(12) United States Patent
Scanlon et al.

(10) Patent No.: US 9,855,371 B2
(45) Date of Patent: Jan. 2, 2018

(54) BIORESORBABLE STENT

(71) Applicants: John James Scanlon, Wilmington, DE (US); Catherine Ann Scanlon, Wilmington, DE (US)

(72) Inventors: John James Scanlon, Wilmington, DE (US); Catherine Ann Scanlon, Wilmington, DE (US)

( * ) Notice: Subject to any disclaimer, the term of this patent is extended or adjusted under 35 U.S.C. 154(b) by 646 days.

(21) Appl. No.: 14/263,851

(22) Filed: Apr. 28, 2014

(65) Prior Publication Data

US 2015/0306282 A1  Oct. 29, 2015

(51) Int. Cl.
| A61L 27/58 | (2006.01) |
| A61F 2/95 | (2013.01) |
| A61L 31/14 | (2006.01) |
| A61L 31/16 | (2006.01) |
| A61L 31/18 | (2006.01) |

(52) U.S. Cl.
CPC ............. *A61L 31/14* (2013.01); *A61L 31/148* (2013.01); *A61L 31/16* (2013.01); *A61L 31/18* (2013.01)

(58) Field of Classification Search
CPC ................ A61F 2/07; A61F 2210/0076; A61F 2250/0018; A61F 2250/0031; A61F 2250/0035; A61F 2310/0097; A61L 31/16; A61L 27/54
See application file for complete search history.

(56) References Cited

U.S. PATENT DOCUMENTS

| 8,012,402 | B2 | 9/2011 | Kleiner | |
| 8,206,635 | B2 | 6/2012 | Ramzipoor | |
| 8,585,753 | B2 | 11/2013 | Scanlon | |
| 2007/0038290 | A1* | 2/2007 | Huang | A61F 2/90 623/1.16 |
| 2007/0179219 | A1* | 8/2007 | Huang | A61F 2/82 524/37 |
| 2009/0216316 | A1* | 8/2009 | Wang | A61L 31/06 623/1.38 |
| 2012/0271396 | A1* | 10/2012 | Zheng | A61L 27/58 623/1.2 |

OTHER PUBLICATIONS

Purac, DataSheet 03, Inherent Viscosity and Molecular Weight Correlations.

* cited by examiner

*Primary Examiner* — Matthew F Desanto

(57) ABSTRACT

Disclosed herein is a high strength, bioresorbable wall thickness suitable for use in an endoprosthesis such as a stent that is produced by first forming a wall thickness by melt processing or solution processing one or more bioresorbable materials into a tubular shape; drawing the shape from shorter length to an optimum longer length and reducing the diameter from a larger diameter to a smaller diameter to orient the molecular chains of the material; fabricating a stent from the tube formed of the oriented material by cutting a strut pattern in its wall thickness; covering the stent's struts with at least one coating to delay degradation of the bioresorbable material; covering the stent's struts with one or more controlled release active ingredients to minimize the risk of restenosis or other side effects; crimping the stent onto a balloon catheter assembly; delivering the stent into an anatomical lumen via percutaneous methods to a treatment location; radially expanding the stent from a smaller size to a larger size at the treatment location wherein the stent temporarily supports the anatomical lumen; and removing the catheter from the lumen.

20 Claims, 18 Drawing Sheets

SECTION A-A

SECTION A-A

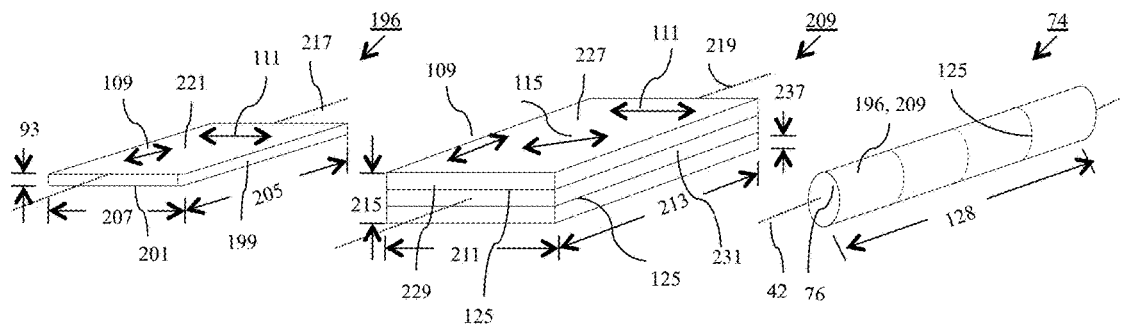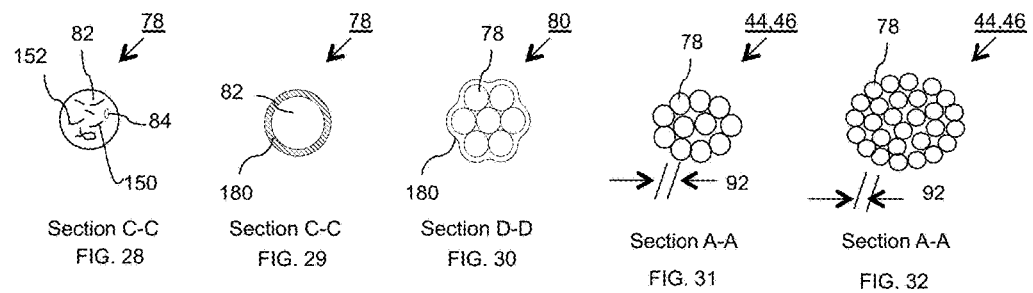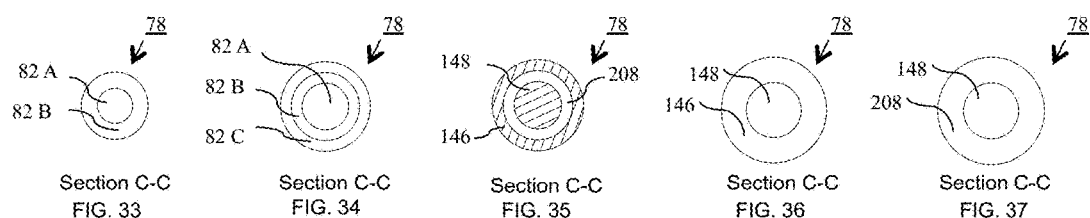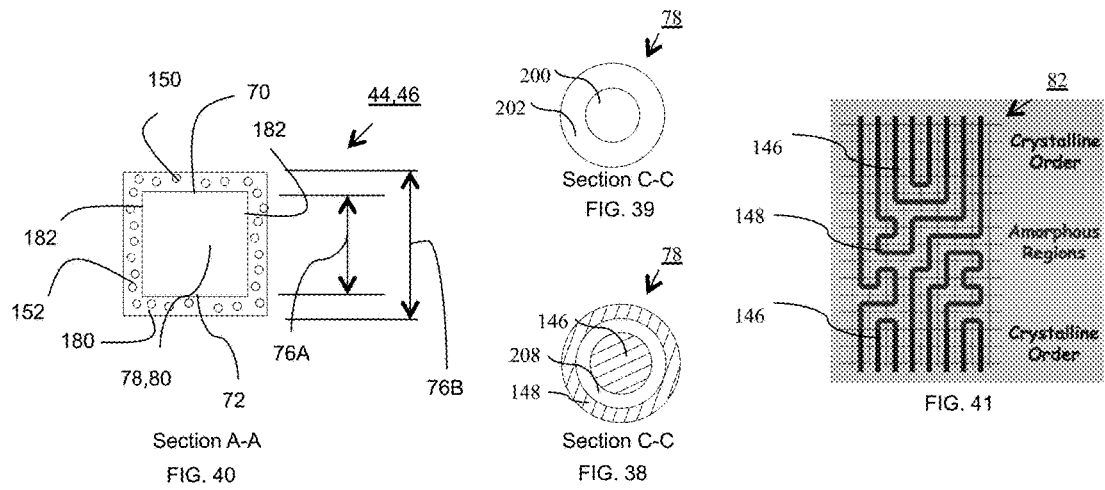

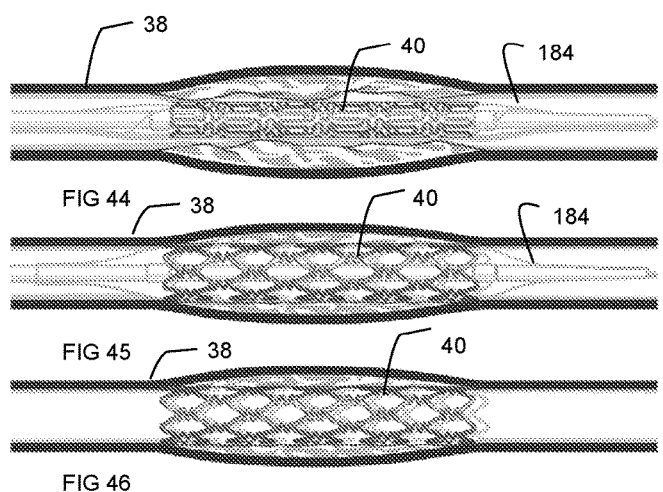
FIG 44
FIG 45
FIG 46
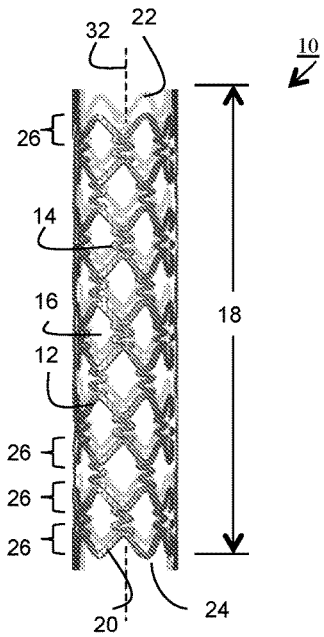
FIG. 49 A
PRIOR ART
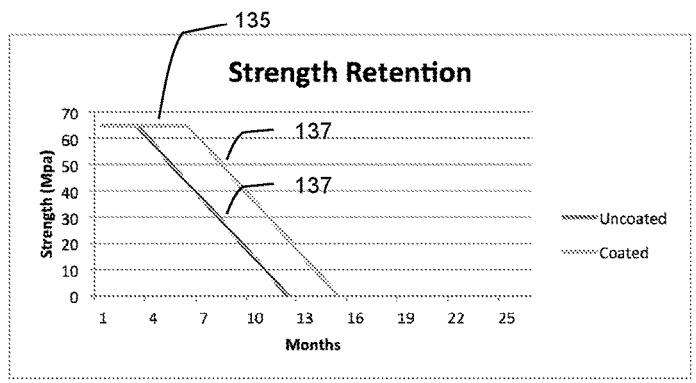
FIG. 47
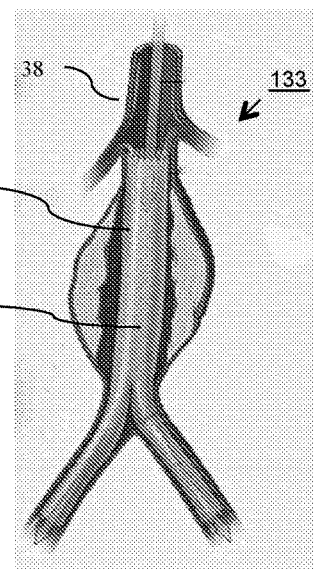
FIG. 49
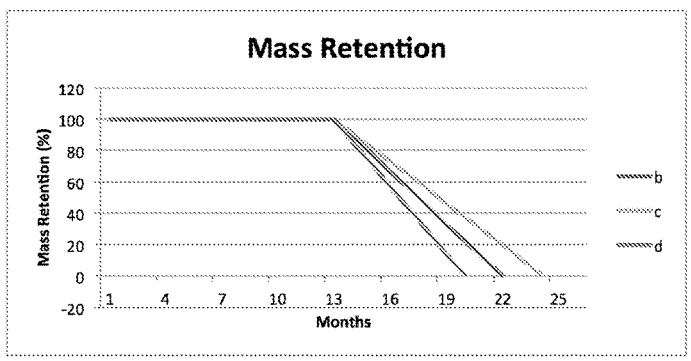
FIG. 48

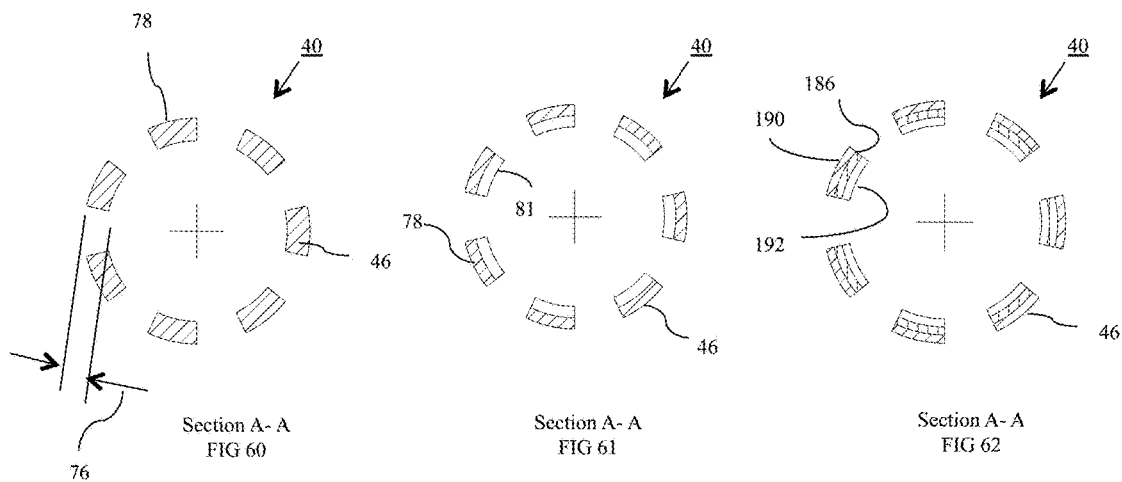
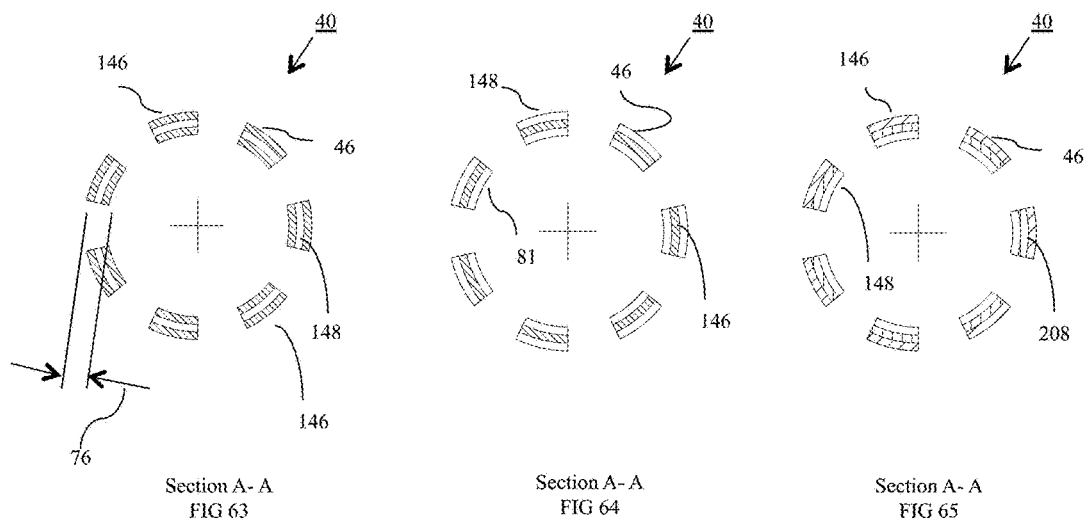

Section B-B

Section B-B

Section B-B

Section B-B

Section B-B

Section B-B

Section B-B

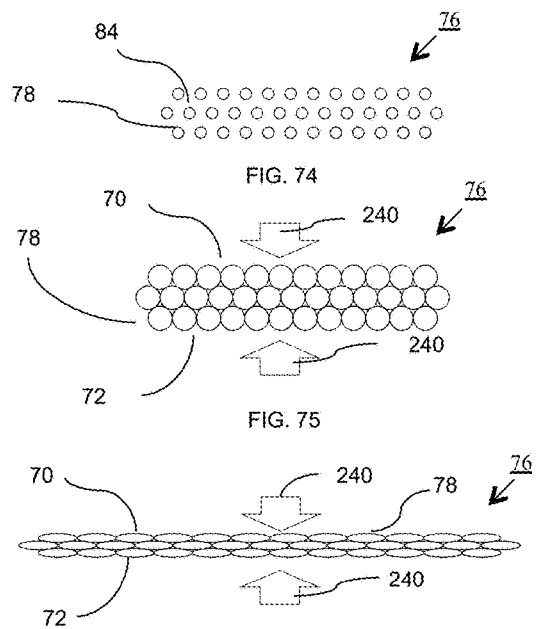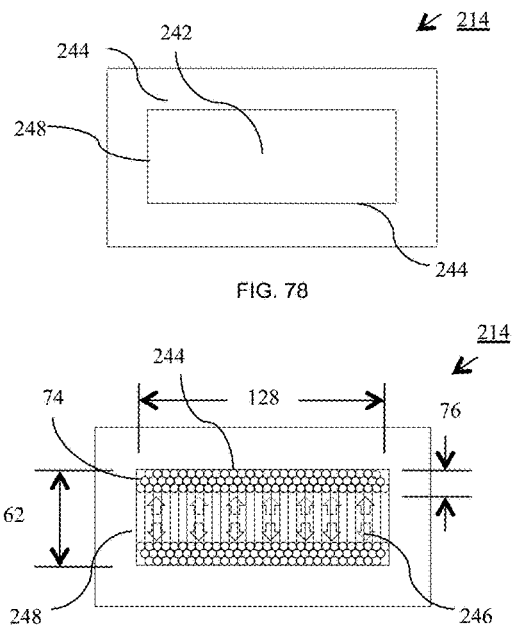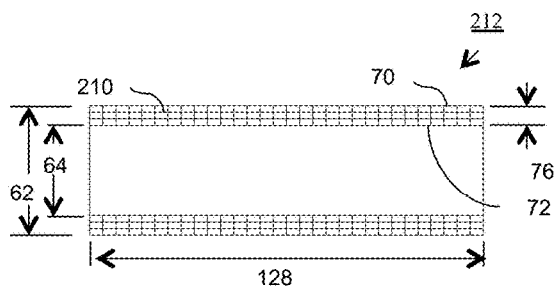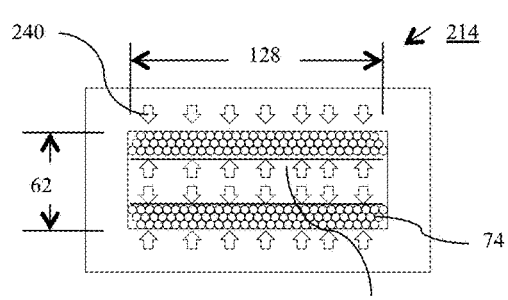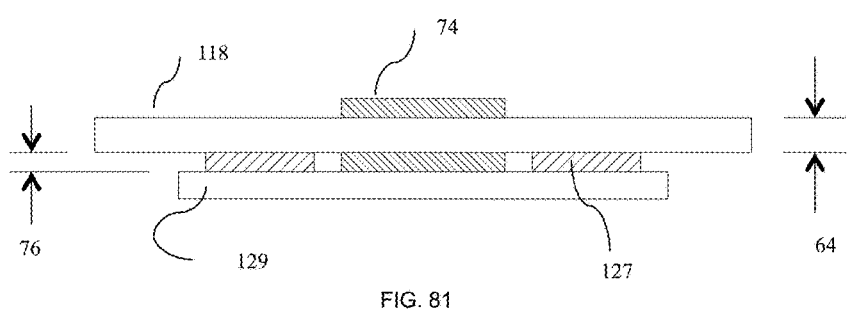

SECTION A-A

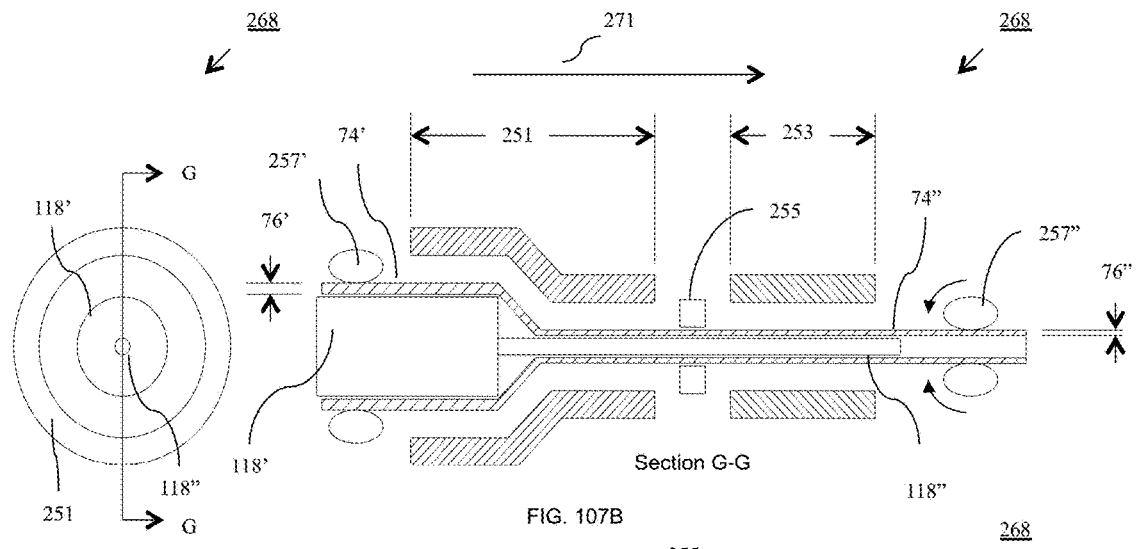
FIG. 107A
FIG. 107B
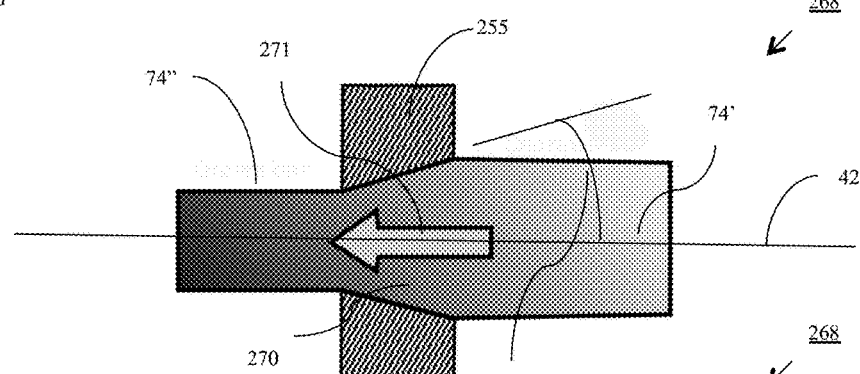
FIG. 108
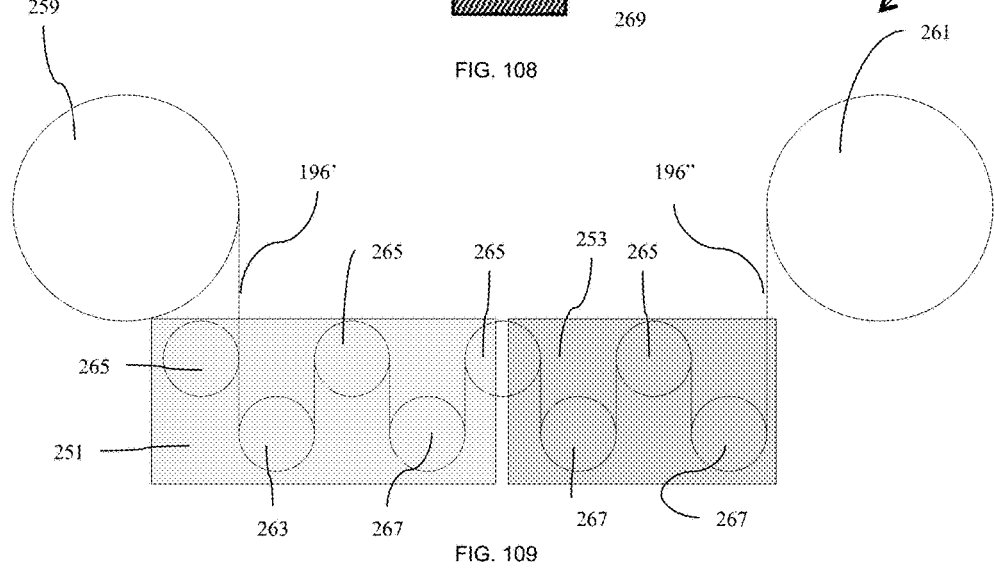
FIG. 109

BIORESORBABLE STENT

PRIORITY CLAIMS

This application claims benefits of Provisional Patent Application Ser. No. 61/816,800 filed Apr. 28, 2013 entitled "BIORESORBABLE STENT WITH STRUTS FORMED OF NANOFIBERS" and Provisional Patent Application Ser. No. 61/975,782 filed Apr. 5, 2014 entitled "BIORESORBABLE STENT."

FIELD OF INVENTION

The present invention relates to drug-eluting medical devices. This invention especially relates to polymeric scaffolds that are expanded by a delivery balloon.

BACKGROUND OF INVENTION

In percutaneous transluminal coronary angioplasty (PTCA), a balloon catheter is inserted through a brachial or femoral artery, positioned across a coronary artery occlusion, and inflated to compress against atherosclerotic plaque to open, by remodeling, the lumen of the coronary artery. Problems with PTCA include formation of intimal flaps or torn artery linings, both of which can create another occlusion in the lumen of the coronary artery. Moreover, thrombosis and restenosis may occur several months after the procedure and create a need for additional angioplasty or a surgical bypass operation. Stents are used to address these issues. Stents are small, intricate, implantable medical devices and are generally left implanted within the patient to reduce occlusions, inhibit thrombosis and restenosis, and maintain patency within the vascular lumens, such as, for example, the lumen of a coronary artery.

Radially expandable endoprostheses are artificial devices implanted in an anatomical lumen. An "anatomical lumen" refers to a cavity, duct, or a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments stents reinforce the walls of the blood vessel and prevent restenosis following angioplasty in the vascular system. "Restenosis" refers to the reoccurrence of stenosis in a blood vessel or heart valve after it has been treated by, for example, balloon angioplasty, stenting, or valvuloplasty with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to the expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen. In the case of a balloon expandable stent, the stent is mounted about a balloon disposed on the catheter.

Mounting the stent typically involves compressing or crimping the stent onto the balloon prior to insertion in an anatomical lumen. At the treatment site, within the lumen, inflating the balloon expands the stent. The balloon may then be deflated and the catheter withdrawn from the stent and the lumen, leaving the stent at the treatment site. In the case of a self-expanding stent, the stent may be secured to the catheter via a retractable sheath. When the stent is at the treatment site the sheath may be withdrawn which allows the stent to self-expand.

The structure of a stent is typically composed of scaffolding that includes a pattern or network of interconnecting structural elements often referred to in the art as struts or bar arms. The scaffolding is designed so that the stent can be radially compressed (to allow crimping) and radially expanded (to allow deployment). A conventional stent is allowed to expand and contract through movement of the individual structural elements of a pattern with respect to each other.

For example, in FIG. A shows a stent 10 having an overall body shape that is hollow and tubular. The stent 10 can be formed from wires, fibers, coiled sheet, with or without openings, or a scaffolding network of rings. The stent 10 can have any geometrical configuration, such as sinusoidal or serpentine strut configuration, and are not limited to what is illustrated in FIG. A. The variation in strut patterns is virtually unlimited.

In FIG. A, the stent 10 includes many interconnecting struts 12, 14 separated from each other by openings 16. The struts 12, 14 can be made of any suitable material, such as biocompatible metal or polymer. The stent 10 has an overall longitudinal length 18 measured from opposite ends, referred to as the distal and proximal ends, 20, 22. The stent 10 has an overall body having a tube shape with a central passageway 24 passing through the entire longitudinal length of the stent 10. At least some of the struts 12 are arranged in series to form sinusoidal or serpentine ring structures 26 that encircle the central axis 32.

The terms "axial" and "longitudinal" are used interchangeably and relate to a direction, line, or orientation that is parallel or substantially parallel to the central axis 32 of the stent 10 or central axis of a cylindrical structure. The terms "circumferential" and "circumferentially" relate to a direction along a circumference of a stent or circular structure. The terms "radial" and "radially" relate to a direction, line, or orientation that is perpendicular or substantially perpendicular to the central axis 32 of a stent 10 or a central axis of a cylindrical structure.

In many treatment applications, the presence of a stent in a body may be necessary for a limited period of time until its intended function of, for example, maintaining vascular patency and/or drug delivery is accomplished. Thus, stents are often fabricated from biodegradable, bioabsorbable, and/or bioresorbable materials such that they completely erode only after the clinical need for them has ended. The term "biodegradable" relates to a compound that can be broken down by natural processes into basic components. The term "bioabsorbable" refers to the breakdown of a compound into a simpler substance or substances that are dispersed and stored within the body but not eliminated by the body. The term "bioresorbable" refers to the breakdown of a compound into a simpler substance or substances that are eliminated by the body. For example, in the case of a bioresorbable polymer the macromolecule is cleaved into low molecular mass by-products, which are eliminated from the body by biological pathways utilizing the kidneys and lungs.

The stent must be able to satisfy a number of basic functional requirements. The stent must be capable of withstanding the structural loads, for example, radial compressive forces, imposed on the stent as it supports the walls of the anatomical lumen after deployment. Therefore, a stent must possess adequate radial strength. Radial strength, which is the ability of a stent to resist radial compressive forces, is due to strength and rigidity around the circumferential direction of the stent. After deployment, the stent must adequately maintain its size and shape throughout its service life despite various forces that may come to bear on it, including the cyclic loading induced by the beating heart. In particular, the stent must adequately maintain an anatomical lumen at a prescribed diameter for the desired treatment time despite these forces. The term "treatment time" refers to the time required for the vessel to remodel, after which the stent is no longer necessary for the vessel to maintain a desired diameter.

Stents implanted in coronary arteries are primarily subjected to radial loads, typically cyclic in nature, which are due to the periodic contraction and expansion of vessels as blood is pumped to and from a beating heart. Stents implanted in peripheral blood vessels, or blood vessels outside the coronary arteries such as iliac, femoral, popliteal, renal and subclavian arteries must be capable of sustaining both radial forces and crushing or pinching loads. These stent types are implanted in vessels that are closer to the surface of the body and are particularly vulnerable to crushing or pinching loads, which can partially or completely collapse the stent and thereby block fluid flow in the vessel. A stent having suitable radial stiffness may not have sufficient crush resistance. Other design considerations for peripheral stents are the degree of bending and axial compression the stent can withstand without mechanical loss of strength or stiffness.

In addition to high radial strength, the stent must also possess sufficient flexibility to allow for crimping on a delivery device, flexure during delivery through an anatomical lumen, and expansion at the treatment site. Longitudinal flexibility is important to allow the stent to be maneuvered through a tortuous vascular path and to enable it to conform to a deployment site that may not be linear or may be subject to flexure. A stent should have sufficient toughness so that it is resistant to crack formation, particularly, in high strain regions during crimping, delivery, and deployment.

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surface a coating of the polymer and the therapeutic substance impregnated in the polymer.

A stent and delivery system typically undergo sterilization to reduce their bioburden to an acceptable sterility assurance level (SAL). There are numerous methods of sterilizing medical devices, the most common being ethylene oxide treatment and treatment with ionization radiation such as electron beam and gamma radiation. Generally, it is desirable for the sterilization procedure to have little or no adverse affects on the performance of a sterilized article.

A polymeric stent or delivery system generally includes means for locating the stent during the percutaneous procedure. Typically, fluoroscopic visualization is used to locate markers either imbedded in the stent or delivery device.

In the prior art there are two primary types of stents: self-expanding and plastically deformed. Self-expanding stents are commonly comprised of super-elastic materials such as Nitinol. This material is known for its ability to return to its original configuration after severe deformation such as a crushing load or longitudinal bending. However, this variety of self-expanding stent has the problem of exerting a "chronic outward force (COF)" on the blood vessel supported by the stent. It is believed that a COF exerted on a blood vessel is a main contributor to high degrees of restenosis of lesions treated by a self-expanding stent even when anti-proliferative drugs are employed.

Stents that are plastically deformed to support a vessel do not suffer from COF. Stents that are plastically deformed by a balloon have the desirable quality of being deployable to the desired diameter for supporting the vessel without exerting outward forces on the vessel exceeding those required to main position of the stent in the vessel during usage. However, plastically deformed stents have the drawback of higher potential for collapsing or becoming kinked in peripheral blood vessels and are generally not used for this reason.

In the prior art, there are generally two classes of materials used to fabricate stents: metal and polymer. A stent comprised of metallic material is generally durable. A durable metallic stent has the drawbacks that it constrains the blood vessel after remodeling has occurred, is subject to frequent strut fractures, requires dual antiplatelet therapy (DAPT) to prevent subsequent thrombosis, sometimes requires revascularization, and sometimes results in the unsatisfactory outcome of late stent thrombosis which often results in patient death. However, a stent comprised of metal offers the benefits of high strength which enables a stent to be fabricated having relatively thin wall thickness and the ability to retain luminal capacity after angioplasty.

A stent comprised of polymer material is generally biodegradable, bioabsorbable, bioresorbable, biosoluble, or bioerodable. The polymeric stent is intended to remain in the body for only a limited period of time because the stent degrades, absorbs, resorbs, or erodes from the implant site. The prior art stents fabricated of bioresorbable polymers generally are comprised of struts 12,14 having a wall thicknesses comprised of a solid polymeric cross section. It is believed that biodegradable stents allow for improved healing of the anatomical lumen as compared to metal stent, which may lead to a reduced incidence of late stage thrombosis.

However, a potential shortcoming of polymer stents compared to metal stents of the same dimension, is that polymer stents typically have less radial strength and rigidity. Relatively low radial strength potentially contributes to relatively high recoil of polymer stents after implantation into an anatomical lumen. "Recoil" refers to the undesirable retraction of a stent radially inward from its deployed diameter due to radially compressive forces that bear upon it after deployment. Moreover, polymer stents of the prior art generally have twice the stent-to-artery coverage of metal stents. The higher stent-to-artery coverage may increase the probability of blocking anatomical lumen side branches or invoking an unfavorable response resulting in restenosis or thrombosis.

Another potential problem with polymer is that struts can crack or fracture during crimping, delivery, and deployment, especially with brittle polymers. Some polymers like poly (L-lactide) ("PLLA") are stiff and strong but can exhibit a brittle fracture mechanism at physiological conditions in which there is little or no plastic deformation prior to failure. A stent fabricated from such polymers can have insufficient toughness for the range of use of a stent. In particular, during deployment of a stent comprised of a material having insufficient ductility, strut fracture can occur when the stent is expanded during deployment with a balloon catheter beyond recommended expansion limits. As a result, cracks can occur particularly in high strain regions, which can result in mechanical failure of the stent. The terms "physiological conditions" refer to conditions within the human body including, but not limited to, body temperature (approximately 37 degrees Celsius), pH, water concentration, oxygen concentration, operating pressure, etc.

A bioresorbable stent of the prior art typically has a wall thickness formed by injection molding, extrusion, or casting. These prior art stents employ polymers with relatively low molecular orientation because the molecular orientation is limited to the random molecular orientation that is imparted on the polymer when it flows through the screw inside the barrel that conveys the material to the mold or die. Instead of building strength in the polymer, these prior art process of molding or extruding can actually reduce the strength of the polymer because the polymer is subjected to relatively high shear stresses at temperatures above the melting point of the polymer which substantially reduces the molecular weight of the polymer. The resultant stents are typically much lower strength than metallic stents and, therefore, have much thicker wall thickness or wider struts to compensate for the polymeric material that is not as strong as a metallic material. Solid wall thickness polymeric stents are sometimes strengthened by radial or longitudinal plastic deformation of the precursor tubes used in manufacturing struts as described in U.S. Pat. No. 8,012,402 B2 filed 15 Apr. 2009, "Tube expansion process for semi-crystalline polymers to maximize fracture toughness." The larger wall thickness is problematic in small diameter stents because the polymeric stents of the prior art reduce luminal capacity because the stent struts consume a significant portion of the orifice in which fluid flows. The terms "plastic deformation" refers to a process when an object is changed permanently in size or shape permanently due to an applied force.

As previously mentioned, polymeric stents are generally produced by cutting a strut pattern in a tube using a laser. A strut pattern creates the interconnecting struts separated by open spaces that define the tubular shape of the stent. The process of cutting a strut pattern in a tube wall thickness generally requires that the tube wall thickness and ovality not vary more than 5-20 microns. Since the struts are typically 75-150 microns in width, it is necessary to use tubes having very little dimensional variation or it is impossible to accurately cut a strut pattern in a tube achieving these narrow strut widths. The prior art methods of have difficulty producing tubes meeting these stringent tolerances, especially when manufacturing a tubular precursor construct having a length greater than 15 cm.

Stents produced from polymer tubes having a wall thickness comprised of filaments, fibers, fibers, and the like can suffer from insufficient stiffness. Mechanical tests suggest that prior art polymeric stents experience less recovery of diameter when expanded by balloon after crimping. The polymeric stents are also more difficult to plastically deform and to properly size in lumen after deployment. Researchers also found that polymeric stents of the prior art have less net gain in luminal capacity at periodic checkpoints after intervention than durable metallic stents. Many polymers used for stents are relatively brittle under physiological conditions. Polymers are susceptible to mechanical instability such as fracturing while in the body. Bioresorbable stents sometimes fracture when expanded more than 17% during deployment. Bioresorbable stents are difficult to see during delivery and deployment because the polymers are not radiopaque, which leads to malposition of the stent.

SUMMARY

The present invention is directed to a strengthened, bioresorbable wall thickness having a controlled degradation rate. The wall thickness is suited for any application but is especially useful as a cylindrical shaped endoprosthesis that functions to temporarily hold open and sometimes expand a segment of an anatomical lumen. The endoprosthesis is crimped onto the end of a catheter and the endoprosthesis is delivered to the treatment area by inserting the catheter through the skin or an opening in the living body into the anatomical lumen. Upon delivery of the endoprosthesis to the treatment area the endoprosthesis is deployed by self-expansion or plastic deformation. Inflating a balloon positioned in the central passageway of the endoprosthesis sometimes assists expansion. The structure of the endoprosthesis is composed of scaffolding that sometimes includes a pattern of struts separated by openings. The scaffolding is designed so that the endoprosthesis can be radially compressed and radially expanded. The endoprosthesis of the present invention degrades and is partially or fully resorbed or otherwise eliminated by a living body after the treatment time. The endoprosthesis of various embodiments is deployed at various treatment sites within a living body.

The invention provides an endoprosthesis addressing the needs for a bioresorbable stent having increased radial strength during the treatment time, thinner struts to increase luminal capacity during the treatment time, narrower struts to minimize luminal wall contact surface area and blockage of side artery branches, reduced strut fracturing, more controlled degradation rate, improved storage stability, improved radiopacity, and a more controlled resorption rate.

The present invention increases the radial strength of the endoprosthesis by cutting a strut pattern into the wall thickness of an inventive tubular precursor construct comprised of bioresorbable material. Bioresorbable materials have considerably lower strength than prior art metallic materials used in the construction of stents. Orienting the molecular chains of the bioresorbable material during processing the material dramatically increases the strength and toughness of the bioresorbable material.

Fundamentally the present invention is produced by the following steps that can be employed independently or in combination with each other: (1) forming one or more materials into a wall thickness by melt processing, solution processing, or combinations thereof; (2) forming the wall thickness into the shape of an tubular precursor construct; (3) orientating and/or extending the molecular chains of the material that comprises the wall thickness by drawing and/or expanding the wall thickness; (4) modifying the morphology of the material comprising the wall thickness by heating and cooling the material in such a way to obtain the best balance between stiffness and ductility. In an embodiment, the wall thickness is comprised of an extruded, cast, or molded wall thickness prior to drawing or expanding. In another embodiment, the wall thickness is comprised of one or more layers of preformed configurations such as fibers or films aligned in the wall thickness in a pattern to optimize mechanical properties of the endoprosthesis before drawing or expanding. In an embodiment, the drawn or expanded tubular precursor construct is further processed by cutting a strut pattern into the wall thickness which produces a stent comprised of ring struts separated by link struts.

An embodiment of the endoprosthesis of the present inventions includes one or more coatings or layers of coatings of the same for different materials positioned on the outside surfaces of the wall thickness, struts, preformed configurations or combinations thereof that delay or control the degradation of the bioresorbable material. A bioresorbable stent generally undergoes a reduction in molecular weight during the treatment time that initially manifests itself as a reduction in strength and ultimately as a loss of material mass. The delay or control of the degradation of the material enables a stent of thinner and/or narrower struts to provide adequate support to the anatomical lumen during the treatment time. One more embodiment of the endoprosthesis includes at least one active ingredient such as a drug. Active ingredients are stored within one or more layers of coating, within the wall thickness, on the surface of the struts, or combinations thereof.

In an embodiment, the stent is crimped onto the end of a delivery catheter, packaged, and sterilized.

BRIEF DESCRIPTION OF DRAWINGS

FIG. 25 is a perspective view of a preformed configuration in the form of a sheet.

FIG. 26 is a perspective view of a preformed configuration in the form of a multi-sheet.

FIG. 27 is a perspective view of a precursor construct tube formed of one or more sheets connected by seams.

FIG. 28 is a cross-sectional view taken through section C-C of FIG. 5 of a preformed configuration in the form of a fiber including additives and voids.

FIG. 29 is a cross-sectional view taken through section C-C of FIG. 5 of a preformed configuration in the form of a fiber including a coating.

FIG. 30 is a cross-sectional view taken through section D-D of FIG. 9 of a preformed configuration in the form of a multi-fiber including a coating.

FIG. 31 is a cross-sectional view of a strut taken through section A-A of FIG. 1 comprising thick preformed configurations in the form of fibers.

FIG. 32 is a cross-sectional view of a strut taken through section A-A of FIG. 1 comprising thin preformed configurations in the form of fibers.

FIG. 33, FIG. 34, FIG. 35, FIG. 36, FIG. 37, FIG. 38, and FIG. 39 are cross-sectional views taken through section C-C of FIG. 5 of preformed configurations in the form of a fiber having two or more core/shell layers.

FIG. 40 is a cross-sectional view taken through section A-A of FIG. 1 of a strut including a coating containing active ingredients.

FIG. 41 is an illustration of a material morphology depicting crystalline sections connected by amorphous region.

FIG. 44, FIG. 45, and FIG. 46 are side view illustrations of a stent being delivered and deployed in an anatomical lumen.

FIG. 47 is a graph illustrating an example of the loss of strength of material comprising the stent when undergoing degradation.

FIG. 48 is a graph illustrating an example of the loss of mass of material comprising the stent when undergoing degradation.

FIG. 49 is an illustration of a bifurcated stent and a stent-graft.

FIG. 60, FIG. 61, FIG. 62, FIG. 63, FIG. 64, and FIG. 65 are examples of cross-sectional views of a stent strut or link strut taken through section A-A of FIG. 1 showing one or more layers of construction of the wall thickness.

FIG. 74 is a cross sectional view of a portion of a wall thickness comprised of preformed configurations in the form of fibers separated by void space.

FIG. 75 and FIG. 76 are cross sectional views of portions of the wall thickness in FIG. 74 being consolidated.

FIG. 77 is a cross sectional view of a precursor construct tube taken through section B-B of FIG. 10A showing the wall thickness after consolidation, densification, sizing, or combinations thereof.

FIG. 78 is a cross-sectional view of a mold for sizing the wall thickness comprised of preformed configurations.

FIG. 79 is a cross-sectional view of mold that produces a precursor construct tube having low dimensional variation by pressurizing the inside diameter of the tube to press the outer surface of the wall thickness against the mold.

FIG. 80 is a cross-sectional view of a mold that produces a precursor construct tube having low dimensional variation by compressing the wall thickness between two surfaces.

FIG. 81 is a cross-sectional view of a device for producing a precursor construct tube having low dimensional variation by rolling the wall thickness of the tube which is positioned on a mandrel over a flat plate wherein the gap between the plate and the mandrel is formed by a shim that sets the thickness of the tube wall thickness.

FIG. 107A is a side view and FIG. 107B is a cross-sectional view taken through section G-G of FIG. 107A of a process for imparting molecular orientation on the wall thickness of the present invention when the wall thickness is in the form of a tube.

FIG. 108 is a cross-sectional view of a process for imparting molecular orientation on the wall thickness of the present invention when the wall thickness is in any configuration.

FIG. 109 is a side view of a process for imparting molecular orientation on the wall thickness of the present invention when the wall thickness is in the form of a sheet or film.

DETAILED DESCRIPTION OF PREFERRED EMBODIMENTS

Stent

The various embodiments of the present invention relate to stents and methods of fabricating stents with favorable mechanical properties. The stent 40 of the present invention focuses on improving the mechanical properties of the stent 40 by manipulating the structure of the wall thickness 76 of the struts 44, 46.

Figure 1:
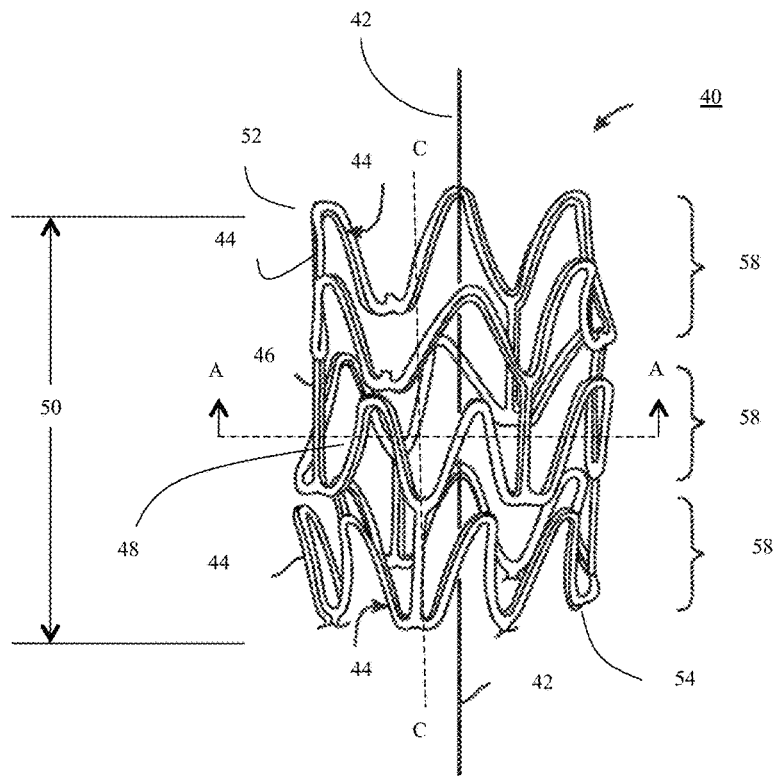
FIG. 1 is a perspective view of a portion of a stent.

Referring now in more detail to the exemplary drawings for purposes of illustrating embodiments of the invention, wherein like reference numerals designate corresponding or like elements among the several views, there is shown in FIG. 1 a partial perspective view of an exemplary stent 40 in un-crimped or expanded state that includes a pattern of a plurality of interconnecting structural elements or struts.

Figure 42:
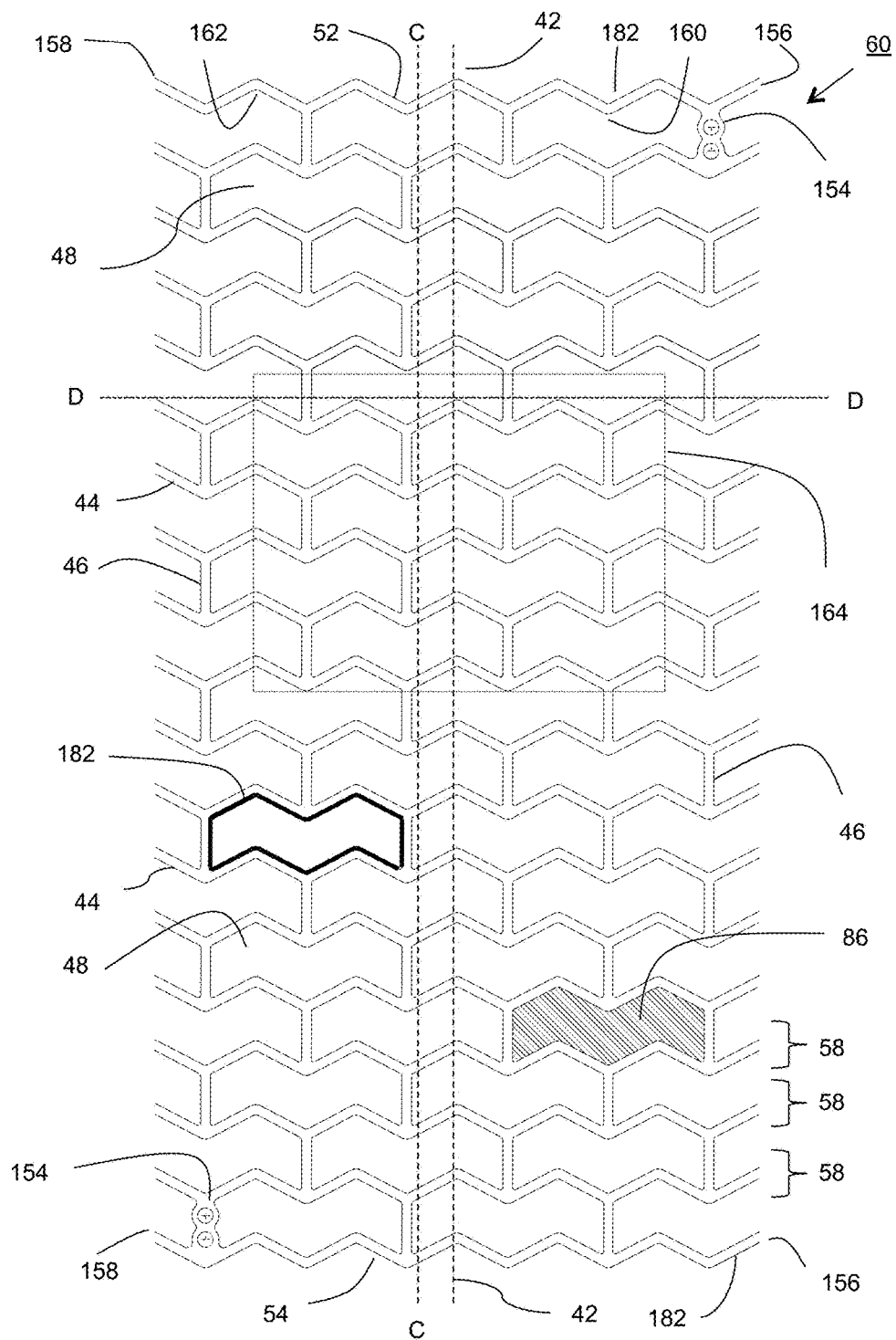
FIG. 42 depicts a strut pattern viewed in a flat or planar state.

Stent 40 has a cylindrical shape with a central axis 42 and includes a pattern with a number of interconnecting structural elements or struts 44 separated by openings 48. In an embodiment, the struts 44 are configured in rings 58 that are connected together by link struts 46. Central axis 42 extends through the center of the cylindrical shape. The stent 40 has an overall body having a tube shape with a central passageway 56 passing through the entire length of the stent. The term "tube" refers to a hollow elongated cylinder such as a channel, conduit, duct, or pipe. The central passageway has two circular openings; there being one opening at each of the distal 54 and proximal ends 52 of the overall body. In general, a strut pattern 60 (FIG. 42) is designed so that the stent can be radially compressed to allow for percutaneous delivery through an anatomical lumen, and then deployed for implantation at the desired treatment site of the anatomical lumen. The strut pattern 60 can have any geometrical configuration and is not limited to what is illustrated in FIG. 1 or FIG. 42. The possible variations of the strut pattern 60 are virtually unlimited. The strut pattern 60 in some embodiments is the same design for the entire length 50 of the stent 40 or in other embodiments has two or more design variations along the length 50 of the stent 40. In other embodiments where a strut pattern is not necessary to facilitate crimping, delivery, or deployment of the stent into the anatomical lumen, the stent 40 does not include a strut pattern 60.

Figure 2:
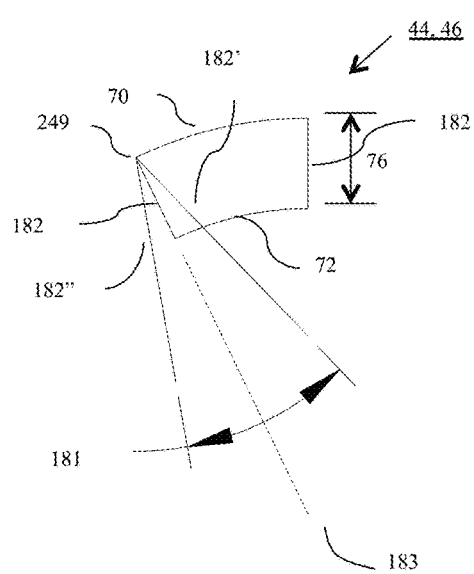
FIG. 2 is a cross-sectional view of a stent strut or link strut taken through section A-A of FIG. 1 showing the range of angles possible for the cutting edges.
Figure 3:
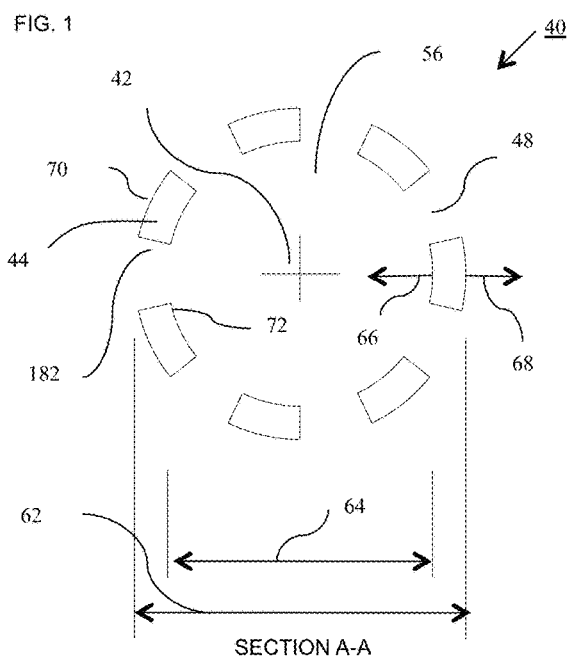
FIG. 3 is a cross-sectional view of a stent taken through section A-A of FIG. 1.

FIG. 3 is an exemplary cross-sectional view of the stent 40 along line A-A in FIG. 1. There can be any number of struts 44 along line A-A. In FIG. 3 the cross-section of seven struts 44 are shown for ease of illustration. The struts 44 in cross-section are arranged in a circular pattern having an outer diameter 62 and inner diameter 64. The circular pattern encircles the central axis 42. A portion of the surface of each strut 44,46 faces radially inward in a direction 66 facing toward the central axis 42. A portion of the surface of each strut 44,46 faces radially outward in a direction 68 facing away from the central axis 42. The various strut 44,46 surfaces that face radially outward collectively form the outer surface 70 of the stent 40. The various strut 44,46 surfaces that face radially inward collectively form the inner surface 72 of the stent 40. The outer surface 70 is commonly referred to as the "abluminal surface" and the inner surface 72 are commonly referred to as the "luminal surface" by those skilled in the art. In an embodiment, the outer surfaces 70 and/or inner surfaces 72 are smooth. In an embodiment, the outer surfaces 70 and/or the inner surfaces 72 are rough. In an embodiment, the struts are curved or angular to minimize or avoid turbulent flow over the struts after deployment. As shown in FIG. 2, the wall thickness 76 is located between the outer surface 70 and the inner surface 72.

Figure 4:
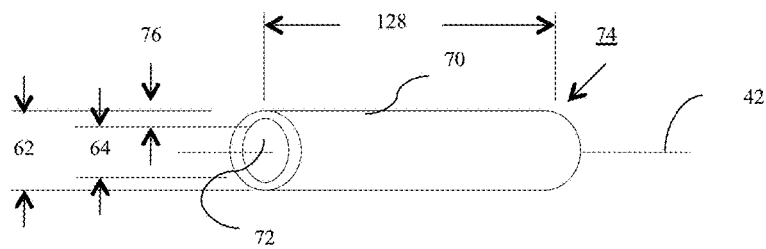
FIG. 4 is a perspective view of a precursor construct tube for use in producing a stent having a wall thickness comprised of preformed configurations.

Cutting the strut pattern 60 in the wall thickness 76 of the precursor construct tube 74 forms the stent 40. Cutting a strut pattern 60, shown in FIG. 42, from the wall thickness 76 of a precursor construct tube 74, as shown in FIG. 4, produces the stent 40. As shown in FIG. 4 the precursor construct tube 74 is a tubular-shaped article comprised of an outer diameter 62, an inner diameter 64, an outer surface 70, an inner surface 72, a length 128, a central axis 42, and a wall thickness 76. The wall thickness 76 of the precursor construct tube 74 is comprised of a drawn and/or expanded extrusion, a drawn and/or expanded molding, a drawn and/or casting, a drawn and/or expanded network of one or more preformed configurations 77 that are aligned in the wall thickness 76 in an engineered design, or any combinations thereof. Drawing and/or expanding the wall thickness 76 as described herein strengthens the tubular precursor construct 74. In an embodiment, the wall thickness 76 includes one or more voids 84. Voids 84 can improve strut ductility and reduce the risk of strut fracturing during deployment.

In an embodiment, the stent 40 includes one or more coatings 180 positioned on the outer surfaces of the struts 44 and link struts 46. In an embodiment, the stent 40 includes one or more active ingredients such as one or more drugs positioned in the wall thickness 76 of the struts 44, 46, coating 180, or combinations thereof. In an embodiment, the stent 40 is temporarily secured on a catheter 184 until it is delivered to a treatment area of an anatomical lumen 38 where it is deployed.

Wall Thickness

In an embodiment, the wall thickness 76 is comprised of one or more materials 82. In an embodiment, the wall thickness 76 is comprised of one or more blends of materials 82. In a preferred embodiment, the wall thickness 76 is comprised of one or more bioresorbable materials 82. For simplicity the terms "absorbable," "resorbable," "biodegradable," "bioresorbable," "bioabsorbable," and "bioadsorbable" are used interchangeably and synonymously in this application. In an embodiment, the wall thickness 76 includes one or more additives 150. In an embodiment, the wall thickness 76 includes one or more nano sized additives 152, which have a size below 0.001 millimeters (mm). In an embodiment, the wall thickness 76 includes one or more voids 84 to create an at least a partially porous wall thickness.

As previously mentioned, the wall thickness 76 of the precursor construct tube 74 is comprised of a drawn or expanded extrusion, a drawn or expanded molding, a drawn or expanded casting, a drawn or expanded network of one or more preformed configurations 77, or combinations thereof. Therefore, in an embodiment, a wall thickness 76 is comprised of one or more preformed configurations 77. In another embodiment the wall thickness 76 is comprised of one or more extruded materials 82. In one more embodiment, the wall thickness 76 is comprised of one or more molded materials 82. In yet another embodiment, the wall thickness 76 is comprised of one or more cast materials 82. In an embodiment, melt processing or solution processing produces the extrusion, molding, casting, or preformed configuration 77.

To produce a wall thickness 76 of enhanced mechanical properties, the wall thickness 76 is comprised of one or more layers 106. In an embodiment, the layers 106 are comprised of extruded, molded, or cast, materials 82. Without intent on limiting, the advantages of producing the wall thickness of layers 106 included: (1) the ability of producing the wall thickness 76 of multiple materials 82; (2) the ability of producing a wall thickness 76 of layers of different configurations such as a film 81, fiber 78, or combination thereof; (3) the ability of producing a wall thickness 76 of materials 82 having different melting temperatures; (4) the ability of producing a wall thickness 76 of materials 82 having different molecular weights; (5) the ability of producing a wall thickness 76 of materials 82 having different physical properties; (6) the ability of producing a wall thickness 76 of materials 82 having different degradation rates; (7) the ability of producing a wall thickness 76 of materials 82 having different resorption rates; (8) the ability to produce a wall thickness 76 with a portion including additives 150, 152 and a portion not including additives 150, 152; (9) the ability to include voids 84 in part or all of the wall thickness 76; (10) the ability of producing a wall thickness 76 of greater crack resistance because the interfaces between layers serve as crack tip arrestors that slow down or stop crack propagation; (11) the ability of producing a wall thickness 76 wherein one portion of the wall thickness 76 has a higher crystallinity or amorphicity than another portion; or (12) combinations thereof.

The advantage of partially or fully producing the wall thickness 76 of preformed configurations 77 such as fibers 78 or films 81 include: (1) the ability of producing the wall thickness 76 of multiple materials 82; (2) the ability of producing a wall thickness 76 of different materials 82 wherein the materials 82 are aligned in the wall thickness 76 in an engineered design that produces a wall thickness 76 having desired physical properties; (3) the ability of producing a fiber reinforced wall thickness 76 comprised of materials 82 having different melting temperatures so that bioresorbable fibers 78 can be included in the wall thickness 76 to reinforce the matrix material 82; (4) the ability of producing a wall thickness 76 of materials 82 having different molecular weights; (5) the ability of producing a wall thickness 76 of materials 82 having different physical properties; (6) the ability of producing a wall thickness 76 of materials 82 having different degradation rates; (7) the ability of producing a wall thickness 76 of materials 82 having different resorption rates; (8) the ability to produce a wall thickness 76 with a portion including additives 150, 152 and a portion not including additives 150, 152; (9) the ability to include voids 84 in part or all of the wall thickness 76; (10) the ability of producing a wall thickness 76 of greater crack resistance because the interfaces between preformed configurations 77 serve as crack tip arrestors that slow down or stop crack propagation; (11) the ability of producing a wall thickness 76 wherein one portion of the wall thickness 76 has a higher crystallinity or amorphicity than another portion (12) or combinations thereof.

In an embodiment, the wall thickness 76 is comprised of one or more materials 82 partially or fully formed into a wall thickness by solution processing. In an embodiment, the wall thickness 76 is comprised of one or more materials 82 partially or fully formed into a wall thickness by melt processing. In an embodiment, the wall thickness 76 is comprised of one or more materials 82 partially or fully formed into a wall thickness by a combination of melt and solution processing. In an embodiment, the wall thickness 76 is comprised of one or more materials 82 that are partially or fully hot drawn. In an embodiment, the wall thickness 76 is comprised of one or more materials 82 that are partially or fully cold drawn. In an embodiment, the wall thickness 76 is comprised of one or more materials 82 that are solution processed followed by one or more hot drawing processes. In an embodiment, the wall thickness 76 is comprised of one or more materials 82 that are wet extruded followed by one or more hot drawing processes. In an embodiment, the wall thickness 76 is comprised of one or more materials 82 that are dry extruded followed by one or more hot drawing processes. In an embodiment, the wall thickness 76 is comprised of one or more materials 82 that are dry-wet or gel extruded followed by one or more hot drawing processes. In an embodiment, the wall thickness 76 is comprised of one or more materials 82 that are melt processed followed by one or more hot drawing processes. In an embodiment, the wall thickness 76 is comprised of one or more materials 82 that are solution processed followed by one or more cold drawing processes. In an embodiment, the wall thickness 76 is comprised of one or more materials 82 that are wet extruded followed by one or more cold drawing processes. In an embodiment, the wall thickness 76 is comprised of one or more materials 82 that are dry extruded followed by one or more cold drawing processes. In an embodiment, the wall thickness 76 is comprised of one or more materials 82 that are dry-wet or gel extruded followed by one or more cold drawing processes. In an embodiment, the wall thickness 76 is comprised of one or more materials 82 that are melt processed followed by one or more cold drawing processes. In an embodiment, the wall thickness 76 is comprised of one or more materials 82 that are melt and solution processed followed by one or more hot drawing processes. In an embodiment, the wall thickness 76 is comprised of one or more materials 82 that are melt and solution processed followed by one or more cold drawing processes. In an embodiment, the wall thickness 76 is comprised of one or more materials 82 that are solution and/or melt processed followed by one or more hot drawing processes and/or one or more cold drawing processes.

In an embodiment, the wall thickness 76 is comprised of one or more materials 82 that are hot expanded. In an embodiment, the wall thickness 76 is comprised of one or more materials 82 that are cold expanded. In an embodiment, the wall thickness 76 is comprised of one or more materials 82 that are solution processed followed by one or more hot expansion processes. In an embodiment, the wall thickness 76 is comprised of one or more materials 82 that are melt processed followed by one or more hot expansion processes. In an embodiment, the wall thickness 76 is comprised of one or more materials 82 that are solution processed followed by one or more cold expansion processes. In an embodiment, the wall thickness 76 is comprised of one or more materials 82 that are melt processed followed by one or more cold expansion processes. In an embodiment, the wall thickness 76 is comprised of one or more materials 82 that are melt and solution processed followed by one or more hot expansion processes. In an embodiment, the wall thickness 76 is comprised of one or more materials 82 that are melt and solution processed followed by one or more cold expansion processes. In an embodiment, the wall thickness 76 is comprised of one or more materials 82 that are solution and/or melt processed followed by one or more hot expanding processes and/or one or more cold expanding processes.

In a more preferred embodiment, the wall thickness 76 has tensile strength above about 5 MPa. In a preferred embodiment, the wall thickness 76 has tensile strength at or less than about 5 MPa. In a more preferred embodiment for use as a vascular stent 40, the wall thickness 76 has a tensile strength above about 40 MPa, more preferably above about 0.3 GPa and most preferably above about 1 GPa. In a preferred embodiment for use as a vascular stent 40, the wall thickness 76 has a tensile strength at or below about 40 MPa. In a more preferred embodiment, the wall thickness 76 has a Young's modulus of elasticity above about 0.1 GPa. In a preferred embodiment, the wall thickness 76 has a Young's modulus of elasticity at or below about 0.1 GPa. In a more preferred embodiment for use as a vascular stent 40, the wall thickness 76 has a Young's modulus of elasticity above about 0.5 GPa, more preferably above about 3.5 GPa. In a preferred embodiment for use as a vascular stent 40, the wall thickness 76 has a Young's modulus of elasticity at or below about 0.5 GPa. In a more preferred embodiment, the wall thickness 76 has an elongation to break above about 1%. In a preferred embodiment, the wall thickness 76 has an elongation to break at or below about 1%. In a more preferred embodiment for use as a vascular stent 40, the wall thickness 76 has an elongation to break above about 2%, more preferably above about 6%, and most preferably above 15%. In a preferred embodiment for use as a vascular stent 40, the wall thickness 76 has an elongation to break at or below about 2%. These figures are based on a tensile machine crosshead speed of 25 millimeters/minute and testing temperature of 24 degrees Celsius.

The terms "melt processing" refers to melting one or more materials 82, forming the material or materials 82 into a desired shape, and cooling the material or materials 82 to lock-in the final shape. The terms "solution processing" refers to dissolving one or more materials 82 in one or more solvents, forming the material or materials 82 into a desired shape, and partially or fully removing the solvent by, for example, evaporating the solvent or solvents to lock-in the final shape. The term "drawing" refers to a process using tensile forces to stretch the material 82 so that the shape's cross sectional area is reduced and/or its length is increased. Without intent on limiting, a tube 74 is drawn through a die to reduce its diameter and increase its length. The term "expanding" refers to stretching the material 82 so that it elongates from a smaller size to a larger size and partially or fully retains the larger size. Without intent on limiting, a tube 74 is expanded to increase its diameter. The term "hot" refers to drawing or expanding the wall thickness at a temperature at or above about 23 degrees Celsius. The term "cold" refers to drawing or expanding the wall thickness 76 at a temperature below about 23 degrees Celsius.

Wall thicknesses 76 formed by solvent process are generally stronger than wall thicknesses 76 formed by melt processing. In melt processing, the highest molecular weight materials 82 cannot be used because they are too viscous to convert into an appropriate shape using commonly available melt extrusion or melt molding machines. It is desirable to use higher molecular weight materials to produce the wall thickness 76 because molecular weight is lost during manufacturing, sterilization, storage, and use of the wall thickness 76. For example, by forming the precursor construct tube's wall thickness 76 by solvent processing there is less thermal, hydrolytic, and mechanical degradation of the material 82 than during melt processing like formation of the material into a tube 74. Moreover, by using a wall thickness 76 produced by solvent processing you can produce the wall thickness 76 of higher molecular weight materials 82 to compensate for the approximately fifty percent or more reduction in molecular weight lost during some crimping, sterilization, and storage conditions.

Precursor Construct Tube

As illustrated in FIG. 4, the precursor construct tube 74 is tubular shaped with an outer diameter 62, an inner diameter 64, an outer surface 70, an inner surface 72, a wall thickness 76, a length 128, and a central axis 42. The term "diameter" refers to a straight line passing from side to side through the center of a body such as, but not limited to, a circle. The tubular shape can be any shape, such as and without intent on limiting, substantially round, elliptical, or oval shaped. The tubular precursor construct 74 of the present invention is of any dimensions that meet the requirements of the end-use applications described herein. In a preferred embodiment for use as a stent 40, the length is greater than 15 centimeters (cm) so that multiple stents of an economic quantity can be cut for the length of the precursor construct tube 74, the inner diameter 64 is greater than 0.5 millimeters (mm), the wall thickness 76 is less than 0.200 millimeters (mm) (more preferably less than 0.160 mm), and the dimensional variation is less than 0.020 millimeters (mm) (more preferably less than 0.010 mm). In other embodiments, the length is at or less than 15 centimeters (cm), the inner diameter is at or less than 0.5 millimeters (mm), and the wall thickness is at or greater than 0.200 millimeters (mm).

Figures 10A, 10B:
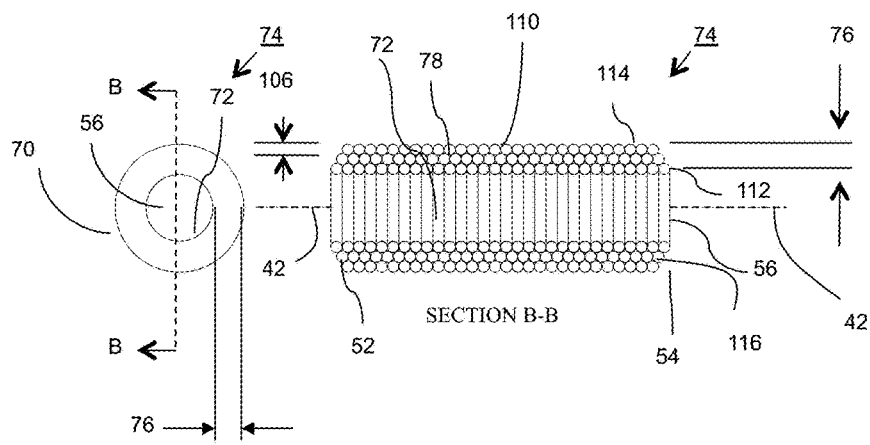
FIG. 10A is a side view and FIG. 10B is cross-sectional view taken through section B-B of FIG. 10A of an embodiment of a precursor construct tube for use in a stent having a wall thickness comprised of preformed configurations in the form of fibers.
Figure 19:
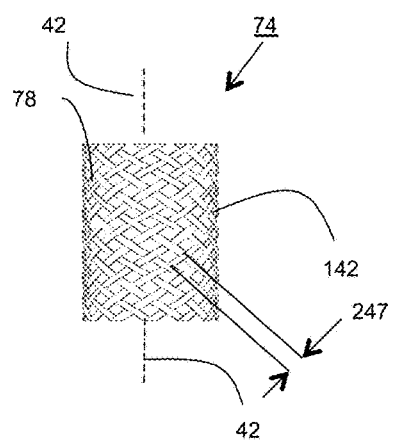
Figure 105:
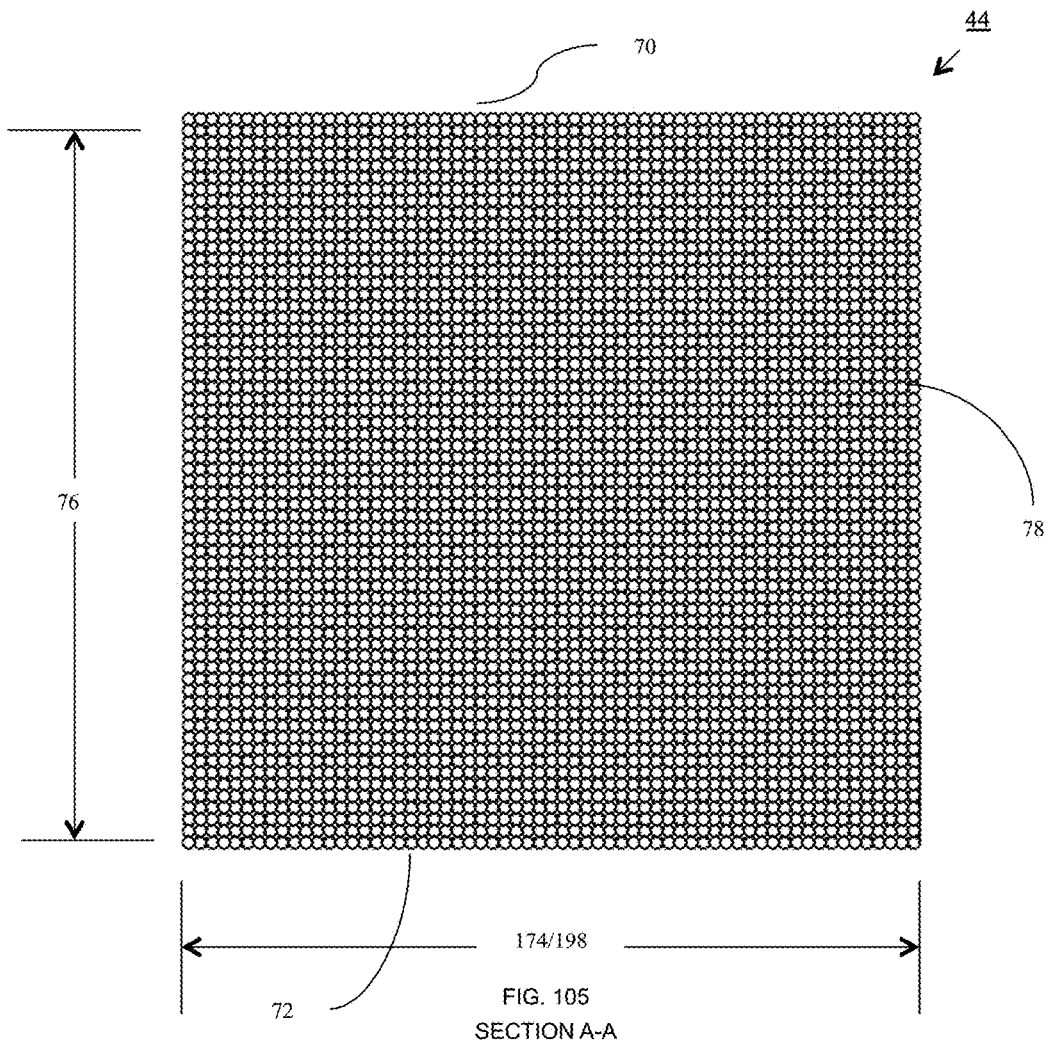
FIG. 105 is an illustration of a wall thickness in cross-sectional view taken through section A-A of FIG. 1 comprised of many preformed configurations in the form of fibers.

Referring to FIG. 4, in an embodiment, the wall thickness 76 of the precursor construct tube 74 is comprised of one or more extruded, molded, or cast materials 82 or layers of materials 82. Referring to FIG. 10A and FIG. 10B, in another embodiment, the wall thickness 76 of the tubular precursor construct 74 is formed of one or more layers 106 of preformed configurations 77 such as fibers 78, films 81, or combinations thereof. Still referring to FIG. 10A and FIG. 10B, to illustrate a layered embodiment, the wall thickness 76 is comprised of an luminal layer 112 of preformed configurations 77, one or more middle layers 116 of preformed configurations 77, and an abluminal layer 114 of preformed configurations 77. The luminal layer 112 is positioned in the wall thickness 76 at the shortest radial distance from the central axis 42, the middle layers 116 at a farther radial distance from the central axis 42, and abluminal layer 114 at the farthest radial distance from the central axis 42. When there are more than three layers 106 of preformed configurations 77 the process of adding preformed configurations 77 to the wall thickness 76 is repeated by sequentially adding more preformed configurations 77 between the luminal layer 112 and the abluminal layer 114 at farther radial distances from the central axis 42 and in direct contact with the underlying preformed configuration 77 or preformed configurations 77 from the proximal end 52 to the distal end 54 of the precursor construct tube 74 until the desired wall thickness is obtained. As an example of an embodiment is shown in FIG. 105, it is possible to have hundreds or more preformed configurations 77 in the wall thickness 76 of the present invention. Upon deposition, in some embodiments the preformed configurations 77 are partially or fully connected at nodes 142 and in other embodiments the preformed configurations 77 are not connected at the nodes 142 as described in more detail in other sections of this specification. The point at which the preformed configurations 77 intersect or crossover other preformed configurations is a node 142. Therefore, the "node" refers to a preformed configuration-to-preformed configuration junction. The term "inter-nodal distance" refers to the length of the fiber 78, 80 between two nodes 142 or the length of the fibers 78, 80 between where a fiber 78 intersects two other fibers 78. An example of the inter-nodal distance 247 is shown in FIG. 19. The inter-nodal distance 247 is of any length that produces a wall thickness 76 having the performance described herein. In an embodiment of wall thickness 76, the inter-nodal distance 247 is in the range of about 0.01 nanometers to 200 millimeters (mm), more preferably in the range of 25 nanometers to 0.200 millimeters (mm), and most preferably in the range of 25 nanometers to 0.050 millimeters (mm). In other embodiments, the inter-nodal distance 247 is less than about 0.01 nanometers. In still other embodiments, the inter-nodal distance 247 is greater than 200 millimeters (mm).

In an embodiment, there are one or more void spaces 84 in the wall thickness 76. In an embodiment, the void spaces 84 are positioned between some or all the preformed configurations 77. As shown in FIG. 25, in an embodiment the wall thickness 76 is comprised of one or more sheets 196 comprised of one or more preformed configurations 77. In an embodiment, the wall thickness 76 is comprised of one or more multi-sheets 209 comprised of one or more preformed configurations 77.

Figure 11:
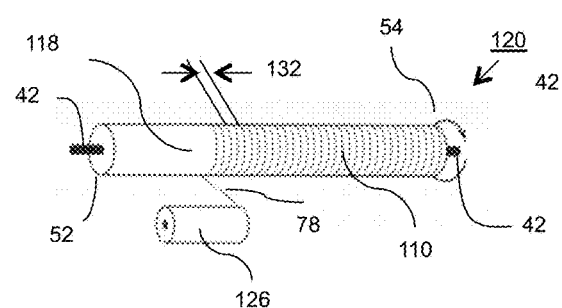
FIG. 11, FIG. 12, and FIG. 13 are perspective views of circumferential, helical, and polar winding processes for use in producing a precursor construct tube having a wall thickness comprised of preformed configurations.
Figure 12:
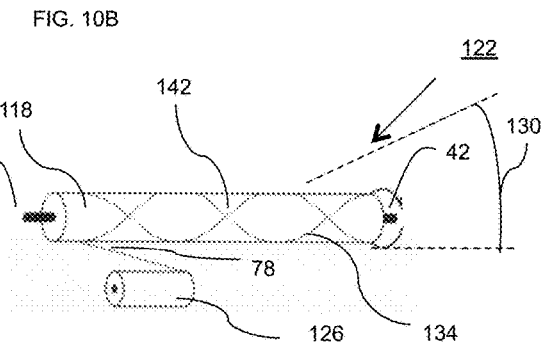
Figure 13:
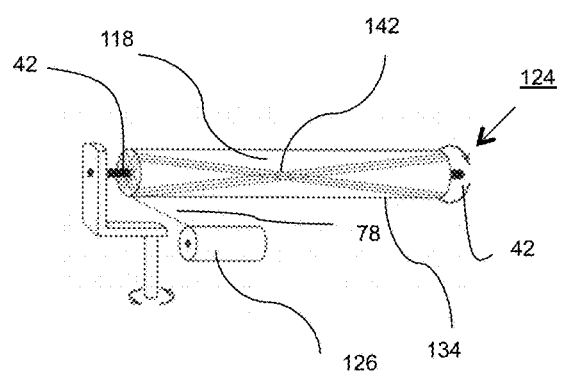
Figure 14:
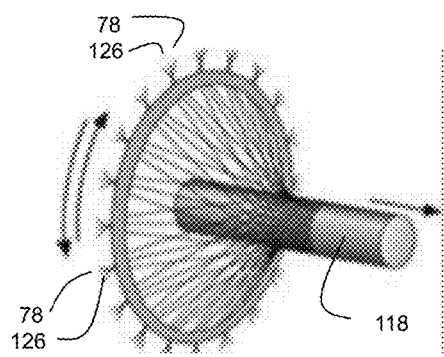
FIG. 14 is a perspective view of a braiding machine for use in producing a precursor construct tube having a wall thickness comprised of preformed configurations.
Figure 18:
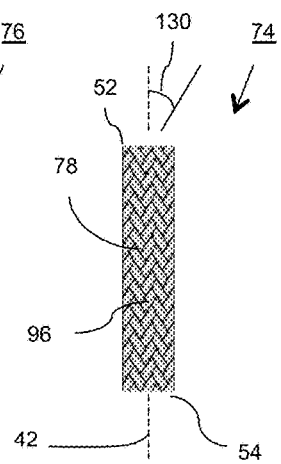
FIG. 18, FIG. 19, and FIG. 20 are examples of braided preformed configurations in the form of fibers in tubular shape for use in formation of the wall thickness of a precursor construct tube for use in producing a stent.
Figure 22:
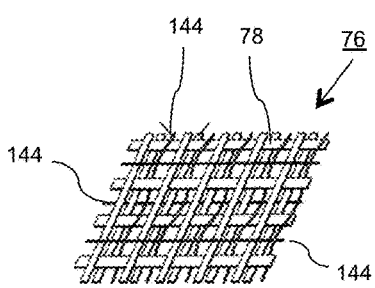
Figure 23:
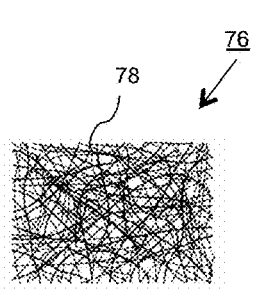
FIG. 23 is a portion of the wall thickness of a tubular precursor construct tube for use in producing a stent having a wall thickness of nonwoven preformed configurations in the form of fibers.
Figure 24:
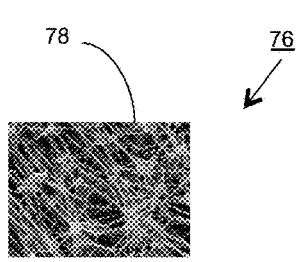
FIG. 24 is a portion of the wall thickness of a precursor construct tube for use in producing a stent having a wall thickness of fibrillated polymer.
Figure 92:
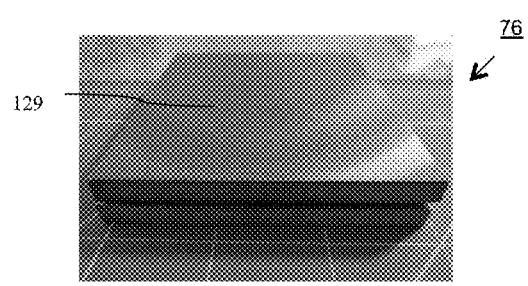
FIG. 92 is a photograph of multiple sheets of preformed configurations in the form of fibers separated by void spaces stacked on top of each other positioned on a bottom flat steel plate and surrounded by a high tolerance shim wherein a second top flat steel plate has been positioned on top of the sheets, shim, and bottom steel plate in a way that the wall thickness can be heated and pressed together to form a wall thickness having low dimensional variation at a thickness substantially equaling the thickness of the shim.
Figure 100:
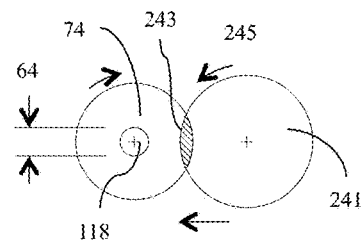
FIG. 100 is an illustration of a sizing device shown in side view comprised of a wall thickness positioned on a high tolerance mandrel wherein the wall thickness is sized by compressing the wall thickness between a rotating mandrel and a rotating roller.
Figure 99:
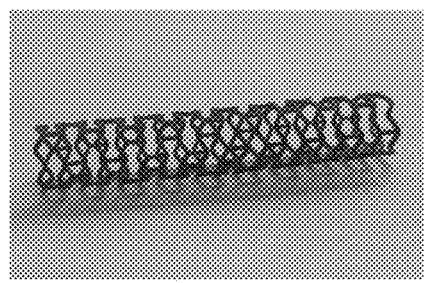
FIG. 99 is a photograph of an exemplary stent produced by the process of the present invention.
Figure 101:
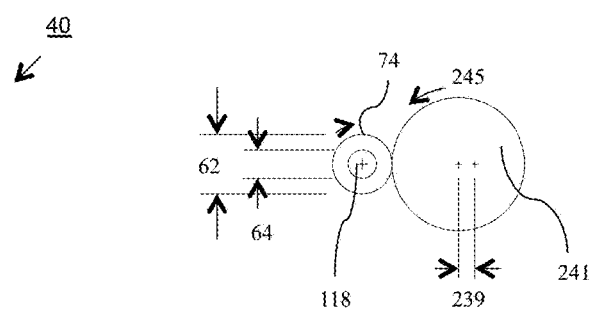
FIG. 101 is an illustration of a sizing device shown in side view comprised of a wall thickness positioned on a high tolerance mandrel where in the wall thickness is sized by compressing the wall thickness between the mandrel and the roller after the precursor construct tube wall thickness has been sized.

In an embodiment, the wall thickness 76 is partially or fully an extrusion. In an embodiment, the wall thickness 76 is partially or fully nonwoven (FIG. 23). In an embodiment, the wall thickness 76 is partially fully a woven (FIG. 22). In an embodiment, the wall thickness 76 is partially or fully a wound (FIG. 11, FIG. 12, FIG. 13). In an embodiment, the wall thickness 76 is partially or fully braided (FIG. 14, FIG. 18). In an embodiment, the wall thickness 76 is partially or fully molded (FIG. 4). In an embodiment, the wall thickness 76 is partially or fully spun (FIG. 53, FIG. 54, FIG. 55, FIG. 56, FIG. 57, FIG. 58, FIG. 59). In an embodiment, the wall thickness 76 is partially or fully blow-molded (FIG. 79). In an embodiment, the wall thickness 76 is partially or fully cast (FIG. 4). In an embodiment, the wall thickness 76 is partially or full drawn (FIG. 107A, FIG. 107B, FIG. 108). In an embodiment, the wall thickness 76 is partially or fully expanded (FIG. 79, FIG. 80). In an embodiment, the wall thickness 76, and features within the wall thickness 76, are partially or fully formed by additive processes. In an embodiment, the wall thickness 76, and features within the wall thickness 76, are partially or fully formed by subtractive processes. In an embodiment, the wall thickness 76 is partially or fully consolidated (FIG. 76). In an embodiment, the wall thickness 76 is partially or fully thermally treated (FIG. 92). In an embodiment, the wall thickness 76 is sized to reduce the dimensional variation of the precursor construct tube 74 (FIG. 100, FIG. 101, FIG. 81). In an embodiment, a strut pattern 60 is cut into the wall thickness 76 of the precursor construct tube 74 (FIG. 99). In an embodiment, the wall thickness 76 includes one or more stent locating means or markers 154 (FIG. 42). In an embodiment, the wall thickness 76 includes one or more coatings 180 (FIG. 40). In an embodiment, the wall thickness 76 includes one or more active ingredients like a drug (FIG. 40). In an embodiment, the wall thickness 76 includes one or more radiopaque coatings 180. In an embodiment, the wall thickness 76 includes a temporary coating 180 that is a partial or full moisture barrier between the wall thickness 76 and the anatomical lumen 38 or ambient conditions. In an embodiment, the wall thickness 76 is produced from any combination or combinations of the manufacturing processes described herein. In an embodiment, the wall thickness 76 is comprised of at least one extruded, nonwoven, woven, wound, braided, molded, spun, blow molded, cast, or any combinations thereof portions that are hot and/or cold draw and/or hot and/or cold expanded as described herein.

In an embodiment, the wall thickness 76 is comprised of one or more materials 82. In an embodiment, the wall thickness is comprised of blends of two or more materials 82. In an embodiment, the wall thickness 76 is comprised of two or more materials 82 of different molecular weight. In an embodiment, the wall thickness 76 is comprised of two or more materials 82 of different melting temperatures. In an embodiment, the wall thickness 76 is comprised of two or more materials of different degradation rates. In an embodiment, the wall thickness 76 is comprised of two or more materials of different resorption rates. In an embodiment, the wall thickness 76 is comprised of two or more materials 82 of different amounts of crystallinity. In an embodiment, the wall thickness 76 is comprised of two or more materials 82 of different amounts of amorphicity. In an embodiment, the wall thickness 76 is comprised of two or more materials 82 with different yield strengths 153. In an embodiment, the wall thickness 76 is comprised of two or more materials 82 of different Young's modulus. In an embodiment, the wall thickness 76 is comprised of two or more materials 82 of different ultimate tensile strengths 151. In an embodiment, the wall thickness 76 is comprised of two or more materials 82 of different elongations to break.

In an embodiment of the wall thickness 76 containing two or more preformed configurations 77, some preformed configurations 77 are comprised of a single material 82 having a single chemical composition and some preformed configurations 77 are comprised of blends of materials 82 of different chemical compositions. In one more embodiment of the wall thickness 76 containing two or more preformed configurations 77, some preformed configurations 77 are comprised of a lower molecular weight material 82 and some preformed configurations 77 are comprised of a higher molecular weight material 82. In a embodiment of the wall thickness 76 containing two or more preformed configurations 77, some preformed configurations 77 are comprised of a lower melting temperature material 82 and some preformed configurations 77 are comprised of a higher melting temperature material 82.

In an embodiment of the wall thickness 76 including multiple preformed configurations 77, some preformed configurations 77 are comprised of material 82 having a relatively higher tensile strength and other preformed configurations 77 are comprised of material 82 having a higher elongation at break. In an embodiment including multiple preformed configurations 77, some preformed configurations 77 are comprised of stiffer material 82 and other preformed configurations 77 are comprised of more flexible material 82. In an embodiment of the wall thickness 76 including multiple preformed configurations 77, the preformed configurations 77 are the substantially the same length. In another embodiment of the wall thickness 76 including multiple preformed configurations 77, the preformed configurations 77 are more than one length. In one more embodiment of the wall thickness 76 including multiple preformed configurations 77, the preformed configurations 77 are comprised of a material 82 or dimensions having the substantially the same degradation rate or resorption rate. In another embodiment of the wall thickness 76 including multiple preformed configurations 77, the preformed configurations 77 are comprised of materials 82 or dimensions having substantially different degradation rate or resorption rates. The term "resorption rate" refers to the time in which the material 83 is substantially loses all its mass within the living body. The term "degradation rate" refers to the time at which the strength of the material 82 is substantially reduced.

Figure 66:
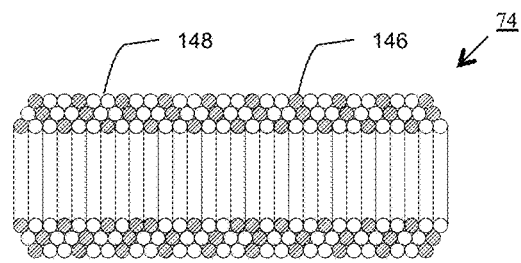
FIG. 66, FIG. 67, FIG. 68, and FIG. 69 are cross sectional views of examples of a precursor construct tubes taken through section B-B of FIG. 10A having preformed configurations in the form of fibers of various compositions and morphology.
Figure 67:
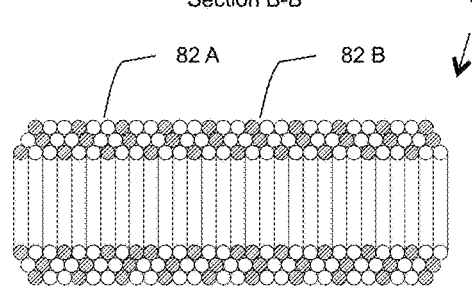
Figure 71:
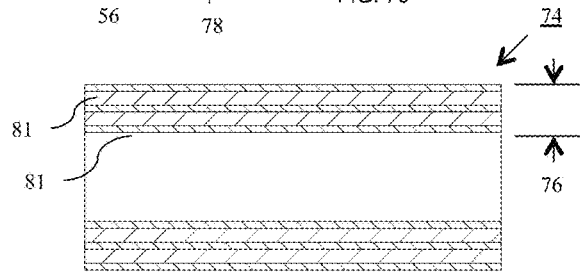
FIG. 71, FIG. 72, and FIG. 73 are cross-sectional views of other embodiments of a precursor construct tubes taken through section B-B of FIG. 10A having wall thickness comprised of sheets of geometric shaped objects in the form of fibers separated and by connected preformed configurations in the form of film.
Figure 68:
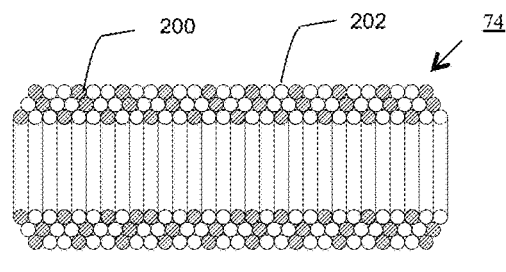
Figure 72:
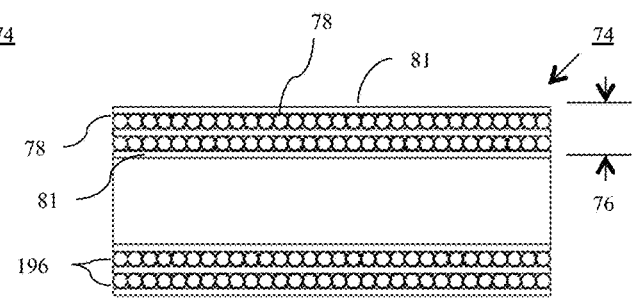
Figure 69:
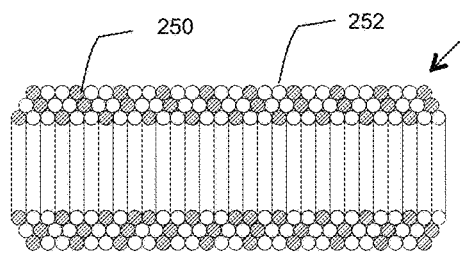
Figure 73:
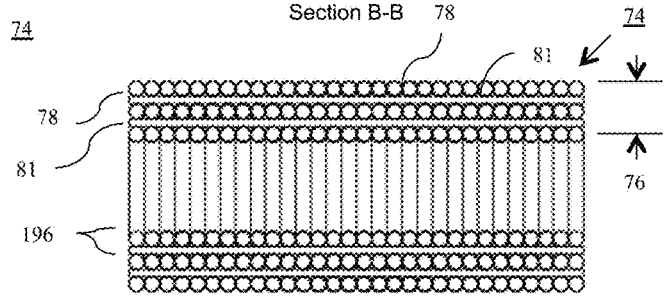

FIG. 66-FIG. 69 and FIG. 71-FIG. 73 are exemplary cross-sectional views of tube 74 along line B-B in FIG. 10A. Without intent on limiting, FIG. 66 depicts an embodiment of a tube 74 in cross-sectional view having some fibers 78 comprised of more crystalline 146 material 82 and some fibers 78 comprised of more amorphous 148 material 82. FIG. 67 depicts an embodiment of a tube 74 having some fibers 78 comprised of a first material 82 A and some fibers 78 comprised of a second material 82 B. FIG. 68 depicts an embodiment of tube 74 in having some fibers 78 comprised of a blend 200 of two or more different materials 82 of any ratio and some fibers 78 comprised of a single 202 material 82. FIG. 69 depicts an embodiment of tube 74 having some fibers 78 comprised of higher molecular weight 250 material and some fibers 78 comprised of lower molecular weight 252 material 82. FIG. 73 depicts an embodiment of a wall thickness 76 in cross sectional view wherein the wall thickness 76 is comprised of one or more layers of film 81 positioned between two or more layers of fiber 78. In another embodiment the wall thickness 76 is comprised of one or more layers of film 81 having lower melting temperature positioned between two or more layers of fiber 78 having a higher melting temperature. In one more embodiment the wall thickness 76 is comprised of one or more layers of film 81 having higher melting temperature is positioned between two or more layers of fiber 78 having a lower melting temperature. FIG. 72 depicts an embodiment of a wall thickness 76 in cross sectional view where one or more layers of fiber 78 are positioned between two or more layers of film 81. In another embodiment of a wall thickness 76 one or more layers of fiber 78 having a higher melting temperature are positioned between two or more layers of film 81 having a lower melting temperature. In another embodiment of a wall thickness 76 one or more layers of fiber 78 having a lower melting temperature are positioned between two or more layers of film 81 having a higher melting temperature.

In an embodiment, the wall thickness 76 is partially or fully porous. In an embodiment, the wall thickness is substantially solid or non-porous. In an embodiment, the void spaces 84 are less than 0.100 millimeters (mm). In an embodiment, the void spaces 84 are at or greater than 0.100 millimeters (mm). In an embodiment, the void spaces 84 are less than ninety percent of the wall thickness 76 volume. In an embodiment, the void spaces 84 are greater than ninety percent of the wall thickness 76 volume.

In an embodiment, the wall thickness 76 is comprised of a plurality of translucent fibers 78 that comprise a wall thickness 76 having a white visual appearance because the void 84 space in the wall thickness 76 reflects light. In an embodiment of a wall thickness 76 comprised of translucent fibers 78, the appearance of the wall thickness 76 is changed from a white or opaque appearance to a substantially translucent appearance by consolidating the wall thickness 76 and substantially removing or reducing the void spaces 84 in the wall thickness 76.

In an embodiment, the wall thickness 76 is formed into the shape of a tube by (1) extrusion, (2) molding, (3) casting, (4) assembling and aligning preformed configurations 77 like fibers 78 or films into the shape of a tube, or (5) combinations thereof, and then hot and/or cold drawing or hot and/or cold expanding the wall thickness 76 one or more times to strengthen the wall thickness 76 and produce a tubular precursor construct 74 suitable for production of stent 40.

In an embodiment, one or more preformed configurations 77 like fibers 78, films 81, or sheets 196 are aligned in the wall thickness 76 in the shape of a tube by braiding, winding, weaving, interlacing, spinning, nonwoven means, or combinations thereof; the tube is heated until the preformed configurations 77 partially or fully melt so that they are interconnected and cool in the form of a stiffer tube. The cooled tube is then hot and/or cold drawn or hot and/or cold expanded one or more times to strengthen the wall thickness 76 and produce a tubular precursor construct 74 suitable for production of stent 40. In another embodiment, the tube is not cooled before drawing and/or expanding. In an embodiment of a wall thickness 76 produced using this assembly process, two or more materials 82 can be strategically positioned in the wall thickness 76 to produce a wall thickness 76 having unusual properties. For example, if the wall thickness 76 is formed of a fibers 78 of higher and lower molecular weight, after melting the wall thickness 76 the higher molecular weight portion remains substantially positioned in the wall thickness 76 after melting and cooling in the engineered pattern in which the preformed configurations 77 were located before melting. So a wall thickness 76 can be produced having veins of higher molecular weight material 82 throughout lower molecular weight material 82. Moreover, a wall thickness 76 can be produced having veins of more crystalline material 82 throughout more amorphous material 82 or having veins of faster degrading material 82 throughout slower degrading material 82. In an embodiment, it is desirable to have veins of faster degrading material 82 positioned in the wall thickness 76 either near the outer surface 70, inner surface 72, or anywhere near the center portion of the wall thickness 76 to facilitate disintegration of the wall thickness 76 during the resorption phase of the stent's deployment. Facilitating disintegration is important because slow to degrade and/or resorb crystalline portions of material 82 can cause inflammation near the deployment site of stent 40. In another embodiment the wall thickness 76 is consolidated before drawing or expanding.

In an embodiment, one or more preformed configurations 77 like fibers 78, films 81, or sheets 196 that are aligned in the wall thickness in the shape of a tube by braiding, winding, weaving, interlacing, spinning, nonwoven means, or combinations thereof; the tube is heated without the preformed configurations 77 melting so that they form a tube. The tube is then hot and/or cold drawn or hot and/or cold expanded one or more times to strengthen the wall thickness 76 and produce a tubular precursor construct 74 suitable for production of stent 40. In another embodiment the wall thickness 76 is consolidated before drawing or expanding.

In an embodiment, one or more preformed configurations 77 like fibers 78 or films 81 that are aligned in the wall thickness in the shape of a tube by braiding, winding, weaving, interlacing, spinning, nonwoven means, or combinations thereof and the tube is not heated. The tube is then hot and/or cold drawn or hot and/or cold expanded one or more times to strengthen the wall thickness 76 and produce a tubular precursor construct 74 suitable for production of stent 40. In another embodiment the wall thickness 76 is consolidated before drawing or expanding.

In an embodiment, the hot and/or cold drawn or expanded tube is thermally treated as described herein to modify the crystallinity or amorphicity of the material or materials 82 comprising the tube so that the tubular precursor construct 74 has optimum physical properties and stability.

In an embodiment, the wall thickness 76 is toughened or tempered. In an embodiment, putting the outer surface of the wall thickness 76 in compression, and the inner surfaces of the wall thickness 76 into tension produces a toughened wall thickness 76. This feature improves the crack resistance of the struts 44, 46 because if there are any surface flaws on the struts 44,46 the compressive forces will force the defects closed preventing crack initiation and propagation. In one embodiment, the toughened wall thickness 76 is produced of an annealed wall thickness 76 by heating the wall thickness 76 and rapidly cooling the outer surface. In one more embodiment a chemical-toughening process produces the toughened wall thickness 76.

Preformed Configurations

Figure 5:
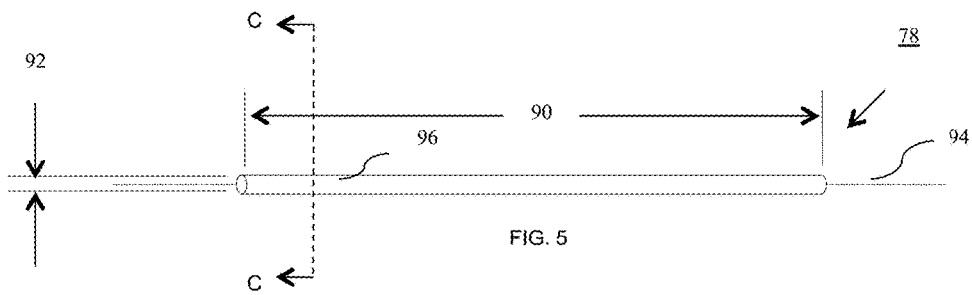
FIG. 5 is a perspective view of a preformed configuration in the form of a fiber.
Figures 6, 7, 8:
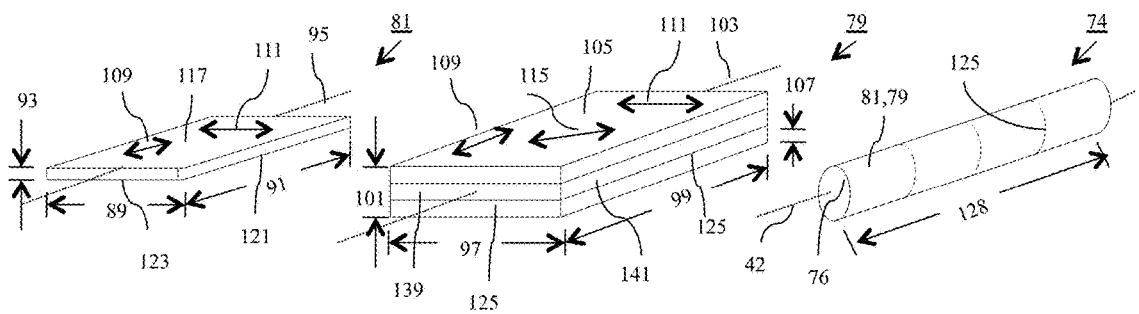
FIG. 6 is a perspective view of a preformed configuration in the form of a film.
FIG. 7 is a perspective view of a preformed configuration in the form of a multi-film.
FIG. 8 is a perspective view of a precursor construct tube formed of one or more films connected by seams.
Figure 9:
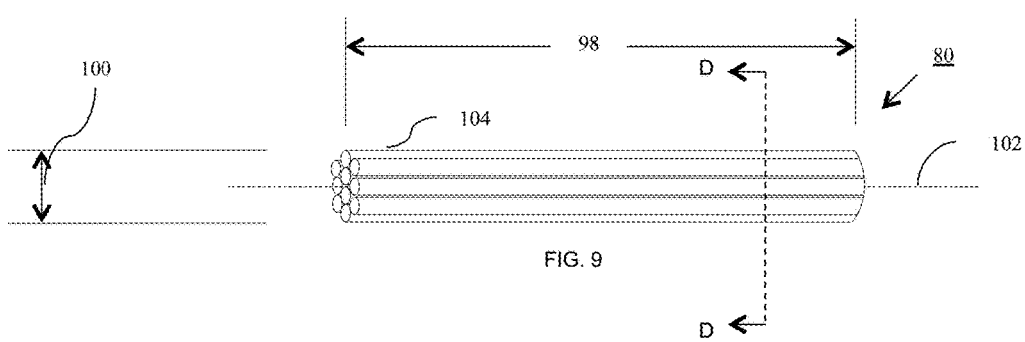
FIG. 9 is a perspective view of a preformed configuration in the form of a multi-fiber.

As previously mentioned, in an embodiment the wall thickness 76 is comprised of one or more preformed configurations 77 of any size and shape. The preformed configurations 77 are comprised of one or more materials 82. In a preferred embodiment, as shown in FIG. 5, the preformed configuration 77 is in the form of a fiber 78. As shown in FIG. 9, in another embodiment the preformed configuration 77 is in the form of a multi-fiber 80. As shown in FIG. 6, in another preferred embodiment, the preformed configuration 77 is in the form of a film 81. In an embodiment, the film 81 is in the form of a membrane. The term "membrane" refers a selective barrier that allows the passage of certain constituents and retains other constituents found in a liquid. As depicted in FIG. 7, in another embodiment the preformed configuration 77 is in the form of a multi-film 79. In an embodiment, the wall thickness 76 is comprised of a combination of preformed configurations 77 in the form of one or more fibers 78 and films 81. The terms "preformed configuration" broadly refers to any preformed geometric shape such as a fiber or a film and any combination of preformed geometric shapes that are capable of being incorporated into the wall thickness 76 and producing a stent 40 having the performance described herein. For simplicity the terms "preformed configuration", "fiber", "multi-fiber", "film", and "multi-film" are used interchangeably and synonymously in this application. The term "preformed configuration" is used more generically. In an embodiment, the wall thickness 76 that is partially or fully comprised of one or more preformed configurations 77 is hot and/or cold drawn or hot and/or cold expanded one or more times as described herein.

As shown in FIG. 5, the fiber 78 is comprised of a length 90, a thickness 92, a lengthwise axis 94, and an outer surface 96. As shown in FIG. 9, the multi-fiber 80 is comprised of a length 98, a thickness 100, a lengthwise axis 102, and an outer surface 104. As shown in FIG. 6, the film 81 is comprised of a width 89, a length 91, a lengthwise axis 95, a thickness 93, an outer surface 117, a short edge 123, and a long edge 121. As shown in FIG. 7, the multi-film 79 is comprised of a width 97, a length 99, a lengthwise axis 103, a thickness 101, an outer surface 105, a short edge 139, and a long edge 141. The preformed configurations 77 have any geometrical shape and are not limited to what is illustrated in FIG. 5, FIG. 6, FIG. 7, and FIG. 9. The possible variations and combinations of the preformed configurations 77 are virtually unlimited. The term "preformed configurations" refers to any geometric shape consisting of, formed by, or characterized by points, lines, curves, or surfaces and is not limited to fibers and films.

In an embodiment, the preformed configurations 77 form an interconnected network in the wall thickness 76 that has a broad range of mechanical properties. The term "network" refers to the interaction of the individual preformed configurations 77 in the wall thickness 76 and their interconnections. An embodiment of the endoprosthesis of the present invention comprises a wall thickness 76 formed of one or more layers of one or more preformed configurations 77.

The inventors discovered a novel process for converting wall thickness 76 comprised of preformed configurations 77 like fibers 78 or films 81 from a pliable state to a stiffer state by thermally treating the wall thickness 76. Although, the fibers 78 and films 81 individually have suitable ultimate tensile strength 151 they do not collectively form a wall thickness 76 that is sufficiently stiff or has a high enough Young's modulus of elasticity to produce a properly functioning precursor construct tube 74 or stent 40 without further thermal treatment. In an embodiment, the wall thickness 76 is thermally treated to form a network of partially or fully interconnected preformed configurations 77. In an embodiment, the thermal treatment modifies the morphology of the material 82. In an embodiment, the preformed configurations 77 are consolidated to increase the density of the wall thickness 76, reduce or eliminate porosity, and reduce the dimensional variation. In an embodiment of the endoprosthesis, the material 82 comprising the wall thickness 76 is partially or fully crystallized or re-crystallized. In an embodiment, the wall thickness 76 is partially or fully amorphized or re-amorphized. The term "amorphized" refers to converting from a more crystalline material to a more amorphous material. The term "crystallized" refers to converting a more amorphous material to a more crystalline material. FIG. 41 depicts a material 82 comprised of crystalline 146 and amorphous 148 regions.

As illustrated in FIG. 74, FIG. 75, and FIG. 76, the wall thickness 76 comprised of preformed configurations 77 is consolidated to increase the density of the wall thickness 76. Consolidating the preformed configurations 77 by reducing or eliminating any void spaces 84 increases the number of preformed configurations 77 present in the wall thickness 76 and therefore strengthens the wall thickness 76. In an embodiment, the wall thickness 76 is heated while the preformed configurations 77 are pressed together and held in a compressed state until sufficiently cooled to retain the consolidated wall thickness 76 in a compressed state. In an embodiment the precursor construct tube 74 is held under compression at these conditions to produce a sized tube 212 that includes an outer diameter 62 and an inner diameter 64 having low dimensional variation. In an embodiment, the precursor construct tube 74 undergoes a thermal treatment process that modifies the crystallinity and/or amorphicity of the material 82 comprising the wall thickness 76.

In an embodiment, some or all the preformed configurations 77 include one or more coatings 180 of the same or different chemical composition positioned on the outer surfaces of the preformed configurations 77 as shown in FIG. 29 in cross-sectional view. In an embodiment, the preformed configurations 77 are comprised of one or more materials 82 of the same or different chemical composition as shown in FIG. 33-FIG. 34 and FIG. 39. In an embodiment, the preformed configurations 77 are comprised of one or more materials 82 of the same or different morphology as some examples are shown in FIG. 35, FIG. 36, FIG. 37, and FIG. 38. The term "morphology" refers to the structure of the molecules in the material 82.

In an embodiment, the preformed configurations 77 are of substantially the same thickness and in other embodiments the preformed configurations 77 are of more than one thickness. In an embodiment, the thickness of the preformed configuration varies from one end to the other end. In an embodiment, the preformed configurations 77 are of a solid thickness. In another embodiment, the preformed configurations 77 are a hollow or tubular thickness. In an embodiment, the preformed configurations 77 include porosity in the thickness. In an embodiment, the preformed configurations 77 are comprised of a single material 82 of a single chemical composition. In an embodiment there are multiple preformed configurations 77 comprised of different materials 82. In further embodiments, the preformed configurations 77 are comprised of blends of two or more materials 82 of different chemical compositions. In an embodiment, the two or more blended materials 82 comprising the preformed configurations 77 are miscible. In an embodiment, the preformed configurations 77 are comprised of two or more blended materials 82 that are immiscible. In other embodiments, the preformed configurations 77 are comprised of two or more blended materials 82 that are compatibilized (made compatible). In embodiment, there is a synergistic effect of using two or more different materials 82 having different chemical compositions in one or more preformed configurations 77. Without intent on limiting, the synergistic effect includes enhanced strength, stiffness, elasticity, flexibility, toughness, rigidity, or degradative properties of the stent 40. When blends of material 82 are used, crystals of faster crystallizing material 82 can nucleate and grow confined in a matrix of slower crystallizing material 82. The term "nucleate" or "nucleation" refers to the process of providing sites for new crystals to form in the material 82. In one more embodiment of the wall thickness 76, the preformed configuration 77 includes multiple materials 82 in coaxial arrangement so that the core material 82 is of a different chemical composition than the material 82 comprising the shell or outer layer or layers of the preformed configuration 77 as shown in FIG. 33-FIG. 39 in cross-sectional view.

In an embodiment, the preformed configuration 77 is comprised of a more amorphous morphology at its core and a more crystalline morphology at its outer layer or shell. In another embodiment, the preformed configuration 77 is comprised of a more crystalline morphology at its core and a more amorphous morphology at its shell or shells. In one more embodiment, the preformed configuration 77 is partially or fully comprised of a semi-crystalline morphology. In another embodiment, the preformed configurations 77 thickness 92, 100, 93, 101 is comprised of a more crystalline morphology. In one more embodiment, the preformed configurations 77 thickness 92, 100, 93, 101 is comprised of a more amorphous morphology.

In an embodiment, the morphology of the fiber 78 is substantially homogenous throughout its entire cross section. In an embodiment, the fiber 78 is comprised of a substantially amorphous material 82. In an embodiment, the fiber 78 is comprised of a substantially semi-crystalline material 82. In an embodiment, the fiber 78 is comprised of a substantially crystalline material 82. Referring to FIG. 33 a fiber 78 in one embodiment includes a different material 82 A at its core than the material 82 B at its shell. As shown in FIG. 34 the, fiber 78 in another embodiment has one material 82 A at its core, another material 82 C at its shell and a third material 82 B between its core and shell. In one more embodiment depicted in FIG. 35, the fiber 78 is comprised of more amorphous material 148 at its core and more crystalline material 146 at its shell and a semi-crystalline material 208 between its core and shell. In one more embodiment, illustrated in FIG. 36, the fiber 78 is comprised of a more amorphous material 148 at its core and a more crystalline material 146 at its shell. In another embodiment shown in FIG. 37, the fiber 78 is comprised of more amorphous material 148 at its core and semi-crystalline material 208 at its shell. As shown in FIG. 39, an embodiment of a fiber 78 is comprised of a blend of materials 82 at the core and a single material 202 at its shell. In one more embodiment shown in FIG. 38, the fiber 78 is comprised of more crystalline material 146 at its core, more amorphous material 148 at its shell, and semi-crystalline material 208 between the core and shell. The crystallinity or amorphicity of the preformed configuration 77 such as the fiber 78 or film 81 can be controlled by numerous process conditions including molecular weight of material 82, processing temperatures, flow rate of material 82, draw down ratio, expansion ratio, material-to-solvent ratios, gap between fiber forming device and target, ambient temperature, solvent selection, solvent blend selection, and thermal treatment (e.g., heating temperature, cooling temperature, heating rate, cooling rate). As can be appreciated there are many variations of the composition of the fiber 78 and the preceding embodiments only show examples of possibilities. Therefore, other suitable embodiments for production of a preformed configuration 77 such as a fiber 78 or film 81 are possible employing any combinations of materials 82, structures, core/shell relationships, morphologies, or molecular weights described in the specification. The number of core and shell layers are not limited to what is shown in FIG. 33-FIG. 39 and it is possible to have more or less core and shell layers of any material composition or morphology.

In an embodiment, the material 82 is converted into one or more preformed configurations 77 by melt processing. In an embodiment, the material 82 is converted into one or more preformed configurations 77 by solution processing. In an embodiment, the material 82 is converted into one or more preformed configurations 77 by melt and solution processing.

The preformed configurations 77 of the present invention such as fibers 78 or films 81 can be of any thickness, width, and length that provides the functionality described herein. However, in an embodiment the thickness of the preformed configurations 77 is preferably less than about 50 mm, more preferably less than about 0.250 mm, and most preferably less than about 0.100 mm. In other embodiments, the thickness of the preformed configuration 77 is greater than 50 mm.

In an embodiment, the wall thickness 76 is comprised of one or more stretched and/or un-stretched preformed configurations 77 such as the fiber 78, multi-fibers 80, sheet 196, film 81, or multi-films 79. In an embodiment, the wall thickness 76 is comprised of one or more preformed configurations 77 drawn down from a larger cross-sectional size to a smaller cross-sectional size and/or elongated from a shorter length to a longer length. In an embodiment, the wall thickness is comprised of one or more preformed configurations 77 having a draw down ratio and elongation ratio of greater than 1, wherein the draw down ratio=original thickness/thickness after drawing and elongation ratio=length after drawing/original length. In another embodiment one or more of the preformed configurations 77 are stretched having a draw ratio in the range of 2 to 14, more narrowly 2 to 10. In an embodiment, one or more of the preformed configurations 77 are stretched having a draw ratio of less than about 2. In an embodiment, the one or more of the preformed configurations 77 are stretched having a draw ratio of greater than about 14. In an embodiment, the preformed configurations 77 comprised of poly-L-lactide (PLLA) are hot drawn at a temperature between 40 to 120 degrees Celsius, more narrowly between 50 to 110 degrees Celsius. In other embodiments, the preformed configurations 77 are drawn at higher or lower temperatures. In an embodiment, the wall thickness 76 is comprised of one or more preformed configurations 77 stretched from a shorter length to a longer length at a rate less than about 300 percent/second. In another embodiment, the wall thickness 76 is comprised of preformed configurations 77 stretched from a shorter length to a longer length at a rate greater than about 300 percent/second.

In a preferred embodiment the preformed configurations 77 suitable for use in the wall thickness 76 have an ultimate tensile strength 151 in the range of 1 MPa to 20 GPa, more narrowly between 10 MPa to 5 GPa. In an embodiment the preformed configurations 77 suitable for use in the wall thickness 76 have an ultimate tensile strength 151 in the range of 1 MPa to 20 GPa prior to thermal treatment during consolidation. In an embodiment, the preformed configurations 77 used in the construction of the wall thickness 76 have an ultimate tensile strength 151 of at or less than or about 1 MPa. In an embodiment, the preformed configurations 77 suitable for use in the wall thickness 76 have an ultimate tensile strength 151 of at or greater than about 20 GPa. In a preferred embodiment, the preformed configurations 77 have a Young's modulus of elasticity in the range of 1 MPa to 20 GPa, more narrowly between about 10 MPa to 15 GPa. In an embodiment, the configurations 77 have a Young's modulus of elasticity at or below 1 MPa. In an embodiment, the configurations 77 have a Young's modulus of elasticity at or above 20 GPa. In a preferred embodiment, the preformed configurations 77 have an elongation at break of between 2 percent and 500 percent, more narrowly between about 4 percent and 250 percent. In an embodiment, the preformed configurations 77 have an elongation at break of at or less than 2 percent. In an embodiment, the preformed configurations have an elongation at break of at or above about 500 percent.

The preformed configurations 77 are manufactured using any process known by those skilled in the art of polymer synthesis and processing and not limited to the guidelines provided herein. Without intent on limiting, a few of the suitable processes for use in producing the present invention are described in "Polymer Synthesis and Processing," Chapter 1 authored by Mahadevappa Y. Kariduranganavar, Arjumand A. Kittur, and Ravindra R. Kamble, published by Natural and Synthetic Biomedical Polymer, Copyright 2014, which is incorporated herein in its entirety as a reference.

Fibers

As previously mentioned, one embodiment of a preformed configuration 77 is in the form of a fiber 78. Without intent on limiting, the term "fiber" in the present invention refers to any nano filament, microfilament, filaments, belts, monofilaments, multi-filaments, fibers, strands, strips, strands, straps, tapes, threads, twine, wires, or yarns. The thickness 92 of the fiber 78 in some embodiments is substantially uniform in size along its entire length 90 and in other embodiments has one or more variations in thickness 92 along the length 90.

In an embodiment, the length of the fiber 78 or multi-fibers 80 is short wherein the length 90, 98, is at or less than 25 centimeters (cm). In another embodiment, the length 90, 98 of the fiber 78 or multi-fibers 80 is long wherein the length 90, 98 is greater than 25 centimeters (cm). The length 90, 98, the fiber 78 or multi-fiber 80 can be any length that meets the performance requirements described herein this specification. The length of fiber 78 or multi-fibers 80 in other embodiments is chopped, broken, or cut so that one longer preformed configuration 77 is converted into several shorter preformed configurations 77 that are incorporated into the wall thickness 76 of the tube 74 or other precursor construct.

The wall thickness 76 can be produced of fibers 78 manufactured using any process that produces a fiber 78 or multi-fiber 80 meeting the specifications described herein. In one embodiment, the fiber 78 or fibers 80 are produced using an electrospinning process 258 shown in FIG. 50-FIG. 52. In another embodiment, the fiber 78 or multi-fibers 80 are produced by solution electrospinning process 258. In another embodiment, a melt electrospinning process 258 produces the fibers 78 or multi-fibers 80. In another embodiment, a coaxial electrospinning process 258 produces the fiber or fibers 78. In another embodiment, an emulsion electrospinning process 258 produces the fiber or fibers 78. In another embodiment, a dry spinning process produces the fiber or fibers 78. In another embodiment, a gel spinning process produces the fiber or fibers 78. In another embodiment, the fiber or fibers 78 are produced by a wet spinning process. In another embodiment, a nonwoven process produces the fiber or fibers 78. In another embodiment, an extrusion process produces the fiber or fibers 78. In an embodiment, the one or more fibers 78 are hot drawn after spinning using temperature conditions provided herein. In another embodiment, the one or more fibers are cold drawn after spinning using temperature conditions provided herein. In other embodiments, the fiber or fibers 78 are produced using fibers 78 produced by any combination of the preceding manufacturing processes. In an embodiment, the wall thickness 76 that is partially or fully comprised of one or more fibers 78 is hot and/or cold drawn or hot and/or cold expanded one or more times as described herein.

The fiber 78 and fibers comprising multi-fiber 80 are comprised of one or more materials 82 and have any cross-sectional shape such as a circle, oval, ellipse, crescent, curved triangle, quatrefoil, parallelogram, square, rectangle, trapezoid, trapezium, triangle, kite, rhombus, pentagon, hexagon, heptagon, octagon, nonagon, decagon, and star shapes. In an embodiment, the fibers 78 and multi-fibers 80 are individually or collectively twisted or braided. Moreover, the tension of the fibers 78 can be variable or constant within a single embodiment having low tension, medium tension, high tension, or combinations thereof.

FIG. 23, FIG. 24, FIG. 53 through FIG. 59 illustrate some embodiments of a wall thickness 76 comprised of preformed configurations 77 in the form of fibers 78 under magnification. In an embodiment, the wall thickness 76 is characterized by fibers 78, 80 that are sequentially laid down on a collecting device 118 so that the fibers 78, 80 collectively take the shape of the tube 74, sheet 196, or other shape suitable for use in making an endoprosthesis. Each successive layer of fibers 78, 80 deposited on the collecting device 118 builds-up the wall thickness 76 of the tube 74, sheet 196, or other suitable shape. As more clearly shown under magnification in FIG. 53-FIG. 59, in some embodiments the fibers 78 form a repeating, non-repeating, or meandering pattern over any previously laid down fibers.

The term "spinning" refers to the process of converting a material 82 or polymer into a fluid state to produce a fiber 78. In one embodiment, if the material 82 or polymer is thermoplastic then the material 82 or polymer is melted to during conversion into a fiber 78. In another embodiment, the material 82 is partially or fully dissolved in a solvent or otherwise treated to form solutions, emulsions, or gels that are suitable for conversion of material 82 into a fiber 78. The fluid material 82 or polymer is then forced through a spinneret, needle, other orifice, where the material 82 or polymer transitions into to a rubbery state, and then into a solidified state in the form of a fiber 78. In some embodiments, while the fibers 78 are solidifying, or in some cases even after they have partially or fully hardened, the fibers 78 are drawn in one or more stages from a first shorter length to a second longer length and from a first larger cross-sectional size to a second smaller cross-sectional size to increase the strength of the fiber 78. Drawing pulls the molecular chains together and orients them along the fiber axis 94, creating a considerably stronger fiber 78.

The term "spinneret" (also spelled spinnerette) refers to a nozzle having one to several hundred or more fine holes through which a spinning solution or melt is forced through to form a fiber 78. The viscous or syrupy solution or melt, prepared by melting or dissolving the material 82, is fed into these tiny openings and emerges as long fibers 78 that are then solidified by coagulation, evaporation, or cooling. The size and shape of the spinneret holes determine the fiber's cross-sectional shape. Each hole forms a single fiber, and the combined fibers 78 in some embodiments can form a yarn or multi-fiber 80. The terms "wet spinning" refers to a fiber manufacturing process wherein the material 82 or polymer is dissolved in a solvent, the resulting solution is forced through a spinneret submerged in a chemical bath that leads the fiber 78 to precipitate, and then solidify, as it emerges out of the spinneret holes. The terms "dry spinning" refers to a fiber 78 manufacturing process wherein the material 82 or polymer is dissolved in a solvent, the resulting solution is forced through a spinneret, and evaporating the solvent forms the fiber 78. The terms "melt spinning" refers to a fiber 78 manufacturing process wherein the material 82 or polymer is melted, the melt is forced through a spinneret, and cooling forms the fiber 78. The terms "gel spinning" (also known as dry-wet spinning) refers to a fiber 78 manufacturing process wherein the material 82 or polymer is dissolved in a first solvent to form a gel, the gel is forced through a spinneret, and solidification of the fiber 78 exiting the spinneret occurs by a combination of precipitation and/or cooling of the material 78 or polymer, and removal of the first solvent with a second solvent by washing the fiber 78 in a liquid bath. The terms "spinneret," "capillary tube," "needle," "orifice," "fiber-forming device," and "die" are used synonymously and interchangeably and relate to any orifice suitable for producing a preformed configuration 77 such as a fiber 78 of any size or shape. In an embodiment, the one or more fibers 78 are formed at the exit of one or more capillary tubes 223 of any gauge size. In an embodiment, the one or more fibers 78 are formed at the exit of one or more capillary tubes 223 of any length. In an embodiment, the one or more fibers 78 are formed at the exit of one or more capillary tubes 223 of a shorter length (less than or equal to about 13 mm). In an embodiment, the one or more fibers 78 formed at the exit of one or more capillary tubes 223 of a longer length (greater than about 13 mm).

In an embodiment, the material 82 flows through one or more capillary tubes 223 having a gauge ranging between 7 and 34 prior to forming into a fiber 78 or fibers. In another embodiment, the material 82 flows through one or more capillary tubes 223 having a gauge greater than 7 prior to forming a fiber 78. In one more embodiment, the material 82 flows through one or more capillary tubes 223 having a gauge smaller than 34 prior to forming a fiber 78. In another embodiment, the material 82 flows through one or more capillary tubes 223 having a gauge ranging from about 7 to 34 at a temperature at or lower than about 23 degrees Celsius prior to and/or during forming a fiber 78. In another embodiment, the material 82 flows through one or more capillary tubes 223 having a gauge ranging from about 7 to 34 at a temperature at or greater than about 23 degrees Celsius prior to and/or during forming a fiber 78. In other embodiments, the material 82 flows through one or more capillary tubes 223 of smaller or larger gauges at temperature greater or lower than 23 degrees Celsius prior to and/or during forming a fiber 78. In an embodiment, the material 82 flows through one or more capillary tubes 223 having an orifice ranging between about 3.8 mm to 0.08 mm prior to forming a fiber 78 or fibers. In an embodiment, the material 82 flows through one or more capillary tubes 223 having in orifice ranging greater than about 3.7 mm prior to forming a fiber 78 or fibers. In an embodiment, the material 82 flows through one or more capillary tubes 223 having an orifice less than about 0.09 mm prior to forming a fiber 78 or fibers. In an embodiment, the material 82 flows through one or mores capillary tubes 223 having a length ranging between about 10 mm to 50 mm prior to forming a fiber 78 or fibers. In an embodiment, the material 82 flows through one or more capillary tubes 223 having a length of less than about 11 mm prior to forming a fiber 78 or fibers. In an embodiment, the material 82 flows through one or more capillary tubes 223 having a length of greater than about 49 mm prior to forming a fiber 78 or fibers. In an embodiment, the orifice of the capillary tube 223 is the same size from entrance to exit of the capillary tube. In an embodiment, the orifice of the capillary tube 223 is a larger size at the entrance than exit. In an embodiment, the orifice of the capillary tube 223 is a smaller size at the entrance than the exit. In an embodiment, the orifice of the capillary tube 223 varies in size one or more times from the entrance to the exit of the capillary tube 223.

In an embodiment, the material 82 is draw down in size from a starting thickness 92 of about 0.08-3 millimeters (mm) to an ending thickness of about 0.0001-0.075 millimeters (mm), more narrowly a starting thickness of about 0.1-1 millimeter (mm) to an ending thickness of about 0.0003-0.050 millimeters (mm). In a preferred embodiment, the fiber 78 or fibers have a draw down ratio of 2-40,000, more narrowly 2-900. In an embodiment, the fiber 78 or fibers have a draw down ratio of less than about 2. In one more embodiment, the fiber 78 or fibers have a draw down ratio of more than about 40,000. The draw down ratio is defined as the ratio of the final diameter to the ending diameter (Starting diameter divided by ending diameter).

In an embodiment, the fiber 78 or fibers are formed by one or more fiber-forming devices separated by a distance between the exit of the fiber-forming devices and the collecting surfaces 118 ranging from about 1 centimeter to 50 centimeters. In another embodiment, the fiber 78 or fibers are formed by one or more fiber-forming devices separated by a distance between the exits of the fiber-forming devices and the collecting surfaces 118 from less than about 2 centimeters. In another embodiment, the fiber 78 or fibers are formed by one or more fiber-forming devices separated by a distance between the exits of the fiber-forming devices and the collecting surfaces 118 from greater than about 50 centimeters. In one embodiment, the fiber 78 or fibers are formed at a fixed distance between the fiber-forming device and the collecting surfaces 118. In another embodiment, the fiber 78 or fibers are formed at a distance between the fiber-forming device and the collecting surfaces 118 that varies during deposition of the fiber 78 on the collecting surfaces 118.

In one embodiment the collecting surface 118 has a surface area between about 1 square millimeter and 1000 square meters. In other embodiments the collecting surface 118 has a surface area of less than about 1 square millimeter and in other embodiments the collecting surface 118 has a surface are of greater than about 1000 square meters. In some embodiments, the fiber or fibers 78 retain the shape of the collecting surface 118. In other embodiments the fiber 78 or fibers are subsequently converted into another shape after removal from collecting surface 118. In one embodiment, the fiber 78 or fibers are formed into a sheet 196.

The collecting surface 118 can be stationary or moving during deposition of fiber 78 or fibers. While the fiber 78 or fibers are being deposited, one layer of fiber 78 or fibers can be deposited or multiple layers of fiber 78 or fibers can be deposited. In an embodiment a moving cylindrical-shaped collecting surface 118 moves at a speed ranging from about 0.01 revolutions per second to about 25,000 revolutions per minute. In other embodiment of a cylindrical-shaped collecting surface 118, the collecting surface 118 moves at less than 0.01 revolutions per second and in other embodiments the collecting surface 118 moves at a rate faster than about 25,000 revolutions per minute. In a preferred embodiment, a moving cylindrical-shaped collecting surface 118 rotates at a speed of 2-20 meters/second, more narrowly 2-10 meters/second. In an embodiment, a moving cylindrical-shaped collecting surface 118 rotates at a speed of at or above 20 meters/second. In and embodiment, a moving cylindrical-shaped collecting surface rotates at a speed of at or at or below 2 meters/second. In an embodiment of a moving flat collecting surface 118, the collecting surface 118 moves at a rate of about 0.001 mm per minute to 25,000 meters per minute. In other embodiments of a flat collecting surface 118, the collecting surface 118 moves at a rate slower than about 0.001 mm per minute and in another embodiment the collecting surface 118 moves at a rate faster than about 25,000 meter per minute. In an embodiment, the rate of movement of the collecting surface 118 is fixed during fiber 78 formation and deposition. In an embodiment, the rate of movement of the collecting surface 118 varies during fiber 78 formation and deposition.

In an embodiment, the collecting surface 118 is at a temperature in the range of about 0 degrees Celsius to the melting temperature of the material 82, more narrowly between about 10-40 degrees Celsius. In other embodiments, the collecting surface 118 is at a temperature in the range of about the glass transition temperature of the material 82 and the melting temperature of the material 82. In other embodiments, the collecting surface 118 is at a temperature at or below about the glass transition temperature of the material 82 and in other embodiments the temperature of the collecting surface 118 is at or above about the melting temperature of the material 82. In an embodiment, the temperature of the collecting surface 118 is fixed during fiber 78 formation and deposition. In another embodiment, the temperature of the collecting surface 118 changes during fiber 78 formation and deposition.

In an embodiment wherein the fiber 78 is stretched multiple times, the fiber 78 is heated during the first stretching followed by cooling and then reheated and cooled for some or all of the subsequent stretching operations. In an embodiment wherein the fiber 78 is stretched multiple times, the fiber 78 is maintained at an elevated temperature during the first and all subsequent stretching operations. Drawing of the fiber 78 results in an increase of the fraction of perfectly oriented material 82 at the expense of un-oriented material 82.

In an embodiment, one or more fibers 78 are formed by a solvent spinning process followed by one or more hot drawing operations. In an embodiment, one or more fibers 78 are formed by a melt spinning process followed by one or more hot drawing operations. In a preferred embodiment wherein the fiber 78 is partially or fully comprised of poly-L-lactide (PLLA) the fiber 78 is hot drawn one or more times at a temperature between 30-150 degrees Celsius, more narrowly between 40-130 degrees Celsius. In an embodiment wherein the fiber 78 is partially or fully comprised of poly-L-lactide (PLLA) the fiber 78 is hot drawn at a temperature at or below about 40 degrees Celsius. In an embodiment wherein the fiber 78 is comprised of poly-L-lactide (PLLA) the fiber 78 is hot drawn at a temperature at or above about 150 degrees Celsius.

In an embodiment, the fiber 78 or fibers are formed by one or more fiber-forming devices and deposited on one or more collecting surfaces 118 having a spray pattern ranging from about 10 mm to 400 mm. In an embodiment, the fiber 78 or fibers are formed by one or more fiber-forming devices and deposited on one or more collecting surfaces 118 having a spray pattern less than about 11 mm. In an embodiment, the fiber 78 or fibers are formed by one or more fiber-forming devices and deposited on one or more collecting surfaces having a spray pattern greater than about 399 mm. The terms "spray pattern" refers to the width or distance that the fiber 78 or fibers are deposited on the collecting surface 118 after exiting one or more fiber-forming devices.

The fiber 78 or fibers of the present invention can be formed on a collecting surface 118 of any shape. In the preferred embodiment, the collecting surface 118 has a cylindrical shape or a flat shape. For example, and without intent on limiting, the shape of the collecting surface 118 is an angle, circle, oval, crescent, curved triangle, quatrefoil, parallelogram, square, rectangle, trapezoid, trapezium, triangle, kite, rhombus, pentagon, hexagon, heptagon, octagon, nonagon, decagon, or star shape.

Figure 51:
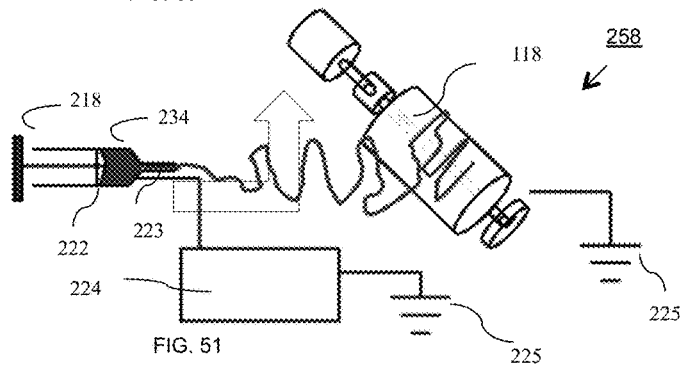

In an embodiment, wherein the collecting surface 118 is a cylindrical shape as shown in FIG. 51, the collecting surface 118 has a diameter ranging from about 0.1 millimeters to 300 centimeters. In another embodiment, the collecting surface 118 has a diameter less than about 0.1 millimeters. In one more embodiment, the collecting surface 118 has a diameter greater than about 300 centimeters.

In an embodiment, the solution 234 or melt 236 is converted into a fiber 78 at a rate of about 0.01 milliliters per hour to about 100 milliliters per second, more narrowly about 0.5 milliliter per hour to 10 milliliter per minute. In another embodiment, the solution 234 or melt 236 is converted into a fiber 78 at a rate at or less than about 0.1 milliliters per hour and in another embodiment the polymer solution or melt is converted into a fiber 78 at a rate at or greater than about 100 milliliters per second.

In an embodiment, when producing one or more fibers 78 the material 82 entering and flowing through the one or more capillary tubes 223 is translucent, remains translucent as it travels the distance between the exit of the capillary tube 223 and the collecting surface 118, and remains substantially translucent after being deposited and removed from the collecting surface 118. In an embodiment, when producing one or more fibers 78 the material 82 entering and flowing through the one or more capillary tubes 223 is translucent, remains translucent as it travels the distance between the exit of the capillary tube 223 and the collecting surface 118, and remains substantially translucent after being deposited and removed from the collecting surface 118 but the multiple layers of fibers 78 collectively have a white appearance.

In an embodiment, when producing one or more fibers 78 the material 82 entering and flowing through the one or more capillary tubes 223 is translucent, turns partially or fully white or opaque as it travels the distance between the exit of the capillary tube 223 to the surface of the collecting surface 118, and remains partially or fully white or opaque after being deposited and removed from the collecting surface 118. In an embodiment, when producing one or more fibers 78 the material 82 entering and flowing through the one or more capillary tubes 223 is translucent, turns partially or fully white or opaque as it travels the distance between the exit of the capillary tube 223 to the surface of the collecting surface 118, and remains partially or fully white or opaque after being deposited and removed from the collecting surface 118. In an embodiment, when producing one or more fibers 78 the molecules comprising the material 82 entering and flowing through the one or more capillary tubes 223 are amorphous, the molecules comprising the material 82 remain about the same amount of amorphicity as they travel the distance between the exit of the capillary tube 223 to the surface of the collecting surface 118, and the molecules comprising the material 82 retain about the same amount of amorphicity after being deposited and removed from the collecting surface 118. In an embodiment, when producing one or more fibers 78 the molecules comprising the material 82 entering and flowing through the one or more capillary tubes 223 are partially or fully amorphous, the molecules comprising the material 82 become more crystalline as they travel the distance between the exit of the capillary tube 223 to the surface of the collecting surface 118, and the molecules comprising the material 82 partially or fully retain the increase in crystallinity after being deposited and removed from the collecting surface 118. In an embodiment, when producing one or more fibers 78 the molecules comprising the material 82 entering and flowing through the one or more capillary tubes 223 are partially or fully unfolded, the molecules comprising the material 82 remain partially or fully unfolded as they travel the distance between the entrance of the capillary tube 223 and the collecting surface 118, and the molecules comprising the material 82 remain partially or fully unfolded after being deposited and removed from the collecting surface 118. In an embodiment, when producing one or more fibers 78 the molecules comprising the material 82 entering and flowing through the one or more capillary tubes 223 are substantially unfolded, the molecules comprising the material 82 become partially or fully folded as they travel the distance between the entrance of the capillary tube 223 and the collecting surface 118, and the molecules comprising the material 82 remain partially or fully folded after being deposited and removed from the collecting surface 118. In an embodiment, when producing one or more fibers 78 the molecules comprising the material 82 entering and flowing through the one or more capillary tubes 223 are partially or fully unfolded, the molecules comprising the material 82 become more folded as they travel the distance between the entrance of the capillary tube 223 and the collecting surface 118, and the molecules comprising the material 82 partially or fully retain the additional folding after being deposited and removed from the collecting surface 118.

In an embodiment having two or more capillary tubes 223, at least one capillary tube 223 deposits material 82 on the collecting surface 118 comprised of more crystalline material 82 and at least one capillary tube 223 deposits material on the collecting surface 118 comprised of more amorphous material 82. In an embodiment having one or more capillary tubes 223, at least one capillary tube 223 deposits material 82 on the collecting surface 118 comprised of crystalline material 82 and amorphous material 82. In an embodiment having one or more capillary tubes 223, at least one capillary tube 223 deposits material 82 on the collecting surface 118 comprised of semi-crystalline material 82. In an embodiment having one or more capillary tubes 223, at least one capillary tube 223 deposits material 82 on the collecting surface 118 comprised of crystalline material 82. In an embodiment having one or more capillary tubes 223, at least one capillary tube 223 deposits material 82 on the collecting surface 118 comprised of amorphous material 82. In an embodiment having two or more capillary tubes 223, at least one capillary tube 223 deposits material 82 on the collecting surface 118 having material 82 mostly comprised of molecules in unfolded configuration and at least one capillary tube 223 deposits material 82 on the collecting surface 118 having material 82 mostly comprised of molecules in folded configuration. In an embodiment having one or more capillary tubes 223, at least one capillary tube 223 deposits material 82 having a combination of folded and unfolded molecules on the collecting surface 118. In an embodiment having one or more capillary tubes 223, at least one capillary tube 223 deposits material on the collecting surface that is more stiff and one capillary tube 223 deposits material on the collecting surface that is more flexible. In an embodiment having one or more capillary tubes, at least one capillary tube 223 deposits one or more fibers 78 that are higher in tensile strength and one capillary tube deposits one or more fibers that are lower in tensile strength. In an embodiment having one or more capillary tubes 223, at least one capillary tube deposits one or more fibers 78 having a higher melting temperature and at least one capillary tube deposits one or more fibers 78 having a lower melting temperature. In an embodiment having one or more capillary tubes 223, at least one capillary tube deposits one or more fibers 78 wherein the solvent has substantially evaporated and at least one other capillary tube 223 deposits one or more fibers 78 wherein the solvent has only partially evaporated. In an embodiment having one or more capillary tubes 223, at least one capillary tube deposits one or more fibers 78 wherein the fibers 78 do not bond together and at least one other capillary tube 223 that deposits one or more fibers 78 wherein the fibers 78 bond together or bond other fibers 78 together upon deposition on the collecting surface 118. In an embodiment having one or more capillary tubes 223, at least one capillary tube 223 deposits one or more preformed configurations 77 such as fibers 78 formed of a material 82 comprised of a higher Young's modulus of elasticity and at least one other capillary tube 223 deposits one or more fibers 78 comprised of a material 82 having a lower Young's modulus of elasticity.

Figure 50:
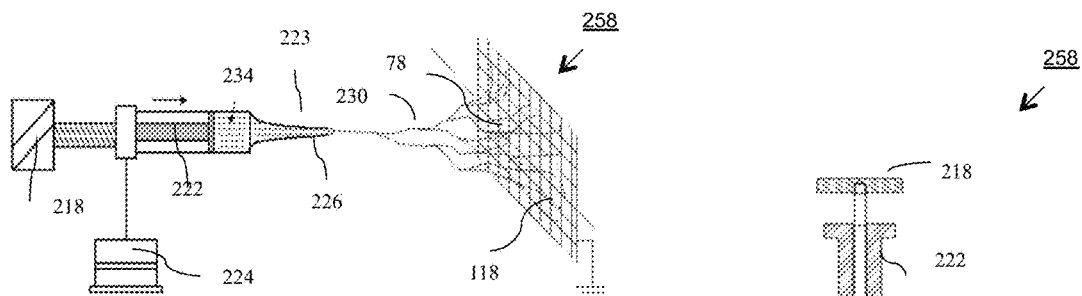
FIG. 50 and FIG. 51 are diagrams of solvent electrospinning manufacturing processes.
Figure 52:
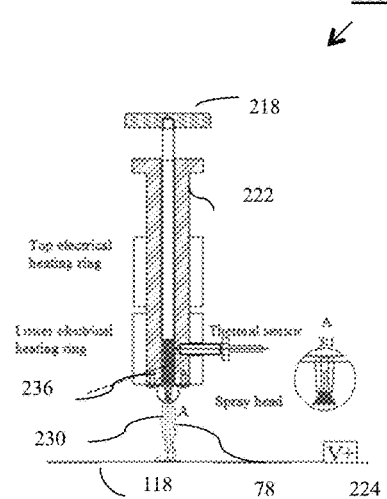
FIG. 52 is a diagram of one melt electrospinning manufacturing process.
Figures 53, 54, 55, 56:
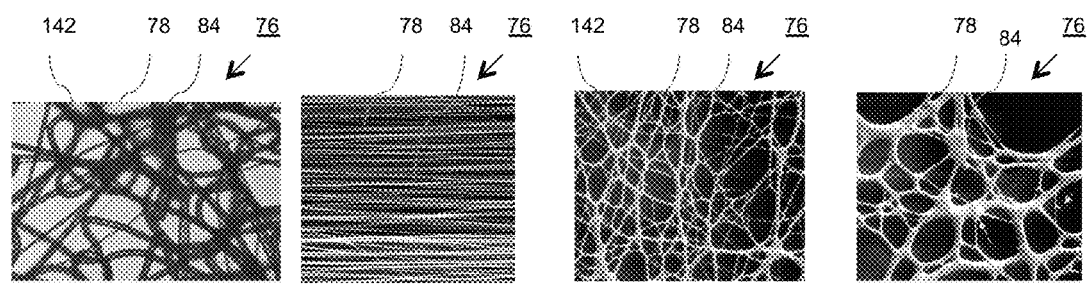
FIG. 53, FIG. 54, FIG. 55, FIG. 56, FIG. 57, FIG. 58, and FIG. 59 are embodiments of a wall thickness including preformed configurations in the form of fibers and voids.

In an embodiment of the present invention, a process known in the art as electrospinning produces one or more preformed configurations 77 in the form of fibers 78. Fibers 78 suitable for use in the present invention can be produced by those skilled in the art of electrospinning. Referring to FIG. 50-FIG. 52, the term "electrospinning" refers to a manufacturing process wherein a high voltage 224 is used to create one or more electrically charged jets 230 of material 82 or solution 234 of material 82, or melt 236 of material 82 which dries or solidifies to produce one or more fibers 78 on a collector 118. Without intent on limiting, a typical electrospinning process 258 includes a syringe 222, capillary tube 223, voltage source 224, and collecting surface 118. The collector 118 can be of an almost infinite amount of shapes and is not limited to the flat or cylindrical shaped collectors 118 described herein and shown in FIG. 50-FIG. 52. In an embodiment, the fibers 78 are collected on the collecting surface 118 in a size and shape suitable for producing a precursor construct tube 74. In another embodiment, the fibers 78 are collected on the collector 118 in a size and shape that requires removal of the fibers 78 from the collecting surface 118 and using a secondary process to form the fibers 78, for example in sheet 196 configuration, into a precursor construct tube 74 or other suitable shape for producing an endoprosthesis. In an embodiment, the electrospun fibers 78 are collected in a nonwoven configuration like shown in FIG. 23, FIG. 53, FIG. 58, and FIG. 59. In an embodiment, the electrospun fibers 78 are collected in an aligned configuration as shown in FIG. 54. In an embodiment, the electrospun fibers 78 are collected in a nonwoven and aligned configuration. The aligned fibers 78 can be at any angle relative to the central axis 42 and are not limited to the example shown in FIG. 54.

In an embodiment, the solution 234 is comprised of material 82 that is partially or fully dissolved in one or more solvents. In another embodiment, the one or more materials 82 are melted to form a fluid or flowing material 82. The solution 234 or melt 236 is placed in a metering device such as a syringe 222 and a pump 218. A capillary tube 223 such as a metallic needle is connected to the exit of the metering device in away that the pump 218 dispenses solution 234 or melt 236 through the exit of the capillary tube 223 at a suitable flow rate. In an embodiment one electrode is placed onto the metallic capillary tube 223 and the other electrode 225 is attached to a collector 118. An electric field is subjected to the end of a capillary tube 223 that contains the melt 236 or solution 234 held by its surface tension. This induces a charge on the surface of the liquid. As the intensity of the electric field is increased, the hemispherical surface of the fluid 234, 236 at the tip of the capillary tube 223 elongates to form a conical shape known as the Taylor cone 226. With increasing field, a critical value is attained when the repulsive electrostatic force overcomes the surface tension and a charged jet 230 of fluid 234, 236 is ejected from the tip of the Taylor cone 226. The discharged material 82 in the form of a jet 230 under some process conditions undergoes a whipping process wherein the solvent evaporates or material cools, leaving behind a charged fiber 78, which lays itself randomly or in an aligned configuration on a grounded collecting surface 118 in one or more layers. In the case of the melt 236 the discharged jet 230 partially or fully solidifies when it travels in the air and is collected on the grounded collecting surface 118. In an embodiment, the electrospun fibers 78 include a static charge that produces a three-dimensional structure on the collector 118.

In one embodiment, the high voltage source 224 can generate up to about 30 kV or more, and the setup can be run on either positive or negative polarity. In an embodiment, the voltage source 224 operates at a voltage about of about 15 kV and amperage of about 90 micro amps. In another embodiment, the voltage source 224 can generate more or less than 30 KV. In one more embodiment, the voltage source can operate at more or less than 90 micro amps. Adjusting the flow of the fluid and the magnitude of the electric field controls the spinning rate. System parameters include molecular weight; molecular-weight distribution and architecture (branched, linear, etc.) of the material 82 or polymer; and solution properties (viscosity, conductivity, temperature, and surface tension). The process parameters include electrical potential, flow rate, and solution concentration; solvent choice; surface tension; distance between the capillary tube 223 and collecting surface 118; ambient parameters (temperature, humidity, and air velocity in the chamber, capillary tube 223 diameter, capillary tube 223 length, and motion of the collecting surface 118. Employing elevated temperature and/or viscosity suppressants can be useful for electrospinning high molecular weight materials 82 or polymers.

Figures 57, 58, 59:
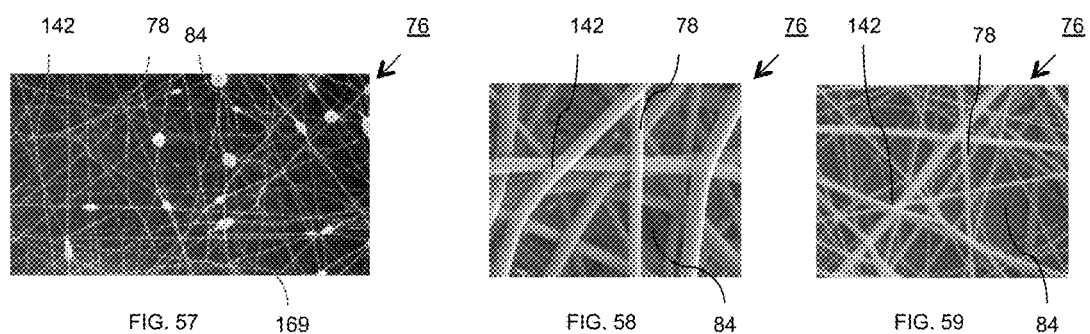

With increasing concentration of the material 82 in the solution 234 (keeping other parameters constant) the average fiber 78 thickness 92 increases. With increasing capillary tube 223 to target 118 distance the average fiber 78 thickness decreases. As shown in FIG. 57, with lower capillary tube 223 to target 118 distances sputtering 169 are sometimes formed. With increasing electric potential, the jet 230 is discharged with greater electrostatic repulsion that causes it to undergo levels whipping action and/or drawing stress. With greater rotational speed of the mandrel 118 the jet 230 undergoes greater drawing stress and the fiber 78 obtains more alignment on the surface of the rotating collecting surface 118.

In an embodiment, to reduce the production time of producing fibers 78, multiple electrospinning devices including multiple syringes 222, pumps 218, capillary tubes 223, or whatever other equipment is necessary are simultaneously employed to deposit multiple fibers 78 on the collection surface 118. The production of multiple fibers 78 simultaneously or in sequence allows the wall thickness 78 to be built up of fibers 78 in a shorter time. In an embodiment, there are multiple capillary tubes 223 depositing material 82 in the form of fiber 78 on the target 118. In one more embodiment, there are multiple capillary tubes 223 positioned at different distances from the target 118 depositing material 82 in the form of fiber 78 on the target 118. In an embodiment, there are multiple capillary tubes 223 wherein the material 82 in the form of a solution 234 or melt 236 is flowing through the capillary tubes 223 are at different flow rates. In an embodiment, there are multiple capillary tubes 223 where the material 82 in the form of a solution 234 is flowing through the capillary tubes 223 at different material-solvent concentrations. In an embodiment, there are multiple capillary tubes 223 wherein the orifices of the capillary tubes 223 are of different sizes. In an embodiment, there are multiple capillary tubes 223 wherein the length of the capillary tubes are of different lengths. In an embodiment, there are multiple capillary tubes 223 wherein the solutions 234 or melts 236 flowing through the capillary tubes 223 are of different temperatures. In an embodiment, there are multiple capillary tubes 223 wherein the solutions 234 or melts 236 flowing through the capillary tubes 223 are of different viscosities. In an embodiment, there are multiple capillary tubes 223 wherein the solutions 234 or melts 236 are comprised of materials 82 of different chemical composition. In an embodiment, there are multiple capillary tubes 223 wherein the solutions 234 are comprised of solvents of different chemical composition. In an embodiment, there are multiple capillary tubes wherein the solutions 234 are comprised of two or more blends of solvents. In an embodiment, there are multiple capillary tubes 223 wherein the solutions 234 or melts 236 are comprised of blends of two or more materials 82 having different chemical compositions.

In an embodiment, the electrospun fiber or fibers 78 comprised of material 82 are strengthened by orienting or extending the molecular chains by electrospinning the material 82 onto a rotating collector, drum, or mandrel 118 or by subsequently stretching the resultant fiber or fibers 78 or mesh. Stretching the fiber 78 imparts molecular orientation, strain hardening 147, or strain crystallization. In this system, the material 82 deposits on the grounded collector, drum, or mandrel 118 as it rotates. Increasing the speed of the rotating drum 118 can increase the degree of molecular orientation and fiber 78 alignment. The wall thickness 76 deposited on the collecting surface 118 is primarily controlled by the length of time that the material 82 is electrospun. In one more embodiment the fiber or fibers 78 are heated during its transit time between its exit from the Taylor cone 226 and the collecting surface 118.

Electrospinning equipment is available from any source such as Elmarco Svarovska p.p.c 1393/7, 460 10 Liberec Ruzodo, (Czech Republic), or Elmarco, 1101 Aviation Parkway Suite E, Morrisville, N.C. 27560 (USA). In an embodiment, the fiber or fibers 78 are produced by a needle-free, high voltage, free liquid surface, electrospinning process developed by Elmarco s.r.o. (Liberec, Czech Republic). This process is known in the art as NANOSPIDER™ technology. In an embodiment, the material 82 is dissolved in a solvent to produce a polymer solution and placed in a container. A cylindrical shaped electrode is at least partially submerged in the polymer solution. When the cylindrical shaped electrode rotates a voltage differential between the electrode and the collecting object causes a multitude of fibers 78 to form as the polymer solution transfers from the electrode to the collecting object. As the polymer solution transfers from the electrode to the collecting object the solvent evaporates leaving fibers 78 on the surface of the collecting object.

Films

In an embodiment of the present invention, the wall thickness 76 is comprised of one or more preformed configurations 77 in the form of one or more films 81. In an embodiment, the wall thickness 76 is comprised of one or more oriented films 81. In an embodiment, the wall thickness 76 is comprised of one or more un-oriented films 81. In an embodiment, the wall thickness 76 is comprised of one or more oriented films 81 and one or more un-oriented films 81. In an embodiment, the wall thickness 76 is comprised of one or more multi-films 79. In an embodiment, the one or more films 81 include a profile such as grooves, indentations, protrusions, or other features that promote intermolecular entanglement when the film 81 is interconnected to another preformed configuration 77 as described herein. In an embodiment, the wall thickness 76 that is partially or fully comprised of one or more films 81 is hot and/or cold drawn or hot and/or cold expanded one or more times as described herein.

In an embodiment, the length of the film 81 or multi-film 79 is short wherein the length 91, 99, is less than 25 centimeters (cm). In another embodiment, the length 91, 99 of the film 81, multi-film 79 is long wherein the length 90, 98 is greater than 25 centimeters (cm). The length 91, 99, of the film 81 and multi-film 79 can be any length that meets the performance requirements described herein this specification. The length of film 81 or multi-film 79 in other embodiments is chopped, broken, or cut so that one longer preformed configuration 77 is converted into several shorter preformed configurations 77 that are incorporated into the wall thickness 76 of the tube 74 or other precursor construct.

In an embodiment the wall thickness 76 is comprised of one or more films 81 or multi-films 79 that are formed by extruding, casting, calendaring, or molding of one or more materials 82 into films 81. In an embodiment the film 81 or multi-films 79 are what is known in the art of manufacturing films as "oriented films." In an embodiment, the film 81 or multi-films 79 are bi-axially oriented films. In an embodiment, the film 81 or multi-films 79 are multi-axial oriented films. In an embodiment, the wall thickness 76 is comprised of any combination of extruded or molded films 81, cast films 81, calendared films 81, oriented films 81, bi-axially oriented films 81, multi-axial oriented films 81, un-oriented films 81, fiber 78, or multi-fibers 80. Generally, oriented films 81 are stronger than un-oriented films.

The thickness 93 of the film 81 or multi-film 79 can be solid or porous. The film 81 can be of any cross-sectional shape such as, for example, rectangular as shown in FIG. 6 or FIG. 7. In an embodiment the width 89 of the film 81 ranges between about 0.5 millimeters (mm) to 3 meters (m). In another embodiment, the width 89 of the film 81 is less than 0.5 millimeters (mm). In one more embodiment, the width of the film 81 is greater than 3 meters (m). The length 91 of the film 81 is indefinite.

Figure 96:
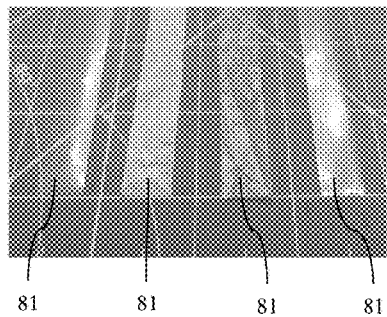
FIG. 96 is a photograph of various embodiments of various preformed configurations comprised of different materials in the form of films.
Figure 97:
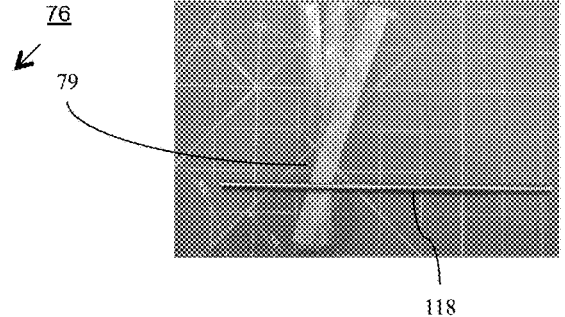
FIG. 97 is a photograph of the films of FIG. 96 assembled in layers being organized to wrap around a mandrel.
Figure 98:
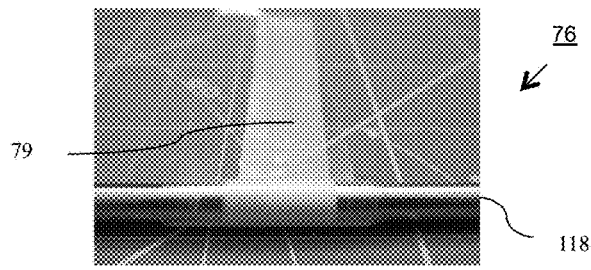
FIG. 98 is a photograph of the films of FIG. 96 assembled in layers being wrapped around a mandrel prior to being heated, formed, and cooled to produce a tube having a wall thickness formed of four layers of different films.

Referring to FIG. 96-FIG. 97, in an embodiment, the wall thickness 76 is formed of one or more films 81 of the same or different material 82. In the example shown in FIG. 96, four films of different chemical composition are laid out on a table in preparation for formation into a wall thickness 76. The films 81 are stacked on top of each other forming a wall thickness 76 comprised of four layers of film 81 as shown in FIG. 97. The four films 81 are wrapped around the mandrel 118 having low dimensional variation as shown in FIG. 98. In an embodiment, the wall thickness 76 is comprised of one or more films 81 wrapped around a mandrel 118 so that from the side view the films 81 take on a spiral appearance. In an embodiment, the one or more films 81 are warmed to facilitate wrapping the films 81 around the mandrel. In some embodiments the films are relatively stiff and by warming them they become more pliable or flexible so that the films 81 can be more easily formed into a wall thickness 76 or more easily wrapped around a mandrel as an example is shown in FIG. 98. The films 81 are thermally treated and sized as described herein to convert the films 81 into a tubular precursor construct 74 having a wall thickness 76 comprised of multiple layers 107 of interconnected film 81. As shown in FIG. 8, the four films include seams 125 at junctions between layers of film 81, junctions of short edges 123 and long edges 121. In an embodiment, the cross section of the tube's 74 wall thickness 76 is stratified so that between each stratum there is a stress crack arresting portion so that if a crack initiates, for example, in a strut 44 that the crack does not easily propagate through the entire wall thickness 76.

As previously mentioned, bi-axial and multi-axial orientation improves the mechanical properties such as Young's modulus and tensile strength of the film 79, 81 and material 82. Orientation can also impact the morphology of the material 82, and the degradation rate and resorption rate of the material 82 after deployment of an endoprosthesis. To obtain molecular orientation in the film, the film 81 or multi-films 79 are stretched one or more times in the machine direction 109, transverse direction 111, or thickness direction 113. In one embodiment, the one or more machine direction 109 and transverse direction 111 stretching is imparted on the film 81 or multi-films 79 consecutively and in another embodiment the one or more machine direction 109 and transverse direction 111 stretching is imparted on the film 81 or multi-films 79 simultaneously. As depicted in FIG. 6, the machine direction 109 runs parallel to the lengthwise axis 95 of the film 81 and the transverse direction 111 runs perpendicular to the lengthwise axis 95 of the film 81.

In an embodiment, one or more films 81 are stretched in the machine direction 109 by means of a machine direction orienter (MDO) by, for example, processing the un-stretched or stretched film 81 through rolls with increasing speed. In an embodiment, one or more films 81 are stretched in the transverse direction 111 by means of a transverse direction orienter (TDO) where the film 81 is fixed at both long ends and stretched, for example using a tenter frame, in a transverse direction 111. In an embodiment the one or more films 81 are stretched in the machine direction 109 and transverse direction 111 sequentially and in another embodiment, the one or more films 81 are stretched in the machine direction 109 and the transverse direction 111 simultaneously. In an embodiment, the film 81 is stretched multiple times in the machine direction 109 and/or transverse direction 111. If the film 81 is stretched multiple times, the film 81 can be heated during the first stretching followed by cooling and then reheated and cooled for all or some of the following stretching operations or the film 81 can be heated and stretched multiple times before cooling.

In an embodiment, using a blown film process (aka double bubble process) simultaneously stretches one or more films 81. Without intent on limiting, a blown process comprises the steps of extruding a tube, cooling the tube, and re-heating the tube during stretching. A synchronous increase in the draw off speed and the bubble expansion by internal pressure results in simultaneous machine direction 109 and transverse direction 111 molecular orientation.

In an embodiment, one or more films 81 are stretched between 10 percent and 10,000 percent of its starting length 91 and/or width 89. In another embodiment, one or more films 81 are stretched to at or below 10 percent of its starting length 91 and/or width 89. In another embodiment, one or more films 81 are stretched to at or above 10,000 percent of its starting length 91 and/or width 89. In an embodiment, one or more films 81 stretched at a rate of 10 percent/minute to 10,000 percent/millisecond. In another embodiment, one or more films 81 are stretched at a rate at or below 10 percent/minute. In one more embodiment, one or more films 81 are stretched at a rate at or above 10,000 percent/millisecond.

In an embodiment, a solvent casting process produces the film 81 or multi-film 79. In an embodiment, solvent casting followed by hot drawing produces the film 81 or multi-film 79. In an embodiment, the one or more materials 82 are dissolved in a solvent or blend of solvents in the range of about 1-15 weight percent material to 99-85 weight percent solvent to form a solution suitable for casting. In another embodiment, the one or more materials 82 are dissolved in a solvent or blend of solvents at lower than 1 weight percent material 82 and the remaining portion solvent. In another embodiment, the one or more materials 82 are dissolved in a solvent or blend of solvents at greater than 15 weight percent material 82 and the remaining portion solvent. In an embodiment, the previously mentioned material solutions are formed into the shape of a film 81, the solvent partially or fully evaporates, and a film 81 is formed upon solidification of the material 82. In an embodiment, the previously mentioned material solutions are formed into the shape of a film 81 by extruding the solution and drawing the solution from a larger cross-sectional size to a smaller cross-sectional size.

Although examples of producing fibers 78 and films 81 have been provided herein, any fiber or film can be used in the present invention provided that it is capable of producing a wall thickness 76 as described in this specification. Fabrication of fibers 78 and/or films 81 by solution casting, melt pressing, melt extrusion, bubble blown method, or any other suitable methods know by those skilled in the art of making films is suitable for the present invention. A description of film production processes suitable for use in the present invention is described in "Polymer Synthesis and Processing," authored by Mahadevappa Y. Kariduraganavar, Arjumand A. Kittur, and Ravindra R. Kamble, as published in Chapter 1 of Natural and Synthetic Biomedical Polymers, Copyright 2014 by Elsevier Inc, and is incorporated herein in its entirety as a reference.

Sheets

Figure 82:
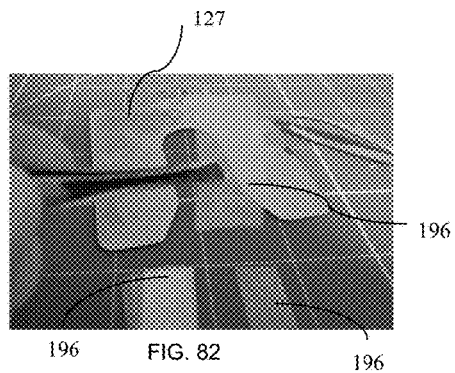
FIG. 82 is a photograph of sheets of interconnected preformed configurations in the form of fibers separated by void spaces having a rectangular shape.

In an embodiment of the present invention, the wall thickness 76 is comprised of one or more sheets 196 or multi-sheets 209. In an embodiment the wall thickness 76 is comprised of one or more sheets 196 as shown in FIG. 25 and FIG. 82. As shown in FIG. 25, the sheet 196 is comprised of a width 207, length 205, lengthwise axis 217, short edge 201, long edge 199, outer surface 221, and thickness 93. As shown in FIG. 26, the multi-sheet 209 is comprised of a width 211, length 213, lengthwise axis 219, short edge 229, long edge 231, seam 125, outer surface 227, and thickness 215. In one embodiment the sheet 196 is comprised of one or more preformed configurations 77. In an embodiment, the sheet 196 is comprised of one or more fibers 78 or multi-fibers 80. In an embodiment, the sheet 196 is comprised of one or more films 81 or multi-films 79. In more embodiments, the sheet 196 is formed of one or more fiber 78, multi-fiber 80, film 81, multi-films 79, or any combination thereof. In an embodiment, the sheet 196 includes one or more void spaces 84. In an embodiment, the thickness 93 of the sheet 196 is substantially the same thickness along its entire length 205 and width 207. In an embodiment, the thickness 93 of the sheet 196 has one or more variations in thickness along its entire length 205 and width 207. The sheets 196 are formed by wet spinning, dry spinning, wet-dry spinning, winding, braiding, extrusion, calendaring, or any other process for producing or organizing one or more preformed configurations 77 in the form of a sheet 196.

Figure 85:
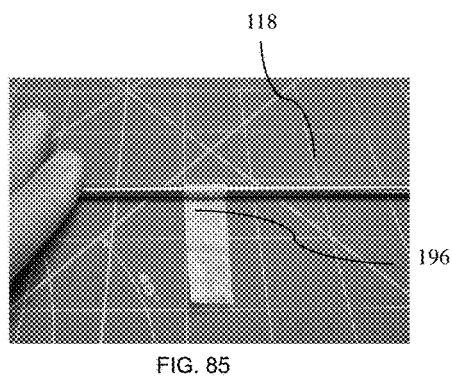
FIG. 85 is a photograph of the two sheets of preformed configurations in the form of fibers stacked on top of each other being wrapped around the outside diameter of a steel mandrel to form the wall thickness of a precursor construct tube.
Figure 86:
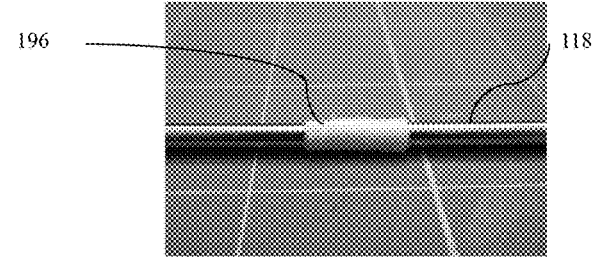
FIG. 86 is a photograph of the two sheets of preformed configurations in the form of fibers wrapped around a steel mandrel to form the wall thickness of a precursor construct tube having a wall thickness comprised of preformed configurations.
Figure 84:
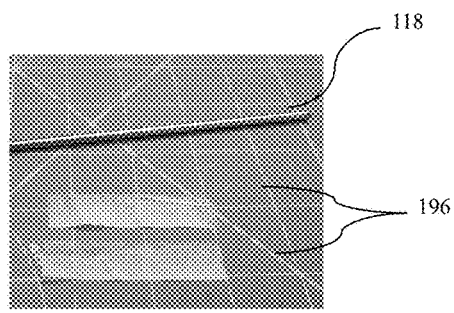
FIG. 84 is a photograph of two sheets of interconnected preformed configurations in the form of fibers separated by void spaces having a rectangular shape wherein one sheet has fibers aligned parallel to the long side of the rectangle and another sheet has fibers aligned parallel to the short side of the rectangle.

In an embodiment, the one or more preformed configurations 77 are first formed into a sheet 196 and the one or more sheets 196 are subsequently formed into the wall thickness 76 of a seamed precursor construct tube 74 or other precursor construct. As shown in FIG. 27, in an embodiment, the sheets 196 are formed into the shape of a tubular precursor construct tube 74 held together with one or more seams 125. Another example of an embodiment having the wall thickness 76 formed of one or more sheets 196 is shown in FIG. 84 and FIG. 86. In the present invention the term "sheet" refers to a relatively thin, normally rectangular or square form, piece, plate or slab wherein its thickness 93 is comprised of one or more preformed configurations 77 like, for example, a fiber 78. As illustrated in FIG. 27, in an embodiment the one or more sheets 196 are formed into a cylindrical shape such as a precursor construct tube 74 by winding or wrapping the sheets 196 around a cylindrical-shaped mandrel 118 in one or more layers of sheet 196 either abutting or overlapping the long edges 199 or short edges 201 of the sheet or sheets 196 to form a seam 125 to interconnect the edges. In an embodiment of the cylindrical shaped precursor construct tube 74 formed of one or more sheets 196 or one or more layers of sheets, the sheets 196 are heated and the sheet's or sheets' edges 199, 201 are interconnected or the layers are interconnected after heating. As shown in FIG. 84 and FIG. 85 two or more sheets 196 can be layered on top of each other and formed into a tubular precursor construct 74.

In an embodiment, the wall thickness 76 is comprised of one or more sheets 196 having one or more preformed configurations 77 aligned substantially parallel to the sheet's lengthwise axis 217. In an embodiment, the wall thickness 76 is comprised of one or more sheets 196 having one or more preformed configurations 77 aligned substantially perpendicular to the sheet's lengthwise axis 217. In an embodiment, the wall thickness 76 is comprised of one or more sheets 196 having one or more fibers 78 aligned substantially at any angle from zero to three hundred sixty degrees to the sheet's lengthwise axis 217. In an embodiment, the wall thickness 76 is comprised of one or more sheets 196 having one or more fibers 78 in a nonwoven configuration.

In an embodiment, the wall thickness 76 is comprised of one or more sheets 196 positioned in the wall thickness 76 so that the sheet's lengthwise axis 217 is aligned parallel to the tube's 74 central axis 42. In an embodiment, the wall thickness 76 is comprised of one or more sheets 196 positioned in the wall thickness 76 so that the sheet's lengthwise axis 217 is aligned perpendicular to the tube's 74 central axis 42. In an embodiment, the wall thickness 76 is comprised of one or more sheets 196 positioned in the wall thickness 76 so that the sheet's lengthwise axis 217 is aligned at any angle from zero to three hundred sixty degrees to the tube's 74 central axis 42.

In an embodiment, the wall thickness 76 is comprised of one or more sheets 196 having each sheet 196 configured so that one or more fibers 78 are aligned substantially parallel to the sheet's 196 lengthwise axis 217, perpendicular to the sheet's 196 lengthwise axis 217, at any angle to the sheet's 196 lengthwise axis 217, in nonwoven configuration, or any combinations thereof. In another embodiment the wall thickness 76 is comprised of one or more sheets 196 including one or more preformed configurations 77 wherein at least one of the sheets 196 has some or all it preformed configurations 77 aligned substantially perpendicular to the sheet's lengthwise axis 217 and another sheet 196 has some or all its preformed configurations 77 aligned substantially parallel to the sheet's lengthwise axis 217. In yet another embodiment the wall thickness 76 is comprised of one or more sheets 196 including one or more preformed configurations wherein at least one of the sheets 196 has some or all it preformed configurations 77 aligned substantially between zero and ninety-one degrees of the central axis 42 of the precursor construct tube 74 and at least one of the other sheets 196 in the wall thickness 76 has one or more preformed configurations aligned between eighty-nine and one hundred eighty degrees from the central axis 42 of the precursor construct tube 74. In an embodiment, the wall thickness 76 that is partially or fully comprised of one or more sheets 196 is hot and/or cold drawn or hot and/or cold expanded one or more times as described herein.

Melt and Solution Processing

In an embodiment, while converting the one or more materials 82 into a preformed configuration 77 or a tubular precursor construct 74 by melt processing, the material 82 is typically heated to a temperature at or above about the melting temperature of the material 82 or until the material 82 is capable of flowing into the shape of the preformed configuration 77 or tubular precursor construct 74. In an embodiment, while converting the material 82 into a preformed configuration 77 or tubular precursor construct 74 by solvent processing, the material 82 is typically dissolved in a solvent at any ratio that forms a viscous liquid capable of being formed into the shape of a preformed configuration 77 or tubular precursor construct 74. Solvent processing includes variations described herein as wet extrusion, dry extrusion and dry-wet or gel extrusion. The solvent processes have the advantage that the material 82 is not subjected to high temperatures and, therefore, thermal degradation of the material 82 is not a problem. The solvent process also has the advantage that when the material 82 is in solution the amount of molecular chain entanglement is lower than when the material 82 is in a melt, and, therefore the material 82 can be more easily drawn into a high strength preformed configurations 77 or tubular precursor construct 74. Moreover, the material 82 experiences more shear forces during melt processing than the material 82 experiences in solvent processing and therefore the molecular weight of the material 82 is preserved during solvent processing and reduced during melt processing. For these reasons, the embodiment of preformed configurations 77 or tubular precursor construct 74 produced by solvent processing is generally significantly stronger than preformed configurations 77 or tubular precursor construct 74 produced by melt processing. Precautions can be taken to prevent thermal degradation of material 82 by removal of catalyst and monomer from the polymerized material 82 or end capping the material's molecular chains to obtain the economical benefits of melt processing the material 82.

The viscous or syrupy solution or melt, prepared by melting or dissolving the material 82, is fed into a die and emerges as long fibers 78, films 81, or tubular profiles that are then solidified by coagulation, evaporation, or cooling. The size and shape of the die determines the cross-sectional shape of the fiber 78, film 81, or tubular precursor construct 74. In an embodiment, the material 82 is at least partially oriented when it fed to or passes through the die. The terms "wet extrusion" refers to a manufacturing process wherein the material 82 or polymer is dissolved in a solvent, the resulting solution 234 is forced through a die submerged in a chemical bath that leads the extrudate to precipitate, and then solidify, as it emerges out of the die. The terms "dry extrusion" refers to a manufacturing process wherein the material 82 or polymer is dissolved in a solvent, the resulting solution 234 is forced through a die, and evaporating the solvent forms the fiber 78, film 81, or tubular precursor construct 74. The terms "melt extrusion" refers to a manufacturing process wherein the material 82 or polymer is melted, the melt is forced through a die, and cooling forms the fiber 78, film 81, or tubular precursor construct 74. The terms "gel extrusion" (also known as dry-wet extrusion) refers to a manufacturing process wherein the material 82 or polymer is dissolved in a first solvent to form a gel, the gel is forced through a die, and solidification of the fiber 78, film 81, or tubular precursor construct 74 exiting the die occurs by a combination of precipitation and/or cooling of the material 82 or polymer, and removal of the first solvent with a second solvent by washing the fiber 78, film 81, or tubular precursor construct 74 in a liquid bath. In an embodiment, the solution is heated or cooled to adjust viscosity, improved dissolution of material 82 in solvent, or to change other processing conditions as required to produce a wall thickness meeting the specifications described herein.

In an embodiment, the solution 234 is at ratio in the range of about one part material 82 and ninety-nine parts solvent to about thirty-five parts material 82 and sixty-five parts solvent. In another embodiment, the solution 234 is at a ratio of at or less than about one part material 82 and remaining parts solvent. In yet another embodiment, the solution 234 is at a ratio at or greater than about thirty-five parts material 82 and remaining parts solvent. In an embodiment, the solution 234 is in the range of about one weight percent (1%) material 82 and ninety-nine weight percent (99%) solvent to about thirty (30%) weight percent material 82 and seventy (70%) weight percent solvent. In another embodiment, the solution 234 is at or less than about one weight percent (1%) material 82 and the remaining percent solvent. In one more embodiment, the solution 234 is at or greater than thirty weight percent (30%) material 82 and the remaining percent solvent. In an embodiment, the solution 234 is in the range of about one weight percent (1%) material 82 and ninety-nine weight percent solvent and other additives 150, 152 to about twenty-five (25%) weight percent material 82 and seventy-five (75%) weight percent solvent and additives 150, 152. In another embodiment, the solution 234 is less than about one weight percent (1%) material 82 and the remaining percent being solvent and other additives 150, 152. In one more embodiment, the solution 234 is greater than twenty-five weight percent (25%) material 82 and the remaining percent being solvent and other additives 150, 152. The term "solution" refers to material 82 partially or fully dissolved in a solvent.

In the present invention any solvent can be utilized that converts the material 82 into a solution, emulsion, gel or other composition that is suitable for converting the material 82 into a preformed configuration 77 and or shape like a tube 74. Those skilled in the art of spinning fibers can select the correct solvent or blends of solvents based on the solubility of the material 82 being used to produce the fibers in the solvent or solvents, the evaporation rate of the solvent, biocompatibility of the solvent, environmental, health, safety, electrical properties, processing parameters, and other considerations. In one embodiment using material 82 partially or fully comprised of poly (L-lactide) (PLLA) or any other material 82 suitable to produce fiber or fibers 78, the processing solvent is comprised of 1,1,1,3,3,3-hexafluoro-2-propanol, $(CF_3)_2CHOH$, $C3H2F6O$, or hexafluoroisopropanol (HFIP). In another embodiment using material 82 partially or fully comprised of poly (L-lactide) (PLLA) or any other material 82 suitable to produce fiber or fibers 78, the processing solvent is comprised of methylene chloride or dichloromethane (DCM). In one more embodiment using material 82 partially or fully comprised of poly (L-lactide) (PLLA) or any other material 82 suitable to produce fiber or fibers 78, the processing solvent is comprised of chloroform. In one more embodiment using material 82 partially or fully comprised of poly (L-lactide) (PLLA) or any other material 82 suitable to produce fiber or fibers 78, the processing solvent is comprised of trichloroethylene. In one more embodiment using material 82 partially or fully comprised of poly (L-lactide) (PLLA) or any other material 82 suitable to produce fiber or fibers 78, the processing solvent is comprised of 1,1,1-trichloroethane or methyl chloroform. In one embodiment using material 82 partially or fully comprised of poly (L-lactide) (PLLA) or any other material 82 suitable to produce fiber or fibers 78, the processing solvent is comprised of benzene. In one embodiment using material 82 comprised of poly (L-lactide) (PLLA) or any other material 82 suitable to produce fiber or fibers 78, the processing solvent is comprised of dioxane. In one embodiment using material 82 partially or fully comprised of poly (L-lactide) (PLLA) or any other material 82 suitable to produce fiber or fibers 78, the processing solvent is comprised tetrahydrofuran (THF). Poly (L-lactide) (PLLA) or any material 82 suitable for use in the present invention can be combined with one or more processing solvents or non solvents of any chemical composition at any ratio that is capable of producing a preformed configuration or a shape like a tube 74 having the specifications described herein.

In an embodiment, the one or more preformed configurations 77 or tubular precursor construct 74 are formed of a single material 82 dissolved in a single solvent. In an embodiment, the one or more preformed configurations 77 or tubular precursor construct 74 are formed of more than one material 82 dissolved in a single solvent. In an embodiment, the one or more preformed configurations 77 or tubular precursor construct 74 are formed of a single material 82 dissolved in blends of two or more solvents. In an embodiment, the one or more preformed configurations 77 or tubular precursor construct 74 are formed of blends of two or more materials 82 dissolved in blends of two or more solvents. In an embodiment, the one or more preformed configurations 77 or tubular precursor construct 74 are formed of one or more materials 82 dissolved in blends of two or more solvents. In an embodiment, the one or more preformed configurations 77 or tubular precursor construct 74 are formed of one or more materials 82 dissolved one or more faster evaporating solvents. In an embodiment, the one or more preformed configurations 77 or tubular precursor construct 74 are formed of one or more materials 82 is dissolved one or more slower evaporating solvents. In an embodiment, the one or more preformed configurations 77 or tubular precursor construct 74 are formed of one or more materials 82 dissolved one or more faster evaporating solvents. In an embodiment, the one or more preformed configurations 77 or tubular precursor construct 74 are formed of one or more materials 82 dissolved in a blend of one or more good solvents and one or more poor solvents. For example, poly-L-lactide (PLLA) is dissolved in a solvent mixture of chloroform (good solvent) and toluene (poor solvent) or a solvent mixture of chloroform (good solvent) and di-n-butyl ether (poor solvent). In an embodiment, the one or more preformed configurations 77 or tubular precursor construct 74 are formed of one or more materials 82 dissolved in a solvent having a low dielectric constant. In an embodiment, the one or more preformed configurations 77 or tubular precursor construct 74 are formed of one or more materials 82 dissolved in a mixture of one or more slower evaporating solvents and one or more faster evaporating solvents. Any material 82 and solvent combination is possible that produces a preformed configuration 77 or tubular precursor construct 74 having the specifications described herein.

The processing solvent or non solvent selection and ratios of polymer-to-solvent can be performed by those skilled in the art of solvent borne coatings or chemistry by using ladder experiments to determine optimum processing conditions and preformed configuration 77 or tubular precursor construct 74 performance. For biocompatibility and environmental reasons, partial or full recovery of processing solvents should be high importance. Steps should be taken to have zero to very low residual solvent in the material 82 comprising wall thickness 76 after manufacturing and zero to very low emissions from manufacturing processes. Without intent on limiting, vacuum dryers, ventilation systems, distillation columns, and scrubbers are effective equipment that can be employed to achieve these objectives. Solvents can be removed from the preformed configurations 77, tubular precursor construct 74, or wall thickness 76 by vacuum drying. Techniques taught in U.S. Patent Application serial no. 2009/0287300 A1 are also useful for partially or fully removing solvents from the material 82 and is incorporated herein in its entirety as a reference.

In an embodiment, the material 82 is used in combination with a super critical fluid. In an embodiment, the material 82 is used in combination with carbon dioxide as a super critical fluid. In an embodiment the material 82 is dissolved in a super critical fluid. In embodiment, the one or more materials 82 are a super critical fluid before and during formation into a preformed configurations 77 or tubular precursor construct 74. In an embodiment, the material 82 or solution 234 is at a super critical temperature upon entering, passing through, or exiting the capillary tube 223. In an embodiment, the material 82 or solution 234 is at a super critical temperature upon entering, passing through, or exiting the an extrusion die. In an embodiment, the solvent used to produce the solution 234 is extracted from the wall thickness 76 with one or more supercritical fluids.

Alignment Process

Figure 15:
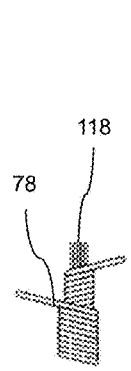
FIG. 15 is an example of another precursor construct tube positioned on a mandrel for use in producing a stent having multiple layers of preformed configurations.
Figure 16:
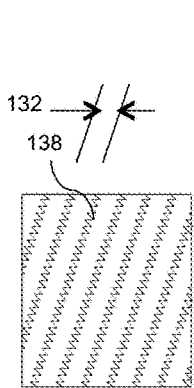
FIG. 16 is a portion of the wall thickness of a precursor construct tube for use in producing a stent having a wall thickness including bent, angled preformed configurations in the form of fibers.
Figure 17:
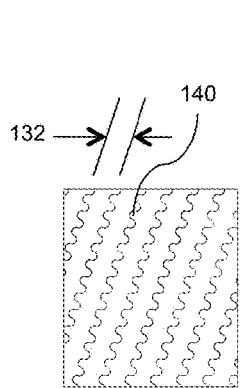
FIG. 17 is a portion of the wall thickness of a precursor construct for use in producing a stent having a wall thickness including curved, angled preformed configurations in the form of fibers.

As previously described, the one or more preformed configurations 77 are aligned in the wall thickness 76 in an engineered design that maximizes the strength of the wall thickness 76. The preformed configurations 77 are aligned in the wall thickness 76 of the precursor construct such as tube 74 in any direction that produces an endoprosthesis such as stent 40 meeting the performance requirements of the end-use applications described herein. In an embodiment, the preformed configurations 77 are aligned in the wall thickness 76 in a single direction. In an embodiment, the preformed configurations 77 are aligned in the wall thickness 76 in multiple directions. In an embodiment the preformed configurations 77 are aligned in the longitudinal direction, which is parallel to the central axis 42 of the stent 40. In an embodiment, the preformed configurations 77 are aligned in the radial direction, which is perpendicular to the central axis 42 of the stent 40. In an embodiment, the preformed configurations 77 are aligned in an angled direction, which is at any angle relative to the central axis 42. In an embodiment, the preformed configurations 77 are aligned in a non-woven pattern like the example shown in FIG. 23. In an embodiment, the preformed configurations 77 are aligned in the wall thickness 76 in an angled, radial configuration as an example is shown in FIG. 15. In an embodiment, the preformed configurations 77 are aligned in an interlaced pattern like the examples shown in FIG. 18-FIG. 22. In an embodiment the wall thickness 76 includes curved or wavy shaped preformed configurations 140 like in the example shown in FIG. 17. In an embodiment, the wall thickness 76 includes bent or zigzag preformed configurations 138 as shown in FIG. 16. The possible variations and combinations of the preformed configuration 77 alignment are virtually unlimited.

As shown in FIG. 12, the alignment angle 130 defines the position of the preformed configuration 77 relative to the central axis 42. The alignment angle of the preformed configuration 77 in the wall thickness 76 of the tube 74 is unlimited. The alignment angle 130 in one embodiment is repeated one or more times for each subsequent preformed configurations 77 positioned, deposited, interlaced, or wrapped in the wall thickness 76. The alignment angle 130 in another embodiment is repeated randomly one or more times for each subsequent preformed configuration 77 positioned, deposited, interlaced, or wrapped in the wall thickness 76. The alignment angle 130 in one embodiment is statistically repeated one or more times for each subsequent preformed configuration 77 positioned, deposited, interlaced or wrapped in the wall thickness 76. The term "alignment" refers to the angle 130 at which the preformed configuration 77 such as the fiber 78, multi-fiber 80, film 81, multi-films 79, or combinations thereof are deposited or positioned within the wall thickness 76 relative to the central axis 42. For example, a circumferential fiber 110 as shown in FIG. 11 has an alignment angle 130 of ninety degrees. The alignment angle 130 of the preformed configuration 77 can vary or be substantially the same within a single embodiment. In the present invention it is also possible to position the adjacent preformed configurations 77 within the wall thickness 76 so that there is a space 132 between the preformed configurations 77 as they are laid down in the wall thickness 76 as an example is shown in FIG. 11. In the present invention it is possible to position the adjacent preformed configurations 77 within the wall thickness 76 so that there is substantially no space 132 between the preformed configurations 77 as they are laid down in the wall thickness 76 as an example is shown in FIG. 10B. In an embodiment, the braided preformed configurations 77 are incorporated into the wall thickness 76 in tubular configuration. In another embodiment, the braided preformed configurations 77 are cut from the mandrel 118 to form a sheet 196 of preformed configurations 77 that are subsequently incorporated into the wall thickness 76 by wrapping the sheet 196 around a mandrel 118 with or without other sheets 196 as described elsewhere herein.

In an embodiment of the wall thickness 76 comprised of multiple layers of preformed configurations 77, the alignment of the preformed configurations 77 is substantially the same in each layer. In an embodiment of the wall thickness 76 comprised of multiple layers of preformed configurations 77, the alignment of the preformed configurations 77 is substantially different in some or all the layers. In an embodiment, one or more layers of preformed configurations 77 are aligned in a uniaxial direction. In an embodiment, one or more layers of preformed configurations 77 are aligned in a biaxial direction. In an embodiment, one or more layers of preformed configurations 77 are aligned in a multi-axial direction. In an embodiment, the wall thickness 76 that is partially or fully comprised of one or more aligned preformed configurations 77 is hot and/or cold drawn or hot and/or cold expanded one or more times as described herein.

The possible patterns and combinations of patterns in which the preformed configurations 77 are positioned in the wall thickness 76 are virtually unlimited in the present invention. The process of the present invention strategically positions the molecules of material 82 in the wall thickness 76 in a predetermined way to improve tensile strength, hoop stress, strength at break, slow crack growth resistance, ductile crack resistance, elongation at break, Young's modulus, flexural strength, flexural strain, flexural modulus, crack resistance, crush resistance, and notched impact strength. In an embodiment aligning one or more preformed configurations 77 in the wall thickness 76 coverts the individual preformed configurations from individual performing structural elements to a bulk performing structural element.

Wound

In an embodiment, the preformed configurations 77 are positioned in the wall thickness 76 partially or fully comprised of wound preformed configurations 77 using a circumferential winding process 120 as shown in FIG. 11. In an embodiment, the preformed configurations 77 are positioned in the wall thickness 76 partially or fully comprised of wound preformed configurations 77 using a helical winding process 122 as shown in FIG. 12. In an embodiment, the preformed configurations 77 are positioned in the wall thickness 76 partially or fully comprised of wound preformed configurations 77 using a polar winding process 124 as shown in FIG. 13. Referring to FIG. 11, an exemplary embodiment of a circumferential winding process 120 is shown for circumferentially winding one or more preformed configurations 77 in a tube shape. Still referring to FIG. 11, the one or more preformed configurations 77 are wound on a mandrel 118 having an outside diameter equal to the inner diameter 64 of tube 74. To produce a tube 74 as an example is illustrated in FIG. 10A, FIG. 10B, and FIG. 11, the bottom layer 112 of the one or more preformed configurations 77 are laid down on the outside surface of the mandrel 118 as the spool containing a supply of preformed configurations or other devices move in the axial direction up the central axis 42 of the mandrel 118 toward the direction of the proximal end 52 so that each preformed configuration 77 is positioned so that it is substantially directly adjacent to the preformed configuration 77 previously laid down on the mandrel 118. Upon reaching the end, the spool or other devices reverse direction by heading toward the distal end 54 or longer laying down a second layer of the preformed configurations 77 on top of the bottom layer of preformed configuration 77. The position of the second layer of preformed configuration 77 can be nested between two preformed configurations 77 underneath or directly on top of the preformed configuration 77 underneath. The process is repeated until the desired wall thickness 76 is obtained.

Another embodiment is shown in FIG. 12, wherein the preformed configurations 77 are positioned using a helical winding process 122. In an embodiment the wall thickness 76 is comprised of one or more angled preformed configurations 134. The position of the angled preformed configurations 134 ranges from zero to three hundred sixty degrees from the central axis 42 of the tube 74. In an embodiment the angle 130 of some or all the preformed configurations 77 substantially matches the angle of the struts 44,46. In an embodiment, the preformed configurations 77 cross over each other forming a node 142, which is a double thickness or intersection of preformed configurations 77.

As shown in FIG. 13, in another embodiment a polar winding process 124 positions the one or more preformed configurations 77 in the wall thickness 76. By utilizing a polar winding technique the one or more preformed configurations are laid down on the mandrel 118 at any angle 130 relative to the central axis 42.

Inter-Laced (Braided)

In an embodiment, as shown in FIG. 14, one or more preformed configurations 77 such as fibers 78, multi-fibers 80, film 81, multi-film 79 or combinations thereof are laid down on a mandrel 118 to partially or fully form the wall thickness 76 of tube 74. The term "braid" refers to interweaving multiple preformed configurations 77 into one or more layers of a wall thickness 76. A tubular braid is formed by crossing a number of preformed configurations 77 in such a way that single or multiple preformed configurations 77 pass alternatively over and under preformed configurations 77 laid up in the opposite direction. Without intent on limiting, a braid configuration suitable for use in the present invention can be selected from the group of: (1) one fiber traveling over one fiber (herringbone pattern); (2) one fiber traveling over two fibers; (3) two fibers traveling in parallel over two fibers, under two fibers (diamond pattern); (4) one fiber under two fibers, over two fibers; (5) two fibers under two fibers, over two fibers; (6) regular (twill); (7) Hercules (panama); (8) 1/1 plain; (9) 2/2 twill; (10) 3/3 twill/2/1; (11) 3/1; (12) three dimensional; (13) 2-diagonal; (14) 3-diagonal; (15) 4-diagonal; (16) round; (17) spiral; or (18) any suitable braid pattern or interlacements known by those skilled in the art of braiding tubes. For example, the preformed configurations 77 feeding the braiding machine may be material 82 of the same chemical composition, of different chemical composition, same thickness, different thickness, material of different molecular weights, or material of same molecular weight, or any other combination described herein.

Referring to FIG. 18, which illustrates a side view of tube 74 having a braided wall thickness 76. The preformed configurations 77 are interlaced so that they are oriented having a braid angle 130 in relation to the central axis 42. The braid angle 130 of the tube 74 used to fabricate one or more layers of the wall thickness 76 can range from zero to three hundred sixty degrees from the central axis 42 wherein an angle of zero degrees has lower radial strength and an angle of ninety degrees has higher radial strength.

Figure 20:
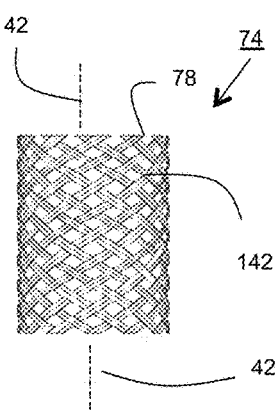

As shown in FIG. 18, in an embodiment of the wall thickness 76 including at least one layer of the braided tube 74 the preformed configurations 77 are closely packed together so that the surface of each preformed configuration 77 is at least partially touching the surface of the adjacent preformed configuration 77. In other embodiments of the wall thickness 76 there are one or more spaces 132 of any distance between the braided preformed configurations 77 as examples are shown in FIG. 19 and FIG. 20. As known by those skilled in the art, the density of the braid can be low or high by changing the tension of the preformed configurations 77 or by changing the take-up rate of the braiding machine. For example, slow take-up rate produces a close braid with tight plait spacing while rapid take-up creates a loose braid with more open plait spacing.

Figure 21:
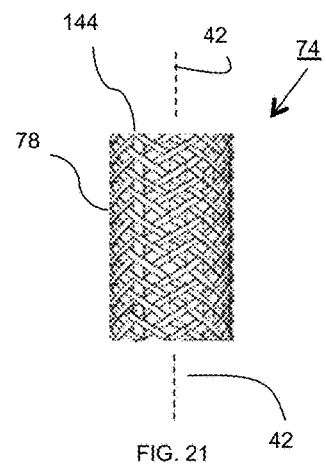
FIG. 21 and FIG. 22 are portions of the wall thickness of a precursor construct tube for use in producing a stent having a wall thickness of braided preformed configurations in the form of fibers including malleable wires.

In one more embodiment of a wall thickness 76 including one or more layers of braided preformed configurations 77, the braids may include one or more additional strands called warp threads 144. As shown in FIG. 21 the warp threads 144 can be utilized to improve dimensional stability, compressive strength, crimpability, foreshortening, or expandability. The warp threads 144 lie in any position in the wall thickness 76 such as parallel, perpendicular, or at an angle to the central axis 42. In an embodiment, the warp threads 144 are interwoven with the diagonal tubular braid strands like what is shown in FIG. 21 and FIG. 22.

As shown in FIG. 14, a braiding machine is fundamentally comprised of a collecting mandrel 118 and a plurality of bobbins 126 that store and feed preformed configurations 77 in an interlaced configuration to the mandrel 118. There are many industrial machines suitable for braiding the tube 74 of the present invention. The machines can be set up vertically or horizontally. In some embodiments, the machine can handle up to 800 spools or bobbins 126. In other embodiment, the machine can handle greater than 800 spools or bobbins 126. One example of a suitable machine is a Maypole braider. Braiding machine suitable for manufacturing the present invention are available from Herzog (Oldenberg, Germany), Steeger USA (Inman, S.C., USA), ETK-Lesmo (Italy), Hsiang Chuan (Taiwan), Penguin Engineers (India), O.M.A. (Italy), OMR, Ratera (Spain), Intertex (Korea), and Trenz-Exports (Santpedor, Spain). Lamb Knitting Machine Corporation (USA) produces suitable knitting machinery.

Nonwoven

Although the process is not illustrated, another embodiment of the wall thickness 76 is comprised of one or more layers of nonwoven preformed configurations 77. The term "nonwoven" refers to a wall thickness 76 comprised of a plurality of preformed configurations 77 bonded together by chemical, mechanical, heat, or solvent treatment. This includes the form known as flash spun. The term "flash spun" refers to a wall thickness 76 formed from the fine fibrillation of a film by the rapid evaporation of solvent and subsequent bonding during extrusion. An exemplary nonwoven wall thickness 76 is illustrated in FIG. 23.

In an embodiment the wall thickness 76 is comprised of one or more layers 106, 017 of a plurality of preformed configurations 77 oriented in a somewhat random or organized fashion around the circumference of the tube 74 from the proximal end to the distal end. The preformed configurations 77 are of uniform or differing lengths, cross section, or shape. Without intent on limiting, the nonwoven process of the present invention is selected from the group of: (1) spun bonding processes; (2) spun melt lay-down processes; (3) wet lay processes; (4) air-laid processes; (5) thermal bonding processes; (6) jet entangled processes; (7) water-entangled processes; (8) solvent-entangled processes; (9) spun lacing processes; (10) carding processes; (11) calendaring processes; (12) aerodynamic processes; (13) electrospinning; (14) dry laid processes; or (15) any processes known in the art that generally produces a fabric-like sheet, tube, or web material made from fibers of indefinite length bonded together by chemical, thermal, adhesive, mechanical, or solvent treatment.

Forming Network

In an embodiment the preformed configurations 77 are transformed into a network by partially or fully interconnecting the preformed configurations 76 in the wall thickness 76. In an embodiment, the network of preformed configurations 77 undergoes a transformation from disconnected or loosely connected objects to partially or fully connected objects that produce a wall thickness 76 having demonstrable changes in its mechanical properties. For example, in an embodiment the wall thickness 76 is transformed from a more flexible to a less flexible wall thickness 76. In an embodiment, the precursor construct tube 74 is transformed from having lower crush resistance to higher crush resistance. In an embodiment, the wall thickness 76 is transformed from being more ductile to less ductile. In an embodiment, the wall thickness 76 is transformed form having a lower Young's modulus of elasticity to a higher Young's modulus of elasticity. In an embodiment, the wall thickness 76 is transformed from having a higher surface area to a lower surface area. In an embodiment, the wall thickness 76 is transformed from having a lower tensile strength to a higher tensile strength. In an embodiment, the wall thickness 76 is transformed from having a faster degradation rate to a slower degradation rate or from a slower degradation rate to a faster degradation rate in anatomical conditions. In an embodiment the wall thickness 76 is transformed from having a poorer crack resistance to a superior crack resistance.

In an embodiment of the wall thickness 76, the one or more preformed configurations 77 are fully disconnected from each other in the wall thickness 76. In an embodiment of the wall thickness 76, the one or more preformed configurations 77 are partially connected to one another in the wall thickness 76. In one more embodiment of the wall thickness 76, the one or more preformed configurations 77 are fully connected to one another in the wall thickness 76. In an embodiment the preformed configurations 77 are partially or fully connected at crossover points or nodes 142. In an embodiment, the preformed configurations 77 are partially or fully connected at the outer surfaces 96, 104, 105, 117; short edges 123, 139; long edges 121, 141; or between any combinations described herein.

In an embodiment of the wall thickness 76, the one or more fibers 78 are fully disconnected from each other in the wall thickness 76. In an embodiment of the wall thickness 76, the one or more fibers 78 are partially connected to one another in the wall thickness 76. In one more embodiment of the wall thickness 76, the one or more fibers 78 are fully connected to one another in the wall thickness 76. In an embodiment of the wall thickness 76, the one or more films 81 are fully disconnected from each other in the wall thickness 76. In an embodiment of the wall thickness 76, the one or more films 81 are partially connected to one another in the wall thickness 76. In one more embodiment of the wall thickness 76, the one or more films 81 are fully connected to one another in the wall thickness 76. In an embodiment of the wall thickness 76, the one or more fibers 78 and films 81 are fully disconnected from each other in the wall thickness 76. In an embodiment of the wall thickness 76, the one or more fibers 78 and films 81 are partially connected to one another in the wall thickness 76. In one more embodiment of the wall thickness 76, the one or more fibers 78 and films 78 are fully connected to one another in the wall thickness 76. In an embodiment, the wall thickness 76 that is partially or fully comprised of a network of one or more preformed configurations 77 is hot and/or cold drawn or hot and/or cold expanded one or more times as described herein.

In an embodiment of the wall thickness 76, the one or more sheets 196 are fully disconnected from each other in the wall thickness 76. In an embodiment of the wall thickness 76, the one or more sheets 196 are partially connected to one another in the wall thickness 76. In one more embodiment of the wall thickness 76, the one or more sheets 196 are fully connected to one another in the wall thickness 76. In an embodiment, the sheets 196 are partially or fully connected at crossover points. In an embodiment the sheets 196 are partially or fully connected at outer surfaces 221, 227; seams 125; short edges 201, 229; long edges 199, 231; between layers 237, or between any combinations of objects described herein.

In an embodiment of the wall thickness 76, the one or more layers 106, 107, 237 are fully disconnected from each other in the wall thickness 76. In an embodiment of the wall thickness 76, the one or more layers 106, 107, 237 are partially connected to one another in the wall thickness 76. In one more embodiment of the wall thickness 76, the one or more layers 106, 107, 237 are fully connected to one another in the wall thickness 76.

In an embodiment of the wall thickness 76, the one or more preformed configurations 77, sheets 196, films 81, fibers 78, or combinations thereof are partially or fully connected by heating and then cooling the wall thickness 76. In an embodiment of the wall thickness 76, the one or more preformed configurations 77, sheets 196, films 81, fibers, or combinations thereof are partially or fully connected by heating the wall thickness 76 to a temperature in the range of about the glass transition temperature (Tg) of the material 82 and the melting temperature (Tm) of the material 82 and then cooling. In an embodiment of the wall thickness 76, the one or more preformed configurations 77, sheets 196, films 81, fibers 78, or combinations thereof are partially or fully connected by heating the wall thickness 76 to a temperature in the range of about the crystallization temperature (Tc) of the material 82 and then cooling. In an embodiment of the wall thickness 76, the one or more preformed configurations 77, sheets 196, films 81, fibers 78, or combinations thereof are partially or fully connected by heating the wall thickness 76 to a temperature at or below about the glass transition temperature (Tg) of the material 82 and then cooling if necessary. In an embodiment of the wall thickness 76, the one or more preformed configurations 77, sheets 196, films 81, fibers 78, or combinations thereof are partially or fully connected by heating the wall thickness 76 to a temperature at or above about the melting temperature (Tm) of the material 82 and then cooling. In an embodiment, the preformed configurations 77, sheets 196, film 81, fiber 78, or any combinations thereof are partially or fully connected by heating and quenching the wall thickness 76. In an embodiment, the preformed configurations 77, sheets 196, film 81, fiber 78, or any combinations thereof are partially or fully connected by heating and quenching the wall thickness 76 followed by one or more operations wherein the wall thickness 76 is reheated and re-cooled one or more times. In an embodiment, the preformed configurations 77, sheets 196, film 81, fiber 78, or any combinations thereof are partially or fully connected by heating and quenching the wall thickness 76 followed by one or more operations wherein the wall thickness 76 is reheated and re-cooled one or more times to anneal the wall thickness 76. In an embodiment, the preformed configurations 77, sheets 196, film 81, fiber 78, or any combinations thereof are partially or fully connected by heating and quenching the wall thickness 76 followed by one or more operations wherein the wall thickness 76 is reheated and re-cooled one or more times to increase the crystallinity of the wall thickness 76. The term "quenching" refers to rapidly cooling.

Figure 106:
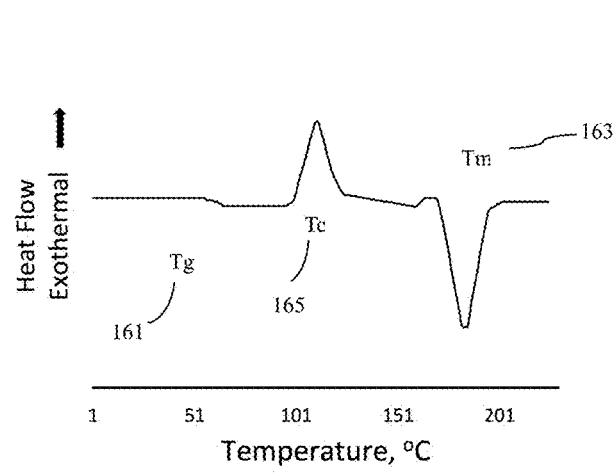
FIG. 106 is an exemplary DSC thermogram.

In a preferred embodiment, after arranging the one or more preformed configurations 77 partially or fully comprised of poly-L-lactide (PLLA) in the wall thickness 76 or sheets 196 as described herein, the preformed configurations 77 are partially or fully interconnected by heating the wall thickness 76 to a temperature in the range of about between the glass transition temperature (Tg) of the material 82 and the melting point (Tm) of the material 82, more narrowly between about 125 degrees Celsius to 195 degrees Celsius. In an embodiment, the wall thickness 76 is heated to a temperature at or above the melting temperature of poly-L-lactide (PLLA), more narrowly at or above 165 degrees Celsius. In an embodiment, the wall thickness 76 is heated a temperature at or below the glass transition temperature (Tg) of Poly-L-lactide (PLLA), more narrowly at or at or below 125 degrees Celsius. The glass transition temperature (Tg), crystallization temperature (Tc), and melting temperature (Tm) can be experimentally determined and obtained by those skill in the are of Differential Scanning calorimetry (DSC) which produces a thermograph 169 as an example is shown in FIG. 106. Referring to the thermograph shown in FIG. 106, the Tg is identified as 161, the Tc is identified as 165, and the Tm is identified as 163.

In an embodiment of the wall thickness 76, the one or more preformed configurations 77, sheets 196, films 81, fibers 78, layers, or combinations thereof are partially or fully connected by compressing the wall thickness 76. In an embodiment of the wall thickness 76, the one or more preformed configurations 77, sheets 196, films 81, fibers 78, layers, or combinations thereof are partially or fully connected by compressing the wall thickness 76 at a pressure in the range of about 0.15 MPa and 10.00 MPa. In an embodiment of the wall thickness 76, the one or more preformed configurations 77, sheets 196, films 81, fibers 78, layers, or combinations thereof are partially or fully connected by compressing the wall thickness 76 at or below about 0.15 MPa. In an embodiment of the wall thickness 76, the one or more preformed configurations 77, sheets 196, films 81, fibers 78, layers, or combinations thereof are partially or fully connected by compressing the wall thickness 76 to a pressure at or above about 10 MPa.

In a preferred embodiment of the wall thickness 76, the one or more preformed configurations 77, sheets 196, films 81, fibers 78, layers, or combinations thereof are partially or fully connected by compressing the wall thickness 76 at a compression ratio in the range of about 1.25 to 14, more narrowly 1.25 to 10. In an embodiment of the wall thickness 76, the one or more preformed configurations 77, sheets 196, films 81, fibers 78, layers, or combinations thereof are partially or fully connected by compressing the wall thickness 76 at a compression ratio at or below about 1.25. In an embodiment of the wall thickness 76, the one or more preformed configurations 77, sheets 196, films 81, fibers 78, layers, or combinations thereof are partially or fully connected by compressing the wall thickness 76 at a compression ratio at or at or above about 14. The compression ratio is calculated by the formula: Compression ratio=wall thickness before compression divided by the wall thickness after compression. Since in some embodiments the wall thickness 76 includes void space 84, the inventors used calipers to lightly compress the wall thickness 76 when measuring the starting thickness. In an embodiment, the length and/or width of the wall thickness increases in size after compression.

In an embodiment, the one or more preformed configurations 77 such as fibers 78, sheets 196, films 81, layers, or combinations thereof are partially or fully melted and interconnected after cooling. In an embodiment, the one or more preformed configurations 77 such as fibers 78, sheets 196, films 81, layers, or combinations thereof are at least partially softened by heating and interconnected after cooling. In an embodiment, the one or more preformed configurations 77 such as fibers 78, sheets 196, films 81, layers, or combinations thereof are heated without melting the material 82 and interconnected after cooling. In an embodiment, the one or more preformed configurations 77 such as fibers 78, sheets 196, films 81, layers, or combinations thereof are heated, entangled, and interconnected after cooling. In an embodiment, the molecules forming the one or more preformed configurations 77 such as fibers 78, sheets 196, films 81, layers, or combinations thereof are heated, entangled and interconnected after cooling. In an embodiment, the one or more preformed configurations 77 such as fibers 78, sheets 196, films 81, layers, or combinations thereof are heated without melting the material 82, pressed together, and held together so that interfacial bonding occurs between the preformed configurations 77, fibers 78, films 81, sheets 196, layers, or combinations thereof after cooling. In an embodiment, the one or more preformed configurations 77 such as fibers 78, sheets 196, films 81, layers, or combinations thereof comprised of materials 82 of more than one melting temperature are heated and interconnected after cooling. In an embodiment, the one or more preformed configurations 77 such as fibers 78, sheets 196, films 81, layers, or combinations thereof that are separated by one or more binding materials 108 are compressed and interconnected. In an embodiment, the wall thickness 76 comprised of one or more preformed configurations 77 such as fibers 78, sheets 196, films 81, layers, or combinations thereof has a white or opaque appearance until the preformed configurations are compressed while heated to form a substantially translucent film after cooling.

In an embodiment, the porous wall thickness 76 comprised of one or more preformed configurations 77 such as fibers 78, sheets 196, films 81, layers, or combinations thereof has a white or opaque appearance until the preformed configurations are compressed while heated to form a substantially translucent film after cooling.

In an embodiment, the physical features of the preformed configurations 77 are substantially retained in the bulk wall thickness 76 after heating, compressing, and cooling. In an embodiment, the physical features of the preformed configurations 77 are partially retained in the bulk wall thickness 76 after heating, compressing, and cooling. In an embodiment, the physical features of the preformed configurations 77 are substantially or fully lost in the bulk wall thickness 76 after heating, compressing, and cooling. The term "bulk" wall thickness refers to the area between the outer surface 70 and the inner surface 72 of the wall thickness 76. As an example, if the wall thickness 76 is comprised of compressed fibers 78, these fibers 78 should be somewhat recognizable by visual examination with or without the aid of magnification if their physical features are at least partially retained. If the physical features were substantially lost, then no parts of the fibers would be recognizable by visual examination with or without the aid of magnification.

In an embodiment, after arranging the one or more preformed configurations 77 in the wall thickness 76 wherein layers of one or more preformed configurations 77 comprised of material 82 having a higher melting temperature are separated by layers of film 81 having a lower melting temperature, the layers of preformed configurations 77 are partially or fully interconnected by heating the wall thickness 76 to a temperature in which the layers of film 81 partially or fully adhere the layers of preformed configurations 77 upon cooling. In an embodiment, after arranging the one or more preformed configurations 77 in the wall thickness 76 wherein layers of preformed configurations 77 comprised of material 82 having a lower melting temperature are separated by layers of film 81 having a higher melting temperature, the layers of film 81 are partially or fully interconnected by heating the wall thickness 76 to a temperature in which the layers of preformed configurations 77 partially or fully adhere the layers of film 81 upon cooling. In an embodiment, after arranging the multiple layers of preformed configurations 77 in the wall thickness 76 wherein some layers of preformed configurations 77 are comprised of material 82 having a higher melting temperature are separated by layers of preformed configurations 77 comprised of material 82 having a lower melting temperature, the layers of preformed configurations 77 are partially or fully interconnected by heating the wall thickness 76 to a temperature in which the preformed configurations 77 comprised of a lower melting temperature material 82 adhere the layers of preformed configurations 77 comprised of material 82 having a higher melting temperature upon cooling. In an embodiment, after arranging the multiple layers of film 81 in the wall thickness 76 wherein some layers of film 81 are comprised of material 82 having a higher melting temperature are separated by layers of film 81 comprised of material 82 having a lower melting temperature, the layers of film 81 are partially or fully interconnected by heating the wall thickness 76 to a temperature in which the film 81 comprised of a lower melting temperature material 82 adhere the layers of film 81 comprised of material 82 having a higher melting temperature upon cooling.

For example, two or more layers comprised of poly (L-Lactide) which has a higher melting temperature of about 185-195 degrees Celsius can be partially or fully connected or bonded together by positioning one or more layers of a material 82 having a lower melting temperature between the layers of poly (L-lactide) and heating the composite wall thickness 76. One or more materials 82 selected from the following group are suitable for connecting layers of Poly (L-lactide) by heating a composite wall thickness: copolymers of L-Lactide and Glycolide (PURASORB PLG 8523 or 8531) having a lower melting temperature of 140-150 degree Celsius, copolymers of L-Lactide and DL-Lactide (PURASORB PLDL 7028, 7038, 7060) having a lower melting temperature of about 115-125 degrees Celsius, copolymers of L-Lactide and DL-Lactide (PURASORB 8038 or 8085) having a lower melting temperature of about 125-134 degrees Celsius, copolymers of L-Lactide and D-Lactide (PURASORB 9655) having a lower melting temperature of about 155-165 degrees Celsius, copolymers L-Lactide and α-caprolactone (PURASORB 7015) having a lower melting temperature of about 110-120 degrees Celsius, or other materials 82 having lower melting temperatures than Poly-L-Lactide so that the layers of Poly-L-Lactide are connected together. Conversely, one or more layers comprised of poly (L-Lactide) having a lower melting temperature of about 185-195 degree Celsius can connect or bond together one or more layers of materials 82 having a higher melting temperature such as poly (Glycolide) (PURASORB PG20) having a higher melting temperature of about 220-230 degrees Celsius or copolymers of L-Lactide and Glycolide (PURASORB 1017) having a melting temperature of about 200-210 degrees Celsius.

The optimum cohesive interconnectivity of the preformed configurations 77 to form a network within the wall thickness 76 can be fine-tuned or optimized by those skilled in the art of processing materials 82 such as polymers to achieve the mechanical properties required for the various end-use applications described herein. Governing factors that affect mechanical properties of the wall thickness 76 are the preformed configurations 77 network, preformed configuration 77 curvature, intrinsic preformed configuration 77 properties, preformed configuration 77 geometry, material 82 crystallinity, material 82 amorphicity, porosity of the wall thickness 76, and preformed configuration 77-to-preformed configurations 77 junctions.

In an embodiment, the wall thickness 76 comprised of one or more preformed configurations 77 includes preformed configurations 77 that are partially or fully connected together or partially or fully encapsulated with one or more binders 108 such as, for example, a coating, adhesive, prepeg, resin, polymer, biodegradable polymer, fast evaporating solvent, slow evaporating solvent, adhesion promoter, bioresorbable polymer, bioabsorbable polymer, biological material, natural material, synthetic material, protein, collagen, or combination thereof. The binder 108 can be located on the outer surface 70; inner surface 72; between multiple layers 106, 107; in voids 84; between adjacent preformed configurations; between sheets 196, or combinations thereof. In one embodiment the binder 108 has an amorphous structure, in another embodiment the binder 108 has a crystalline structure, in one more embodiment the binder 108 has a semi crystalline structure, and in other embodiments the binder 108 has an amorphous and crystalline structure. Including a crystalline binder in the present invention can improve the stent's 40 rigidity or stiffness and including an amorphous binder can improve the stent's flexibility and crack resistance. The binder 108 forms a strong wall thickness 76 matrix in conjunction with the preformed configurations 77.

In other embodiments the preformed configurations 77 are connected together using a fusion, thermal weld, solvent weld, ultrasonic weld, friction weld, or weld.

The preformed configuration 77 can be single continuous lengths chopped into two or more lengths. Employing preformed configurations 77 of differing melting temperatures can be useful in bonding preformed configurations 77 at crossover points. Moreover, since molecular orientation of the material 82 can increase the melting point of the preformed configurations 77, the preformed configurations 77 that are not highly drawn can be employed as thermal binding preformed configurations 77. Without intent on limiting, method for bonding the preformed configurations 77 together can be selected from the group of: mechanical needling; thermal bonding; through-air thermal bonding; calendaring; hot calendaring; belt calendaring; embossing; use of one or more binders 108; ultrasonic bonding; radiant heat bonding; pressure bonding; hydraulic entanglement; solvent bonding; adhesive; and chemical bonding.

In an embodiment of the wall thickness 76, the one or more preformed configurations 77 such as fibers 78, sheets 196, films 81, layers, or combinations thereof are partially or fully connected by compressing, heating, and cooling the wall thickness 76 at any combination of the conditions specified herein.

Fabricating Shaped Wall Thickness

In an embodiment, extruding, casting, or molding a wall thickness 76 using melt processing or solution processing forms the wall thickness 76 of the tubular precursor construct 74. In another embodiment, the wall thickness 76 of the tubular precursor tube 74 is formed as shown in FIG. 84-FIG. 88. In an embodiment, the tube 74 is formed by wrapping one or more sheets 196 of one or more thicknesses 93 around a mandrel 118 having low dimensional variation to form a tube 74. In an embodiment, the tube 74 is formed by wrapping one or more sheets 196 around a mandrel 118 having low dimensional variation, heating the sheets 196 to partially or fully interconnect the sheets 196 while the sheets 196 are wrapped around the mandrel 118, cooling the sheets 196 while the sheets 196 are wrapped around the mandrel 118, and removing the tube 74 from the mandrel 118. In some embodiments, the tube 74 is partially or fully cooled on the mandrel 118 or alternatively as the tube 74 slides off the mandrel 118 during removal. If the tube is not substantially cooled to room temperature before removal from the mandrel 118, the tube 74 should be quickly cooled as it slides off the mandrel 118 to obtain tube 74 having low dimensional variation. In an embodiment, the tube 74 is formed by wrapping one or more sheets 196 around a mandrel 118 having low dimensional variation, heating the sheets 196 while the sheets 196 are wrapped around and compressed on the mandrel 118 to partially or fully consolidate the wall thickness 76, cooling the sheets 196 while the sheets are partially or fully wrapped around and compressed on the mandrel, and removing the tube 74 from the mandrel 118. In an embodiment, the tube 74 is formed by wrapping one or more sheets 196 around a mandrel 118 having low dimensional variation, heating and compressing the sheets 196 while the sheets 196 are wrapped around the mandrel 118 to partially or fully consolidate the wall thickness 76 and conform the wall thickness 76 to the mandrel 118 so that the inner diameter 64 has low dimensional variation, modifying the outer diameter 62 so that it has low dimensional variation, cooling the sheets 196 while the sheets are partially or fully wrapped around and compressed on the mandrel 118, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118, cooling the sheets 196 while the sheets 196 are partially or fully wrapped around the mandrel 118, and removing the tube 74 from the mandrel 118 when the mandrel 118 includes one or more materials positioned between the outside of the mandrel 118 and the inner diameter of the tube 74 that facilitates removal of the tube 74 from the mandrel 118. Without intent on limiting, materials that can facilitate removal of the tube 74 from the mandrel include: mold release agents, polytetrafluoroethylene (PTFE), silicone, oils, vegetable oils, vegetable shortening (e.g. CRISCO, available from Pillsbury Best, USA), hydrogenated vegetable oils, lubricants, non-stick surfaces, lubricious coatings, polished surfaces, coatings, coatings comprised of water-soluble polymers, sacrificial coatings, temporary coverings, or any other materials that facilitate removal. In an embodiment, the tube 74 is formed by wrapping one or more sheets 196 around a mandrel 118 having low dimensional variation, heating the sheets 196 while the sheets 196 are wrapped around the mandrel 118 and in a partially or fully inert environment like under nitrogen blanket, cooling the sheets 196 while they are partially or fully wrapped around the mandrel 118 and partially or fully under said inert environment, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 and in a negative pressure (vacuum) environment, cooling the sheets 196 while the sheets 196 are partially or fully wrapped around the mandrel 118 and partially or fully under said negative pressure (vacuum) environment, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 and in a oxygen-free or oxygen-reduced environment, cooling the sheets 196 while partially or fully wrapped around the mandrel 118 and in said oxygen-free or oxygen-reduced environment, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 and in a moisture-free or moisture-reduced environment, cooling the sheets while the sheets are partially or fully wrapped around the mandrel 118 in moisture-free or moisture-reduced environment, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 until the molecules comprising the material 82 partially or fully contract so that the tube 74 has an inner diameter 64 closely matching the outer diameter of the mandrel 118, cooling the sheets 196 while partially or fully wrapped around the mandrel, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 until the molecules comprising the material 82 partially or fully fold so that the tube 74 has an inner diameter 64 closely matching the outer diameter of the mandrel 118, cooling the sheets 196 while partially or fully wrapped around the mandrel 118, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 and at a temperature between about the glass transition temperature of the material 82 and about the melting temperature of the material 82, cooling the sheets 196 while they are partially or fully wrapped around the mandrel 118, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 and at a temperature at or below about the glass transition temperature of the material 82, cooling the sheets while partially or fully wrapped around the mandrel 118, and removing the tube 74 from the mandrel 118. In an embodiment, the tube 74 is formed by wrapping one or more sheets 196 around a mandrel 118 having low dimensional variation, heating the sheets 196 while the sheets 196 are wrapped around the mandrel 118 and at a temperature at or above about the melting temperature of the material 82, cooling the sheets 196 while partially or fully on the mandrel, and removing the tube 74 from the mandrel 118. In an embodiment, the tube 74 is formed by wrapping one or more sheets 196 around a mandrel 118 having low dimensional variation that is pre-heated or pre-cooled to a temperature at or below about the glass transition temperature of the material 82, heating the sheets 196 while the sheets 196 are wrapped around the mandrel 118, cooling the sheets while the sheets are partially or fully wrapped around the mandrel 118, and removing the tube 74 from the mandrel 74. In an embodiment, the tube 74 is formed by wrapping one or more sheets 196 around a mandrel 118 having low dimensional variation that is pre-heated to a temperature between about the glass transition temperature of the material 82 and about the melting temperature of the material 82, heating the sheets 196 while the sheets 196 are wrapped around the mandrel 118, cooling the sheets 196 while the sheets are partially or fully wrapped around the mandrel 118, and removing the tube 74 from the mandrel 74. In an embodiment, the tube 74 is formed by wrapping one or more sheets 196 around a mandrel 118 having low dimensional variation that is pre-heated to a temperature at or above about the melting temperature of the material 82, heating the sheets 196 while the sheets 196 are wrapped around the mandrel 118, cooling the sheets 196 while the sheets 196 are partially or fully wrapped around the mandrel 118, and removing the tube 74 from the mandrel 118.

Figure 87:
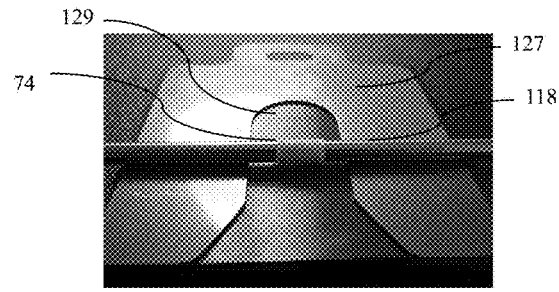
FIG. 87 is a photograph of a process of sizing the wall thickness of a precursor construct tube by rolling the heated tube over a flat plate and shim in a way that the wall thickness is formed into the proper thickness by compressing the wall thickness in the gap formed between the shim top surface and the top surface of the flat plate.

In an embodiment, the tube 74 is formed by wrapping the one or more sheets 196 around a cylindrical-shaped mandrel 118 having low dimensional variation, heating the sheets 196 to the temperature conditions described herein, rolling the heated sheets 196 while still positioned on the mandrel 118 to size the wall thickness 76 using processes like or similar to those examples shown in FIG. 81, FIG. 87, or FIG. 101, quenching the tube 74 in cold water or other cooling means while the tube 74 is still positioned on the mandrel 118, reheating the tube 74 while it is still positioned on the mandrel 118 at the temperature conditions described herein to increase the crystalline portion of the material 82, and removing the tube 74 from the mandrel 118 by sliding the tube 118 off the mandrel 118 into cold water or other cooling means so that at least the outer diameter 62 and inner diameter 64 of the tube 74 are substantially retained as the tube 74 partially or fully exits the mandrel 118 and enters the cold water or other cooling means. In an embodiment, the tube 74 is formed by wrapping the one or more sheets 196 partially or fully comprised of Poly-L-Lactide (PLLA) around a cylindrical-shaped mandrel 118 having low dimensional variation, heating the sheets 196 to a temperature at or above the glass transition temperature of the material 82 (preferably between 150-250 degrees Celsius) for any period of time (more narrowly less than 25 minutes), rolling the heated sheets 196 while still positioned on the mandrel 118 to size the wall thickness 76 using processes like or similar to those examples shown in FIG. 81, FIG. 87, or FIG. 101 wherein the temperature of the roller 241 or flat plate 129 contacting the outer surface 70 of the tube 74 is a any hot or cold temperature (preferably at or above the glass transition temperature of the material 82 and more preferably between about 15-65 degrees Celsius), quenching the tube 74 in cold water or other cooling means at a temperature at or below the glass transition temperature of the material 82 (more narrowly at or below about 23 degrees Celsius) while the tube 74 is still positioned on the cylindrical-shaped mandrel 118, reheating the tube 74 at temperature at or above about 80 degrees Celsius (more narrowly between about 80-160 degrees Celsius) while it is still positioned on the cylindrical shaped mandrel 118 for any period of time (more narrowly between 30 seconds and 10 minutes) to increase the crystalline portion of the material 82, and removing the tube 74 from the mandrel 118 by sliding the tube 74 off the mandrel 118 into cold water or other cooling means at a temperature at or below the glass transition temperature of the material 82 (more narrowly at or below 23 degrees Celsius) so that at least the outer diameter 62 and inner diameter 64 of the tube 74 are substantially retained as the tube 74 partially or fully exits the mandrel 118 and enters the cold water or other cooling means. In an embodiment, the tube 74 is formed by wrapping the one or more sheets 196 partially or fully comprised of Poly-L-Lactide (PLLA) around a cylindrical-shaped mandrel 118 having low dimensional variation, heating the sheets 196 to a temperature at or above the glass transition temperature of the material 82 (preferably between 150-250 degrees Celsius) for any period of time (more narrowly less than 25 minutes), rolling the heated sheets 196 while the sheets 196 are still positioned on the mandrel 118 to size the wall thickness 76 using processes like or similar to those examples shown in FIG. 81, FIG. 87, or FIG. 101 wherein the temperature of the roller 241 or flat plate 129 contacting the outer surface 70 of the tube 74 is a any temperature (preferably at or above the glass transition temperature of the material 82 and more preferably between about 15-65 degrees Celsius), quenching the tube 74 in cold water or other cooling means at a temperature at or below the glass transition temperature of the material 82 (more narrowly at or below about 23 degrees Celsius) while the tube 74 is still positioned on the cylindrical-shaped mandrel 118, reheating the tube 74 at temperature at or above about 80 degrees Celsius (more narrowly between about 80-160 degrees Celsius) while it is still positioned on the cylindrical shaped mandrel 118 for any period of time (more narrowly between 30 seconds and 10 minutes) to increase the crystalline portion of the material 82, and removing the tube 74 from the mandrel 118 by twisting and sliding the tube 74 off the mandrel 118 into cold water or other cooling means at a temperature at or below the glass transition temperature of the material 82 (more narrowly at or below 23 degrees Celsius) so that at least the outer diameter 62 and inner diameter 64 of the tube 74 are substantially retained as the tube 74 partially or fully exits the mandrel 118 and enters the cold water or other cooling means. Twisting the heated tube 74 one or more times at one or more locations along the length 128 of the tube 74 while still positioned on the cylindrical-shaped mandrel 118 induces at least some strain hardening on the material 82 comprising the wall thickness 76 because only part of the tube 74 rotates on the mandrel at a time due to the friction between the inner surface 72 of the tube 74 and the outer surface of the mandrel 118 which imparts stress on the wall thickness 76. In an embodiment, the tube 74 is twisted one or more times in the range of about 0-45 degrees around the central axis 42 of the tube 74. In other embodiments, the tube is twisted more than about 45 degrees around the central axis of the tube 74. The water used for quenching the tube 74 can be substituted by any cool liquid or gas that is at a temperature at or below the glass transition temperature of the material 82 comprising the wall thickness 76. In other embodiments, the tube 74 is not reheated to produce a wall thickness 76 comprised of less crystalline material 82. In other embodiments, the tube 74 is rolled over a heated plate 129 as shown in FIG. 81, FIG. 87, or FIG. 101 or other sizing means as described herein at a temperature at or below about the glass transition temperature of the material 82 so that the wall thickness 76 and the outer diameter 62 are roughly sized by partially or fully reducing the void space 84 in the wall thickness 76 prior to heating the tube 74 at temperatures at or above the glass transition temperature of the material 82.

Referring to FIG. 84, FIG. 85, FIG. 86, FIG. 87, and FIG. 88, in an embodiment the tubular wall thickness 76 is formed by positioning and/or compressing one or more sheets 196 around a mandrel 118 having low dimensional variation, heating the sheets 196 while the sheets 196 are positioned and/or compressed on the mandrel 118, cooling the sheets 196 while partially or fully positioned and/or compressed on the mandrel 118, and removing the tubular wall thickness 76 from the mandrel 118, wherein one or more of said sheets 196 are comprised of a material 82 having a higher melting temperature and one or more sheets 196 are comprised of a material 82 having a lower melting temperature. In an embodiment, the tubular wall thickness 76 is formed by positioning and/or compressing one or more sheets 196 comprised of one or more fibers 78, films 81, or combinations thereof on a mandrel 118 having low dimensional variation, heating the sheets 196, films 81, or combinations thereof while the sheets 196, films 81, or combinations thereof are positioned and/or compressed on the mandrel, cooling the sheets 196, films 81, or combinations thereof while partially or fully positioned and/or compressed on the mandrel 118, and removing the tubular wall thickness 76 from the mandrel 118, wherein one or more of said sheets 196 or films 81 are comprised of one or more materials 82 having a higher melting temperature and one or more sheets 196 or film 81 are comprised of a material 82 having a lower melting temperature. In an embodiment, the tubular wall thickness 76 is formed by positioning and/or compressing one or more sheets 196 comprised of one or more fibers 78, films 81, or combinations thereof on a mandrel 118 having low dimensional variation, heating the sheets 196, films 81, or combinations thereof while the sheets 196, films 81, or combinations thereof are positioned and/or compressed on the mandrel 118, cooling the sheets 196, films 81, or combinations thereof while partially or fully positioned and/or compressed on the mandrel 118, and removing the tubular wall thickness 76 from the mandrel 118, wherein the one or more of the material or materials 82 comprising the one or more of said sheets 196 or films 81 are cross-linked. In an embodiment, the tubular wall thickness 76 is formed by positioning and/or compressing one or more sheets 196 comprised of preformed configurations 77 in the form of one or more fibers 78 and one or more films 81 on a mandrel 118 having low dimensional variation, heating the sheets 196 and film 81 while the sheets 196 and film 81 are positioned and/or compressed on the mandrel 118, cooling the sheets 196 and film 81 while partially or fully positioned on the mandrel 118, and removing the tubular wall thickness 76 from the mandrel 118. In an embodiment, the tubular wall thickness 76 is formed by positioning and/or compressing one or more sheets 196 comprised of preformed configurations 77 in the form of one or more fibers 78 and one or more films 81 on a mandrel 118 having low dimensional variation, heating the sheets 196 and film 81 while the sheets 196 and film 81 are positioned and/or compressed on the mandrel 118, cooling the sheets 196 and film 81 while partially or fully positioned and/or compressed on the mandrel 118, and removing the tubular wall thickness 76 from the mandrel 118, wherein the layers of film 81 interconnect the layers of sheets 196. In an embodiment, the tubular wall thickness 76 is formed by positioning and/or compressing one or more sheets 196 comprised of preformed configurations 77 in the form of one or more fibers 78 and one or more films 81 on a mandrel 118 having low dimensional variation, heating the sheets 196 and film 81 while the sheets 196 and film 81 are positioned and/or compressed on the mandrel 118, cooling the sheets 196 and film 81 while partially or fully positioned and/or compressed on the mandrel 118, and removing the tubular wall thickness 76 from the mandrel 118, wherein the material 82 comprising the layers of film 81 partially or fully flows into the void space 84 in the layers of sheets 196 during heating and partially or fully retains this position after cooling. In an embodiment, the tubular wall thickness 76 is formed by positioning and/or compressing one or more sheets 196 and/or films 81 on a mandrel 118 having low dimensional variation, heating the sheets 196 and/or film 81 while the sheets 196 and/or film 81 are positioned and/or compressed on the mandrel 118, cooling the sheets 196 and/or film 81 while partially or fully positioned on the mandrel 118, and removing the tubular wall thickness 76 from the mandrel 118, wherein some or all of said sheets 196 and/or film 81 are comprised of a material 82 having been surface treated to improve adhesion between sheets 196 and/or film 81. The amount of sheets 196, layers of sheets, and configurations of sheets 196 is virtually unlimited in the present invention. The amount of sheets 196 and films 81, the configurations of sheets 196 and films 81, and the combinations of sheets 196 and films 81 employed in the present invention are virtually unlimited.

Figure 88:
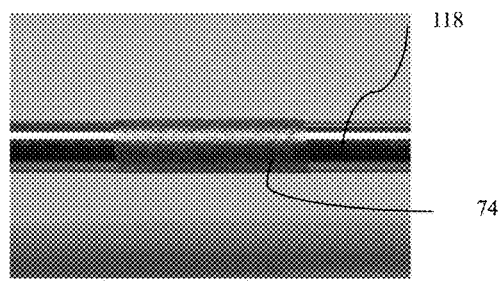
FIG. 88 is a photograph of the tube formed in FIG. 84-FIG. 87 wherein the material comprising the preformed configurations in the form of fibers transforms from an opaque white color to being translucent after heating the fibers while positioned on a high tolerance mandrel, and sizing the wall thickness by the process shown in FIG. 87.

In another embodiment, the tube 74 is formed by wrapping one or more sheets 196 around a mandrel 118 having low dimensional variation, rolling the tube 74 while still positioned on the mandrel 118 over an object having low dimensional variation like the flat steel plate 129 shown in FIG. 87 wherein a shim 127 having the thickness of the tube's final wall thickness 76 is employed to separate the mandrel 118 from the flat plate 129 so that the wall thickness 76 of the tube 74 is compressed between the gap separating the mandrel 118 from the flat plate 129 until the wall thickness 76 adequately cools to retain a thickness of proper dimensions and with little variability such a diameter or ovality. FIG. 88 shows an example of the tube 74 after rolling the outer surface 70 over the flat plate 129 shown in FIG. 87. In an embodiment, the tube 74 that is removed from the mandrel 118 is hot and/or cold drawn or hot and/or cold expanded one or more times as described herein.

Seams

As shown in FIG. 27, in an embodiment one or more sheets 196 comprised of one or more preformed configurations 77 are converted into a wall thickness 76 of a tube 74 or other precursor construct using seams 125 or other suitable means. In an embodiment, the sheet 196 is constructed of one or more layers 237 of preformed configurations 77 to form a multi-sheet 209 as illustrated in FIG. 26. In an embodiment, the wall thickness 76 is comprised of one sheet 196. In an embodiment the wall thickness 76 is comprised of one or more sheets 196 as shown if FIG. 89-FIG. 91. In an embodiment, the wall thickness 76 is comprised of one film 81. In an embodiment, the wall thickness 76 is comprised of more than one film 81 or multi-film 79. In an embodiment, the wall thickness 76 is comprised of one or more sheets 196 and one or more films 81. In an embodiment of a wall thickness 76 comprised of one or more sheets 196, films 81, or combinations thereof, the sheets, films, or combinations thereof are held together in a shape suitable for use as an endoprosthesis with one or more seams 125. In an embodiment, the wall thickness 76 including one or more seams 125 is hot and/or cold drawn or hot and/or cold expanded one or more times as described herein.

In an embodiment, one or more seams 125 or other connection means are used to partially or fully interconnect the one or more layers 237 of sheet 196. In an embodiment, the one or more seams 125 are positioned between layers 237 of sheet 196. In another embodiment, the one or more seams 125 are positioned between two long edges 199, 231 of sheets 196, 209. In an embodiment, the one or more seams 125 are positioned between two short edges 201, 229 of sheets 196, 209.

In an embodiment, one or more seams 125 or other connection means are used to partially or fully interconnect the one or more layers 107 of film 81. In an embodiment, the one or more seams 125 are positioned between layers 107 of film 81. In another embodiment, the one or more seams 125 are positioned between two long edges 121, 141 of film 81, 79. In an embodiment, the one or more seams 125 are positioned between the short edges 123,139 of film 81, 79.

In an embodiment, one or more seams 125 or other connection means are used to partially or fully interconnect the one or more layers of film 81 and one or more layers of sheet 196. In an embodiment, the one or more seams 125 are positioned between layers of film 81, layers of sheet 196, layers of film 81 and sheet 196, or combinations thereof. In an embodiment, the one or more seams 125 are positioned between two long edges 121, 141 of film 81, 79 and two long edges 199, 231 of sheet 196, 209. In an embodiment, the one or more seams 125 are positioned between the short edges 201, 229 of sheets 196, 209 and the short edges 123,139 of film 81, 79. The seam 125 can be at any position required to form the sheet 196 or film 81 into a wall thickness or precursor construct such as tube 74 as described herein.

In an embodiment including seams 125, the seams 125 are oriented in the wall thickness 76 in anyway necessary to form a wall thickness 76 of the desired shape such as in the form of a precursor construct tube 74, 75. In an embodiment, the seams 125 are oriented in any angle relative to the central axis 42 of the tube 74 or other precursor construct. In an embodiment, the seams 125 can range from zero to three hundred sixty degrees from the central axis of the tube 74 or at any angle or combinations of angles required to convert the one or more sheets 196, one or more films 81, or combinations thereof into the wall thickness 76 of a tube 74 or other precursor construct. The edges of the sheets 196 or films 81 can overlap the adjacent sheet 196 or film 81 or abut the adjacent sheet 196 or film 81 when connected by the seam 125. The seams 125 can be straight, curved, zigzag or any shape that partially or fully interconnects the sheets 196, films 81, or combinations thereof. Any means known by those skilled in the art of connecting and/or sealing is suitable for use in interconnecting the sheets 196, films 81, or combinations thereof. Without intent on limiting, the sheets 196, films 81, or combinations thereof are partially or fully interconnected by thermal fusion, welding, ultrasonic, shrinking, clamping, compression, adhesives, attachment, biological, chemical, bonding, mechanical, interlocking, sewing, tapes, solvent bonding, any combination thereof, or any other method that produces an endoprosthesis as described herein.

Layering Process

Figure 70:
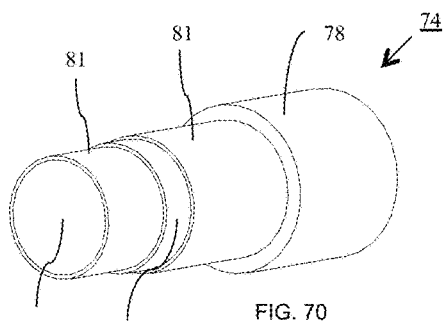
FIG. 70 is a perspective view of a wall thickness of a precursor construct tube fabricated of multiple layers.

In an embodiment, the wall thickness 76 is comprised of one or more layers 106. Referring to FIG. 70, which shows an example of a wall thickness 76 of a tubular precursor construct 74 comprised of four layers 106 in exploded isometric view. For illustration purpose only, starting at the inner diameter, the tube 74 is comprised of a ("luminal") layer of film 81 that surrounds the central passageway 56. Positioned at a farther radial distance from the central axis 42 and in direct contact with the interior layer is a layer of braided reinforcing fiber 78 oriented in an axial, radial, curved, or angled configuration. Positioned at an even farther radial distance from the central axis 42 and in direct contact with the first layer of fibers 78 is a second layer of oriented film 81. Positioned at the farthest radial distance from the central axis 42 and in direct contact with the second layer of film 81 is an exterior ("abluminal") layer of fiber 78. These layers are sandwiched together to form a high-strength, integrally connected network of fibers bound together in the form of a tube 74.

In an embodiment, the layers 106 are partially or fully interconnected. In an embodiment, one or more binders 108 are included in the wall thickness 76 to partially connect the layers 106. In an embodiment, one or more binders 108 are included in the wall thickness 76 to fully connect the layers 106. The term "binder" refers to any material that interconnects one layer to one or more layers or one preformed configuration 77 to one or more preformed configurations 77. Without intent on limiting, a binder 108 can be selected from the group of: a coating, adhesive, prepeg, resin, polymer, biodegradable polymer, fast evaporating solvent, slow evaporating solvent, adhesion promoter, bioresorbable polymer, bioabsorbable polymer, biological material, natural material, synthetic material, protein, collagen, or combination thereof. In an embodiment, the layers are compressed, heated, and cooled in a way that produces wall thickness 76 comprised of consolidated fibers 78, films 81, or combinations thereof. In an embodiment, the wall thickness 76 that is partially or fully comprised of one or more layers 106 is hot and/or cold drawn or hot and/or cold expanded one or more times as described herein.

A portion of the wall thickness 76 of a strut 44, 46 is shown in cross sectional view A-A in FIG. 105. As shown, in an embodiment the wall thickness 76 is comprised of one or more layers of preformed configurations 77. In an embodiment, the wall thickness 76 is comprised of many layers of preformed configurations 77 such as the fibers 78 positioned at an increasing radial distance from the central axis 42 of the stent 40 between the inner surface 72 and the outer surface 70. In a more preferred embodiment the wall thickness 76 of the stent 40 is comprised of between about 1-2,000 layers of preformed configurations 77, more narrowly 1 to 400 layers of preformed configurations 77. In an embodiment, the wall thickness 76 of the stent 40 is comprised of more than 2,000 layers of preformed configurations 77.

As shown in FIG. 72 and FIG. 73, in an embodiment the wall thickness 76 is a composite of one or more layers of fibers 78 and one or more layers of films 81. In an embodiment, the fibers 78 have a higher melting temperature than the films 81 so that when the wall thickness 76 is consolidated at an optimum temperature the film 81 adheres the fibers 78 together in the wall thickness 76. In an embodiment, the fibers 78 have a lower melting temperature than the films 81 so that when the wall thickness 76 is consolidated at an optimum temperature the fibers 78 adhere the film 81 together in the wall thickness 76. In a multilayer embodiment, the wall thickness 76 is comprised of some layers of fibers 78' having a higher melting temperature and some layers of fibers 78" having a lower melting temperature so that when the wall thickness 76 is consolidated at an optimum temperature the second layer of fibers 78" adheres the first layer of fibers 78' together in the wall thickness 76. In a multilayer embodiment, the wall thickness 76 is comprised of some layers of film 81' having a higher melting temperature and some layers of film 81" having a lower melting temperature so that when the wall thickness 76 is consolidated at an optimum temperature the second layers of films 81" adhere the first layers of film 81' together in the wall thickness 76. In multilayer embodiment, the wall thickness 76 is comprised of layers of fiber 78 and/or film 81 having a mixture of fibers 78 and/or films 81 comprised of materials 82 having a higher and lower melting point material 82 so that when the wall thickness 76 is consolidated at an optimum temperature the layers adhere to each other.

Without intent on limiting, a few embodiments wall thicknesses 76 comprised of a composite of materials 82 of different melting temperatures are described herein. In an embodiment, one or more layers of fibers 78 comprised of poly (L-lactide) having an I.V. ideally ranging from about 1.0 to 6.5 dl/g (available from Purac as PL) are separated by one or more layers of film 81 comprised of a copolymer of L-lactide and glycolide at a molar ratio of about 70 to 90 percent L-lactide and about 10 to 30 percent glycolide and an IV ideally ranging from about 2 to 7 dl/g (available from Purac as PLG 85) wherein the composite wall thickness 76 is heated and consolidated at an optimum temperature to adhere the layers together to form a composite wall thickness of high strength.

In an embodiment, one or more layers of fibers 78 comprised of poly (L-lactide) having an I.V. ideally ranging from about 1.0 to 6.5 dl/g (available from Purac as PL) are separated by one or more layers of fibers 78 comprised of a copolymer of L-lactide and glycolide having a molar ratio of about 10 percent L-lactide and about 90 percent glycolide and an IV ideally of about 1.7 dl/g (available from Purac as PLG 1017) where in the composite wall thickness 76 is heated and consolidated at an optimum temperature to adhere the layers together to form a composite wall thickness 76 of high strength. In an embodiment, one or more layers of film 81 comprised of poly (L-lactide) having an I.V. ideally ranging from about 1.0 to 6.5 dl/g (available from Purac as PL) are separated by one or more layers of film 81 comprised of a copolymer of L-lactide and glycolide having a molar ratio of about 10 percent L-lactide and about 90 percent glycolide and an IV ideally of about 1.7 dl/g (available from Purac as PLG 1017) where in the composite wall thickness 76 is heated and consolidated at an optimum temperature to adhere the layers together to form a composite wall thickness 76 of high strength.

In an embodiment, one or more layers of film 81 comprised of poly (L-lactide) having an I.V. ideally ranging from about 1.0 to 6.5 dl/g (available from Purac as PL) are separated by one or more layers of fibers 78 comprised of a copolymer of L-lactide and glycolide having a molar ratio of about 10 percent L-lactide and about 90 percent glycolide and an IV ideally of about 1.7 dl/g (available from Purac as PLG 1017) where in the composite wall thickness 76 is heated and consolidated at an optimum temperature to adhere the layers together to form a composite wall thickness 76 of high strength. In an embodiment, one or more layers of film 81 comprised of poly (L-lactide) having an I.V. ideally ranging from about 1.0 to 6.5 dl/g (available from Purac as PL) are separated by one or more layers of fibers 78 comprised of a copolymer of L-lactide and glycolide having a molar ratio of about 10 percent L-lactide and about 90 percent glycolide and an IV ideally of about 1.7 dl/g (available from Purac as PLG 1017) where in the composite wall thickness 76 is heated and consolidated at an optimum temperature to adhere the layers together to form a composite wall thickness 76 of high strength. In other embodiments, the I.V. is of the materials 82 are higher or lower. In other embodiments, the molar ratio of L-Lactide and glycolide copolymers is higher or lower.

In an embodiment, one or more fibers 78 comprised of poly (L-lactide) having an I.V. ideally ranging from about 1.0 to 6.5 dl/g are separated by one or more layers of film 81 comprised of a copolymer of L-lactide and DL-lactide having an molar ratio of about 70 to 80 percent L-lactide and about 20 to 30 percent DL-lactide having and I.V. ideally ranging from about 2 to 8 dl/g (available from Purac as PLDL) where the composite wall thickness 76 is consolidated at an optimum temperature that adheres the layers together to form a composite wall thickness 76 of high strength. In an embodiment, one or more fibers 78 comprised of poly (L-lactide) having an I.V. ideally ranging from about 1.0 to 6.5 dl/g are separated by one or more layers of film 81 comprised of a copolymer of L-lactide and D-lactide having an molar ratio of about 96 percent L-lactide and about 4 percent D-lactide having and I.V. ideally ranging from about 4 to 6 dl/g (available from Purac as PLD) where the composite wall thickness 76 consolidated at an optimum temperature to adhere the layers and to form a composite wall thickness 76 of high strength. In an embodiment, one or more fibers 78 comprised of poly (L-lactide) having an I.V. ideally ranging from about 1.0 to 6.5 dl/g are separated by one or more layers of film 81 comprised of a poly caprolactone having an I.V. ideally ranging from about 1 to 2 dl/g (available from Purac as PC12) where the composite wall thickness 76 is consolidated at an optimum temperature that adheres the layers to form a composite wall thickness 76 of high strength. In an embodiment, one or more layers of fibers 78 comprised of poly (L-lactide) having an I.V. ideally ranging from about 1.0 to 6.5 dl/g (available from Purac as PL) are separated by one or more layers of fibers 78 comprised of polyglycolide having an I.V. ideally ranging from about 0.5 to 2 dl/g (available from Purac as PG S) wherein the composite wall thickness 76 is consolidated at an optimum temperature that adheres the layers to form a composite wall thickness 76 of high strength. The optimum temperature is experimentally determined by those skilled in the art of polymer processing for each material 82 combination using the thermal treatment guidelines described herein. The variations in layer composition of the present invention is extensive and, therefore, any number of layers comprised of any of the materials 82 described herein in any configurations such as fiber 78 or film 81 and combinations thereof is within the scope of the present invention so long as the materials and combinations produce a composite wall thickness 76 suitable for production of a stent 40 having the performance described herein. In an embodiment, the wall thickness 76 applies the "Sandwich Theory" like, for example, a wall thickness 76 being comprised of a low-to-moderate stiffness core that is connected to one or more stiff exterior films 81 or a stiff core connected to one or more low-to-moderate stiffness exterior films 81. The term "stiffness" refers to the rigidity of the wall thickness or to the extent the wall thickness resists deformation in response to an applied force. The "Rule of Mixtures" known by those skilled in the art of material science can be useful in estimating the theoretical boundaries of the proprieties of the composite wall thicknesses 76 of the embodiments described herein.

In an embodiment, the wall thickness 76 is a combination of one or more solvent processed preformed configurations 77 and one or more melt processed preformed configurations 77. For example, glycolide-based polymers are not easily dissolved and must be melt processed. Therefore, in an embodiment melt processed fibers 78 and/or films 81 can be combined with solvent processed fibers 78 and/or films 81. In other embodiments, the preformed configurations 77 are comprised of all solvent processed materials 82 or all melt processed materials 82.

In an embodiment, as illustrated in FIG. 60 in cross-sectional view, the wall thickness 76 is comprised of one layer comprised of only fibers 78. In another embodiment, the wall thickness 76 is comprised of one layer of only film 81. In other embodiments like in FIG. 61-FIG. 65, the wall thickness 76 is comprised of multiple layers comprising at least one layer of fibers 78 layer and other layers of different structures. As an embodiment is shown in cross-sectional view in FIG. 61, the abluminal layer is comprised of one or more fibers 78 and the luminal layer is comprised of one or more films 81. In other layers comprising the tube 74 can, for example and without intent on limiting, be an extruded or molded porous or non-porous wall tube, deformed extruded or molded porous or non-porous wall tube, braided tube, knitted tube, non-woven tube, woven tube, or combinations thereof.

An embodiment of the wall thickness 76 shown in cross-sectional view in FIG. 62 is comprised of a formed material 192 on the luminal layer, electrospun fiber or fibers 190 on the abluminal layer, and woven fiber or fibers 186 in the middle layer. Without intent on limiting, the formed material 192 is extruded or molded material 82. In an embodiment, the formed material 192 is porous. In an embodiment, the formed material 192 is deformed after formation to increase its strength. As shown in cross-sectional view in FIG. 63, an embodiment of the wall thickness 76 is comprised of a more crystalline layer 146 on the abluminal and luminal layers, an a more amorphous layer 148 between the abluminal and luminal layers. As shown in cross-sectional view in FIG. 64, an embodiment of the wall thickness 76 is comprised of a more amorphous layer 148 on the abluminal and luminal layers, and a more crystalline or semi-crystalline layer 146 between the abluminal and luminal layers. As shown in cross-sectional view in FIG. 65, an embodiment of a wall thickness 76 is comprised of a more crystalline layer 146 on the abluminal layer, a more amorphous layer 148 on the luminal layer, and a semi-crystalline layer 208 positioned between the abluminal and luminal layers. In other embodiments the one or more crystalline layers, semi-crystalline layers, and the amorphous layers are positioned in other arrangements relative to each other and not limited just to the examples shown herein. In other embodiments the position of the one or more layers of fiber 78 or fibers can be in different positions relative to the films 81, formed layers, deformed layers, woven layers, or non-woven layers and not limited to the examples shown herein.

The number of layers of fibers 78 or film 81 is dependent on the desired wall thickness 76 of tube 74 and the thickness of the preformed configurations 77 such as the fiber 78 thickness 92 or the film thickness 93. The number of layers will vary depending on the end-use application. There can be any number of layers of fibers 78, film 81, or combinations thereof in the wall thickness 76 of the tube 74 or other precursor construct of present invention.

In an embodiment, the layers 106 are formed in the wall thickness 76 of a tubular precursor construct tube 74 by any suitable process that produces embodiments as specified herein such as by layering multiple preformed configurations 77 on top of each other (FIG. 10B or FIG. 105), by rolling one or more sheets 196 and or films 81 like a jelly roll (FIG. 96, FIG. 97, FIG. 98), assembling one or more concentric tubes (FIG. 70), or by any combinations thereof.

Consolidation Process

As previously mentioned, in an embodiment of the wall thickness 76 is compressed to compact the preformed configurations 77 and consolidate the wall thickness 76. Consolidation is the process of compacting the preformed configuration 77 in the wall thickness 76. Compression promotes molecular entanglement between preformed configurations 77, layers, and combinations thereof, which produces a stronger wall thickness 76. To maintain the consolidated wall thickness 76 after it is compacted, the wall thickness 76 is usually heated and cooled during consolidation. In an embodiment having a porous wall thickness prior to consolidation, the density of the wall thickness is generally increased after consolidation. In an embodiment, the wall thickness 76 is fully consolidated and is comprised of substantially solid material 82 including zero void space 84. In an embodiment, the wall thickness 76 is partially consolidated and is at least partially comprised of porous material 82 including void space 84. In an embodiment, the wall thickness 76 has white or opaque appearance before consolidation and a substantially translucent appearance after consolidation. In an embodiment, the preformed configurations 77 positioned in the wall thickness 76 are pressed together and remain substantially pressed together without melting the material 82 comprising the preformed configurations 77. In an embodiment, the preformed configurations 77 positioned in the wall thickness 76 are pressed together and remain substantially pressed together after partial or full melting and cooling of the material 82 comprising the preformed configurations. In an embodiment, the consolidated wall thickness 76 is hot and/or cold drawn or hot and/or cold expanded one or more times as described herein.

Referring to an example of a densification system depicted in FIG. 74-FIG. 77, the one or more preformed configurations 77 such as fiber 78, multi-fibers 80, film 81, or multi-films 79 separated by void spaces 84 are compacted using a compressive force 240 to move the fibers 78 in close proximity to each other. The compressive force 240 is applied in one embodiment in the direction facing the outer surface 70 of the tube 74, in a second embodiment the compressive force 240 is applied in the direction facing the inner surface 72 of the tube 74, and in a third embodiment the compressive force 240 is applied in the direction facing the outer surface 70 and the inner surface 72 of the tube 74. In embodiments having a small amount of void 84 space the compressive force 240 is stopped at the desired porosity in the wall thickness 76. If the desired goal is to remove most or all the porosity in the wall thickness 76 the compressive force 240 is increased to obtain a substantially solid wall thickness 76 comprised of compressed preformed configurations 77 as an embodiment is illustrated in FIG. 77. In yet other embodiments, ultra sonic energy or other heating sources are employed to retain the wall thickness 76 in compressed or sized state in one or more locations.

The inventors discovered that if the wall thickness 76 comprised of one or more preformed separated by void 84 spaces is not constrained, that it tends to shrivel, wrinkle, or contract into an undesirable and unpredictable shape. However, if the wall thickness 76 is constrained the wall thickness 76 does not shrivel, wrinkle, or contract.

By using the present invention of forming a wall thickness 76 of preformed configurations 77 and consolidation of the wall thickness 76 by compressing the preformed configurations 77 together while heated and cooled under a constrained condition, a stronger wall thickness 76 is produced than simply molding or extruding a wall thickness of as-polymerized material. The terms "as-polymerized" refer to material 82 obtained immediately after polymerization of one or more monomers and conversion into a form suitable for use in an injection molding machine, extruder, or other conversion equipment.

The terms "constrain," or "constraining," "constrains" refer to prohibiting the wall thickness 76 from shrinking or wrinkling, except for any amount of shrinking or wrinkling that is desirable to meet the functional requirement of the wall thickness 76 in the applications discussed herein.

Thermal Treatment Processes

Thermal treatment is the process of heating and cooling. Thermal treatment further includes the rate at which the present invention is heated and cooled. Thermal treatment also includes the period of time the present invention is heated and cooled. The terms "heat," "heated," or "heating" refer to increasing the temperature of the material 82 from a lower to a higher temperature. The terms "cool, "cooled," "cooling" refers to decreasing the temperature of the material 82 from a higher temperature to a lower temperature.

In an embodiment, the wall thickness 76 is comprised of one or more materials 82 that have been thermally treated. In an embodiment, the wall thickness 76 is thermally treated one or more times. In an embodiment, the wall thickness 76 is comprised of preformed configurations 77 that have been thermally treated after being positioned in the wall thickness 76. In an embodiment, the precursor construct tube 74 is comprised of a wall thickness 76 that has been thermally treated. In an embodiment, the stent 40 is comprised of a wall thickness 76 that has been thermally treated. In an embodiment, the wall thickness 76 is comprised of preformed configurations 77 that have been thermally treated after being positioned in the wall thickness 76 and consolidated. In an embodiment, thermal treatment occurs in any combination of the processes of producing the present invention described herein. In an embodiment, the wall thickness 76 is heated and cooled between some or all the processing steps. In an embodiment, the wall thickness 76 is not heated and cooled between some or all the processing steps.

As non-limiting example is shown in FIG. 106, the glass transition temperature 161, the crystallization temperature 165, and the melting temperature 163 of a material 82 or combination of materials 82 can be determined from a DSC thermograph 169.

Thermal Treatment—Formation of Tube or Preformed Configurations

In an embodiment, thermal treatment occurs during conversion of the as-polymerized material 82 into a wall thickness 76 by melt processing the material 82 by extrusion or molding the materials 82 into a shape like a tubular precursor construct tube 74. In another embodiment, thermal treatment occurs during conversion of the as-polymerized material 82 into a preformed configuration 77. In melt processing the one or more materials 82 are heated to at or above the melting temperature (Tm) of the material 82 or whatever temperature is required to form the material 82 into the shape of a tube or preformed configuration 77. In a preferred embodiment, the material 82 is held in the die, mold, or other formation device for a period of time ranging from about 1 microsecond to 15 minutes. In another embodiment, the material 82 is held in the die, mold, or other formation device for a period of time of at or less than 1 microsecond. In one more embodiment, the material 82 is held in the die, mold, or other formation device for a period of time at or more than 15 minutes. In an embodiment the material 82 is heated at a rate in the range of about 7 degrees Celsius/minute to 200 degrees Celsius/second. In another embodiment, the material is heated at a rate at or below 7 degrees Celsius/minute. In one more embodiment, the material 82 is heated at a rate at or higher than 200 degrees Celsius/minute. In an embodiment, the material 82 is cooled to room temperature (about 23 degrees Celsius) at a rate between 7 degrees Celsius/minute and 200 degrees Celsius/second. In another embodiment, the material 82 is cooled to room temperature at a rate at or slower than 7 degrees Celsius/minute. In one more embodiment, the material is cooled to room temperature at a rate at or faster than 200 degrees Celsius/second. In an embodiment, the material 82 is cooled quickly (quenched) to form a more amorphous wall thickness 76. In an embodiment, the material 82 is cooled slowly to form a more crystalline wall thickness 76.

Thermal Treatment—Consolidation of Wall Thickness

In an embodiment, thermal treatment occurs during consolidation of the wall thickness 76 from a thicker wall thickness 76 to a thinner wall thickness 76 or from a lower density to a higher density wall thickness by reducing or eliminating void 84 space.

To consolidate a wall thickness 76 comprised of one or more preformed configurations 76, the wall thickness 76 is preferably heated in the range between about the glass transition temperature (Tg) of the material 82 and the melting temperature (Tm) of the material 82 or whatever temperature is required to substantially retain the consolidated wall thickness 76 after cooling. In another embodiment, the wall thickness 76 is consolidated at a temperature at or below the glass transition temperature (Tg) of the material 82. In one more embodiment, the wall thickness 76 is consolidated at a temperature at or above the melting temperature (Tm) of the material 82. In a preferred embodiment, the material 82 is held in the consolidation device for a period of time ranging from 1 microsecond to 30 minutes. In another embodiment, the material 82 is held in the consolidation device for a period of time of at or less than 1 microsecond. In one more embodiment, the material 82 is held in the consolidation device for a period of time at or more than 30 minutes. In an embodiment the material 82 is heated at a rate in the range of about 7 degrees Celsius/minute to 200 degrees Celsius/second. In another embodiment, the material is heated at a rate at or below 7 degrees Celsius/minute. In one more embodiment, the material 82 is heated at a rate at or higher than 200 degrees Celsius/second. In an embodiment, the material 82 is cooled to room temperature (about 23 degrees Celsius) at a rate between 7 degrees Celsius/minute and 200 degrees Celsius/second. In another embodiment, the material 82 is cooled to room temperature at a rate at or slower than 7 degrees Celsius/minute. In one more embodiment, the material 82 is cooled to room temperature at a rate at or faster than 200 degrees Celsius/second. In an embodiment, the material 82 is cooled quickly (quenched) to form a more amorphous wall thickness 76. In an embodiment, the material 82 is cooled slowly to form a more crystalline wall thickness 76.

Thermal Treatment—Drawing or Expanding Tubular Precursor Construct and/or Preformed Configurations In an embodiment, thermal treatment occurs during the process of drawing the melt or solution processed preformed configuration 77 or tubular precursor construct 74 from a larger cross-sectional size to a smaller cross-sectional size. In an embodiment, thermal treatment occurs during the process of stretching the melt or solution processed preformed configurations 77 or precursor construct 74 from a shorter length to a longer length. In an embodiment, thermal treatment occurs during the process of expanding the diameter of the melt or solution processed tubular precursor construct 74 from a smaller diameter to a larger diameter and/or from a shorter length to a longer length.

To draw or expand a wall thickness 76 comprised of an extrusion, molding, casting, an assembly of one or more preformed configurations 77, the wall thickness 76 is preferably heated in the range between about the glass transition temperature (Tg) of the material 82 and the melting temperature (Tm) of the material 82 or whatever temperature is required to allow adequate stretching to achieve the draw down ratios or expansion ratios prescribed herein and substantially retain the stretched wall thickness 76 after cooling. In another embodiment, the wall thickness 76 is drawn or expanded at a temperature at or below the glass transition temperature (Tg) of the material 82. In one more embodiment, the wall thickness 76 is drawn or expanded at a temperature at or above the melting temperature (Tm) of the material 82. In a preferred embodiment, the material 82 is held in substantially constant tension during drawing or expansion for a period of time ranging from 1 microsecond to 60 minutes. In another embodiment, the material 82 is held in the in tension during drawing and or expansion for a period of time of at or less than 1 microsecond. In one more embodiment, the material 82 is held in tension during drawing or expansion for a period of time at or more than 60 minutes. In an embodiment the material 82 is heated at a rate in the range of about 10 degrees Celsius/minute to 200 degrees Celsius/second. In another embodiment, the material 82 is heated at a rate at or below 10 degrees Celsius/minute. In one more embodiment, the material 82 is heated at a rate at or higher than 200 degrees Celsius/second. In an embodiment, the material 82 is cooled to below the glass transition temperature of the material 82 or to room temperature (about 23 degrees Celsius) at a rate between 7 degrees Celsius/hour and 300 degrees Celsius/second. In another embodiment, the material 82 is cooled to room temperature at a rate at or slower than 7 degrees Celsius/hour. In one more embodiment, the material 82 is cooled to room temperature at a rate at or faster than 300 degrees Celsius/second. In an embodiment, the material 82 is cooled quickly (quenched) to form a more amorphous wall thickness 76. In an embodiment, the material 82 is cooled slowly to form a more crystalline wall thickness 76.

Thermal Treatment—Sizing or Shape Formation

To size or form a wall thickness 76 comprised of an extrusion, molding, casting, an assembly of one or more preformed configurations 77, the wall thickness 76 is preferably heated in the range above about the glass transition temperature (Tg) of the material 82 or whatever temperature is required to achieve low dimensional variation, reshape the wall thickness 76 (if applicable), and substantially retain the sized wall thickness 76 after cooling. In another embodiment, the wall thickness 76 is sized at a temperature at or below the glass transition temperature (Tg) of the material 82. In a preferred embodiment, the material 82 is held in sized formation for a period of time ranging from 1 microsecond to 60 minutes. In another embodiment, the material 82 is held in sized formation for a period of time of at or less than 1 microsecond. In one more embodiment, the material 82 is held in sized formation for a period of time at or more than 60 minutes. In an embodiment the material 82 is heated at a rate in the range of about 10 degrees Celsius/minute to 200 degrees Celsius/second. In another embodiment, the material 82 is heated at a rate at or above 200 degrees Celsius/second. In one more embodiment, the material 82 is heated at a rate at or below degrees 10 Celsius/minute. In an embodiment, the material 82 is cooled to below the glass transition temperature (Tg) or room temperature (about 23 degrees Celsius) at a rate between 7 degrees Celsius/hour and 300 degrees Celsius/second. In another embodiment, the material 82 is cooled to room temperature at a rate at or slower than 7 degrees Celsius/hour. In one more embodiment, the material 82 is cooled to room temperature at a rate at or faster than 300 degrees Celsius/second. In an embodiment, the material 82 is cooled quickly (quenched) to form a more amorphous wall thickness 76. In an embodiment, the material 82 is cooled slowly to form a more crystalline wall thickness 76.

Thermal Treatment—Modifying Morphology (Crystallinity and Amorphicity)

In an embodiment, thermal treatment occurs during the process of modifying the morphology of the material 82 from a more amorphous material 82 to more crystalline material 82. In an embodiment, thermal treatment occurs during the process of modifying morphology of the material 82 from a more crystalline material 82 to a more amorphous material 82.

To modify the morphology of a wall thickness 76 comprised of an extrusion, molding, casting, an assembly of one or more consolidated or unconsolidated preformed configurations 77, the wall thickness 76 is preferably heated in the range above about the glass transition temperature (Tg) of the material 82 and the melting temperature (Tm) of the material 82, more narrowly around the mid point between the glass transition temperature (Tg) and the melting point (Tm) of the material 82. In an embodiment, the wall thickness is heated to a temperature within plus or minus thirty percent of the crystallization temperature (Tc) of the material 82. In another embodiment, the wall thickness 76 has its morphology modified at a temperature at or above the melting temperature (Tm) of the material 82. In a preferred embodiment, the material 82 is constrained to minimize or prevent dimensional changes during morphology modification for a period of time ranging from 1 microsecond to 24 hours. In another embodiment, the material 82 is constrained to minimize or prevent dimensional changes during morphology modification for a period of time of at or less than 1 microsecond. In one more embodiment, the material 82 is constrained to minimize or prevent dimensional changes during morphology modification for a period of time at or more than 24 hours. In an embodiment the material 82 is heated at a rate in the range of about 10 degrees Celsius/minute to 200 degrees Celsius/second. In another embodiment, the material 82 is heated at a rate at or below 10 degrees Celsius/minute. In one more embodiment, the material 82 is heated at a rate at or higher than 200 degrees Celsius/second. In an embodiment, the material 82 is cooled to below the glass transition temperature or to room temperature (about 23 degrees Celsius) at a rate between 7 degrees Celsius/hour and 300 degrees Celsius/second. In another embodiment, the material 82 is cooled to room temperature at a rate at or slower than 7 degrees Celsius/hour. In one more embodiment, the material 82 is cooled to room temperature at a rate at or faster than 300 degrees Celsius/second. In an embodiment, the material 82 is cooled quickly (quenched) to form a more amorphous wall thickness 76. In an embodiment, the material 82 is cooled slowly to form a more crystalline wall thickness 76.

In a more preferred embodiment, the crystallinity of the material or materials 82 comprising the wall thickness 76 is in the range of about 20 percent to 70 percent crystalline and 30 to 80 percent amorphous, more narrowly between 40 and 60 percent crystalline and 40 to 60 percent amorphous. In a preferred embodiment, the crystallinity of the material or materials 82 comprising the wall thickness 76 is at or less than 20 percent crystalline and the balance amorphous. In a preferred embodiment, the crystallinity of the material or materials 82 comprising the wall thickness 76 is at or more than 60 percent crystalline and the balance amorphous.

Thermal Treatment—Coating

In an embodiment, thermal treatment occurs during the process of coating the stent 40. In a preferred embodiment, the coating 180 is applied and/or dried on the wall thickness 76 or stent 40 at a temperature above about 5 degrees Celsius. In another embodiment, the coating 180 is applied and dried on the wall thickness 76 or stent 40 at a temperature at or below 5 degree Celsius.

Thermal Treatment—Crimping & Packaging

In an embodiment, thermal treatment occurs during the process of crimping the stent 40 on the end of a catheter 184. In an embodiment, the stent 40 is crimped and/or packaged at a temperature above about −17.8 degrees Celsius. In an embodiment, the stent 40 is crimped and/or packaged at a temperature at or below −17.8 degrees Celsius.

Thermal Treatment—Environmental Conditions

In an embodiment, the material 82 is dried before thermal processing and/or melt processing. In an embodiment, the material 82 is dried at a temperature at or below the gas transition temperature (Tg) of the material 82 before formation into a wall thickness 76. In a preferred embodiment, the material 82 and preformed configurations 77 are dried to moisture content at or below about 250 parts per million (ppm) before formation into a wall thickness 76. In an embodiment, the material 82 is dried to moisture content at or above about 250 parts per million (ppm) before formation into a wall thickness 76. In an embodiment, the material 82 is dried for about 1-6 hours, at 60-120 degrees Celsius, and at low vacuum (less than about 200 mbar). In an embodiment, the heating and/or cooling of the wall thickness 76 occurs under negative pressure (vacuum) in the range of about negative 0.05 MPa to negative 0.2 MPa. In another embodiment, the heating and/or cooling of the wall thickness occurs under negative pressure (vacuum) at or less than about negative 0.05 MPa. In one more embodiment the heating and/or cooling of the wall thickness 76 occurs under negative pressure (vacuum) at or greater than negative 0.2 MPa.

In an embodiment, unless otherwise specified the temperature of the environment surrounding the processing steps described herein ranges from about 0 degrees Celsius to the melting temperature of the material 82, more narrowly about 0-40 degrees Celsius. In other embodiments, the temperature of the environment surrounding the processing steps described herein is at or below about 0 degrees Celsius and in other embodiments the environment is at or above the melting temperature of the material 82. In an embodiment, the environment surrounding the processing steps described herein has a relative humidity ranging from about 15 to 90 percent relative humidity. In another embodiment, the environment has a relative humidity at or below about 15 percent relative humidity. In an embodiment, the environment has a relative humidity at or above about 90 percent relative humidity.

In an embodiment, the wall thickness 76 comprised of one or more preformed configurations 77 is sintered. The term "sinter" refers to the process of partially or fully connecting the preformed configurations 77 by atomic diffusion. In an embodiment formed by sintering, the preformed configurations 77 are held in a mold and heated to a temperature below the melting temperature of the material 82. The atoms in the preformed configurations 77 diffuse across the boundaries of the preformed configurations 77, fusing the preformed configurations 77 together and creating a consolidated piece.

In an embodiment, the wall thickness 76 is heated while the preformed configurations 77 are under compression. In an embodiment, the wall thickness 76 comprised of preformed configurations 77 is heated while the preformed configurations 77 are not under compression. In an embodiment, the wall thickness 76 comprised of preformed configurations 77 is cooled while the preformed configurations 77 are under compression. In an embodiment, the wall thickness 76 comprised of preformed configurations 77 is cooled while the preformed configurations 77 are not under compression. In an embodiment, the wall thickness 76 comprised of preformed configurations 77 is heated and cooled while the preformed configurations 77 are under compression. In an embodiment, the wall thickness 76 comprised of preformed configurations 77 is heated while not under compression and cooled while under compression. In yet another embodiment, the wall thickness 76 comprised of preformed configurations 77 are heated while under compression and cooled while not under compression. In one more embodiment, the wall thickness 76 comprised of preformed configurations 77 is heated while constrained in one or more directions. In an embodiment, the wall thickness 76 comprised of preformed configurations 77 is heated and cooled while constrained in one or more directions. In an embodiment, the wall thickness 76 comprised of preformed configurations 77 is heated while unconstrained. In an embodiment, the wall thickness 76 comprised of preformed configurations 77 is cooled while unconstrained. In still one more embodiment, the wall thickness 76 comprised of preformed configurations is heated and cooled while unconstrained.

An embodiment of the endoprosthesis of the present invention comprises a wall thickness 76 formed of one or more preformed configurations 77 wherein the material 82 comprising the preformed configurations 77 has a partially or fully white or opaque appearance and the wall thickness 76 is heated to a temperature wherein the material 82 comprising the preformed configurations 77 partially or fully becomes translucent in appearance while heated and partially or fully retains this translucent appearance after cooling. Another embodiment of the present invention comprises a wall thickness 76 formed of one or more preformed configurations 77 separated by one or more void spaces 84 wherein the material 82 comprising the preformed configurations 77 has a partially or fully white or opaque appearance and the wall thickness 76 is heated to a temperature wherein the material 82 comprising the preformed configurations 77 partially or fully becomes translucent in appearance while heated and partially or fully retains this translucent appearance after cooling. One more embodiment of the present invention comprises a wall thickness 76 formed of one or more preformed configurations 77 wherein the material 82 comprising the preformed configurations 77 has a partially or fully white or opaque appearance and the wall thickness 76 is heated to a temperature wherein the material 84 comprising the preformed configurations 77 partially or fully becomes translucent in appearance, the void spaces 84 in the wall thickness 76 are reduced or eliminated, and the material 82 comprising the preformed configurations 77 partially or fully retains its translucent appearance after heating and cooling. An embodiment of the present invention comprises a wall thickness 76 formed of one or more preformed configurations 77 wherein the material 82 comprising the preformed configurations 77 has a white or opaque appearance and the wall thickness 76 is heated to a temperature wherein the material 82 comprising the preformed configurations 77 partially or fully becomes translucent in appearance, the void spaces 84 in the wall thickness 76 are reduced or eliminated, the material 82 comprising the preformed configurations 77 partially or fully retains its translucent appearance, and the tubular precursor construct 74 has low dimensional variation after heating and cooling.

In an embodiment, the material 82 includes spherulites of a substantially uniform size in the wall thickness 76. In an embodiment, the material 82 includes spherulites of varying size in the wall thickness 76. In an embodiment, the wall thickness 76 includes larger spherulites on the outer diameter 62 of the wall thickness 76 than the remaining portion of the wall thickness 76. In an embodiment, the wall thickness 76 includes smaller spherulites on the outer diameter 62 than the remaining portion of the wall thickness 76. In an embodiment, the wall thickness 76 includes larger spherulites on the inner diameter 64 than the remaining portion of the wall thickness 76. In an embodiment, the wall thickness 76 includes smaller spherulites on the inner diameter 64 of the wall thickness 76. In an embodiment, the wall thickness 76 includes larger spherulites on the inner diameter 64 and outer diameter 62 than on the remaining portion of the wall thickness 76. In an embodiment, the wall thickness 76 includes smaller spherulites on the inner diameter 64 and outer diameter 62 than on the remaining portion of the wall thickness 76. In an embodiment, the size of the spherulites changes from a smaller size to a larger size in part or all the wall thickness 76 after heating and cooling the wall thickness. In an embodiment, the size of the spherulites changes from a larger size to a smaller size in part or all of the wall thickness 76 after heating and cooling. In an embodiment, the some or all the spherulites change from a smaller size to a larger size after heating and cooling the wall thickness 76. In an embodiment, some or all the spherulites change from a larger size to a smaller size after heating and cooling the wall thickness 76. The size of the spherulites can be measured using an optical microscope under cross-polarized light.

In an embodiment, the inner diameter 64 changes from a more ductile to less ductile material 82 after heating and cooling, and the remaining portion of the wall thickness 76 remains more ductile than the inner diameter 64. In an embodiment, the outer diameter 62 changes from a more ductile material 82 to a less ductile material 82 after heating and cooling, and the remaining portion of the wall thickness 76 remains more ductile than the outer diameter 62. In an embodiment, the inner diameter 64 and outer diameter 62 change from a more ductile to less ductile material 82 after heating and cooling, and the remaining portion of the wall thickness 76 remains more ductile than the inner diameter 64 and outer diameter 62. In an embodiment, most or all the wall thickness 76 changes from a more ductile material to a less ductile material 82 after heating and cooling the wall thickness 76.

In an embodiment, the inner diameter 64 changes from a less ductile to a more ductile material 82 after heating and cooling, and the remaining portion of the wall thickness 76 remains less ductile than the inner diameter 64. In an embodiment, the outer diameter 62 changes from a less ductile material 82 to a more ductile material 82 after heating and cooling, and the remaining portion of the wall thickness 76 remains less ductile than the outer diameter 62. In an embodiment, the inner diameter 64 and outer diameter 62 change from a less ductile to a more ductile material 82 after heating and cooling, and the remaining portion of the wall thickness 76 remains less ductile than the inner diameter 64 and outer diameter 62. In an embodiment, most or all the wall thickness 76 changes from a less ductile material 82 to a more ductile material 82 after heating and cooling the wall thickness 76.

An embodiment of the present invention comprises a wall thickness 76 formed of one or more preformed configurations 77 wherein the wall thickness 76 has a partially or fully white or opaque appearance and the wall thickness 76 is heated to a temperature wherein the wall thickness 76 becomes translucent in appearance while heated and partially or fully retains this translucent appearance after cooling. An embodiment of the present invention comprises a wall thickness 76 formed of one or more preformed configurations 77 separated by one or more void spaces 84 wherein the wall thickness 76 has a partially or fully white or opaque appearance and the wall thickness 76 is heated to a temperature which the wall thickness 76 partially or fully becomes translucent in appearance while heated and partially or fully retains this translucent appearance after cooling. An embodiment of the present invention comprises a wall thickness 76 formed of one or more preformed configurations 77 wherein the wall thickness 76 has a partially or fully white or opaque appearance and the wall thickness 76 is heated to a temperature at which the wall thickness 76 partially or fully becomes translucent in appearance, the void spaces 84 in the wall thickness 76 are reduced or eliminated, and the wall thickness 76 retains its translucent appearance after heating and cooling.

An embodiment of the present invention comprises a wall thickness 76 formed of one or more preformed configurations 77 wherein the material 82 comprising the preformed configurations 77 or network of preformed configurations 77 produces a wall thickness 76 having mechanical properties that are initially more flexible, more limp, or softer which are changed to a final less flexible, more rigid, or harder mechanical properties after heating and cooling the wall thickness 76. An embodiment of the present invention comprises a wall thickness 76 formed of one or more preformed configurations 77 separated by one or more void spaces 84 wherein the material 82 comprising the preformed configurations 77 or network of preformed configurations 77 produces a wall thickness 76 having mechanical properties that are initially more flexible, more limp, or softer which are changed to a final less flexible, more rigid, or harder mechanical properties after heating the wall thickness 76 and cooling the wall thickness. An embodiment of the present invention comprises a wall thickness 76 formed of one or more preformed configurations 77 wherein the material 82 comprising the preformed configurations 77 or network of preformed configurations 77 produces a wall thickness 76 having mechanical properties that are initially more flexible, more limp, or softer which are changed to a less flexible, more rigid, or harder mechanical properties, the void spaces 84 in the wall thickness 76 are reduced or eliminated, and the material 82 comprising the preformed configurations 77 or network of preformed configurations 77 partially or fully retains the less flexible, more rigid, less porous, or harder mechanical properties after heating and cooling the wall thickness 76.

In an embodiment, the wall thickness 76 is heated to a temperature that changes the ductility of some or all of the material 82 comprising the wall thickness 76 after the material 82 is cooled to any temperature at or below the melting temperature of material 82. In an embodiment, the wall thickness 76 is heated to a temperature that changes the ductility of some or all the material 82 when the material 82 is at physiological conditions.

Figure 83:
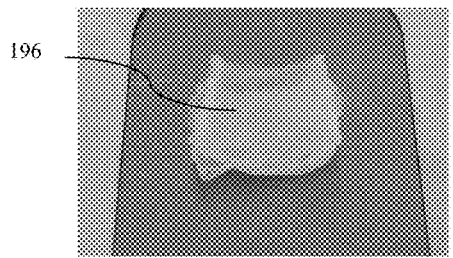
FIG. 83 is a photograph of multiple heated sheets of preformed configurations in the form of fibers separated by void spaces having undergone shrinking, wrinkling, or distortion when heated unconstrained.

As shown in FIG. 83, the material 82 when in the form of preformed configuration 77 has a tendency to shrink or wrinkle when heated. To produce a stent 40 having a wall thickness 76 of little dimensional variation, the material 82 or preformed configuration 77 are preferably heated while partially or fully constrained. By constraining the preformed configurations 77 during heating and/or, the wall thickness 76 retains its formed shape until it is cooled and can partially or fully retains its own shape.

Figure 104:
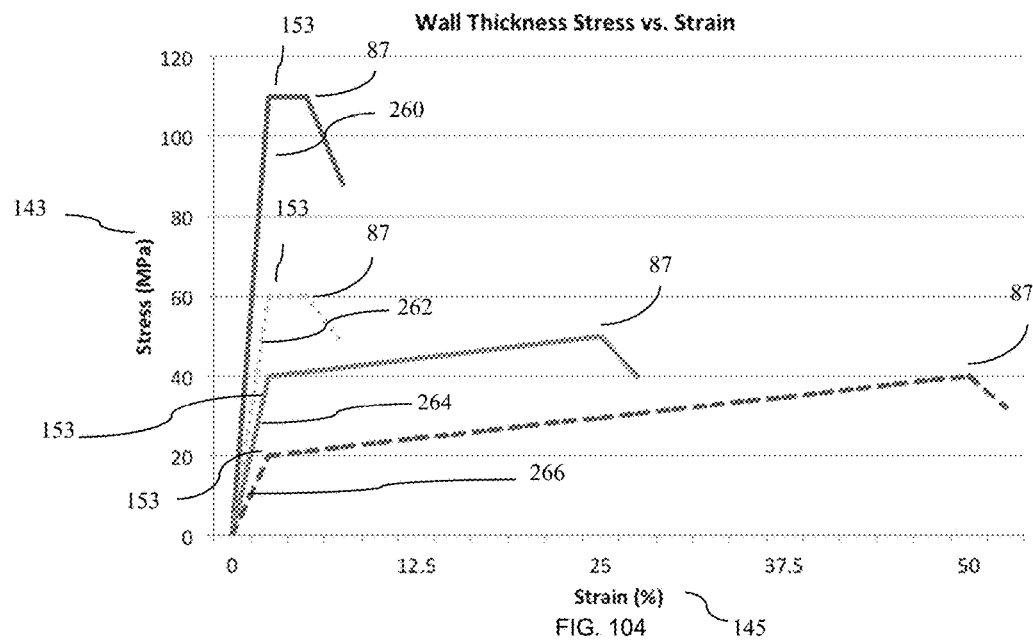
FIG. 104 includes examples stress-strain curves of wall thicknesses of various degrees of strength, stiffness, and ductility.

The wall thickness 76 of the present invention has a large variety of physical properties that are dependent on the thermal processing and consolidation of the wall thickness 76. The wall thickness 76 of the present invention can be customized to meet the requirements of the end-use application. For example, the strength, stiffness, and elasticity can be customized in each embodiment to meet the end use application. Without intent on limiting, referring to FIG. 104 there are a few examples of wall thicknesses 76 of varying amounts of strength, stiffness, and elasticity produced by utilizing the thermal processing conditions described herein. The stiffness of the wall thickness 76 increases as the slope of line in the elastic region 83 increases. Therefore, line 260 represents an embodiment of the stiffest wall thickness 76 shown in FIG. 104. Line 262 represents the next most stiffest wall thickness shown in FIG. 104. Conversely, line 266 shows the most pliable embodiment of a wall thickness 76 in FIG. 104. Line 264 represents the next most pliable wall thickness 76 in FIG. 104. The embodiments having the more stiffness where obtained by using higher temperatures, longer heating cycles, more consolidation, or combinations thereof. In embodiments represented by line 264 and line 266 the elongation to break was much greater than that of line 260 and line 262. The inventors found that under the thermal treatment conditions described herein, that a wall thickness 76 could be produced having an elongation to break of up to 250% or more. This is a remarkable increase in elasticity a the manufacture of the Poly (L-Lactic) acid material 82 reports the elongation to break of the PL-38 (available from Purac, the Netherlands) material 82 has an as-polymerized elongation to break of 2-6 percent. Employing a wall thickness 76 having a high elongation to break is useful to prevent strut cracking during crimping or after deployment in an anatomical lumen 38. An embodiment, having a high elongation to break is also useful for increase the safety margin that prevents strut cracking in vivo because as the material 82 undergoes degradation in some embodiments it becomes more brittle and becomes more inclined to crack. A wall thickness 76 having a high elongation to break can also be useful stent's 40 implanted in area of high flexure like for example in a peripheral stent. A noted herein, the physical properties of the wall thickness 76 or stent 40 can be customized or tailored specifically to the requirements of the end use application. The variations of strength, stiffness, and elasticity of the present invention are not limited to what is shown in FIG. 104. In other embodiments, the wall thickness 76 has lesser or greater strength, stiffness, and elasticity than what are shown in FIG. 104. In other embodiments, the wall thickness 76 has strength, stiffness, and elasticity between the examples shown in FIG. 104.

Once again referring to FIG. 104, the embodiments represented by line 264 and line 266 show that the ultimate tensile strength 151 of the wall thickness 76 is increased by stretching the wall thickness 76. The stress-strain graph clearly shows that the ultimate tensile strength of the wall thickness 76 increased as the strain on the wall thickness 76 increased. The graph proves that a wall thickness 76 comprised of consolidated preformed configurations 77 can be further strengthened by radial or axial expansion of a tubular precursor construct tube 74 fabricated following the specifications described herein.

Sizing and Orientation Process

As previously described, in one embodiment the wall thickness 76 is formed by solution or melt processing the material 82 into a shape like a precursor construct tube 74. In another embodiment, the wall thickness 76 is formed by first forming preformed configurations 77 by solution or melt processing the material 82 into a shape like a fiber 78 or film 81 and then forming these preformed configurations 77 into the shape of a precursor construct tube 74.

In order to be able to cut an accurate strut pattern 60 in the wall thickness 76 of the tube precursor construct tube 74, the tube 74 must have very little variation in outer diameter 62, inner diameter 64, wall thickness 76, or ovality. Therefore, in a preferred embodiment the outer diameter 62 and/or the inner diameter 64 are controlled to have low dimensional variation.

In a preferred embodiment the tube 74 having a wall thickness 76 is subjected to any sizing process that minimizes the dimensional variation of the tube's 74 outer diameter 62, inner diameter 64, wall thickness 76, ovality, or combination thereof. The term "ovality" refers to the amount the cross-sectional shape of the tube 74 is out-of-round. An example of a sized tube 212 is shown in cross-sectional view in FIG. 77. In the preferred embodiment of the sized tube 212, the outer diameter 62, inner diameter 64, wall thickness 76, and ovality along the entire length 128 of the tube 212 preferably does not vary more than about +/−15 microns, more preferably does not vary more than about +/−10 microns, and most preferably does not vary more than about +/−2.5 microns. In another embodiment of the sized tube 74, the outer diameter 62, inner diameter 64, wall thickness 76, and ovality along the entire length of the tube 212 varies less than 10 microns. In one more embodiment, of the sized tube 74 the outer diameter 62, inner diameter 64, wall thickness 76, and ovality along the entire length of the tube 212 varies greater than +/−15 microns. The term "micron" refers to a dimension equal to one micrometer or 0.001 millimeter (mm).

In one embodiment of a system for producing a sized tube 212, as depicted in FIG. 78-FIG. 79, the tube 74 having a wall thickness 76 is inserted into the cavity 242 of a mold 214 as illustrated in FIG. 79 in cross sectional view. There exists in the un-sized tube's 74 wall thickness 76 dimensional variation related to variation in molding, extrusion, shrinkage, warpage, preformed configuration 77 thickness, fiber 78 thickness 92, film thickness 93, variation size of the void 84 space between fibers 78, and due to other factors. As shown in FIG. 79, the dimensional variation can be reduced by pushing the wall thickness 76 against the cavity of a mold 214 to form the wall thickness 76 into the size and shape of the mold 214. By heating and cooling the material 82 during the forming process the tube 74 retains the shape of the cavity 242 of the mold 214.

In an embodiment of a sized-tube 212, the un-sized tube 74 is inserted into the cavity 242 of a mold 214 so that it is substantially centered in the tubular-shaped cavity 242. As depicted in FIG. 79, in an embodiment the tube 74 is radially expanded to produce a sized-tube 212 by increasing the pressure 246 inside the tube 74 so that the wall thickness 76 is compressed between the pressure 246 and the mold horizontal wall 244, vertical wall 248, or combination thereof. In one more embodiment, the tube 74 is radially expanded to produce a sized-tube 212 by increasing the pressure 246 inside the tube 74 so that the wall thickness 76 is compressed between the pressure 246 and the mold horizontal wall 244, vertical wall 248, or combination thereof when the tube 74, mold 214, or combination thereof are at an temperature at or above about 20 degrees Celsius, more narrowly at or above the glass transition temperature of the material 82. In one more embodiment, the tube 74 is radially expanded to produce a sized-tube 212 by increasing the pressure 246 inside the tube 74 so that the wall thickness 76 is compressed between the pressure 246 and the mold horizontal wall 244, vertical wall 248, or combination thereof when the tube 74, mold 214, or combination thereof are at an temperature at or above about 20 degrees Celsius, more narrowly at or above the glass transition temperature of the material 82, and the sized-tube 212, mold 214, or combinations thereof are cooled until the sized-tube 212 substantially retains it sized configuration. In another embodiment the tube 74 is radially expanded from a smaller size to a larger size by creating a vacuum between the tube 74 wall thickness 76 and the mold's 214 horizontal interior wall 244. In another embodiment the tube 74 is radially expanded from a smaller size to a larger size by creating a vacuum between the tube 74 wall thickness 76 and the mold's 214 horizontal interior wall 244 when the tube 76, mold 214, or combination thereof are at temperature at or above 20 degrees Celsius, more narrowly at or above the glass transition temperature of the material 82. In another embodiment the tube 74 is radially expanded from a smaller size to a larger size by creating a vacuum between the tube 74 wall thickness 76 and the mold's 214 horizontal interior wall 244 when the tube 74, mold 214, or combination thereof are at temperature at or above 20 degrees Celsius, more narrowly at or above the glass transition temperature of the material 82, and the sized-tube 212, mold 214, or combination thereof are cooled until the sized-tube 212 substantially retains its sized configuration. In an embodiment, some or all the void 84 space within the wall thickness 76 is partially or fully filled with material 82 or otherwise sealed or the outer 70 or inner 72 surfaces are coated to make the wall thickness 76 less permeable or impermeable prior to sizing. In another embodiment the un-sized tube 74 is inserted into the cavity 242 of a mold 214 and axially elongated from a shorter length 128 to a longer length 128 to produce a sized tube 212 by closing off one end of the tube 74, increasing the pressure 246 inside the tube 74, and creating a tensile force in the wall thickness 76 that results in axial elongation. In another embodiment the un-sized tube 74 is inserted into the cavity 242 of a mold 214 and axially elongated from a shorter length 128 to a longer length 128 to produce a sized-tube 212 by closing off one end of the tube 74, increasing the pressure 246 inside the tube 74, and creating a tensile force in the wall thickness 76 that results in axial elongation when the tube 74, mold 214, or combination thereof are at an temperature at or above about 20 degrees Celsius, more narrowly at or above the glass transition temperature of the material 82. In another embodiment the un-sized tube 74 is inserted into the cavity 242 of a mold 214 and axially elongated from a shorter length 128 to a longer length 128 to produce a sized-tube 212 by closing off one end of the tube 74, increasing the pressure 246 inside the tube 74, and creating a tensile force in the wall thickness 76 that results in axial elongation when the tube 74, mold 214, or combination thereof are at an temperature at or above about 20 degrees Celsius, more narrowly at or above the glass transition temperature of the material 82, and the sized-tube 212, mold 214, or combinations thereof are cooled until the sized-tube 212 substantially retains it sized configuration. In one more embodiment of a sized tube 212, the un-sized tube 74 is inserted into the cavity 242 of a mold 214 and radially expanded and axially elongated to produce a sized-tube 212 by increasing the pressure 246 inside the tube 74 using temperature to facilitate expansion and sizing of the sized-tube 212.

Once again referring to FIG. 79, conveying a fluid into the tube 74 to increase the internal pressure in the tube increases the pressure 246 inside of the tube. Without intent on limiting, in an embodiment the fluid that produces the pressure 246 imposed on the wall thickness 76 during compression of the wall thickness 76 is partially or fully comprised of air, nitrogen, substantially oxygen-free or low oxygen containing gas, liquid, or other inert gas or liquid. A removable or non-removable, air impermeable or liquid impermeable liner or bladder is optionally used to separate the fluid from the inner surface 72 of the tube 74. In one embodiment, during the radial expansion and/or axial elongation processes, the tube 74 is heated to a temperature between the glass transition temperature and the melting temperature of the material 82 to allow the radial expansion and/or axial elongation of the tube 74. In another embodiment, during the radial expansion or axial elongation processes, the tube 74 is heated to a temperature at or above about melting temperature of the material 82 to allow the radial expansion and/or axial elongation of the tube 74. In one more embodiment, during the radial expansion or axial elongation processes, the tube 74 is heated to a temperature at or below about the glass transition temperature of the material 82 to allow the radial expansion and/or axial elongation of the tube 74.

In another embodiment, a tube 74 having a wall thickness 76 comprised of preformed configurations 77 such as fibers 78, multi-fibers, film 81, multi-film 79 and voids 84 is inserted into the cavity 242 of the mold 214 and a second tube having a solid wall thickness is inserted in the inner diameter 64 of the tube 74. As in the previously described process, in an embodiment the two tubes are expanded radially and/or axially elongated by creating an expansion force that compresses the wall thickness 76 of the two tubes while at an elevated temperature as described herein against the inner surface of the mold cavity until cooled to produce a sized tube 212.

In one more embodiment, a first tube having a solid wall thickness is inserted into the cavity 242 of the mold 214, a second tube 74 having a wall thickness comprised of pre-formed configurations 77 such as fibers 78, multi-fibers 80, film 81, multi-films 79, and voids 84 is inserted into the inner diameter of the first tube, and a third tube having a solid wall thickness is inserted in the inner diameter 64 of the tube 74 comprised of preformed configurations 77. As in the previously described processes, the three tubes are expanded radially and/or axially elongated by creating an expansion force that compresses the wall thickness of the three tubes while at an elevated temperature as described herein against the inner surface of the mold 214 cavity 242 until cooled to produce a sized tube 212.

In one embodiment the heat is applied to the wall thickness 76 by introducing a heated fluid into the inside of the tube 74, in another embodiment the heat is applied to the wall thickness 76 by heating the mold 214 wall 244, 248, in another embodiment the heat is introduced in the cavity of the mold 242, and in another embodiment the heat is applied to the wall thickness 76 by a combination of introducing a heated fluid into the inside of the tube 74 and by heating the mold 214 wall 244, 248. In one embodiment the cooling is applied to the wall thickness 76 by introducing a cooled fluid into the inside of the tube 74, in another embodiment the cooling is applied to the wall thickness 76 by cooling the mold 214 wall 244, 248, in another embodiment the cooling is introduced in the cavity of the mold 242, and in another embodiment the cooling is applied to the wall thickness 76 by a combination of introducing a cooling fluid into the inside of the tube 74 and by cooling the mold 214 wall 244, 248.

The inside diameter of the mold's cavity 242 has a precise diameter having low dimensional variation so that when the wall thickness 76 of the un-sized tube 74 presses against the inside surface of the cavity 242 in the mold 214 the tube 74 substantially assumes the shape, dimensions, and tolerances of the mold's cavity 242. The wall thickness 76 of the tube 74 is held in an expanded state against the surface of the cavity's 242 horizontal interior wall 244 and/or vertical interior wall 248 and cooled until the sized-tube 212 substantially retains its new shape and dimensions. In an embodiment, the sized-tube 212 is cooled to a temperature at or below the material's 82 melting temperature. In another embodiment, the sized-tube 212 is cooled to a temperature at or below the material's 82 glass transition temperature. In one more embodiment, the sized-tube is cooled at a temperature at which the sized-tube 212 substantially retains a shape such as a tube having low dimensional variation and performance as described herein. In an embodiment, the sized tube 212 is preferably cooled at a rate allowing the material 82 comprising the wall thickness 76 to at least partially crystallize or re-crystallize so that the wall thickness 76 is comprised of material 82 having crystalline and amorphous portions. In one embodiment the cooling is applied to the wall thickness 76 by introducing a cooled fluid into the inside of the tube 74, in another embodiment the cooling is applied to the wall thickness 76 by cooling the mold 214 wall 244, in another embodiment the cooling is introduced into the mold, and in another embodiment the cooling is applied to the wall thickness 76 by a combination of introducing a cool fluid into the inside of the tube 74 and by cooling the mold 214 wall or walls 244, 248. In some embodiments one or more vents (not shown) are incorporated in the mold 214 wall or walls 244, 248 to allow any air trapped in compressed void 84 spaces, residual vapors, or volatile materials to escape the wall thickness 76. The sized-tube 212 is removed from the mold 214 for subsequent processing like applying a coating 180 or cutting a strut pattern 60

In an embodiment of the mold 214 the horizontal interior wall 244 is adapted to be smooth or include protrusions, indentations, or protrusions and indentations of any size and shape that form a pattern on the outer surfaces 70, inner surfaces 72, or combinations thereof of the sized-tube 212. In an embodiment, the wall thickness 76 includes barbs to minimize or prevent the stent 40 from migrating from its deployed position. These protrusions, for example, can be used to prevent the stent 40 from migrating from the installed position during delivery or to penetrate the anatomical lumen and deliver therapeutic drugs. Likewise, the indentations can, for example, be useful for storing therapeutic drugs or stent location marking materials. These surface modifications can also be useful for strengthening the tube or stent. In an embodiment, the mold's 214 horizontal wall 244, vertical wall 248, core 256 or combination thereof includes one or more patterns that are transferred onto part or the entire outer surface 70 of the wall thickness 76. The mold's 214 walls and core in some embodiments have straight surfaces and in other embodiments have curved or angled surfaces. In yet one more embodiment, the mold's 214 horizontal wall 244, vertical wall 248, core 256, or combination thereof includes one or more patterns that are transferred onto part or the entire inner surface 72 of the wall thickness 76. Without intent on limiting, in an embodiment the pattern imparts grooves, radial grooves, grooves aligned 0-360 degrees from the central axis 42, straight grooves, curved grooves, zigzag grooves, crisscross grooves, helical grooves, ridges, radial ridges, ridges aligned 0-360 degrees from the central axis, straight ridges, curved ridges, zigzag ridges, crisscross ridges, helical ridges, cylindrical-shaped indentations, spherical-shaped indentations, triangular-shaped indentations, rectangular-shaped indentations, or any pattern that modifies the surface or surface area of the wall thickness 76. The grooves, ridges, or indentations can be of any size, shape, depth, height, or configuration. In another embodiment, a mold 214 can also be used to form or modify the shape of a strut pattern. In an embodiment, the mold 214 walls are smooth to produce a tube 74 having one or more smooth surfaces 70, 72.

FIG. 80 illustrates another embodiment of sizing the tube 74 so that it meets the dimensional requirements of the strut pattern 60 cutting process. In this system, the tube 74 is inserted into a mold 214 while it is positioned on a tubular shaped core 256. The cavity of the mold 242 and the core 256 have low dimension variation and form the tube 74 into a sized-tube 212 shown in FIG. 80 by compressing the wall thickness 76 between the mold's horizontal interior wall 244, vertical interior wall 248, core 256, or combinations thereof. In an embodiment the tube 74 wall thickness 76 is compressed in the mold 214 at a temperature between the glass transition temperature and melting temperature of the material 82. In another embodiment, the tube 74 wall thickness is compressed in the mold 214 at a temperature at or above the melting temperature of the material. In yet one more embodiment, the tube 74 wall thickness 76 is compressed in the mold 214 at a temperature at or below the glass transition temperature of the material 82. In an embodiment the wall thickness 76 of the tube is held in a compressed state using a compressive force 240 against the surface of the cavity's 242 horizontal interior wall 244, core 256, and/or vertical interior wall 248 and cooled until the sized-tube 212 substantially retains its new shape and dimensions. In an embodiment, the sized tube 212 is preferably heated and cooled at a rate allowing the material 82 comprising the wall thickness 76 to at least partially crystallize or re-crystallize so that the wall thickness 76 is comprised material having appropriate stiffness and pliability for the end-use application. In an embodiment, the sized tube 212 is heated and cooled at a rate allowing the material 82 comprising the wall thickness 76 to at least partially amorphisize or re-amorphisize so that the wall thickness 76 comprised of material having appropriate stiffness and pliability for the end-use application. In an embodiment, the sized tube 212 is subjected to uniform or non-uniform heating and uniform or non-uniform cooling so that the wall thickness 76 is comprised of material 82 including at least some deformation induced residual stresses. In an embodiment, the sized tube 212 includes non-uniform wall thickness 76 so that, for example, the wall thickness 76 in one section of the tube 212 is thicker or thinner than in another section of the tube 212. In one embodiment the cooling is applied to the wall thickness 76 by introducing a cooled fluid into the inside of the core 256, in another embodiment the cooling is applied to the wall thickness 76 by cooling the mold 214 wall 244, 248, and in another embodiment the cooling is applied to the wall thickness 76 by a combination of introducing a cool fluid into the inside of the core 256 and by cooling the mold 214 wall 244, 248. In some embodiments one or more vents (not shown) are incorporated in the mold 214 wall 244, 248 to allow any air trapped in compressed void 84 spaces, residual vapors, or volatile materials to escape the wall thickness 76. The sized-tube 212 is removed from the mold 214 for subsequent processing like applying a coating 180 or cutting a strut pattern 60. In an embodiment forging produces the sized-tube 212. The term "forging" refers to a manufacturing process involving the shaping of the wall thickness using localized compressive forces. Forging can occur at any temperature including cold, warm, and hot forging.

In an embodiment of the mold 214, the wall 244,248 and/or core 256 is adapted to include protrusions, indentations, or protrusions and indentations of any size and shape that form a pattern on the outer surface 70 and/or inner surface 72 of the sized-tube 212. These protrusions, for example, can be used to prevent the stent 40 from migrating from the installed position during delivery or to penetrate the anatomical lumen and deliver therapeutic drugs. Likewise, the indentations can, for example, be useful to storing therapeutic drugs or stent location marking materials. These surface modifications can also be useful for strengthening the tube or stent. In one more embodiment of the mold 214, the wall 244, 248 and or core 256 is adapted to produce thru holes in one or more struts 44, 46. Thru holes can also be used to store therapeutic drugs, impart greater flexibility or crack resistance on the stent 40. In another embodiment, the thru holes are added to the wall thickness 76 of one or more struts by cutting the holes in the wall thickness with a laser. In an embodiment, the mold 214 walls are smooth to produce a tube having one or more smooth surfaces 70, 72.

Another embodiment of a tube sizing process that minimizes the dimensional variation of the tube's 74 outer diameter 62, inner diameter 64, wall thickness 76, ovality, or combination thereof consists of using one or more rollers 241 to compress the wall thickness 76 of the tube 74 from a thicker to thinner wall thickness 76 to obtain a sized-tube 212. The surface of the roller or rollers can be smooth or include a pattern such as those examples previously described such as grooves, indentation, protrusions, etc. In an embodiment, the one or more of the rollers 241 includes cutting or grinding means so that when the mandrel 118 rotates or the mandrel 118 and roller 241 rotate the roller 242 trims the excess material 82 for the outer surface 70 of the precursor construct tube 74 to ensure that the tube 74 has low dimensional variation. In the present invention, the roller and mandrel can rotate clockwise, counter clockwise, or combination thereof. Referring to FIG. 100 and FIG. 101, wherein FIG. 100 shows a tube 74 at the start of consolidation and/or sizing process and FIG. 101 shows a tube 74 at the end of the consolidation and/or sizing process, in this embodiment the tube 74 positioned on a rigid cylindrical-shaped mandrel 118 having low dimensional variation is mounted on a rigid stand and a cylindrical-shaped roller 241 is mounted next to the mandrel 118 so that a gap exists between the outside diameter of the mandrel 118 and the outside diameter of the roller 241 that equals the final wall thickness 76 of the sized tube 212. Referring to FIG. 101, in an embodiment, the gap is incrementally reduced by moving the roller 241 closer to the mandrel 118 by distance 239 to gradually consolidate the wall thickness 76 over time. The amount of compression that occurs during consolidation is represented by the wall thickness compression 243 shown in FIG. 100. The mandrel 118 and roller 241 rotate in a clockwise or counter clockwise direction 245 one or more times so that the wall thickness 76 is fully or incrementally compressed to the distance equaling the gap between the mandrel 118 and the roller 241.

Referring to FIG. 81, a precursor construct tube 74 sizing process includes a flat plate 129 having low dimensional variation, a shim 127 having low dimensional variation and a thickness substantially equal to the final wall thickness 76 of the precursor construct tube 74, and a cylindrically shaped mandrel 118 having low dimensional variation. The tube 74 is positioned on the mandrel 118 in the using any process or combination of processes described herein. While the tube 74 is positioned on the mandrel 118, the tube is heated to consolidate the preformed configurations 77 around the outside diameter of the mandrel 118. As mentioned herein, the preformed configurations 77 tend to shrink and form a tight grip around the mandrel 118 during heating which ensures an inner diameter 64 having low dimensional variation. While the preformed configurations 77 are still heated, as shown in FIG. 81 and FIG. 87, the mandrel 118 is rolled one or more times over the surface of the shim 127 so that the outer surface 70 of the precursor construct tube 74 is pressed against the flat plate 129 and the wall thickness 76 is formed into the thickness of the gap between the mandrel 118 and the flat plate 129. After forming the wall thickness 76 to the size of the gap between the mandrel 118 and the flat plate 129, the precursor construct tube 74 is cooled. As described herein, the tube 74 is cooled rapidly to form a more amorphous material 82 or cooled slowly to form a more crystalline material 82. In other embodiments, the tube 74 is cooled rapidly by quenching and then followed by reheating and cooling slowly during a secondary annealing process to modify the morphology of the material 82. The precursor construct tube 74 is removed from the mandrel 118 after processing.

In an embodiment, the compression of the wall thickness 76 occurs at a temperature in the range between the glass transition temperature and the melting temperature of the material or materials 82. In another embodiment, the compression of the wall thickness 76 occurs at a temperature at or above about the melting temperature of the material or materials 82. In one embodiment, the compression of the wall thickness 76 occurs at a temperature at or below about the glass transition temperature material or materials 82. In an embodiment, the surface of the flat plate 129 and/or roller 241 is at a temperature in the range of between about the glass transition temperature and the melting temperature of the material 82 during sizing. In another embodiment, the surface of the flat plate 129 and/or roller 241 is at a temperature at or above about the melting temperature of the material 82. In another embodiment, the surface of the flat plate 129 and/or roller 241 is at a temperature at or below about the glass transition temperature of the material 82.

Figure 103:
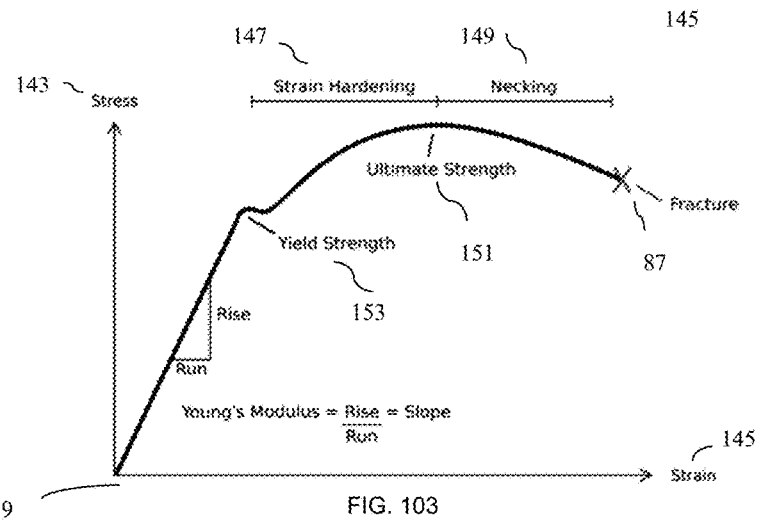

In another embodiment, the wall thickness 76 is partially or fully hot rolled, which is the process of compressing the wall thickness 76 at a temperature at or above about the recrystallization temperature of the material or materials 82. In another embodiment, the wall thickness 76 is partially or fully cold rolled, which is process of compressing the wall thickness 76 at a temperature at or below about the recrystallization of the material or materials 82. In an embodiment wherein the wall thickness 76 is partially or fully comprised of poly (L-lactide) or PLLA, as an example of a DSC thermogram 169 shows in FIG. 106, the glass transition temperature (Tg) 161 of as-polymerized PLLA is about 60-65 degrees Celsius, the melting temperature (Tm) 163 is about 185-195 degrees Celsius, and the crystallization temperature (Tc) 165 is about 90-140 degrees Celsius. However, these temperatures may vary and should be experimentally determined for each material. In another embodiment, the wall thickness 76 is hammered, which is process of compressing the wall thickness 76 comprised of preformed configurations 77 at a temperature at or below or at or above about the recrystallization of the material or materials 82. In another embodiment, the wall thickness 76 is rolled, so that the wall thickness 76 includes strain-hardening 147 of the material or materials 82. Referring to FIG. 103, the terms "strain hardening 147 (aka work hardening or cold working) refers to the process of strengthening the material 82 by plastic deformation. This strengthening occurs because of the dislocation movement and the dislocation generation within the crystal structure of the material 82. In material science, the term "dislocation" refers to a crystallographic defect, or irregularity, within a crystal structure. In another embodiment, the wall thickness 76 is rolled, so that the wall thickness 76 includes strain hardening 147 of the material or materials 82 and the strain-hardened wall thickness 76 is partially or fully annealed to obtain some or full recrystallization to reduce dislocation density. In a more preferred embodiment of an annealed wall thickness 76 comprised of poly (L-lactide), the wall thickness 76 is heated to a temperature between 90-140 degrees Celsius for a period of 0.1-120 minutes, more narrowly 1-60 minutes. In other embodiments, the wall thickness 76 is annealed at higher or lower temperatures for shorter or longer periods of time.

Referring to FIG. 100 and FIG. 101, the wall thickness 76 of the tube 74 is held in a compressed state against the surface of the mandrel 118 and the roller 241 and cooled until the sized-tube 212 substantially retains its new shape and dimensions. Alternatively, referring to FIG. 81, the wall thickness 76 of the tube 74 while positioned on a mandrel 118 having low dimensional variation is rolled on a heated plate 129 to compress the wall thickness 76 to the desired thickness 76 set by shim 127 during consolidating and/or sizing. Any rolling process known by those skilled in the art can be utilized to form or shape the wall thickness 76 of the present invention. Without intent on limiting, the wall thickness 76 can be processed using ring rolling, roll bending, roll forming, profile rolling, foil rolling, and controlled rolling. In an embodiment, the wall thickness 76 is rolled in a mill of any configuration that produces parts as described herein.

The wall thickness 76 is strengthened in other embodiments by using process selected from the group of squeezing, swaging, extrusion, forging, sizing, riveting, staking, coining, peening, burnishing, heading, hubbing, thread rolling, bending, drawing, expanding, compression, flanging, straightening, shearing, slitting, piercing, lancing, perforation, shaving, trimming, dinking, spinning, embossing, stretching, ironing, forming, superplastic forming, or any other process that imparts strain hardening on the wall thickness 76.

Another embodiment of a tube 74 sizing process that minimizes the dimensional variation of the tube's 74 outer diameter 62, inner diameter 64, wall thickness 76, ovality, or combination thereof consists of using the jaws of a crimping machine similar to the one described in U.S. Pat. No. 8,245,559. Crimping equipment is available from Machine Solutions Inc., 2951 W. Shamrell Blvd, Flagstaff, Ariz. 86001 (USA) part numbers HH100/2000, SC100/150, SC500/600, SC700/800, SC7755/875S, SC1775S/1875S, or modified versions thereof or functional equivalents thereof. In this embodiment, a tube 74 is positioned in a radial compression mechanism that clamps the tube 74 while mounted on a mandrel having an outside diameter equal to the inner diameter 64 of the tube 74 so that the outer diameter 62 is reduced from a larger diameter to a smaller diameter. The wall thickness 76 is held in compression until the desired dimensions are achieved. In one embodiment, the compression occurs at a temperature in the range between the about the glass transition temperature and about the melting temperature of the material or materials 82. In another embodiment, the compression occurs at a temperature at or above about the melting temperature of the material or materials 82. In another embodiment, the compression occurs at a temperature at or below about the glass transition temperature of the material or materials 82. In another embodiment, the compression occurs at a temperature in the range between about the crystallization temperature 165 of the material or materials 82. The wall thickness 76 of the tube 74 is held in a compressed state against the surface of the mandrel 118 and the radial compression mechanism and cooled until the sized-tube 212 substantially retains its new shape and dimensions and optimum morphology that provides an appropriate balance between stiffness and pliability for the end-use application.

In an embodiment multiple sizing processes are employed. For example, first the un-sized tube 74 is rolled to consolidate the wall thickness 76 so that it is with +/−50 microns of the finished outer diameter 62. Then the consolidated tube 74 is placed in a mold 214 as previously described to complete the sizing process. By using multiple size modification processes in sequence, a tube 74 can be formed without developing substantial flashing at mold knit lines. The wall thickness 76 can be formed or sized using any combination or combinations of the processes described herein or processes similar to those described herein or that processes that produce a wall thickness 76 having the mechanical or degradative properties described herein.

There are many other embodiments capable of sizing a tube 74 so that it has low dimensional variation. For example, the tube 74 can be passed through a sizing die. Any way of modifying the tube 74 so that it meets the low dimensional variation specified herein is suitable for use in the present invention.

In an embodiment, the tube 74 or sized tube 212 is subjected to deformation by expanding the wall thickness 76 to further enhance its mechanical properties. In an embodiment, the wall thickness 76 is formed by melt processing before radial expansion and/or axial elongation. In an embodiment, the wall thickness 76 is formed by solution processing before radial expansion and/or axial elongation. In an embodiment, the wall thickness 76 is formed by a combination of solution and melt processing before radial expansion and/or axial elongation. By imparting radial expansion and/or axial elongation on the tube 74 or sized-tube 212 provides biaxial or multi-axial orientation around the circumference of the tube and along the longitudinal axis of the tube. This deformation or strain is shown to provide further increase in strength of tube 74 along the axis of deformation. The terms "radial expansion" are defined by the ratio of the inside diameter of the expanded tube 74 divided by the original inside diameter of tube 74. The terms "axial elongation" are defined by the ratio of the length of the elongated tube divided by original length of the tube.

In embodiments, the tube 74 or sized-tube 212 are subjected to radial expansion preferably in the range of 50 percent to 1000 percent, more narrowly in the range of about 100 percent to about 500 percent and axial elongation in the range of 50 percent to 1000 percent, more narrowly in the range of about 10 percent to about 800 percent. In another embodiment, the radial expansion and/or axial elongation is greater than 1000 percent. In an embodiment, the radial expansion and/or axial elongation is less than about 50 percent. A deformed tube 74 or 212 can have any combination of radial expansion and axial elongation within the ranges previously specified. Furthermore, the tube 74 or 212 can have any ratio of radial expansion divided by axial elongation within the ranges of radial expansion and axial elongation specified herein. The tube 74 or sized tube 74 can be radially and/or axially elongated one or more times.

In the present invention, it is preferred that the tubular precursor construct 74 includes a radial expansion ratio and/or axial elongation ratio greater than 1, wherein the radial expansion ratio=expanded inner diameter/original inner diameter and the axial elongation ratio=elongated length/original length. In embodiments, the tube 74 or sized-tube 212 are subjected to radial deformation and/or axial elongation at any rate but preferably in the range of 500 percent/minute to 500 percent/microsecond. In other embodiments, the tube 74 or sized tube 212 is subjected to radial deformation and/or axial elongation at a rate faster than about 500 percent/microsecond. In one more embodiment, the tube 74 or sized tube 212 is subjected to radial deformation and/or axial elongation at a rate slower than 500 percent/minute.

The radial expansion and/or axial elongation of the tubes 74, 212 can occur in a single process, multiple processes, or combined processes. In one embodiment, the temperature during deformation of the tubes 74, 212 is between the glass transition temperature and the melting temperature of the material 82. In another embodiment, the temperature during deformation of the tubes 74, 212 is at or below about the glass transition temperature of the material 82. In yet one more one embodiment, the temperature during deformation of the tubes 74, 212 is at or at or above about the glass transition temperature of the material 82. For tubes 74 or 212 comprised of Poly-L-Lactide (PLLA) the tubes are preferably deformed in a temperature in the range of about 40 to 140 degrees Celsius, more preferably in the range of about 40 to 120 degrees Celsius, and most preferably in the range of about 50-115 degrees Celsius.

In an embodiment, the tubular precursor construct 74 is subjected to deformation by drawing the wall thickness 76 to further enhance its mechanical properties. In an embodiment, the wall thickness 76 is formed by melt processing before drawing. In an embodiment, the wall thickness 76 is formed by solution processing before drawing. In an embodiment, the wall thickness 76 is formed by a combination of solution and melt processing before drawing. In an embodiment, the wall thickness 76 is formed into the shape of a tubular precursor construct 74 by melt and/or solution processing before drawing. In a preferred embodiment, the material 82 comprising the wall thickness 76 has crystallinity below 80% before drawing. In another embodiment, the material comprising the wall thickness 76 has crystallinity at or above 80% before drawing. In an embodiment, the wall thickness 76 is formed into the shape of a tubular precursor construct 74 by melt and/or solution processing by extrusion, molding, or casting before drawing. In an embodiment, the wall thickness 76 is formed of one or more layers of preformed configurations 77 such as films 81, fibers 78, or combinations thereof before drawing. The preformed configurations 77 are positioned in the wall thickness 76 as described elsewhere in this specification. At least partially forming the wall thickness 76 of preformed configurations 77 before drawing in some embodiments includes porosity in the drawn wall thickness 76. In an embodiment, the wall thickness 76 is consolidated before drawing. In an embodiment the wall thickness 76 includes one or more voids 84 before drawing. In an embodiment, the wall thickness 76 is formed into a network before drawing. In an embodiment, the wall thickness 76 is comprised of one or more layers 106 before drawing. In an embodiment, the wall thickness 76 includes one or more seams 125 before drawing. In an embodiment formed by melt processing the one or more materials 82 are melted and extruded through a die into any suitable shape like a precursor construct tube 74. In an embodiment formed by solvent processing, the one or more materials 82 are dissolved in one or more solvents at any material-to-solvent ratio and extruded through a die into any suitable shape like a precursor construct tub 74. The wall thickness 76 configured into a shape like a tube 74 in any configuration described herein can be fed into the drawing process 268 to impart greater molecular orientation on the material 82 comprising the wall thickness 76. By imparting radial compression and/or axial elongation on the precursor construct tube 74 provides biaxial or multi-axial orientation of the material 82 around the circumference of the tube and along the longitudinal axis of the tube. This deformation or strain is shown to provide further increase in strength of tube 74 along the axis of deformation. The terms "draw down ratio" is defined by the ratio of the inside diameter of the drawn tube 74 divided by the original inside diameter of tube 74. The terms "axial elongation" are defined by the ratio of the length of the elongated tube divided by original length of the tube.

Without intent on limiting, FIG. 107A shows in side view and FIG. 107B shows in cross-sectional view through section G-G of FIG. 107A an illustration of an example process 268 for drawing a precursor construct tube 74. The process 268 consists of two mandrels 118', 118" of different diameters, a heating zone 251, a sizing die 255, a cooling zone 253, and two pullers 257', 257". The tube 74' having a starting larger wall thickness 76' and a larger inner diameter 64' is placed on the larger portion of the mandrel 118', the tube 74' is moved under a heating zone 251 in direction 271 wherein the material 82 comprising the wall thickness 76 is conditioned to allow drawing. A tensile force, created by puller 257" advancing the tube 74 from left to right at a faster rate than puller 257', is applied onto the wall thickness 76' while under the heating zone 251 so that when the wall thickness slides off the larger mandrel 118' the inner diameter 64 of the tube 74 and/or the wall thickness 76 are reduced as a result of the tensile force or drawing force. The tensile force created in the wall thickness 76 and temperatures are optimized to create the correct drawing conditions for creating a tube 74 having the desired final diameters 62", 64", final wall thickness 76", and dimension variation. In some embodiments, the drawn tube 74" is formed onto a smaller mandrel 118" having low dimensional variation to facilitate setting the inner diameter 64 and/or passing the outer diameter 62 through a sizing die 255 having low dimensional variation to facilitate setting the outer diameter 62" to achieve the tube's optimum dimensions before and/or during movement through the cooling zone 253. In an embodiment, the orifice 270 of the sizing die 255 is tapered so that the entrance diameter is larger than the exit diameter. In an embodiment, the orifice 270 of the sizing die 255 is not tapered. In an embodiment, the sizing die 255 is positioned nearby where the tube 74 diameter is reduced from a larger diameter to a smaller diameter to assist with the drawing process. In an embodiment, the sizing die 255 is positioned downstream from the tube 74 size reduction location. To minimize drag of the drawn tube on the smaller diameter mandrel 118", the length of the smaller diameter mandrel 118" only needs to be sufficient to form the inner diameter 64 of the tube 74 as it cools and solidifies. In an embodiment, the outer diameter 62 is controlled during heating, drawing, cooling or combinations thereof. In an embodiment, the inner diameter is controlled during heating, drawing, cooling, or combinations thereof. In an embodiment, the outer diameter 62 and the inner diameter 64 are controlled during heating, drawing, cooling, or combinations thereof. In an embodiment, one or more lubricants and/or nonstick surfaces are positioned between the inner diameter 64 of the tube 74 and the outer diameter of the mandrel 118 are used to facilitate moving the tube 74 over the mandrel or mandrels 118. In an embodiment, the tube 74 is drawn down from a larger size to a smaller size multiple times. In an embodiment, the tube 74 is drawn down from a larger size to a smaller size multiple times wherein the tube 74 is thermally treated between draw down operations to improved ductility of the tube prior to the two or more secondary draw down operations. In an embodiment, the tube 74 is drawn down and thermally treated to increase the crystallinity of the wall thickness 76.

Again without intent on limiting, FIG. 108 shows an illustration of another example process 268 for drawing a precursor construct tube 74. The process 268 consists of a sizing die 255 wherein the orifice 270 of the sizing die 255 is tapered so that the diameter of the orifice 270 is larger at the entrance and smaller at the exit of the sizing die 255. The draw down angle 269 of the sizing die 255 can range from 0-90 degrees from the central axis 42 of the tube 74. As shown in FIG. 108, in an embodiment the tube 74 having a larger outer diameter 62' and thickness 76' is inserted into the larger orifice 270' of the sizing die 255 and pushed, pulled, or pushed and pulled through the sizing die 255 wherein the outer diameter 62" of the tube is reduced and the wall thickness 76" of the tube 74" is reduced. In an embodiment the tube 74 having a larger outer diameter 62' and thickness 76' is inserted into the larger orifice 270' of the sizing die 255 and pushed, pulled, or pushed and pulled through the sizing die 255 wherein the outer diameter 62" of the tube is reduced and the wall thickness 76" of the tube 74" remains substantially the same as the starting thickness 76'. In an embodiment the tube 74 having a larger outer diameter 62' and thickness 76' is inserted into the entering orifice 270' of the sizing die 255 and pushed, pulled, or pushed and pulled through the sizing die 255 wherein the outer diameter 62" of the tube is substantially the same as the starting outer diameter 62' and the wall thickness 76" of the tube 74" is reduced. In one embodiment, the tube 74 is cold drawn through the die. In another embodiment, the tube 74 is hot drawn through the die. A similar process 268 can be used to produce drawn films or sheets by substituting the circular shaped orifice with a rectangular shaped orifice. Likewise, a similar process 268 can be used for producing rods of material 82. In an embodiment, the tube 74 is drawn down from a larger size to a smaller size multiple times by, for example, passing the tube 74 through multiple dies 255 sequentially that have smaller and smaller orifices 270.

In an embodiment wherein the application requires the wall thickness 76 in a film or sheet 196 configuration, the wall thickness 76 is drawn using a process 268 like the example shown in FIG. 109. The drawing process 268 consists of an unwind roll 259 that stores and dispenses the starting film or sheet 196' into the process, a heated section 251, a cooling section 253, a slower rotating drive roll 263, a series of faster rotating drive rolls 267, a series of idling rolls 265 that rotate at a speed that does not impart tension on the sheet 196, and a take-up roll which collects and stores the drawn film or sheet 196". The sheet 196' entering the process 268 has a thicker wall thickness 76' and a shorter length 205'. The sheet 196 enters the heated area over the idle roller 265 and over a slower rotating drive roll 263 which starts pulling the sheet 196 through the process. After leaving the slower rotating drive roll 263 the sheet 196 passes over an another idle roller 265 and then over a faster rotating drive roll 267 so that the sheet 196 while in the heated section is placed in tension so that it is drawn to a thinner wall thickness 76 "and longer length 205". The drawn sheet 196" then passes over a series of drive rolls 267 and idle rolls 265 that maintain the drawn sheet 196" in a substantially constant amount of tension through the remaining portion of the heated zone 251 and the cooling zone so that the optimum oriented molecules and morphology of the drawn wall thickness 76" are maintained before collection of the drawn sheet 196" on the take-up roll 261. In the sheet 196 drawing process 268 of the present invention there can be any number of slower rotating drive rolls 263, faster rotating drive rolls 267, and idle rollers 265 that produce a wall thickness 76 meeting the specifications described herein. In an embodiment, the wall thickness 76 in the form of a sheet 196 includes bi-axial or multi-axial stretching by drawing the sheet 196 in the transverse and machine direction as described under the film section herein. Moreover, the heating zone 251 and cooling zone 253 can be of any length that produces a wall thickness 76 meeting the specifications described herein.

In a preferred embodiment, the wall thickness 76 is heated to a temperature between about the glass transition temperature and the melting temperature of the material 82 during drawing. In an embodiment, the wall thickness 76 is heated to a temperature at or below about the glass transition temperature of the material 82 during drawing. In an embodiment, the wall thickness 76 is heated to a temperature at or above about the melting temperature of the material 82 during drawing. In an embodiment, the wall thickness 76 or tubular precursor construct 74 includes any draw down ratio and/or axial elongation ratio greater than 1, wherein the draw down ratio=starting inner diameter/drawn inner diameter and the axial elongation ratio=drawn down length/ starting length. In a more preferred embodiment, the draw down ratio is between 1 and 20. In a preferred embodiment, the draw down ratio is at or greater than 20. In an embodiment, the wall thickness 76 is drawn at a rate of about 0.005 millimeters/second to 50 centimeters/second. In an embodiment, the wall thickness 76 is drawn at a rate at or below about 0.005 millimeters/second. In an embodiment, the wall thickness 76 is drawn at a rate at or above about 50 centimeters/second. In an embodiment, the wall thickness 76 is held at a substantially constant tension for a sufficient time during heating and cooling to maintain the drawn configuration, achieve the optimum crystallinity, or combinations thereof. The terms "draw down ratio" refer to the ratio of the tube 74 inner diameter 64 before drawing to the tube 74 inner diameter 64 after drawing (draw down ratio=inner diameter (before drawing) 64 divided by inner diameter (after drawing) 64 or to the sheet 196 thickness 93 before drawing to the sheet 196 thickness 93 after drawing (draw down ratio=thickness (before drawing) 93 divided by thickness (after drawing) 93). For a wall thickness 76 comprised of poly-L-lactide, in an embodiment the preferred draw down ratio is in the range of 1 to 20, more narrowly 4 to 12. For a wall thickness 76 comprised of poly-L-lactide, in an embodiment the preferred drawing temperature is in the range of 40-160 degrees Celsius, more narrowly 60-120 degrees Celsius. For a wall thickness 76 comprised of poly-L-lactide, in an embodiment the preferred as-polymerized molecular weight is above 200,000 g/mol, more preferably above 670,000 g/mol, and most preferred above 1,300,000 g/mol. For preservation of molecular weight, in an embodiment the wall thickness 76 is drawn in an inert atmosphere like nitrogen. In an embodiment, the wall thickness 76 was dried as described herein before drawing. Furthermore the tube 74 or 212 can have any ratio of radial compression divided by axial elongation within the ranges of radial compression and axial elongation specified herein.

Strut Pattern Cutting Process

In an embodiment, the cutting of the material 82 from the wall thickness 76 of the precursor construct tube 74 or sized tube 212 removes sections of the wall thickness 76 in the shape of a closed cell 86 as an example is shown in FIG. 42. In another embodiment, the stent 40 wall thickness 76 includes open cells 88. In an embodiment, the stent 40 wall thickness 76 includes open 88 and closed cells 86. A closed cell 86 is completely surrounded by one or more struts 44,46 and one or more struts 44,46 incompletely surround an open cell 88.

In an embodiment a pattern of struts 44, 46 is formed on the un-sized tube 74, consolidated tube, or sized-tube 212 by removing portions of the wall thickness 76 by chemical etching, mechanical cutting, or laser cutting material away from the tube 74 wall thickness 76. Representative examples of lasers that may be used include without limitation excimer, carbon dioxide, YAG, diode lasers, ultra short pulse lasers, Er/YB-doted cw fiber lasers, pulsed Nd:YAG lasers, athermal ablation, femto second laser, lasers which emit optical pulses with a duration at or below 1 ps, bulk lasers (pulses with durations between 30 fs and 30 ps, fiber lasers, dye lasers, semiconductor lasers, color center lasers, free electron lasers, solid state lasers, and ultra fast lasers. Athermal ablation or other cutting equipment suitable for manufacturing scaffold 40 of the present invention is available from Raydiance, 2199 S. McDowell Boulevard, Petaluma, Calif. 94954, USA, or Rofin-Sinar Laser GmbH, Berzeliusstrabe 87, 22113, Hamburg or Peterbrunner Str. Lb, 82319, Starnberg, Germany. In an embodiment, the outer surface 70 precursor construct tube 74 is smooth and in another embodiment the outer surface 70 is rough. In an embodiment, one or more layers of the coating 180 are applied to the outer surface of the precursor construct tube 74 prior to cutting the strut pattern 60 into the wall thickness 76 to provide a substantially smooth surface for feeding the tube 74 through a cutting process such as a laser. In another embodiment, the outer surface 70 is treated or coated with a solvent or other surface treatment to increase the smoothness of the outer surface 70. A smooth outer surface 70 on a tube 74 having low dimensional variation facilitates the strut pattern 60 cutting process by enabling the tube 74 to be more accurately moved under for example, a laser, as the strut pattern 60 is cut in the wall thickness 76.

Referring to FIG. 2, the strut is comprised of an outer surface 70, an inner surface 72, and two cutting edges 182. Using point 249 that lies at the intersection of the outer surface 70 and the cutting edge 182 as a reference, there is an angle 181 that defines the cutting angle into wall thickness 76. The cutting edge 182 extends between the outer surface 70 and the inner surface 72 of the tube 74 and can be of any angle or curvature. In one embodiment, the cutting edge is perpendicular to the outer surface 70 of the tube 74 as shown in FIG. 2 as line 183. In another embodiment, the angle 181 is between negative 45 degrees to positive 45 degrees from the line 183 as shown by line 182' and line 182". In one more embodiment, the angle 181 is less than negative 45 degrees. In one more embodiment, the angle 181 is greater than positive 45 degrees.

After forming the tubular precursor construct tube 74 as described herein, sections of the wall thickness 76 are cut away, leaving stent struts 44, 46 having the pattern 60 shown in FIG. 42. The remaining struts 44, 46 have a wall thickness 76 comprised of fibers 78, 80. The strut pattern 60 is illustrated in a planar or flattened view for ease of illustration and clarity, and is representative of the pattern of struts before the stent 40 is crimped or after the stent 40 is deployed. In some embodiments, however, the strut pattern 60 changes after the stent 40 is deployed because the material 82 undergoes plastic deformation during deployment because the stent 40 is expanded beyond the original outer diameter 62 to the extent that plastic deformation occurs and the stent 40 does not revert back to its original size when the balloon catheter is retracted. The strut pattern 60 actually forms a tubular stent structure, as shown in FIG. 1, so that line C-C is parallel to the central axis 42 of the stent 40. FIG. 1 shows the stent in a state prior to crimping or after deployment. As can be seen from FIG. 1, the stent 40 comprises an open framework of struts that define a generally tubular body.

As shown in FIG. 42, the strut pattern 60 includes various struts 44, 46 oriented in different directions and openings 48 between the struts. Each opening and the struts 44, 46 immediately surrounding the opening defines a closed cell 86. At the proximal 52 and distal 54 ends of the stent 40, an optional marker strut 154 includes depressions, blind holes, or through holes adapted to hold a radiopaque marker that allows the position of the stent 40 inside of a patient to be determined. One of the closed cells 86 is shown with cross-hatch lines to illustrate the shape and size of the cells.

The strut pattern 60 is illustrated with a bottom edge 156 and a top edge 158. On the stent 40, the bottom edge 156 meets the top edge 158 so that line D-D forms a circle around the stent central axis 42. In this way, the strut pattern 60 forms sinusoidal hoops or rings 58 that include a group of struts arranged circumferentially. The rings 58 include a series of crests 160 and troughs 162 that alternate with each other. All points on the outer surface of each ring 58 are at the same or substantially the same radial distance away from the central axis 42 of the stent 40.

In an embodiment, the stent 40 preferably has a stent-to-anatomical lumen coverage in the range of about less than ninety-nine percent, more preferably in the range of about one to forty-five percent, and most preferably less than about thirty-five percent or whatever is experimentally determined to be the optimum stent-to-anatomical lumen coverage for the end-use application determined by those skilled in the art.

Still referring to FIG. 42, the rings 58 are connected to each other by another group of link struts 46 that have individual lengthwise axes parallel or substantially parallel to line C-C. The rings 58 are capable of being collapsed to a smaller diameter during crimping and expanded to their original diameter or to a larger diameter during deployment in a vessel.

Figure 43:
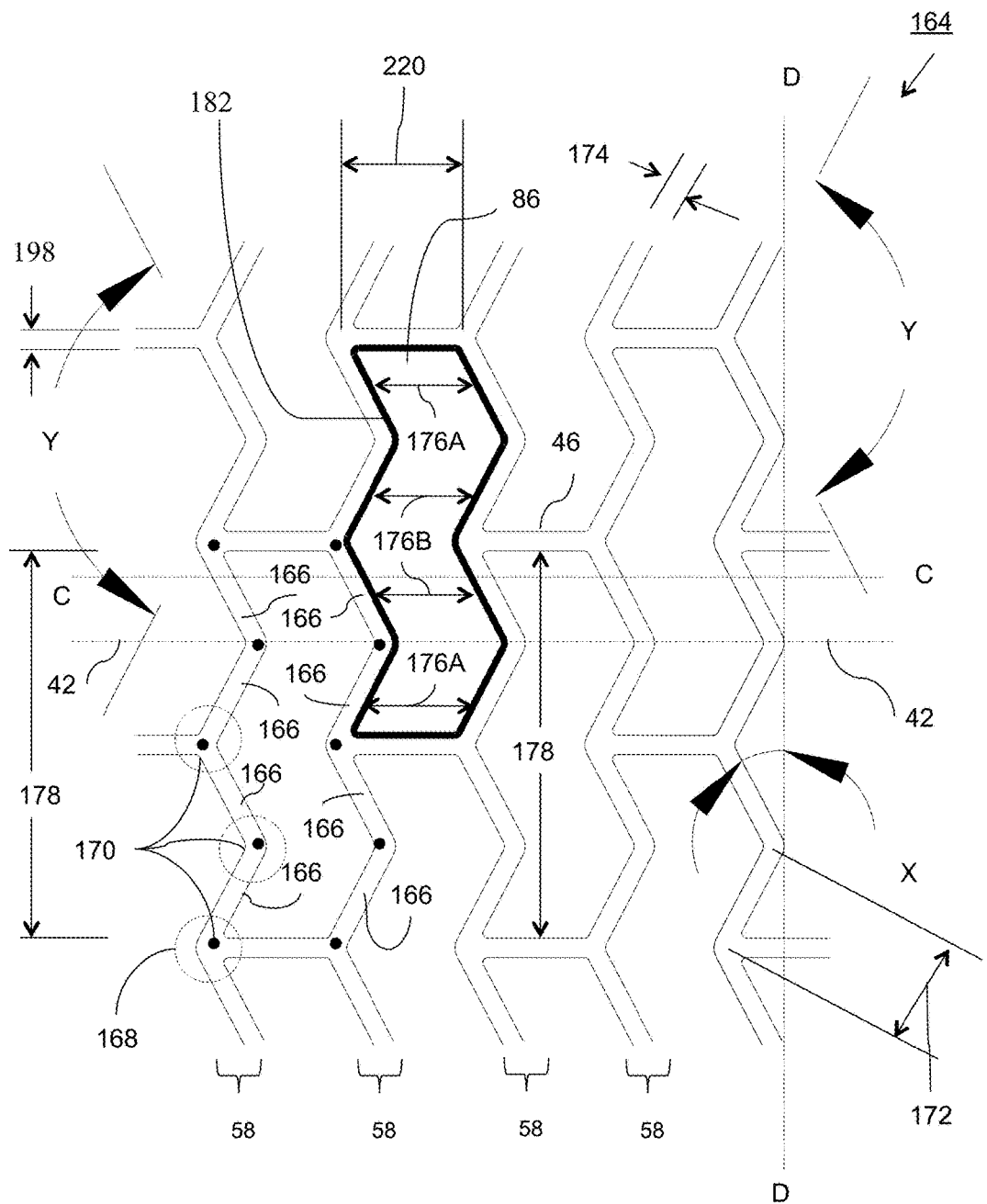
FIG. 43 is a detailed view of an intermediate portion of the strut pattern of FIG. 42.

FIG. 43 shows a detailed view of an intermediate portion 164 of the strut pattern 60 of FIG. 28. The intermediate portion 164 is located between the distal 54 and proximal 52 end rings of the stent. The rings 58 include linear ring struts 166 and curved hinge elements 168. The ring struts 166 are connected to each other by the hinge elements 168.

The hinge elements 168 are adapted to flex, which allows the rings 58 to move from a non-deformed configuration to a deformed configuration. As used herein in connection with the strut pattern 60, "non-deformed configuration" refers to the state of the rings prior to being crimped to a smaller size for delivery through an anatomical lumen. As used herein in connection with the strut pattern 60, "deformed configuration" refers to the state of the rings upon some type of deformation, such as crimping or deployment to a size smaller or greater than the original size prior to crimping.

Still referring to FIG. 43, line D-D lies on a reference plane perpendicular to the central axis 42. When the rings 58 are in the non-deformed configuration, as shown in FIG. 43, each ring strut 166 is oriented at a non-zero angle X relative to the reference plane. The non-zero angle X is between 20 degrees and 30 degrees, and more narrowly at or about 25 degrees. In other embodiments, the angle X can have other values.

Also, the ring struts 166 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the stent is deployed. Having the interior angle be less than 180 degrees allows the stent to be crimped while minimizing damage to the stent struts during crimping, and may also allow for expansion of the stent to a deployed diameter that is greater than its initial diameter prior to crimping. In other embodiments, the interior angle Y can have other values.

While continuing to refer to FIG. 43, the stent 40 also includes link struts 46 connecting the rings 58 together. The link struts 46 are oriented parallel or substantially parallel to line C-C and the central axis 42. The ring struts 166, hinge elements 168, and link struts 46 define a plurality of closed cells 86. The boundary or perimeter of one closed cell 86 is darkened in FIG. 43 for clarity. Except for those positioned on the ends of the stent 40, each of the closed cells 86 is immediately surrounded by six other closed cells 86, meaning that the perimeter of each closed cell 86 merges with a portion of the perimeter of six other closed cells 86. Each closed cell 86 abuts or touches six other closed cells 86 except for those positioned on the proximal and distal ends, which only abut or touch four other closed cells 86. In other embodiments, the close cell 86 or open cell 88 can be surrounded by more or less other closed or open cells.

Still referring to FIG. 43, the perimeter of each closed cell 86 includes eight of the ring struts 166, two of the link struts 46, and ten of the hinge elements 168. Four of the eight ring struts form a proximal side of the cell perimeter and the other four ring struts form a distal side of the cell perimeter. The opposing ring struts on the proximal and distal sides are parallel or substantially parallel to each other. In other embodiments, there can be more or less ring struts 166, link struts 46, or hinge elements 168.

Within each of the hinge elements 168 there is an intersection point 170 toward which the ring struts 166 and link struts 46 converge. There is an intersection point 170 adjacent each end of the ring struts 166 and link struts 46. A radius is preferably located near the junction of a ring strut 166 and a ring strut 166 and a ring strut 166 and link strut 46 to minimize stress concentration or crack initiators during crimping and deployment. Distances 172 between the intersection points adjacent the ends of rings struts 166 are the same or substantially the same for each ring strut 166 in the intermediate portion 164 of the strut pattern 60. The distances 220 are the same or substantially the same for each link strut 46 in the intermediate portion 164.

In an embodiment for use in a vascular stent, the ring struts 166 have widths 174 that are uniform in dimension along the individual lengthwise axis of the ring strut. The ring strut widths 174 are between 0.07 mm and 0.30 mm, and more narrowly at or under about 0.200 mm. The link struts 46 have widths 198 that are also uniform in dimension along the individual lengthwise axis of the link strut. The link strut widths 198 are between 0.07 mm and 0.300 mm, and more narrowly at or under about 0.200 mm. The ring struts 166 and link struts 46 have the same or substantially the same thickness 76 (FIG. 2) in the radial direction, which is between 0.08 mm and 0.250 mm, and more narrowly at or under about 0.200 mm.

As shown in FIG. 43, the interior space of each closed cell 86 has an axial dimension 176 parallel to line C-C and a circumferential dimension 178 parallel to line D-D. The axial dimension 176 is constant or substantially constant with respect to circumferential position within each closed cell 86 of the intermediate portion 164. That is, axial dimensions 176A adjacent the top and bottom ends of the cells 86 are the same or substantially the same as axial dimensions 176B further away from the ends. The axial and circumferential dimensions 176, 178 are substantially the same among the closed cells 86 in the intermediate portion 164.

It will be appreciated that FIG. 42 that the strut pattern 60 for a stent 40 that comprises linear ring struts 166 and linear link struts 46 is formed from a tube 74 comprised of a wall thickness 76 including one or more layer of preformed configurations such as fibers 78, film 81, or combinations thereof. The ring struts 166 define a plurality of rings 58 capable of moving from a non-deformed configuration to a deformed configuration. Each ring 58 has a center point, and at least two of the center points of the adjacent rings define the stent 40 central axis 42. The link struts 46 are oriented parallel or substantially parallel to the stent 40 central axis 42. The link struts 46 connect the rings 58 together. The link struts 46 and the ring struts 166 define closed cells 86 or openings 48. Each closed cell 86 abuts other closed cells.

The ring struts 166 and hinge elements 168 on each ring 58 define a series of crests 160 and troughs 162 (FIG. 42) that alternate with each other. Every other crest 160 on each ring 58 is connected by one of the link struts 46 to another crest on an immediately adjacent ring, thereby forming an arrangement of the closed cells. An example of stent 40 having a wall thickness 76 formed of preformed configurations 77 wherein a strut pattern 60 has been cut in the wall thickness 76 is shown in FIG. 99.

In other embodiments, adjustments to the above specified strut pattern 60 design may be made to compensate for unique characteristics of materials 82 used to construct the stent 40, manufacturing processes used to produce the stent 40, end-use application, or equipment utilized to deploy the stent 40. For example, in another embodiment of the stent 40 the perimeter of closed cell 86 may include a discontinuity to make the cell an open cell 88 (not shown). In an embodiment, some or all of the ring struts 166 or link struts 46, are equal in length, width, or thickness. In an embodiment, some or all of the ring struts 166 or link struts 46, unequal in length, width or thickness. In other embodiments some or all the crests 160 may be connected to some or all the troughs 162 of adjacent rings 58 with link struts 46, some or all the crests 160 may be connected to some or all the crests 160 of adjacent rings 58 with the link struts 46, some or all the troughs 162 may be connected to some or all the troughs 162 of adjacent rings 58 with the link struts 46, or combinations thereof. In yet more embodiments some or all the ring struts 166 or link struts 46 many include curved or bent portions. Moreover, in other embodiments some or all of the ring struts 166, link struts 46, or hinged elements 168 may include one or more features such as and without limitation indentations, radii, grooves, cuts, and other features that enhance operability during crimping and deployment. In another embodiment the shape of the cells 88, 86 are a mixture of different shapes and configurations. In one more embodiment there can be more or less than eight ring struts 166 and more or less than two link struts 46 to form cells 88 or 86. In yet one more embodiment, the size and shape of the cells 88, 86 vary in different portions of the strut pattern 60. For example, the cells 88,86 are different near the proximal and distal ends than near the central portion of the stent 40. And, in other embodiments the width 174, 198 and thickness 76 of the ring struts 166 and link struts 46 vary in one or more portions of the stent 40. In an embodiment, the thickness 76 of the stent 40 is thinner in one or more portions of the stent 40 such as thinner near the proximal and distal ends than near the center portion of the length 50 so that stress concentrations do not develop at the intersection of the stent and the lumen.

In an embodiment, heat is present during the cutting of the strut pattern 60. In an embodiment, little or no heat is present during the cutting of the strut pattern 60. In an embodiment as shown in FIG. 42 and FIG. 43, the strut pattern 60 in an embodiment includes a thermal fusion between some or all of the ends of the preformed configurations 77 at the location wherein the wall thickness 76 is cut or removed from the tube 74, 212. At the cutting edges 182 there is sometimes sufficient heat generated during cutting that the ends of the preformed configurations located at the cutting edges 182 are at least partially thermally fused together to connect the severed ends of the fibers in the wall thickness 76 at the juncture between the struts 44, 46 and the openings 48. Care is taken to ensure the heat generated during cutting is sufficient to weld or fuse the edges together but does not excessively melt, degrade, or distort the material 82 comprising the struts 34, 46. For easy identification of the cutting edges 182, the lines illustrating the cutting edges are shown in bold in FIG. 42 and FIG. 43. In another embodiment, the cutting edges 182 do not include thermal fusion between the fibers 78.

The struts 44,46 are of any shape, width, cross section, or thickness that enables the stent 40 to have the functionality described herein. For example, and without intent on limiting, the cross sectional shape of the struts 44, 46 is a circle, oval, crescent, curved triangle, quatrefoil, parallelogram, square, rectangle, trapezoid, trapezium, triangle, kite, rhombus, pentagon, hexagon, heptagon, octagon, nonagon, decagon, or star shape. In some embodiments the cross section of the struts 44, 46 includes one or more void 84 spaces between the preformed configurations 77 or within the cross section of the wall thickness 76.

FIG. 99 is a photograph of a stent 40 including a strut pattern 60 cut into a wall thickness 76 of a tube 74 having a wall thickness 76 comprised of preformed configurations 77. The strut pattern 60 was cut with a Rofin FemtoFX (available from Rofin-Basel Lasertech GmbH, Starnberg, Germany). If necessary the stents 40 are finished by deburring or polishing operations.

Surface Treatment Process

In an embodiment, some or all the surfaces 70, 72, 96, 104, 117, 105, 221, 227, 182 include one or more surface treatments.

In an embodiment, some or all the surfaces include a treatment comprised of a flame or corona treatment. Flame or corona treatment modifies the surface of the material 82 to, for example, improve adhesion of other films, fibers, coatings, or other materials, or in some case improve biocompatibility. In an embodiment, some or all the surfaces include one or more acid treatments. In an embodiment, some or all the surfaces include one or more sulfuric acid treatments. In an embodiment some or all the surfaces include one or more perchloric acid treatments. In an embodiment some or all the surfaces include one or more potassium chlorate treatments. In an embodiment, one or more include one or more potassium hydroxide treatments. In an embodiment, one or more surfaces include one or more hydrochloric acid treatments. In an embodiment one or more surfaces include one or more ultra dry petroleum ether treatments. In an embodiment, one or more surfaces include a treatment with one or more agents that modify the carbon/oxygen ratio. In an embodiment, one or more surfaces include a treatment with one or more agents that generate oxygen in the form of hydroxyl form. In an embodiment, one or more surfaces include a formalin-fixed paraffin-embedding (FFPE) treatment. In an embodiment one or more surfaces include an ultraviolet light treatment. In an embodiment, one or more surfaces include one or more ozone treatments. In an embodiment, one or more surfaces include a chromic acid treatment. In an embodiment, one or more surfaces include treatment with agents that produce hydroxyl, aldehyde, carboxyl, or other enhancing groups on the surface. In an embodiment one or more surfaces include a treatment comprised of one or more charged groups that are anions. In an embodiment, the one or more surfaces include a treatment with one or more cations. In an embodiment the one or more surfaces include a treatment with one or more serums. In an embodiment the one or more surfaces include a treatment with one or more proteins. In an embodiment, the one or more surfaces are treated with one or more oxidizing agents. In an embodiment, the one or more surfaces are treated with one or more treatments of radiation. In other embodiments, the material 82, stent 40, preformed configurations 77, or combinations thereof have any surface modification that improves patency. Without intent on limiting, in other embodiments, the surface modifications includes modifying the surface tension, surface energy, increasing or decreasing the surface charge density, charge, hydrophobicity, hydrophilicity, wettability, polylysine coating, agents that enhance cell or tissue culture growth, or any combinations thereof.

Coating Process

In an embodiment, some or all the surfaces 70, 72, 96, 104, 117, 105, 221, 227, 182 include one or more coatings 180. In an embodiment, the one or more coatings 180 are rigidly affixed to the one or more surfaces of the wall thickness 76. In an embodiment, the one or more coatings 180 are not rigidly affixed to the one or more surfaces of the wall thickness 76. In an embodiment, the coating 180 is permeable. In an embodiment, the coating 180 is impermeable. In an embodiment, the one or more coatings 180 substantially conform to the wall thickness 76. The coating 180 is applied to the wall thickness 76 using any process known by those skilled in the art of coating. The thickness of the coating 180 preferably ranges from 50 nanometers to 0.030 millimeters. In other embodiments the coating 180 thickness is thicker or thinner.

As shown in FIG. 40, which is a cross-sectional view of strut a 44, 46 of stent 40, in an embodiment the struts include one or more layers of a coating 180. The coating or coatings 180 are positioned on the outer surface 70, inner surface 72, cutting edges 182, void 84 or combinations thereof. In other embodiments, the coating or coatings 180 are positioned on the outside surface of one or more preformed configurations 77 such as fibers 78 (FIG. 29), on the outside surface of one or more multi-fibers 80 (FIG. 30), on the outside surfaces of one or more films 81, on the outside surfaces of one or more multi-films 79, on the outside surface of one or more sheets 196; on the outside surface of one or more multi-sheets 209; or combinations thereof.

The one or more coatings 180 serve a variety of functions including: (1) storage of active ingredients such as a drug; (2) delivery of an active ingredient such as a drug after deployment; (3) controlled release of an active ingredient such as a drug after deployment; (4) controlled onset of degradation of material 82 (e.g., lengthen time to loss of strength); (5) controlled onset of resorption or rate of resorption of material 82 (e.g., lengthen time to loss of mass); (6) improved storage stability; (7) improving visibility or radiopacity/radiodensity of the wall thickness 76 after deployment; or (8) combinations thereof. One additional purpose of the coating 180 is to improve the patency of the lumen after deployment of the stent 40.

The coating or coatings 180 of the present invention can be any surface modification of the wall thickness 76, stent 40, struts 44, 46, preformed configurations 77, film 79, 81, cutting edges 182, fibers 78, 80, or combinations thereof that meet the performance specifications described herein. Without intent on limiting useful materials for use as a coating 180 in the present invention can be selected from the group of: acrylate-based, acrylic, alkyds, alginates, amorphous polymers, C10 polymer, C19 polymer, C19 polymer with hydrophobic and hydrophilic polyvinyl-pyrrolidinone groups, collagen, crystalline polymers, crystalline materials, epoxy-based, ethylene co-polymers, fluropolymers, heparin, high molecular weight polymers, hydrophilic materials, hydrophobic materials, hydrocolloids, hydroxyapatite, hydrophilic polyvinyl-pyrrolidinone, hydrophobic hexyl methacrylate, hydrogels, hydrophobic hexyl methacrylate and hydrophilic vinyl pyrrolidinone and vinyl acetate monomers, hydrophobic butyl methacrylate, lactide-based materials, light curing materials, low molecular weight polymers, lubricious materials, parylene, materials 82 listed herein, materials having glass transition temperature less than 40 degrees centigrade, materials having a glass transition temperature at or above 40 degrees centigrade, modified derivatives of caprolactone polymers, moisture curing materials, olefins, oxides, photo-curable hydrogels, phosphorylcholine, polyacrylates, polyalkelene esters, polyamides, polyamides esters, poly (n-butyl methacrylate), polycaprolactone, poly (ε-caprolactone), polyethylene glycol, poly-DL-Lactide, poly (L-lactide)/poly (butylene succinate-co-L-lactate) blends, poly trimethyl carbonate, polyesters, poly (ethylene succinate), polyhydroxyalkanoates, poly-L-lactide, poly (L-lactide), poly (D-lactide), poly (DL-lactide), DL-lactide/glycolide copolymer of any monomer ratio, polyglycolide, L-lactide/D-lactide copolymers of any monomer ratio, L-lactide/DL-lactide copolymers of any monomer ratio, povidone-iodine (PVP-I), any chemical complex of polyvinylpyrrolidone and elemental iodine, any polymer and radiopaque materials, lactones, L-lactide copolymers, L-lactide/glycolide copolymers of any monomer ratio, L-lactide/ε-caprolactone copolymers of any monomer ratio, polymers having degradation time 0.5 months to 48 months, polymers having degradation time less than 0.5 months, polymers having degradation time greater than 48 months, biodegradable polymers having molecular weight (Mw) 10 kg/mol to 200 kg/mol, biodegradable polymers having molecular weight (Mw) less than 10 kg/mol, biodegradable polymers having molecular weight (Mw) greater than 200 kg/mol, any material that temporarily prevents the substantial penetration of water from the area of the anatomical lumen to the material 82 comprising the wall thickness 76, any material that prevents the substantial penetration of water from the area of the anatomical lumen into the material 82 comprising the wall thickness 76 for a period of time less than 6 months, any material that prevents the substantial penetration of water from the area of the anatomical lumen into the material 82 comprising the wall thickness 76 until the material preventing the penetration is partially or fully eliminated from the surface of the wall thickness by biological means, any material that temporarily controls the penetration of water from the area of the anatomical lumen into the material 82 comprising the wall thickness 76, any material that controls the substantial penetration of water from the area of the anatomical lumen into the material 82 comprising the wall thickness 76 for a period of time less than 6 months, any material that increase the storage stability of the wall thickness 76 at ambient storage conditions, any material that increases the storage stability of the wall thickness at temperatures above 23 degrees Celsius, any material that increases the storage stability of the wall thickness at a relative humidity above 30% relative humidity, any materials that affect the pH of the area nearby the place of deployment of the wall thickness in the anatomical lumen at or below about 7.4 pH, materials that affect the pH of the area nearby the place of deployment of the wall thickness in the anatomical lumen above about 7.4 pH, poly (butylene succinate) (PBS), polycaprolactone copolyglycolic acid, polycaprolactone glycerylmonostearate, polysaccharides, polytrimethylene carbonate, polyethylene co-vinyl acetate, polyolefins, polyvinyl pyrrolidinone (PVP), polyvinyl alcohols, polyethylene glycol, polyvinyl esters, proteins, styrene-based, starch acetate, styrene isoprene butadiene (SIBS) Block copolymers, terminal diols, urethane-based, vinyl-based, wax, carnauba wax, beeswax, animal waxes, vegetable waxes, mineral waxes, synthetic waxes, petroleum waxes, homopolymers, co-polymers thereof, terpolymers thereof, complexes thereof, combinations thereof, derivatives, analogs, and functional equivalents.

In some embodiments surface treatments or primers are utilized to improve adhesion to surfaces. The previously mentioned coatings materials 180 are also useful to produce binder 108. In an embodiment of the coating 180, one or more of the coating materials are dissolved in a solvent to produce a liquid coating 180 that is applied to the stent 40, and the solvent evaporates upon deposition of the coating 180 on the stent 40 leaving the dried coating 180 material on the stent 40. In an embodiment of the coating 180, one or more of the coating materials are emulsified in a liquid carrier to produce a liquid coating 180 that is applied to the stent 40, and the liquid carrier evaporates upon deposition of the coating 180 on the stent 40 leaving the dried coating 180 material on the stent 40.

In the preferred embodiments, the controlled release coatings 180 are comprised of copolymers of DL-Lactide and glycolide (aka Poly (DL-Lactide-co-Glycolide) or poly (DL-Lactide). In the preferred controlled release embodiments, the one or more coatings 180 have an IV ranging from about 0.1-1.5 dl/g, a molecular weight ranging from about 5-200 kg/mol, and a degradation time ranging from 0.1 months to 24 months. In other embodiments, the controlled release coatings 180 have higher or lower IV, molecular weight, and degradation time. In an embodiment, a homopolymer of α-caprolactone is useful as a coating 180 to delay the onset of degradation or hydrolysis of the stent 40.

Any coating 180 that has a degradation time greater than the materials 82 comprising the wall thickness 76 is useful in delaying the onset of degradation or hydrolysis of the stent 40. In another embodiment, a coating 180 that slows down the uptake of water into the wall thickness 76 of the stent 40 or modifies the pH of the wall thickness 76 is useful for delaying or slowing the loss of strength of the stent 40 under anatomical conditions. In an embodiment, the one or more moisture barrier or retarding coatings 180 that delay the onset of degradation, hydrolysis, or loss of strength is comprised of one or more materials having a moisture vapor transmission rate (also known as water vapor transmission rate) of between 0.10 $g/h/m^2$ to 10 $g/h/m^2$, more narrowly 0.6 to 5 $g/h/m^2$. In an embodiment, the one or more moisture barrier or retarding coatings 180 that delay the onset of degradation, hydrolysis, or loss of strength is comprised of one or more materials having a moisture vapor transmission rate of at or less than 0.10 $g/h/m^2$. In an embodiment, the one or more moisture barrier or retarding coatings 180 that delay the onset of degradation, hydrolysis, or loss of strength is comprised of one or more materials having a moisture vapor transmission rate of at or greater than about 10 $g/h/m^2$. In a more preferred embodiment, the one or more moisture barrier or retarding coatings 180 that delay the onset of degradation, hydrolysis, or loss of strength of the material 82 comprising the linear ring struts 166 and connecting struts 46 has a perm in the range of about 0.01 to 100, more narrowly 0.01 to 10 using the ASHRAE standards (or equivalent), wherein one perm equals one grain (avoirdupois) of water vapor per hour flowing through one square foot of a material induced by a vapor pressure difference of one inch of mercury across two surfaces. In a preferred embodiment, the one or more moisture barrier or retarding coatings 180 that delay the onset of degradation, hydrolysis, or loss of strength of the material 82 comprising the linear ring struts 166 and connecting struts 46 has a perm in the range of at or above about 100 using the ASHRAE standards. In an embodiment, the one or more moisture barrier or retarding coatings 180 that delay the onset of degradation, hydrolysis, or loss of strength of the material 82 comprising the linear ring struts 166 and connecting struts 46 has a perm in the range of at or below about 0.01 using the ASHRAE standards. In an embodiment of the present invention, the one or more moisture barrier or retarding coatings 180 are temporary, which means they serve as a substantial barrier or substantially retard moisture from reaching the material 82 comprising the struts 166, 46 until about the time at which the degradation or hydrolysis is desired to start. The desired time can vary depending on environmental conditions. In the preferred embodiment, the thickness of the one or more moisture barrier or retarding coatings 180 is in the range of about 80 nanometers (nm) to 0.030 millimeters (mm). In an embodiment, the thickness of the one or more moisture barrier or retarding coatings 180 is in the range of at or below about 80 nanometers (nm). In an embodiment, the thickness of the one or more moisture barrier or retarding coatings 180 is in the range of at or above about 0.030 millimeters (mm).

In an embodiment the one or more coating or coatings 180 dissolve, degrade, erode, bioresorb, or partially or fully disappear after deployment of the stent 40 in the anatomical lumen. In these embodiments, the coating or coatings 180 dissolve, degrade, erode, bioresorb, or partially or fully disappear in a timeframe after deployment of the stent 40 in the anatomical lumen selected from the group of: (1) less than two years, (2) less than 1 year, (3) less than six months, or (4) any time experimentally determined by those skilled in the art for the end-use application describe herein. In another embodiment, the coating or coatings 180 is partially or fully dissolved, degraded, eroded, bioresorbed, or disappears in a time frame of greater than about 2 years.

In an embodiment the coating or coatings 180 includes one or more additives 150, nano size additives 152, or combinations thereof. In an embodiment, the additives 150 and nano size additives 152 are in the form of one or more active ingredients. The term "active ingredient" refers to any substance that is biologically active, therapeutically active, or an active pharmaceutical ingredient (API). The term "nano" refers to any substance that has one dimension in the size range of about less than 0.001 millimeter (mm).

In an embodiment the coating or coatings 180 delay or control the onset and/or rate of degradation and/or resorption of material 82. In an embodiment, delaying the onset of degradation improves patency by enabling the stent 40 to substantially maintain its strength for a longer period of time than an uncoated stent. In an embodiment, the stent 40 provides support to the lumen until the struts 44,46 are partially or fully covered with endothelial cells. In an embodiment, the stent 40 provides support to the lumen until the lumen remodels and becomes self-supporting.

Delaying Degradation

In an embodiment the stent 40 provides two functions: (1) provide mechanical support to the anatomical lumen 38 until remodeling occurs after deployment and (2) deliver active ingredients after deployment of the stent 40 that, for example, control neointimal cellular growth.

In an embodiment, the stent 40 retains a sufficient portion of its original strength at deployment until the lumen 38 is capable of holding itself substantially open and no longer requires the support of the stent 40. In an embodiment, the original strength of the stent 40 at deployment is substantially retained until the struts 44, 46 are partially encapsulated by the endothelial cells on the inside surface of the anatomical lumen 38. In a preferred embodiment, the vascular lumen 38 has about a 0.5-10% reduction in the inside diameter of the anatomical lumen at about 6-48 months after deployment of the stent 40. In a more preferred embodiment, the vascular lumen 38 has less than about 0.5% reduction in the inside diameter of the anatomical lumen 38 at about 6-48 months after deployment. In an embodiment, the inside diameter of the anatomical lumen 38 has more than 10% reduction in the inside diameter of the anatomical lumen at about 6-48 months after deployment of the stent 40. In other embodiments, the anatomical lumen 38 has more or less reduction in the inside diameter of the anatomical lumen 38 at shorter or longer time periods.

In an embodiment, the stent 40 provides sufficient structural support to the anatomical lumen 38 for sufficient time by delaying or slowing down the onset of degradation of the material 82 comprising the stent struts 44, 46. In an embodiment, the one or more coatings 180 delay the onset of loss of strength of the stent 40. In an embodiment, the one or more layers of the coating 180 control the rate at which water penetrates the outside surface of the material 82 comprising the struts 44, 46. Referring to FIG. 47, in an embodiment an uncoated stent having a wall thickness 76 starts to lose mechanical strength 137 several months after deployment and substantially all its strength about three to twelve months after deployment because the polymer 82 undergoes hydrolysis upon exposure to water in the living body. In an embodiment, one or more coatings 180 on the surface of the stent 40 delay the onset of degradation 135 of the material 82 so that the stent 40 does not substantially lose all its strength for a longer period of time. The variations in the delay in the time of degradation and time to substantial loss of strength are virtually unlimited and not limited to the example shown in FIG. 47. In an embodiment, the water uptake of the stent 40 is partially or fully delayed or reduced to increase the period of time that the bioresorbable stent 40 provides mechanical stability to the lumen. The loss of strength in some embodiments is linear as shown in FIG. 47. In other embodiments the loss of strength is not linear.

Once again referring to FIG. 47, in an embodiment, the delay 135 in the onset of degradation or hydrolysis is in the range of 3-12 months. In an embodiment, the delay in the onset of degradation, loss of strength 137, or hydrolysis is less than 3 months. In an embodiment, the delay in the onset of degradation, loss of strength 137, or hydrolysis is greater than 12 months. In a preferred embodiment of a vascular stent 40, the stent 40 substantially maintains sufficient strength to support a vascular lumen until remodeling occurs and the lumen is self supporting, which is about 3-12 months after deployment of the stent 40. In other embodiments the stent 40 maintains a strength for longer or shorter periods of time. At a some time after deployment, in an embodiment of the wall thickness 76, the material 82 comprising the wall thickness 76 degrades and loses sufficient strength that the anatomical lumen in which the stent 40 is implanted is partially or fully free to expand and contract thus partially or fully restoring vasomotion.

As previously discussed, in a preferred embodiment, once the material 82 comprising the wall thickness 76 starts to degrade and lose strength after deployment in an anatomical lumen 38 the degradation process is followed by the material 82 partially or fully losing mass so that the material 82 comprising the wall thickness 76 is resorbed.

Referring to FIG. 48, in an embodiment the material 82 comprising the wall thickness 76 loses mass and the degradative products are eliminated by the body through biological pathways. In an embodiment, the material 82 comprising the wall thickness 76 preferably substantially loses most or all of its mass in the period of time ranging from about 1 month to five years after deployment. In an embodiment, the material 82 comprising the wall thickness 76 substantially loses most or all of its mass in a period of time of less than 1 month after deployment. In another embodiment, the material 82 comprising the wall thickness 76 substantially loses most or all its mass in a period of time of greater than 5 years after deployment.

In an embodiment, the coating 180 delays the onset and/or rate of loss of mass. The modification of the time it takes to lose mass after implantation with one or more coatings 180 is virtually unlimited and not limited to the example shown in FIG. 48. The loss of mass in some embodiments is linear as shown in FIG. 48. The loss of mass in other embodiments is not linear.

Slowing the rate of hydrolysis of material 82, slowing the rate of degradation of material 82, or extending the maintenance of radial strength of stent 40 after deployment is controlled by durability of the coating 180 under physiological conditions, thickness of the coating or coatings 180, hydrophilicity of the coating or coatings 180, hydrophobicity of the coating or coatings 180, morphology of the coating or coatings 180, crystallinity of the coating or coatings 180, amorphicity of the coating 180, crystallinity of the material or materials comprising the struts 44,46, amorphicity of the material or materials 82 comprising the struts 44, 46, material or materials comprising the coating or coatings 180, number of layers of coating 180, porosity of the coating or coatings 180, permeability of the coating or coatings 180, environmental conditions surrounding the coating or coatings 180, pH of environment surrounding stent 40, temperature of area surrounding stent 40 after deployment in lumen, additives in the coating, or combinations thereof.

One significant factor that controls the degradation rate of the stent 40 upon deployment in a living body is the surface area of the struts 44, 46. If, for example, the struts 44, 46 are comprised of many relatively thin preformed configurations such as fibers 78 as shown in the cross sectional view of the strut 44, 46 in FIG. 32 the stent 40 has a relatively higher surface area and it degrades more quickly. Conversely, if the struts 44, 46 are comprised of few relatively thick fibers 78 as shown in cross sectional view in FIG. 31 then the stent 40 has a lower surface area and it degrades more slowly. Moreover, if the wall thickness 76 includes more material 82 mass in nodes 142 than in fibers 78 then the surface area is lower and the stent 40 degrades more slowly than a stent 40 containing more material 82 mass in fibers 78 than in nodes 142.

In an embodiment, to avoid large spikes in degradative byproducts, in an embodiment of stent 40, preformed configurations 77 having different thicknesses are employed in the fabrication of wall thickness 76 to stage the degradation of the preformed configurations 77 over time. To further avoid spikes in degradative byproducts, other embodiments of the stent 40 are designed to have a balance or preferable unbalance of the amount of mass of material 82 in nodes 142 and the amount of mass of material 82 in fibers 78 depending on desired stent 40 mass loss vs. time resorption profile sought to minimize lumen inflammation from high local acidity or other side affects related to degradative products.

The rate at which degradative byproducts are generated during the degradation of stent 10 can be managed by selecting materials 82 having different degradation rates. For example, in an embodiment the wall thickness 76 is comprised partially of slow degrading a homopolymer of L-lactide (PLLA) and partially of faster degrading polymers or copolymers of glycolide (PG). In another embodiment, the degradation rate is managed by using blends of polymers or copolymers. For example, a wall thickness 76 includes fibers 78 comprised of co-polymers of L-lactide (PLLA) and glycolide (PG) wherein the PLLA is slower to degrade and the PG is faster to degrade. The degradation rate can be fine tuned to achieve the performance specifications of stent 40 as described herein, for example, by varying the molar ratio from ten percent L-lactide and ninety percent glycolide to ninety percent L-lactide to ten percent glycolide. The rate of material 82 mass loss after deployment in anatomical lumen 38 in other embodiments is controlled by degree of crystallinity or molecular weight of material 82.

Referring back to FIG. 10B, which is a cross sectional view of an embodiment of the precursor construct tube 74 that is suitable to be converted into stent 40 of the present invention, the degradation of stent 40 is managed by having a wall thickness 76 comprised of material 82 having the same chemical composition but having differing molecular weights. In one such embodiment the abluminal layer 114 is comprised of a higher molecular weight material 82 than the luminal layer 112. In another embodiment the molecular weight of the material 82 in the abluminal layer 114 is comprised of a lower molecular weight material than the luminal layer 112. In the case wherein there are one or more middle layers, these layers 106 can be comprised of material 82 having molecular weight progressively higher to lower molecular weight from abluminal layer 114 to luminal layer 112 or comprised of material progressively decreasing in molecular weight from abluminal layer 114 to luminal layer 112.

Drug Delivery

In an embodiment, the endoprosthesis such as a stent 40 includes one or more active ingredients. In an embodiment the one or more active ingredients are stored in one or more coatings 180. In an embodiment, the one or more active ingredients are stored in the wall thickness 76. In an embodiment, the one or more active ingredients are stored in one or more coatings 180 and the wall thickness 76. In an embodiment of an endoprosthesis including active ingredients, the active ingredients are released or eluted after deployment at any rate experimentally determined by those skilled in the art meeting the requirements of the end-use application. In one embodiment the release or elution of one or more active ingredients is immediately after deployment, in another embodiment the release or elution of one or more active ingredients is sustained over all or part of the period of time the endoprosthesis is deployed, in one more embodiment the release or elution of one or more active ingredients is at an ascending rate over all or part of the period of time the endoprosthesis is deployed, in yet one more embodiment the release or elution of one or more active ingredients is at a descending rate over all or part of the period of time the endoprosthesis is deployed, and in other embodiments the release or elution of one or more active ingredients is any combination of the preceding rates. In some embodiments, the one or more active ingredients, additives 150, 152, and material 82 are formulated to improve patency, stability, biocompatibility, compatibility with other ingredients comprising stent 40, coating 180, or combinations thereof.

Without intent on limiting, examples of active ingredients included in the stent 40, coating 180, wall thickness 76, struts 44, 46, material 82, fiber 78,80, film 81, 79, voids 84, or combinations thereof are selected from the group of: a vascular cell growth inhibitor, abciximab, ABT-578 (Abbott Laboratories), actinomcin D, actinomycin, agents affecting extracellular matrix production and organization, agents that interferes with endogenous vasoactive mechanisms, agents affecting extracellular matrix production and organization, agents that bind to the FKBP12 binding protein, agents that binds to the mammalian target of rapamycin (mTOR) and thereby blocks the cell cycle mainly of the smooth muscle cell from the G1 to S phase, agents that block T-cell activation or proliferation, agents that decrease cytokine expression on the cell surface membrane and results in an inhibition of T-cell activation and lower smooth muscle cell selectivity, agents that fight cancer, agents that have ability to stabilize microtubules and thereby inhibit cell division in the G0/G1 and G2/M phases, agents that inhibit platelet aggregation, agents that inhibit smooth muscle cell proliferation, agents that inhibits the calcineurin receptor, agents that interfere with endogenous vasoactive mechanisms, agents that prevent or reduce blood clotting, agents that prevent or reduce local allergic reactions, agents that promote endotheliazation, agents that reduce neointimal hyperplasia, agents that reduce allergic reaction, agents that reduce the size of tumors, agents that reduce vascular hyperplasia, an inhibitor of mammalian target of rapamycin (mTOR), analgesics, anesthetic agents, anti-cancer agents, anti-coagulants, anti-inflammatory agents, anti-irritant agents, anti-migratory agents, anti-mitotic agents, anti-proliferative agent, anti-thrombotic agents, antibodies, antibiotics, antineoplastic agents, antiproliferative drugs, antimicrobials, anti-sense nucleotides and transforming nucleic acids, Ap-17, bARKct inhibitors, bacteria, batistimat, beta-blockers, bioactive agents, Biolimus A9, bisphosphonates, buffering agents, cholesterol-lowering agents, chaperone inhibitors, chemotherapeutic agents, corticosteroids, cilostazole, clopidogrel, crystalline materials, crystalline forms of drugs, cyclosporine, cytostatic drugs, dexamethasone, dexamethasone, DNA, modified DNA, drugs, Epo D, epidermal growth factor inhibitors, endothelial progenitor cells (EPC), estradiol, estrogen, everolimus, everolimus (certican or RAD-001), flunisolide, FKBP-12 binding agents, geldanamycin, genetic therapeutic agents, genistein, glucocorticosteroids, growth factors and delivery vectors including recombinant micro-organisms and liposomes, halofuginone, hormones, human apolioproteins (e.g., AI, AII, AIII, AIV, AV, etc.), hypothemycin, hydrocortisone, imiquimod (as well as other imidazoquinoline immune response modifiers), immunosuppressive agents, leptomycin B, limus drugs, liprostin, living cells, macrolide antibiotics including FKBP-12 binding compounds, materials that influence pH in environment surrounding stent 40, materials that promote improvement in elasticity of anatomical lumen, materials that promote remodeling of anatomical lumen, materials that provide reparative effect on anatomical lumen, materials that slow down aging process of anatomical lumen, mitotic inhibitors, mTOR inhibitors, mometasone furoate, mometasone furoate monohydrate, mineralocorticoids, myolimus, natural materials, non-genetic therapeutic agents, novolimus, nitric oxide, nucleic acids, paclitaxel, peroxisome proliferator-activated receptor gamma ligands (PPARγ), peptides, pharmaceutically active agents, pharmaceutically active agents having optimized morphology, pharmaceuticals, phospholamban inhibitors, pimecrolimus, polypeptides, proteins, protein-tyrosine kinase inhibitors, protease inhibitors, proteasome inhibitors, progestin, rapamycin, rapamycin derivatives, rapamcin hydroxyesters as disclosed in U.S. Pat. No. 5,362,718), resiquimod, Resten-NG, Ridogrel, Serca 2 gene/protein, sirolimus, sirolimus salicylate, statins, steroids, synthetic materials, tacrolimus, tacrolimus (FK506), taxol, temsirolimus, temsirolimus (CCI-779 or amorphous rapamycin 42-ester with 3-hydroxy-2-(hydroxymethyl)-2-methyl-propionic acid as disclosed in U.S. patent Ser. No. 10/930,487), toxic compounds, therapeutic agents, trapidil, vascular cell growth inhibitors, vascular cell growth promoter, vascular endothelial growth factors (e.g., VEGF-2), vasodilating agents, virus, zotarolimus, zotarolimus (reference U.S. Pat. Nos. 6,015,815 and 6,329,386), combinations thereof, derivatives of thereof, analogs thereof, or functional equivalents thereof. In an embodiment of the coating 180 including a therapeutic drug, the drug is released at a time approximately equal to about half the degradation time of the material comprising the coating 180.

Without intent on limiting, in an embodiment including one or more anti-cancer agents, the agent or agents are selected from the group of: Adrucil™ (Fluorouracil), Adriamycin PFS (Doxorubicin Hydrochloride), Adriamycin RDF (Doxorubicin Hydrochloride), Avastin™ (Bevacizumab), Bevacizumab, Bleomycin, Camptosar (Irinotecan Hydrochloride), Carboplatin, Carboplatin AUC 6, Capecitabine (Xeloda™), Capox, Camptosar™ (Irinotecan), Cetuximab, Cisplatin, Doxorubicin Hydrochloride, Docetaxel, Drugs that interfere with cells ability to reproduce, Efudex™ (Fluorouracil), Eloxatin (Oxaliplatin), Epirubicin (Ellence™), Erbitux (Cetuximab), Folfiri, Folfiri-Bevacizumab, Folfiri-Cetuximab, Folfox, Fluorplex (Fluorouracil), 5-Fluorauracil (5-FU), Fluorouracil, Gefitinib (Iressa™), Gemcitabine, Irinotecan Hydrochloride, Lomustine (CCNU), Leucovorin Calcium, Methotrexate, Mitomycin, Oxalipatin, Panitumumab, Paclitaxel (Taxol™), Pegylated liposomal doxorubicine, Platinol (Cisplatin), Platinol-AQ (Cisplatin), Radiation, Regorafenib, Stivarga (Regoranfenib), Topotecan, Trastuzumab, Vectibix (Panitumumab), Vinorelbine (Navelbine™), Wellcovorin (Leucovorin Calcium), Xeloda (Capecitabine), Xelox, Zaltrap (Ziv-Afibercept), chemical equivalents, analogues, functional equivalents, or combinations thereof.

In an embodiment, one or more layers of the coating 180 include one or more active ingredients that improve patency of the anatomical lumen 38 after deployment of the stent 40 in the anatomical lumen 38. In an embodiment, the one or more layers of the coating 180 are comprised of a material comprised of one or more polymers. In an embodiment, the one or more layers of the coating 180 are comprised of a material comprised of one or more controlled release polymers. In an embodiment, one or more layers of the coating 180 are comprised of a hydrophilic material. In another embodiment, one or more layers of the coating 180 are comprised of a hydrophobic material. In another embodiment, one or more layers of the coating 180 are comprised of a hydrophobic and hydrophilic material. In an embodiment, one or more layers of the coating 180 are comprised of a crystalline material. In another embodiment, one or more layers of the coating 180 are comprised of an amorphous material. In yet one more embodiment, one or more layers of the coating 180 are comprised of a crystalline and amorphous material. In an embodiment, the one or more layers of coating 180 are comprised of a material that has an release time of the one or more active ingredients of about half of the degradation time of the material or materials comprising the coating 180. In another embodiment, the one or more layers of coating 180 are comprised of a material that has a release time of the one or more active ingredients of less than half of the degradation time of the material or materials comprising the coating 180. In another embodiment, the one or more layers of coating 180 are comprised of a material that has a release time of the one or more active ingredients of more than half of the degradation time of the material or materials comprising the coating 180. In an embodiment, one or more layers of the coating 180 comprise a material having an intrinsic viscosity (IV) in the range of about 0.2 dl/g to 1.0 dl/g. In an embodiment, one or more layers of the coating 180 comprise a material having an intrinsic viscosity (IV) in the range of at or greater than about 1.0 dl/g. In an embodiment, one or more layers of the coating 180 comprise a material having an intrinsic viscosity (IV) in the range of about at or less than about 0.2 dl/g. In an embodiment, one or more layers of the coating 180 comprise a material having a molecular weight in the range of about 17 kg/mol to 153 kg/mol. In an embodiment, one or more layers of the coating 180 comprise a material having a molecular weight in the range of at or greater than about 153 kg/mol. In an embodiment, one or more layers of the coating 180 comprise a material having a molecular weight in the range of at or less than about 17 kg/mol. In an embodiment, one or more layers of the coating 180 comprise a material having a degradation time in the range of about 0.5 months to 16 months. In an embodiment, one or more layers of the coating 180 comprise a material having a degradation time in the range of about at or greater than 16 months. In an embodiment, one or more layers of the coating 180 comprise a material having a degradation time in the range of about at or less than 0.5 months. The terms "degradation time" as used in this specification of a degradation time for a coating 180 on the wall thickness 76 refers to the time to complete mass loss of the coating material and this time can vary from specification shown herein depending on ingredients included in coating material, coating formulation, device geometry and other factors known by those skilled in the art of coating medical devices. In a preferred embodiment, the thickness of the drug release or active ingredient containing coating 180 is in the range of 0.001 mm to 0.015 mm. In an embodiment, the thickness of the drug release active ingredient coating 180 is at or greater than 0.015 mm. In an embodiment, the thickness of the drug release active ingredient coating 180 is at or less than 0.001 mm.

In an embodiment of the coating 180 discussed herein containing one or more active ingredients, the stent 40 is designed to provide a specific dose of active ingredient or active ingredients locally after deployment. In an embodiment, the dose is the ratio of the weight percent of active ingredient to weight percent of the coating material after the coating 180 dries on the stent 40. In an embodiment, the dry coating 180 applied to the stent 40 includes 0 to 1000 grams of active ingredient, more narrowly 5 μg to 1000 μg of active ingredient. In other embodiments, the dry coating 180 applied to the stent 40 includes more than 1000 grams of active ingredient. In an embodiment, the dry coating 180 applied to the stent 40 includes a ratio of one part active ingredient to one part dry coating material. In another embodiment, the dry coating 180 applied to the stent 40 includes a ratio of one part active ingredient to one-five parts dry coating material. In another embodiment, the dry coating 180 applied to the stent 40 includes a ratio of one part active ingredient to one to nine parts dry coating material. In another embodiment, the dry coating 180 applied to the stent 40 includes a ratio of one part active ingredient to 1 to 20 parts dry coating material. In another embodiment, the dry coating 180 applied to the stent 40 includes a ratio of one part active ingredient to more than 20 parts dry coating material.

In another embodiment of the drug eluting stent, the stent 40 includes directional drug delivery functionality. For example, the coating 180 including an active ingredient delivery is on the surface of the stent 40 facing the lumen (abluminal surface) and another coating 180 facing the interior of the lumen (luminal surface) where blood flows contains a coating 180 that controls the onset and rate of hydrolysis of the bioresorbable material comprising the strut 44,46. The term "lumen" refers to a cavity of a tubular organ or part such as a blood vessel or artery. The term "abluminal" refers to the outermost radial surface having the greatest radial distance from the central axis 42 of the stent 40. The term "luminal" refers to the innermost surface having the shortest radial distance from the central axis 42 of the stent 40.

In an embodiment of the present invention the active ingredients are partially or fully encapsulated and feature the capability of controlled release of the active ingredients so that for example drug delivery kinetics can be customized. In an embodiment of the present invention including controlled release, the one or more active ingredients are released from the endoprosthesis after deployment at a predetermined rate. In an embodiment of the present invention including controlled release, the one or more active ingredients are released from the endoprosthesis after deployment at substantially equal amounts over a predetermined period of time. In an embodiment of the present invention including controlled release, the one or more active ingredients are released for the endoprosthesis after deployment at a sporadic rate. In an embodiment of the present invention including controlled release, the one or more active ingredients burst off the endoprosthesis after deployment. In an embodiment of the present invention including controlled release, the one or more active ingredients are released from the endoprosthesis after deployment at first order kinetics. In an embodiment of the present invention including controlled release, the one or more active ingredients are released from the endoprosthesis after deployment at zero order kinetics. In other embodiments, additives 150, 152 disperse, suspend, or disperse and suspend the active ingredients in the coating 180 and/or material 82 comprising preformed configurations 77 such as the fibers 78, multi-fibers 80, film 81, multi-film 79, or combinations thereof. In yet other embodiments, additives 150, 152 modify the solubility of active ingredients by either making active ingredients more soluble or less soluble in environment of the stent 40 after deployment in anatomical lumen. In still other embodiments additives 150, 152 modify the process of hydrolyzing or degrading/resorption process of material 82 comprising the preformed configurations 77 such as the fibers 78, multi-fibers 80, film 81, multi-films 79, or combinations thereof by increasing or decreasing the degradation/resorption time after deployment of stent 40 in the anatomical lumen 38.

In an embodiment of a vascular stent, the drug dosage preferably ranges from about 50 µg/stent to 200 µg/stent (assuming a 3 mm diameter by 18 mm long stent). In an embodiment of a vascular stent, the drug dosage is about 50 µg/cm$^2$ to 1000 µg/cm$^2$ drug dose density, more narrowly 77 µg/cm$^2$ to 250 µg/cm$^2$. In a preferred embodiment, the cumulative in vivo 100% drug release occurs in 180 days. In an embodiment, 80% of the drug release occurs in less than 45 days. In other embodiments the drug release is faster or slower or the drug dosage is higher or lower.

Material Composition

The wall thickness 76 is comprised of any material 82 providing the performance described herein. In the preferred embodiment, the wall thickness 76 and/or preformed configurations 77 are comprised of one or more bioresorbable materials 82. In an embodiment, the wall thickness and/or preformed configurations 77 are comprised of one or more biodegradable materials 82. In an embodiment, the wall thickness 76 and/or preformed configurations 77 are comprised of one or more absorbable materials. In an embodiment, the wall thickness 76 and/or preformed configurations 77 are comprised of two or more materials 82 having different melting temperatures. In an embodiment, the wall thickness 76 is comprised of two or more materials 82 having one or more different physical properties. In a preferred embodiment for use as a vascular stent 40, after deployment of the stent 40 in an anatomical lumen 38, the material 82 initially loses strength after remodeling of lumen is substantially completed and then loses mass.

The term "bioresorbable" refers to any material 82 that is: biodegradable; bioabsorbable; bio-adsorbable; bioresorbable; bio-erodible; dissolvable; degradable; soluble; metabolizable; erodible in physiological conditions; degradable via hydrolytic mechanism; able to disappear via phagocytosis; able to disappear via chemical breakdown by physiological environment; degradable at a rate that matches remodeling stages of cells; broken down by a living body and does not require mechanical removal; broken down in a living body; eliminated by a living body; eventually dispersed throughout the living body; a macromolecule that experiences cleavage of the main chain and is broken down into by-products and can be eliminated by biological pathways such as through the kidneys or lungs; soluble in blood or broken down to materials that are soluble in blood; or any substance that partially or fully disappears in the living body after installation. The terms "physical properties" or "mechanical properties" refer to the modulus of elasticity, yield strength, elongation to break, degradation rate, molecular weight, solubility, and resorption rate of the material 82.

Without intent on limiting, the wall thickness 76 and/or preformed configurations 77 such as fibers 78, multi-fibers 80, film 81, multi-film 79, coating 180, binder 108, or combinations thereof are comprised of one or more materials 82 selected from the following group: α-hydroxyesters; aliphatic polyesters; amorphous material; asymmetrically 3,6-substituted poly-1,4-dioxane-2,5-diones; asymmetrically 3,6-substituted poly-1,4-dioxane-2,5-diones; biodegradable glass; β-tricalcium phospante; $(C_6H_8O_4)_n$; poly[(3S-cis)-3,6-dimethyl-1,4-dioxane-2,5-dione]; carboxyl-capped tetraaniniline; chitin polymers; chitosan; copolymers; copolymer DL-lactide/glycolide; copolymer L-lactide/ε-caprolactone; copolymer L-lactide/glycolide; copolymer of lactic acid and ε-caprolactam; copolymer of hydroxybutyric acid and hydroxyvaleric acid; copolymers of lactic acid; copolymers of lactic acids with hydroxyl acids; collagen; cross linked gelatin; cross linked hyaluronic acid; crystalline material; degradable polycarbonates; degradable polycarboxylates; desaminotyrosyl-tyrosine alkyl ester; desaminotyrosyl-tyrosine ethyl ester; emulsions; fibroin; homopolymers; homopolymer of L-lactide; fibrin; glycosaminoglycan; hydrolyzable polyesters; hyaluronic acid; hyaluronic acid with cross linking agents like glutaraldehyde, or water soluble carbodiimide; iodinated poly(DTE carbonate); lactide based polymers; biodegradable magnesium; biodegradable magnesium alloy nano particles; biodegradable magnesium alloy wires; magnesium based alloys; materials broken down by proteolytic enzyme process; materials susceptible to hydrolytic breakdown; materials having glass transition temperature at or above 37 degrees Celsius; materials that degrade in less than about three months at physiological conditions; materials that degrade in greater than about three months at physiological conditions; materials that are resorbed into a living body in less than about two years physiological conditions; materials that are resorbed into a living body in greater than about two years at physiological conditions; materials that release active ingredients at physiological conditions in less than about three months; materials that release active ingredients at physiological conditions in greater than about three months; materials that substantially retain mechanical properties at physiological conditions for less than about six months; materials that substantially retain mechanical properties at physiological conditions for greater than about six months; materials that dissolve at physiological conditions in less than about six months; materials that dissolve at physiological conditions in greater than about six months; materials that affect hydrophobicity; materials that affect hydrophilicity; materials that affect crystallinity; materials that affect molecular weight; materials that affect rate of reduction in molecular weight at physiological conditions; materials that degrade at constant rate at physiological conditions; materials that degrade at descending rate at physiological conditions; materials that degrade at ascending rate at physiological conditions; oligomers; poly (1,3-dioxane-2-one); poly (1,4-dioxane-2,3 dione); poly (1,5-dioxepan-2-one); polymers containing functional groups for connecting/grafting/bonding active ingredients; polymer including an acid containing group; a polymer including an acid containing group wherein said acid containing group is carboxylic acid; a polymer including a backbone containing one or more of side chains; a polymer comprising a backbone including a plurality of side chains wherein said side chains include a plurality of hydrolytically degradable functional groups; an un-branched polymer; an un-branched polymer including a an acid group at each end; an un-branched polymer including an acid group at one end; an un-branched polymer having a functional group at each end; an un-branched polymer having a functional group at one end; poly (4 hydroxy butyrate)[P4BH]; methylmethacrylate-N-vinylpyrrolidone copolymers; poly (beta-alkanoic acid); poly (beta-dioxanone) (PDS); poly (beta-hydroxybutyrate-co-beta-hydroxyvalerate); poly (beta-hydroxybutyrate) (PHBA); poly (beta-hydroxypropionate) (PHPA); poly (beta-maleic acid) (PMLA); poly (butylene adipate-co-terephthalate); poly(butylene succinate-co-L-lactate); poly (delta-valerolactone); poly (dioxanone); poly (DL-lactide-co-glycolide) [DLPLG]; poly (DL-lactide); poly (epsilon-caprolactone); poly (ethylene oxide) (PEO); poly (ethylene glycol); poly (glycine-co-DL-lactide); poly (glycolic acid) [PGA]; poly (glycolide-co-lactide) (PGLA); poly (glycolide-co-trimethylene carbonate (PGA/TMC); poly (glycolide); poly (hydroxyacids); poly hydroxyacetic ester; polyhydroxyalkanoate; polyhydroxybutyric acid; poly (hydroxybutyrate/hydroxyvalerate) [PHBV]; poly (L-lactic acid) [PLLA]; poly (L-lactide); poly (lactic acid-coglycolic acid) [PLGA]; poly (lactic acid) [PLA]; poly (lactide-co-delta-valerolactone); poly (lactide-co-epsilon-caprolactone); poly (lactide-co-ethylene oxide); poly (lactide-co-glycolide); poly (lactide-co-tetramethylene glycolide); poly (lactide-co-trimethylene carbonate); poly (orthoester) [POE]; poly (para-dioxanone); poly (trimethylene carbonate); poly (tyrosine carbonates); poly (urethane-based); poly (β-R,S-malic acid); polylactide; poly-D-lactide (PDLA); poly-DL-lactide (PDLLA); poly-L-lactide (PLLA); poly(∝-malic acid); poly-∝-hydroxy acids; polyanhydrides; polyarylates; polydihydropyranes; poly (alkyl-2-cyanoacrylate); polymers; polymer chains formed of lactic acid monomer units; polydioxanone polymers; polyesters of oxalic acid; polygluconate; polylactide anhydride; polylactide-polyethylene glyxol; polymers and copolymers of glycolide; poly (oxyethylene); polymers and copolymers of polylactide (PLA); poly (p-dioxanon); polymers manufactured by ring-opening polymerization; polylactones; polypeptides; polyphosphoester; polysaccharides; polyvalerolactone [PVL]; polyvinyl alcohol (PVA); purified polymers; polymers having low residual monomer; polymers having residual monomer less than about 0.1 wt %; polymers with low isomer content; proteins; proteic materials; salicylate based polymers; salicylic acid; salicylate-based polyanhydrides; siloxane-doped vaterite; semi-crystalline material; tyrosine-derived polycarbonate; thermoplastics; thermoset polyesters; thermoset plastics; their functional equivalents, analogs, or combinations thereof in any proportion. These materials are also useful for producing a coating 180 or binder 108. In another embodiment, at least one layer of the coating 180 is comprised of durable material 82. In one more embodiment, at least one layer of the coating 180 is comprised of semi-durable material. In a preferred embodiment, the substantially all or all the residual monomer is eliminated from the polymers comprising the wall thickness 76.

In a preferred embodiment, the wall thickness 76 and/or preformed configurations 77 are comprised of poly-L-Lactide (PLLA) having an as-polymerized molecular weight ranging from about 43 kg/mol to 2,682 kg/mol, more narrowly ranging from about 121 kg/mol to 1,534 kg/mol. In another embodiment, the wall thickness 76 and/or preformed configurations 77 are comprised of poly-L-lactide having an as-polymerized molecular weight at or less than about 121 kg/mol. In another embodiment, the wall thickness 76 and/or preformed configurations 77 are comprised of poly-L-lactide having an as-polymerized molecular weight at or greater than about 2,682 kg/mol. In an embodiment a material 82 comprised of one or more molecular weights is employed in the fabrication of the wall thickness 76 and/or preformed configurations 77 to achieve the optimum mechanical and degradation performance.

By utilizing poly-L-lactide or other materials 82 having differing molecular weights to fabricate the wall thickness 76, preformed configurations 77, binder 108, or combinations thereof an optimum morphology can be obtained in the wall thickness 76. For example, the lower as-polymerized molecular weight PLLA in the range of 43 kg/mol to 473 kg/mol have shorter molecular chains and can be used to produce wall thickness 76 and/or preformed configurations 77 of very thin thicknesses 92, 100, 93, 101 that are easier to crystallize during annealing, make preformed configuration-to-preformed configuration connections, consolidation, or tube sizing secondary processes. These lower molecular weight portions that have a crystalline morphology tendency contribute to the matrix of materials 82 comprising the wall thickness 76 by providing stiffness and radial strength. Crystalline materials 82 are also slower to degrade and be resorbed. The higher as-polymerized molecular weight PLLA in the range of about 473 kg/mol to about 2682 kg/mol or more contribute to the matrix of materials 82 by utilizing their long molecular chains to toughen or strengthen the wall thickness 76 and prevent cracking. Since the higher molecular weight materials are longer molecular chains they have a tendency to be more difficult to crystallize so they remain more semi-crystalline or amorphous after annealing, consolidation, or tube sizing secondary processes. These materials, however, can become more crystalline if slower cooling rates are employed after processing or slower to evaporate solvents are employed during processing the material 82 into a preformed configuration 77 such as a fiber 78 or film 81. The higher as-polymerized molecular weight materials 82 having molecular weights at or above 1014 kg/mol can be used but they can be difficult to process because the produce very viscous solutions and melts. The advantage of solution processing of poly-L-lactide into the configuration of a wall thickness 76 and/or preformed configuration 77 is that higher molecular weight materials 82 can be used than melt processing poly-L-lactice which enables stronger wall thicknesses 76 to be produced. Moreover, since molecular weight is destroyed during melt processing and sterilization, starting with a higher molecular weight polymer is beneficial because it enables a higher molecular weight material in the final product after the material 82 is formed into a wall thickness 76 and sterilized. For example, a wall thickness 76 partially or fully comprised of poly-L-lactide is preferably produced of a material 82 having an as-polymerized molecular weight greater than 100,000 g/mol, more preferably greater than 500,000 g/mol, and most preferably greater than 1,300,000 g/mol to preserve sufficient molecular weight after conversion into a wall thickness 76 suitable for use in stent 40.

The term "polymer" refers to natural or synthetic compounds consisting of up to millions or more of repeated units linked by chemical bonds. The term "copolymer" refers to a chemical compound form by uniting the molecules of two or more different compounds or monomers. The term "oligomer" refers to a compound containing up to five monomer units. The term "monomer" refers to a molecule that can combine with others to form a polymer. The terms "degree of polymerization" refers to the number of monomeric units in a molecule of a polymer. The terms "molecular chain" refers to two or more like or different atoms linked together by forces. The terms "molecular orientation" refers to the orientation of the atoms in an individual chain relative to each other such as linear or folded or relative to other separate chains of molecules. The terms "molecular extension" refers to lengthening the chain of atoms linked together by forces either by straightening or by addition of atoms.

In some embodiments, part or all the wall thickness 76 and/or preformed configurations 77 are comprised of branched polymers, block polymers, star polymers, comb polymers, brush polymers, star block $AB_n$ polymers, coil-cycle-coil polymers, star $A_nB_n$ polymers, $AB_2$ star polymers, palm tree $AB_n$ polymers, H-shaped $B_2AB_2$ polymers, dumbbell polymers, ring block polymers, copolymers having alternating monomer residue, copolymers having monomer residue organized in repeating sequence, copolymers having monomer residue arranged in random or statistical sequence, polymers having hydrophobic modification, diblock polymers, surface active polymers, triblock polymers, grafted polymers, polymers having side chains of different composition or configuration than main chain, or any material meeting the performance specifications described herein.

In an embodiment the polymer is ester terminated. In another embodiment the polymer end group is free carboxylic acid. In one more embodiment, the polymer end group is alkyl ester. In one more embodiment the polymer end group is decyl ester. In another embodiment the end group of the polymer is dodecyl ester. In another embodiment, the polymer is 2-hydroxyethyl methacrylate terminated. In one more embodiment, the polymer is propargyl terminated. In an embodiment the polymer is 2-bromoisobutyryl terminated. In other embodiments, active ingredients are grafted onto the polymer backbone or side branches.

Lactide-based polymers mentioned herein are available from PURAC, 111 Barclay Building, Lincolnshire, Ill. 60069, USA under the trade name PURASORB™ Biomaterials, EVONIK, Germany, or from NATUREWORKS LLC (owned by Cargrill), 15305 Minnetonka, Boulevard, Minn., 55345, USA.

Without intent on limiting, examples of lactide-based polymer suitable for use in the present invention (available from Purac under the trademark PURASORB) include poly (L-Lactide) (PLLA) having a molecular weight ranging from about 43 kg/mol or below to about 2,682 kg/mol or above; poly (DL-lactide) (PDL) having a molecular weight ranging from about 17 kg/mol or lower to about 1,134 kg/mol or higher; copolymers of L-lactide and glycolide having an 85/15 molar ratio (PLG 85) having a molecular weight ranging from about 276 kg/mol to about 869 kg/mol; copolymers of poly (DL-lactide) and glycolide having a 50/50 molar ratio (PDLG 50) having a molecular weight ranging from about 17 kg/mol to about 196 kg/mol; copolymer of L-lactide and DL-lactide in an 80/20 molar ratio (PLDL 80) having a molecular weight ranging from about 507 kg/mol to about 1,593 kg/mol; and copolymers of poly (L-lactide) and caprolactone in a 70/30 molar ratio (PLC 70) having a molecular weight ranging from about 83 kg/mol to about 753 kg/mol. Other materials 82 providing the performance specified herein are suitable for use in the present invention by copolymerizing or combining polymers comprised of L-lactide, D-lactide, DL-lactide, glycolide, or caprolactone in any molar ratio. Manufacturers of lactide-based polymers sometime specify products in terms of their inherent viscosity (IV). There is a correlation between IV and molecular weight that can be provided by the polymer manufacturers. The inherent viscosity is determined by viscometry of diluted polymer solutions. Measurements are performed in chloroform at 25 degrees Celsius at a concentration of 0.1 g/dl. For low IV values higher concentrations are used: 2.0 g/dl for IV<0.2 dl/g, 1.0 g/dl for 0.2 dl/g<=IV<0.3 dl/g 0.5 dl/g for 0.3 dl/g<=IV<1.0 dl/g. To illustrate the correlation using material 82 comprised of PLLA, a material having a molecular weight of 43 kg/mol has an IV of 0.6 dl/g, a material having a molecular weight of 674 kg/mol has an IV of 3.8 dl/g, and a material having a molecular weight of 2,682 kg/mol has and IV of 9.6.

Partially or fully employing low molecular weight material 82 or polymers and/or slow to evaporate solvents can be useful for crystallizing or re-crystallizing a material 82 or polymer after formation of fiber 78, 80. Crystallizing or re-crystallizing the some or all the material 82 or polymers can improve the stiffness or radial strength of the stent 40. Having an experimentally selected balance of crystalline and amorphous material 82 or polymer within wall thickness 76 provides optimized mechanical properties having superior radial strength, flexibility, and crack resistance.

Once again referring to FIG. 103, in an embodiment the wall thickness 76 is comprised of one more materials 82 having an as-polymerized yield strength 153 in the range of about 5 to 125 mPa, more narrowly 10 to 100 mPa. In another embodiment, the wall thickness is comprised of one or more materials that have an as-polymerized yield strength 153 at or below about 5 mPa. In one more embodiment, the wall thickness is comprised of one or more materials 82 having an as-polymerized yield strength 153 at or at or above about 125 mPa. Referring to FIG. 103, the wall thickness is comprised of one or more materials 82 having an as-polymerized ultimate strength 151 in the range of about 5 to 200 mPa, more narrowly 10 to 125 mPa. In another embodiment, the wall thickness 76 is comprised of one or more materials 82 having an as-polymerized ultimate strength 151 of at or greater than about 200 mPa. In one more embodiment, the wall thickness 76 is comprised of one or more materials 82 having an as-polymerized ultimate strength 151 of at or less than about 5 mPa. The term "stress" refers to the applied load divided by the original cross sectional area of the specimen. The term "strain" refers to the change in the specimen's length divided by its original length.

Referring to FIG. 103, in a preferred embodiment the as-polymerized material 82 has a strain 145 of greater than about 2% before the material 82 breaks under load, more narrowly a strain 145 greater than about 4%. In an embodiment, the as-polymerized material 82 has a strain 145 at or less that about 2% before the material 82 breaks under load. In the present invention the amount of strain 145 under stress 143 that wall thickness 76 can support before the wall thickness 76 breaks is dependent on the material 82 selection, molecular weight of the material 82, orientation of the material 82, the amount of porosity in the wall thickness 76, the amount of consolidation, the thermal treatment, and other factors. The wall thickness 76 comprised of preformed configurations 77 of the present invention is unique in that when produced of Poly (L-Lactide), which according to the manufacturer has an elongation at break of 2-6%, can be converted into a wall thickness 76 having an elongation at break of over 15% and in some cases over 200% and still have adequate stiffness to serve as a suitable precursor construct tube 74 and/or stent 40 in the applications described herein. The amount of stiffness is increased at the expense of elongation to break by greater compression and/or exposure to higher temperatures of the wall thickness 76. The optimum stiffness and elongation to break can be experimentally determined for each application by varying the amount of compression and thermal treatment using the specifications provided herein as a guide.

In an embodiment of the present invention, the as-polymerized material 82 has a Young's modulus of elasticity ranging from about 0.01 to 4.0 GPa. In an embodiment of the present invention, the as-polymerized material 82 has a Young's modulus of elasticity ranging from about 4-10 GPa. In another embodiment, the as-polymerized material 82 has a Young's modulus of elasticity of at or greater than 10 GPa. In one more embodiment, the as-polymerized material has a Young's modulus of elasticity of at or less than about 0.01 GPa. In an embodiment, the wall thickness 76 includes multiple materials 82 wherein one material 82 has a higher modulus of elasticity and one material 82 has a lower modulus of elasticity. By employing materials 82 of having a higher modulus of elasticity, the stiffness of the stent 40 or precursor construct tube 74 is increased.

Those skilled in the art of polymer science can measure the degree of crystallinity of a material 82. Those skilled in the art can, for example, measure the degree of crystallinity of a material 82 by using differential scanning calorimetry (DSC), X-ray diffraction (XRD), wide-angle x-ray diffraction (WAXD), infrared spectroscopy, and nuclear magnetic resonance (NMR). The distribution of crystalline and amorphous regions can be visualized with microscopic techniques such as polarized light microscopy and transmission electron microscopy. The terms "chemical composition" refer to a chemical formula indicating the proportion of each element present in a molecule (empirical formula), a chemical formula indicating the numbers and types of atoms in a molecule (molecular formula), a chemical formula showing the composition and structure of a molecule (structural formula), or combinations thereof.

The bioresorbable materials 82 such as polymers are prone to loss in degree of polymerization. The degree of polymerization is vulnerable for reduction during polymerization, conversion of as-polymerized material 82 to a wall thickness 76 and/or preformed configuration 77, consolidation, thermal treatment, cutting, crimping, sterilization, and other secondary operations. During processing or conversion of the as-polymerized material 82 into a wall thickness 76, the material 82 can undergo various types of degradative processes: (1) hydrolytic, (2) thermal, (3) mechanical, or (4) combinations thereof. In the present invention, the degree of polymerization is partially or fully preserved by one or more of the following processing steps: (1) minimizing the temperature at which the material 82 is processed; (2) minimize the number of times the material 82 is exposed to elevated temperatures; (3) partially or fully removing any catalyst from the material; (4) partially or fully removing any monomer from the as-polymerized material 82; (5) partially or fully end-capping the molecular chains; (6) minimizing hydrolytic degradation by drying the material 82 before processing; (7) thermal processing in an inert environment like nitrogen; and/or (8) minimizing shear stresses imposed on the material 82 especially at elevated temperatures during processing. Using solution processing of material 82 into a wall thickness 76 and/or preformed configuration preserves more of the as-polymerized degree of polymerization than melt processing.

Additives

In an embodiment, the wall thickness 76 includes one or more additives 150 or nano-sized additives 152. As shown in FIG. 28, in an embodiment the preformed configuration 77 such as a fiber 78 includes one or more additives 150 or nano-sized additives 152. As shown in FIG. 40, in an embodiment the one or more coatings 180 include one or more additives 150 or nano-sized additives 152. In an embodiment, the additives 150 or nano-sized additives 152 are comprised of an active ingredient. The additives 150 or nano-sized additives 152 are in the form of a solid, liquid, gas, or combination thereof. The additives 150 or nano-sized additives 152 can be of any shape or configuration such as a particle or fiber.

In an embodiment, the additives 150 and/or nano sized additives 152 comprise between 0.01% and 98% of the volume of the wall thickness 76. In other embodiments, the additives 150 and/or nano sized additives 152 comprise between 0.001 weight percent and 99 weight percent of the wall thickness 76. In other embodiments, the additives 150 and/or nano-sized additives 152 comprise more or less volume or weight percent of the wall thickness 76.

Without intent on limiting, in an embodiment additives 150 and nano-size additives 152 are included in the wall thickness 76 and/or coating 180 selected from the group of: active ingredients, acidic materials, acid salts, agents that increase porosity, agents that promote absorption of active ingredients or material 82 into living body, amorphous materials, antimicrobials, antioxidants, anti-hydrolyzing agents, barium, barium sulfate, basic salts, bicarbonates, binders, bismuth sub-carbonate, blow agents, bismuth trioxide, bone morphogenetic protein 2 (BMP-2), buffering agents, buffering salts, calcium carbonate, calcium phosphates, carbon, carbon nano tubes, cell culture, ceramics, chalk, citric acid, citrates, clay, collagen, crystalline materials, disintegrants, dispersants, DNA, modified DNA, encapsulated materials, emulsifiers, emollients, excipients, enzymes, elastomeric materials, foaming agents, fillers, filters, glass, bioresorbable glass, gold, hydrophobic modifiers, hydrolyzing agents, iodine, povidone-iodine (PVP-I), any chemical complex of polyvinylpyrrolidone and elemental iodine, lime, living cells, magnesium alloys, magnesium particles, materials that prevent additives or active ingredients from agglomerating, materials that promote polymer crystallization, materials that promote polymer re-crystallization, materials that modify material 82 alkalinity, materials that modify material 82 acidity, materials that modify material 82 pH below about 7.4, materials that modify material 82 pH above about 7.4, materials that modify stent alkalinity, materials that modify stent acidity, materials that modify stent 40 pH above about 7.4, materials that modify stent 40 pH below about 7.4, materials that accelerate the Kreb's cycle, materials that decelerate the Kreb's cycle, materials that accelerate the rate of hydrolysis of material 82, materials that decelerate the rate of hydrolysis of material 82, materials that reduce the molecular weight of material 82, materials that increase the molecular weight of material 82, material capable of cleaving a polymeric backbone at anatomical conditions, material that degrade upon exposure to radiation, materials that degrade upon exposure to radiation including sources from ultraviolet, x-ray, e-beam, laser, or gamma, materials that degrade upon exposure to ultrasonics, materials that impart shape memory on the endoprosthesis, minerals, microencapsulated materials, monosodium phosphates, monosodium citrate, multi-wall carbon nano tubes, nano tubes, nano encapsulated materials, neutralizers, nucleating agents, particles, pH modifiers, phosphates, platinum, potassium bicarbonate, proteins, preservatives, radioactive materials, radiation, rheology modifiers, sodium bicarbonate, sodium bisulfate, titanium dioxide, salts, solvents, solubilizers, silica, starch, stabilizers, surfactants, suspension aids, talc, titanium, tri-calcium phosphate, tungsten, xylan esters, zirconium oxide, or functional equivalents, combinations thereof, other materials that improve the functionality of stent 40.

Polymeric stents are more difficult to adjust in size when deployed because a polymer is viscoelastic. In an embodiment of the present invention, the wall thickness 76 and/or preformed configurations 77 includes one or more ductile or deformable additives 150, 152, fibers 78, 80, or combinations thereof. Preferably these additives 150, 152 and/or fibers 78, 80 are biodegradable, bioresorbable, or combinations thereof. The term "ductile" refers to the wall thickness 76 being fashioned into a new form and the term "deformable" refers to altering the shape of the wall thickness 76 by stress. These deformable additives 150, 152 in an embodiment enable the stent 40 to be more effectively incrementally changed in size or shape during crimping (reduction in size) or deployment (expansion in size). This inventive feature of including ductile, malleable, or deformable additives 150, 152 in the wall thickness 76 or surfaces 70, 72, 182 of the stent 40 of the present invention is significant because it improves the clamping force of the stent 40 on the catheter during delivery provides additional protection against premature dislodgement of the stent from the catheter. In addition it enables the surgeon implanting the stent 40 to incrementally achieve the optimum size of the stent 40 (avoiding malpositioning) during deployment so that the stent 40 properly fits the anatomical lumen 38 in which it is being deployed.

In other embodiments, the one or more additives 150, 152 impart improved shape memory characteristics of the tube 74 or stent 40. Shape memory additives are useful in deployment of self-expanding stents 40. In another embodiment, the additives 150, 152 increase the rigidity of the stent 40 to, for example, increase the radial strength or crush resistance of the tube 74 or stent 40. Without intent on limiting, additives 150, 152 that can increase the rigidity of the tube 74 or stent 40 are biodegradable glass or metals. In an embodiment, the additives 150, 152 increase the maximum tensile strength 151 of the wall thickness 76 or tubular precursor construct 74. In an embodiment, the additives 150, 152 increase the yield strength 153 of the wall thickness 76 or tubular precursor construct 74. In an embodiment, the additives 150, 152 increase the Young's modulus of the wall thickness 76 or tubular precursor construct 74. In an embodiment, the additives 150, 152 increase the elongation to break or fracture 87. In an embodiment, the additives 150, 152 modify the physical properties of the material or materials 82 comprising the wall thickness 76 or tubular precursor construct 74.

In an embodiment, the wall thickness 76 includes one or more bioresorbable metals or includes one or more bioresorbable metal additives 150, 152 to, for example, enable the stent 40 to be more malleable or ductile so that the stent 40 can be adjusted in size and substantially retain the adjusted size after deployment of the stent 40 with a balloon catheter. In addition, the additives 150, 152 can improve the stent 40 retention on a catheter 184 during stent 40 delivery. For example, in one embodiment the wall thickness 76 is partially or fully comprised of magnesium, a magnesium alloy, or a magnesium alloy additive 150, 152, and other materials. In an embodiment, the magnesium alloy is comprised of a combination of magnesium and any combination of aluminum, zinc, lithium, rare earth metals, zirconium, or calcium at any ratio or formulation that meets the performance described herein. In an embodiment, the magnesium alloy is comprised of any combination of magnesium and aluminum. In another embodiment, the magnesium alloy is comprised of any combination of magnesium and zinc. In yet one more embodiment, the magnesium alloy is comprised of a combination of magnesium, aluminum, and zinc. In still one more embodiment, the magnesium alloy is comprised of a combination of between about 0.9 percent and 10 percent aluminum and between about 0.45 and 10 percent zinc. In another embodiment, the magnesium alloy includes less than about 0.9 percent aluminum. In one more embodiment, the magnesium alloy includes at or more than about 10 percent aluminum. In still one more embodiment, the magnesium alloy includes less than about 0.45 percent zinc. In yet one more embodiment, the magnesium alloy includes at or more than about 10 percent zinc. Magnesium alloys are available from Sumitomo Electric Industries, Osaka, Japan. An exemplary wall thickness 76 including one or more malleable or ductile wires is illustrated in FIG. 22 or FIG. 28. A stent 40 having one or more malleable wires included in the wall thickness 76 produces a stent 40 suitable for enhanced plastic deformation similar to that of a metallic balloon expandable stent but it has the benefit of being resorbed after the treatment time. In an embodiment, the wall thickness 76 includes one or more additives 150, nano sized additives 152, or combinations thereof that are incorporated in the material 82 prior to, during, or after formation of the preformed configurations 77 to improve the mechanical properties of the stent 40.

In one embodiment, the additive 150, 152 or additives are included in the one or more solvents prior to the addition of the one or more materials 82 in the solvent or solvents when producing a solution 234 that is converted into a wall thickness 76 or preformed configuration 77. In another embodiment the additive 150,152 or additives are included in the one or more solvents after including the one or more materials 82 in the solvent or solvents when producing a solution 234 that is converted into a wall thickness 76 or preformed configuration 77. In an embodiment, the additive 150, 152 or additives included in the solution 234 are partially or fully dissolvable in the one or more solvents comprising the solution 234. In an embodiment, the additive 150 or additives included in the solution 234 are not dissolvable in the one or more solvents comprising the solution 234. In an embodiment, the additive 150, 152 or additives are included in the one or more materials 82 that are converted into a wall thickness 76 or preformed configuration 77.

Crimping

An embodiment of bioresorbable stent 40 is crimped onto a balloon catheter 184. In an embodiment of stent 40, the stent 40 is crimped onto a balloon catheter 184 that includes one or more protrusions or other mechanical attachment devices located on the outer surface of the balloon that at least temporarily assist in retaining the stent 40 on the balloon catheter 184 during storage and delivery of the stent 40 through the anatomical lumen to the treatment area. These protrusions can be positioned adjacent to the proximal 52 and distal 54 ends of the stent 40, between the openings 48, or any other location that assists in retaining the stent 40 on the balloon catheter 184 until at or about the time of deployment. Moreover, adhesives or other additives can be employed in some embodiments to help retain the stent 40 on the balloon catheter 184. In one embodiment, the protrusions range in thickness from about 5 percent of the stent's 40 wall thickness 76 to 500 percent of the stent's wall thickness 76, more narrowly from ten percent to 200 percent. In another embodiment, the protrusions are less than five percent of the stent's 40 wall thickness 76. In one more embodiment, the protrusions are greater than 5 percent of the stent's 40 wall thickness 76.

In an embodiment, when the stent 40 is in the crimped position, one or more of the linear ring struts 166 or link struts 46 or any other location along the stent 40 are connected to the catheter through spot-bonding or spot-welding. In an embodiment, the spot-bonding or spot-welding includes less than about 90 percent of the surface area of the stent 40 or whatever is required to securely hold the stent 40 securely on the catheter 184 until the stent 40 is deployed, at which time the spot-bonding or spot-welding locations allow separation of the stent 40 from the catheter 184. For example, lasers or ultrasonics can be utilized to lightly or temporarily spot-weld or spot-bond the struts 44 to the outer surface of a balloon catheter 184 so that when the balloon expands to deploy the stent 40 the welds or bonds break allowing deployment of the stent 40 in the anatomical lumen 38.

In an embodiment, when the stent 40 is in the crimped position, one or more of the linear ring struts 166 or link struts 46 or any other location along the stent 40 are partially or fully connected together through spot-bonding or spot-welding. The spot bonding or spot welding temporarily assists in keeping the stent 40 in a substantially crimped position so that the catheter 184 including the stent 40 has a low profile during delivery. In an embodiment, the spot-bonding or spot-welding includes less than about 90 percent of the surface area of the stent 40 or whatever is required to hold the stent 40 securely on the catheter 184 until the stent 40 is deployed, the balloon is expanded, or combination thereof at which time the spot-bonding or spot-welding locations allow separation of the stent 40 from the catheter 184. For example, lasers or ultrasonics can be utilized to lightly or temporarily spot-weld, tack-weld, or spot-bond the struts 44 together when the stent 40 is in the crimped position on the catheter so that when the balloon at the end of the catheter expands to deploy the stent 40 the welds or bonds break allowing deployment and/or expansion of the stent 40 in the anatomical lumen 38 to hold open and support the lumen.

Bioresorbable stents 40, especially those comprised of polymer materials 82, are difficult to retain in the crimped position on a catheter 184. The stents 40 have a tendency to partially or fully revert back to their original un-crimped size. By spot welding, tack-welding, or spot bonding the linear ring struts 166 or link struts 46 partially or fully together or to the catheter 184 has the advantage that the stents 40 have better retention during storage and better retention during delivery. In some embodiments, the stent 40 does not have to be stored at in cold storage to maintain the stent 40 substantially securely positioned on the catheter 184 until deployment.

Crimping of a stent onto a catheter can be performed using equipment produced by Machine Solutions, 2951 W. Shamrell Blvd., Flagstaff, Ariz. 86001 (USA) using model numbers HH100/200, SC100/150, SC200/250, SC500/600, SC700/800, SC7755/875S, SC1775S or modified variations thereof or functional equivalents. In other embodiments, the stent 40 is substantially retained on the catheter using an external sleeve that is temporarily positioned over the stent's 40 outer surface 70 to retain stent in a crimped state until deployment in an anatomical lumen. In other embodiments, the stent 40 is substantially retained on the catheter using an external sleeve that is temporarily positioned over the stent's 40 outer surface 70 to retain stent 40 in a crimped state until deployment in an anatomical lumen at which time the sleeve is pealed back like a banana to allow expansion and deployment of the stent 40. For stent 40 including one or more active ingredients or surface coatings, a removable or changeable protective layer can be positioned between the crimping mechanism and the stent to avoid contamination of the crimping mechanism. Alternatively, in another embodiment, a stent 40 including or excluding a strut pattern 60 can be folded on a balloon catheter. In this embodiment the stent can be folded onto a balloon catheter using balloon pleating and folding machines such as those available from Machine Solutions, 2951 W. Shamrell Blvd., Flagstaff, Ariz. 86001 (USA) using model numbers LB1000, MS 700S, TB725, VS1000, or VS1100, or functional equivalents.

Packaging and Sterilization

In an embodiment, the stent 40 is stored in a sealed package. In an embodiment, the stent 40 is packaged in a substantially airtight package that has its interior space wherein the stent 40 and/or stent and catheter are stored under negative pressure or a vacuum. In an embodiment, wherein the packaging is under negative pressure the packaging substantially fully surrounds the outer surface 70 of the stent 40 keeping it's inner surface 72 substantially compressed on the outside surface of the balloon catheter. Since the packaging is under negative pressure, substantially all the oxygen and moisture is removed from the very small space surrounding the stent 40 thereby substantially preventing or minimizing hydrolysis or other degrading processes during storage of the stent 40. In an embodiment, the stent 40 is stored in a package wherein the remaining space in the package not consumed by the stent 40 or stent and/or catheter assembly is at least partially filled with an inert gas and/or moisture absorbing material. In an embodiment, the package includes a temperature sensor.

Different sterilization method may be employed in the present invention. Without intent on limiting, the sterilization processes suitable for use in the present invention include: (1) gamma irradiation; (2) electron beam irradiation (e-beam); (3) ethylene oxide (EtO); (4) low temperature plasma, (5) molding processes; (6) steam and (7) dry heat, (8) ultraviolet light, and (9) any other process capable of sterilizing the components described herein. The components can be sterilized prior to or after the packaging stages. Aseptic production and packaging environments are suitable alternative approaches. Depending on the application the minimum sterility requirements are explained in $SAL^{-6}$ and $SAC^{-3}$. Those skilled in the art of sterilization of medical devices may preform sterilization on the present invention. Care must be taken to minimize the impact on the molecular weight of the material 82, crystallinity of the material 82, mechanical properties of the material 82, and efficacy of the active ingredients.

Deployment

In an embodiment the stent 40 is deployed by percutaneous transluminal coronary angioplasty (PTCA). As illustrated in FIG. 44, in an embodiment the stent 40 is crimped onto a balloon catheter 184 and the assembly is inserted through a brachial or femoral artery 38 and positioned across a coronary artery occlusion. As shown in FIG. 45, the balloon is inflated to compress the stent 40 against atherosclerotic plaque to open to open the lumen 38 of the coronary artery 38. In another embodiment, the stent 40 is self-expanding and is positioned on the end of the catheter, which includes a mechanism to hold the stent 40 in a compressed condition until deployment. As shown in FIG. 46, after deployment, the catheter 184 is withdrawn from the anatomical lumen 38. In an embodiment, the anatomical lumen 38 is pre-dilated prior to deployment of the stent 40.

In an embodiment, the stent 40 is expanded during deployment to an outer diameter 62 that is in the range of about negative 75 percent to positive 35 percent of it's pre-crimped diameter, more narrowly negative 67 percent to 25 percent of it's pre-crimped diameter, without fracturing the stent's 40 struts 44, 46. In, another embodiment, the stent 40 is expanded during deployment to an outer diameter 62 that is in the range of less than about negative 75 percent of it's pre-crimped diameter. In one more embodiment, the stent 40 is expanded during deployment to an outer diameter 62 that is greater than about positive 35 percent of its pre-crimped diameter without fracturing the stent's 40 struts 44, 46. In an embodiment, after deployment the stent's outer surface 70 is in close proximity to the inner surface of the anatomical lumen 38 so that the struts 44, 46 can be covered with endothelial cells. In an embodiment, after deployment the stent's struts 44, 46 are partially or fully embedded in the wall of the anatomical lumen 38. In an embodiment, the strut's 44, 46 of one stent partially or fully overlap the struts 44, 46 of a second stent after deployment. In an embodiment, the stent 40 is deployed in a curved anatomical lumen 38. In an embodiment, the stent 40 is deployed in a tapered anatomical lumen 38. In an embodiment, the stent 40 is deployed in a curved and tapered anatomical lumen 38. In an embodiment, the stent 40 is deployed at a bifurcated anatomical lumen 38. In an embodiment, the anatomical lumen 38 contracts in size after deployment of the stent 40. In an embodiment, the anatomical lumen expands in size after deployment of the stent 40.

Figure 102:
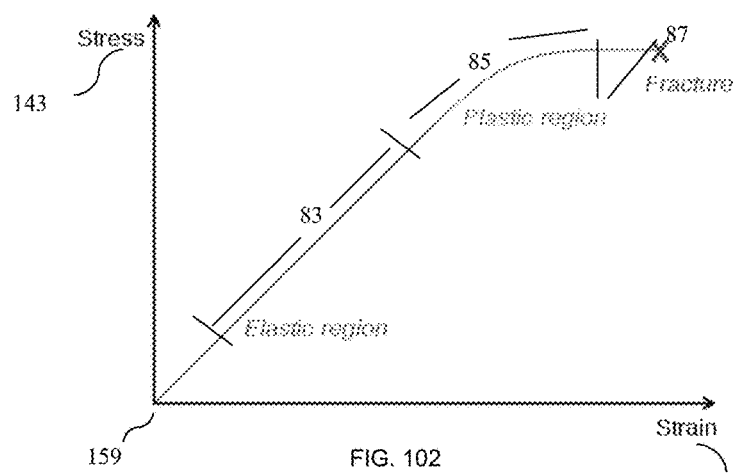
FIG. 102 and FIG. 103 are examples of stress-strain curves.

Referring to FIG. 102 and FIG. 103, in one embodiment the stent 40 is expanded during deployment from a stress 143 ranging from zero stress 159 on the stent 40 to a stress 143 on the stent 40 at the just below where the stent 40 reaches the point of fracture 87. In another embodiment, the material 82 comprising stent 40 experiences stress in the elastic region 83 of the stress-strain curve shown in FIG. 102. In one more embodiment, the stent 40 experiences stress in the plastic region 85 of the stress-strain curve shown in FIG. 102. Referring to FIG. 103, in an embodiment the stent 40 experiences stress 143 in the strain-hardening region 147. Still referring to FIG. 103, in another embodiment, the stent 40 experiences stress 143 in the necking region 149. In an embodiment, the stent 40 is deployed with a balloon catheter pressurized to between about 3 to 20 atmospheres (atm). In an embodiment, the stent 40 is deployed with a balloon catheter pressurized at or below 3 atmospheres (atm). In an embodiment, the stent 40 is deployed with a balloon catheter pressurized at or above 20 atmospheres (atm). In an embodiment, the stent 40 is temporarily retained on the delivery catheter with a sheath that partially or fully surrounds the outer diameter of the crimped stent 40 and substantially maintains the stent 40 in a crimped position until delivery and/or deployment. In an embodiment, the stent 40 is not retained on the delivery catheter with a sheath that maintains the stent 40 in a crimped position until delivery and/or deployment.

Degradation and Resorption Processes

In an embodiment the bioresorbable stent 40 undergoes five stages of degradation. First, the stent 40 starts absorbing water from the surrounding tissue when the stent 40 is implanted in the body. Second, the water reacts with the covalent bonds and segments the material's 82 molecular chain into smaller molecular chains, decreasing the molecular weight. Third, the stent 40 experiences a loss of mass when the implant essentially has no cohesive strength. Fourth, absorption via assimilation by phagocytes or further hydrolysis leads to soluble monomeric anions (such as L-lactate), which dissolve into the intercellular fluid. Fifth, the soluble L-lactate is converted into pyruvate, which enters the Krebs cycle. There it is converted into carbon dioxide and water, finally resulting in the complete resorption of the stent. In an embodiment, the degradation process is accelerated after lumen remodeling through the use of ultrasonic or laser treatment of the stent 40 while it is implanted in the anatomical lumen 38. In an embodiment, the implanted a stent's struts are partially or fully dissolved, destroyed, softened, weakened, degraded, eliminated, or broken into fragments or particulate with any noninvasive or invasive ultrasonic or laser treatment to accelerate the resorption process when mechanical support of the stent is no longer needed. In an embodiment, selective photothermolysis (SPTL) is used by matching a specific wavelength of light ad pulse duration to obtain optimal effect on targeted tissue and minimal effect on surrounding tissue. In an embodiment, non-invasive or invasive use of a laser, ultrasound, or intense pulsed light epilators are used to reduce inflammation after implantation of a stent in an anatomical lumen. In an embodiment, the wavelength is between 200-1500 nm, power 1-1000 mv, and irradiance 2 $mW/cm^2$-25 $mW/cm^2$. In other, embodiments the wavelength, power, and irradiance are higher or lower. In an embodiment, after deployment the vascular tissue, fiber, or cells grow into the porosity of the wall thickness 76 and accelerate the resorption process.

Applications

Although the above embodiments have been described in terms of a stent, it will be appreciated that the present invention can be applied to endoprostheses in general. An "endoprosthesis" corresponds to an artificial device that is placed inside the body, more particularly, within an anatomical lumen. An "anatomical lumen" refers to a cavity, duct, of a tubular organ such as a blood vessel, urinary tract, and bile duct. Devices or end-use applications to which the present invention may be applied include without limitation a coronary vascular stent; a vascular stent; a peripheral vascular stent; a carotid stent; a cerebral stent; a cell transportation device; a cell growth platform; a device for supporting an anatomical lumen; a device for reinforcing an anatomical lumen; a device for delivering a drug or drugs to an anatomical lumen; a renal stent; a iliac stent; a superficial femoral artery stent; a urethral stent; a ureter stent; a urinary stent; a biliary stent; a implantable scaffold; a tracheal stent; a trachea stent; a large bronchi stent; a nasal stent; a gastrointestinal stent; an esophageal stent; a drug delivery stent; a drug delivery device; a self-expandable stent; a balloon-expandable stent; a coil stent; a helical spiral stent; a woven stent; an individual ring stent; a ratcheting stent; a modular stent; a bifurcated stent; a stent-graft; a graft; a birth control device; an intrauterine device (IUD); an anatomical lumen repair or splicing device; a device for local delivery of active ingredients to tubular shaped lumen or organs for treatment of cancer; a device for treatment of colon or rectal cancer; an implant; a patch; a mechanical support device; a reinforcement device; a repair device; an attachment device; an oncology treatment device; a device for treatment of cancer within or near an anatomical lumen; a device to assist in remodeling of diseased anatomical lumens; a tissue engineering application (bone, cartilage, blood vessels, bladder, skin, muscle, etc.); a bone fixation device; bone plates; a medical textile; a repair, a device for reconstruction, or replacement/repair of ligaments; a device for maxillofacial surgery; a device for repair, reconstruction, or replacement of rotator cuffs; a device for repair, reconstruction, replacement of hollow organ tissue; a screw; a plate; any implantable devices, patches, regenerative medicine; and a device for the treatment of cancer.

As shown in FIG. 49, in one embodiment the stent 40 includes one or more bifurcations. In another embodiment the stent 40 includes one or more grafts 131 that cover the outer surface 70, inner surface 72, or inner and outer surfaces of the stent 40 to produce a stent-graft 133 as an example is depicted in FIG. 49. In another embodiment, the stent 40 includes a graft 131 comprised of a solid wall thickness. In one more embodiment, the stent 40 includes a graft 131 comprised of a porous wall thickness. In one embodiment the graft 131 is comprised of bioresorbable material 82. In an embodiment, the stent 40 and graft 131 are comprised of bioresorbable material 82. In another embodiment the stent 40 is comprised of bioresorbable material 82 and the graft 131 is comprised of durable material 82. In an embodiment the stent 40 is comprised of durable material and the graft 131 is comprised of bioresorbable material 82. In an embodiment the graft 131 is a cylindrical shape that partially or fully covers the openings 48 of one or more stents 40 and the graft 131 is at least partially attached to one or more struts 44, 46. In an embodiment, the cylindrical-shaped graft 131 covers the openings 48 in the stent 40, the graft 131 is at least partially attached to the struts 44,46, and the graft's 131 wall thickness is formed of one or more fibers 78, 80. In an embodiment, the cylindrical-shaped graft 131 covers the openings 48 in the stent 40, the graft 131 is at least partially attached to the struts 44,46, the graft's wall thickness is formed of one or more layers including seams, and the graft's 131 wall thickness includes one or more fibers 78, 80. In an embodiment, the cylindrical-shaped graft 131 covers the openings 48 in the stent 40, the graft 131 is at least partially attached to the struts 44,46, and the graft's 131 wall thickness is formed of one or more fibers 78, 80 and void spaces 84. In an embodiment, the cylindrical-shaped graft 131 covers the openings 48 in the stent 40, the graft 131 is at least partially attached to the struts 44,46, the graft's 131 wall thickness is formed of one or more fibers 78, 80, and the graft 131 includes living cells. In an embodiment the graft 131 retains atherosclerotic plaque or other materials that may loosen during deployment of the stent 40.

Performance

The stent 40 of the present invention can be of any dimensions that meet the requirements of the application. In some embodiments of stents 40, the diameter is typically be in the range of 2.0 mm to 30 mm and the length ranging from about 6 mm to 200 mm. In other embodiments, the stents 40 are larger or smaller. These stent sizes generally incrementally increase in diameter in 0.5 mm increments and in length by 4 mm to 6 mm increments.

In an embodiment, the stent 40 preferably has a radial strength in the range of about 200 to 1800 mmHg, more preferably in the range of about 600 to 1800 mmHg, and most preferably in the range about 900 to 1200 mmHg during the healing period. Other embodiments of the stent 40 have lower or higher radial strength.

Stent 40 radial strength and other performance parameters such as radial stiffness, radial reactive force, track force, push efficiency, and torqueability can be tested in equipment available from Machine Solutions, 2951 W. Shamrell Blvd., Flagstaff, Ariz. 86001 (USA) using model numbers IDTE2000, RX550/650, RX750/850 or modifications thereof or functional equivalents. In an embodiment of stent 40 the flexibility of the stent is in the range of 0.5-200 $g_f$, more preferably in the range of 50-90 $g_f$ for vascular stent applications. In other embodiments the stent 40 flexibility is more or less than these values.

In an embodiment, the stent 40 preferably has recoil of less than about 15%, more narrowly less than about 10%. In another embodiment the stent 40 has recoil of greater than 15%. In this specification, as known by those skilled in the art of stenting, the term "recoil" refers to the amount the outer diameter 62, or more generally the size, of the stent 40 changes or shrinks after deployment in the anatomical lumen 38 or during the vascular remodeling process. The amount of recoil can be measured at various time intervals after deployment of the stent 40 in an anatomical lumen by those skilled in the art of IVUS echogencity.

Ramifications & Scope

As indicated in the specification herein, it is preferred that the wall thickness 76 described herein is comprised of bioresorbable materials 82. However, in other embodiments the wall thickness 76 is partially or fully comprised of non-bioresorbable or durable materials. In other embodiments the wall thickness 76 is comprised of any variations and any combinations of embodiments described herein to produce a wall thickness 76 employed in any medical application, industrial application, electrical application, mechanical application, chemical application, physical application, or other application. In some embodiments, all of the processing steps or operations described herein are used to produce a wall thickness 76, tubular precursor construct 74, or stent 40 and in other embodiments only some of the processing steps or operations described herein are used to produce a wall thickness 76, tubular precursor construct 74, or stent 40. In some embodiments, the processing steps or operations are performed in a continuous process and in other embodiments the processing steps or operations are performed in one or more discontinuous or batch processes. In an embodiment, some or all the processing steps described herein are combined into one or more processing steps or operations.

Although it is preferred to prepare a wall thickness 76, tubular precursor construct 74, or stent 40 using processes described herein, it will be apparent that modifications to the processes or sequences of processes can be made without departing from the scope and intent of the invention. Moreover, the stent 40 of the present invention can be any embodiment or any combinations of two or more embodiments described herein in all possible variations unless otherwise indicated herein or otherwise clearly contradicted by context. The variations of features are endless and therefore it is impossible to list all these herein. Without intent on limiting, other processes suitable for manufacturing the wall thickness 76, tubular precursor tube 74, or stent 40 of the present invention include solid freeform manufacturing; 3D printing; and any process that lays down successive layers of liquid, powder, or sheet material and builds up a three dimensional parts having the specific features described herein are all within the scope of the present invention. Without intent on limiting additional suitable manufacturing approaches include selective laser sintering, direct metal laser sintering, fused deposition modeling, stereo lithography, digital light processing, fused filament fabrication, melted and extrusion modeling, molten polymer deposition (available by Straasys), laminated object manufacturing, electron beam melting, selective heat sintering, powder bed and inkjet head 3d printing, photo polymerization, solvent casting, use of porogen particles (e.g. sodium chloride, crystals of saccharose, gelatin spheres, or paraffin spheres), gas foaming, emulsification/freeze-drying, thermally induced phase separation, or other processes know by those skilled in the art of additive process manufacturing that are capable of producing scaffolds having struts comprised of the fiber and void features described herein are considered within the scope of the present invention.

Figure 89:
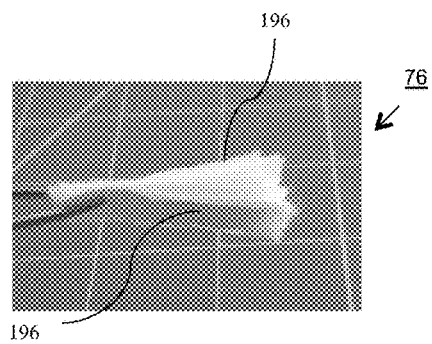
FIG. 89 is a photograph of multiple sheets of preformed configurations in the form of fibers separated by void spaces stacked on top of each other shown in side view.
Figure 90:
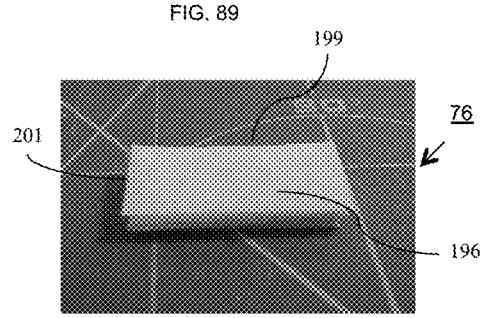
FIG. 90 is a photograph of multiple sheets of preformed configurations in the form of fibers separated by void spaces stacked on top of each other shown from a top view.

Although the specification clearly describes the novel construction of a wall thickness 76 in the form of a tubular precursor construct 74 suitable for use in manufacturing a stent 40, the wall thickness 76 of the present invention has broader applicability and is formable into any shape suitable for use in any application. Without intent on limiting, the wall thickness 76 of the present invention is formed into a shape using a process selected from the group of compression mold, injection mold, reaction injection mold, blow mold, extrusion mold, or calendaring. For example, in an embodiment, one or more sheets 196 comprised of preformed configurations 77 are assembled between two or more plates 129 of any shape or configuration to form a wall thickness 76. As an example is shown in FIG. 89 and FIG. 90, multiple sheets 196 are placed on a flat plate 129. The sheets are surrounded by a high tolerance shim 127 that sets the thickness of the shaped wall thickness 76. As shown in FIG. 92 a second flat plate 129 is positioned on top of the sheets 196 and shim 127. The assembly is heated, compressed, and cooled to form a shaped wall thickness 76. The plates that form the shape of the wall thickness 76 are not limited to the flat shape shown in FIG. 91. The shape or configuration of the plates 129 of the present invention 129 is virtually unlimited. In an embodiment, the shaped wall thickness 76 is formed by positioning one or more sheets 196 between two or more plates 129 having low dimensional variation, heating the sheets 196 to partially or fully interconnect the sheets 196 while the sheets 196 are positioned between the plates 129, cooling the sheets 196 while positioned between the plates 129, and removing the shaped wall thickness 76 from the plates 129. In an embodiment, the shaped wall thickness 76 is formed by positioning one or more sheets 196 between two or more plates 129 having low dimensional variation, heating the sheets 196 while the sheets 196 are positioned and compressed between the plates 129, cooling the sheets 196 while positioned between the plates 129, and removing the shaped wall thickness 76 from the plates 129.

Also, within the scope of the present invention is forming a wall thickness 76 wherein there is a temperature gradient across the wall thickness 76 during formation. In a "half-baked" embodiment the shaped wall thickness 76 is formed by following the following steps: (1) positioning one or more sheets 196 between two or more plates 129; (2) heating only the bottom plate to heat the sheets 196 from the bottom so that for part or all of the heating cycle the top plate is at a lower temperature than the bottom plate while the sheets 196 are positioned and compressed between the plates 129; (3) cooling the sheets 196 while positioned between the plates 129; and (4) removing the shaped wall thickness 76 from the plates 129 so that the bottom portion of the sheet or sheets become substantially translucent and the top portion of the sheet or sheets remain white or opaque because the top sheets were not heated to as high of a temperature. A "half-baked" embodiment of a wall thickness 76 has interesting properties because the translucent portion of the wall thickness 76 is substantially more stiff and the white portion of the wall thickness 76 is substantially more pliable or flexible. The term "half-baked" does not mean that the wall thickness is 50% translucent and 50% white or opaque. In an embodiment the "half-baked" wall thickness 76 is comprised of up to 99 percent of its wall thickness being white (flexible) and the remaining portion being translucent (stiff). In another embodiment, the wall thickness 76 is comprised of up to 99 percent of its wall thickness being translucent (stiff) and the remaining portion being white or opaque (flexible). In other embodiments, the percentages of translucent (stiff) and white/opaque (flexible) in the wall thickness are greater or lesser.

In an embodiment, the shaped wall thickness 76 is formed by positioning one or more sheets 196 between two or more plates 129 having low dimensional variation, heating the sheets 196 while the sheets 196 are positioned and compressed between the plates 129, cooling the sheets 196 rapidly by quenching them in, for example, ice water while positioned between the plates 129, and removing the shaped wall thickness 76 from the plates 129. In an embodiment, the shaped wall thickness 76 is formed by positioning one or more sheets 196 between two or more plates 129 having low dimensional variation, heating the sheets 196 while the sheets 196 are positioned and compressed between the plates 129, cooling the sheets 196 rapidly by quenching them while positioned between the plates 129, removing the shaped wall thickness 76 from the plates 129, and annealing them at a temperature around the crystalline temperature (Tc) of the material 82 for a period of time sufficiently long to increase the crystallinity of the material 82.

In an embodiment, the shaped wall thickness 76 is formed by positioning and/or compressing one or more sheets 196 between two or more plates 129 that are pre-heated to a temperature at or below about the glass transition temperature of the material 82 so that there is a substantially uniform temperature across the wall thickness 76 during formation, heating the sheets 196 while the sheets 196 are positioned and/or compressed between the plates 129, cooling the sheets 196 while the sheets are positioned and/or compressed between the plates 129, and removing the shaped wall thickness 76 from the plates 129. In an embodiment, the shaped wall thickness 76 is formed by positioning and/or compressing one or more sheets 196 between two or more plates 129 that are pre-heated to a temperature between about the glass transition temperature of the material 82 and about the melting temperature of the material 82, heating the sheets 196 while the sheets 196 are positioned and/or compressed between the plates 129, cooling the sheets 196 while positioned and/or compressed between the plates 129, and removing the shaped wall thickness 76 from the plates 129. In another embodiment, the shaped wall thickness 76 is formed by positioning and/or compressing one or more sheets 196 between two or more plates 129 that are preheated to a temperature at or above about the melting temperature of the material 82, heating the sheets 196 while the sheets 196 are positioned and/or compressed between the plates 129, cooling the sheets 196 while the sheets 196 are positioned and/or compressed between the plates 129, and removing the shaped wall thickness 76 from the plates 129.

In an embodiment, the shaped wall thickness 76 is formed by positioning and/or compressing one or more sheets 196 between two or more plates 129 having low dimensional variation, heating the sheets 196 while the sheets 196 are positioned and/or compressed between the plates 129, cooling the sheets 196 while positioned and/or compressed between the plates 129, and removing the shaped wall thickness 76 from the plates 129, wherein one or more of said sheets 196 are partially or fully comprised of a material 82 having a higher melting temperature and one or more sheets 196 are partially or fully comprised of a material 82 having a lower melting temperature. In an embodiment, the shaped wall thickness 76 is formed by positioning and/or compressing one or more sheets 196, films 81, or combinations thereof between two or more plates 129 having low dimensional variation, heating the sheets 196, films 81, or combinations thereof while the sheets 196, films 81, or combinations thereof are positioned and/or compressed between the plates 129, cooling the sheets 196, films 81, or combinations thereof while positioned and/or compressed between the plates 129, and removing the shaped wall thickness 76 from the plates 129, wherein one or more of said sheets 196 or film 81 are comprised of a material 82 having a higher melting temperature and one or more sheets 196 or film 81 are comprised of a material 82 having a lower melting temperature. In an embodiment, the shaped wall thickness 76 is formed by positioning and/or compressing one or more sheets 196, films 81, or combinations thereof between two or more plates 129 having low dimensional variation, heating the sheets 196, films 81, or combinations thereof while the sheets 196, films 81, or combinations thereof are positioned and/or compressed between the plates 129, cooling the sheets 196, films 81, or combinations thereof while positioned and/or compressed between the plates 129, and removing the shaped wall thickness 76 from the plates 129, wherein the one or more of the material or materials 82 comprising the one or more of said sheets 196 or films 81 are cross-linked. The term "cross-linked" refers to connecting one molecule or polymer chain to another molecule or polymer chain through a bond. In an embodiment, the shaped wall thickness 76 is formed by positioning and/or compressing one or more sheets 196 comprised of preformed configurations 77 in the form of one or more fibers 78 and one or more films 81 between two or more plates 129 having low dimensional variation, heating the sheets 196 and films 81 while the sheets 196 and films 81 are positioned and/or compressed between the plates 129, cooling the sheets 196 and film 81 while positioned and/or compressed between the plates 129, and removing the shaped wall thickness 76 from the plates 129. In an embodiment, the shaped wall thickness 76 is formed by positioning and/or compressing one or more sheets 196 comprised of preformed configurations 77 in the form of one or more fibers 78 and one or more films 81 between two or more plates 129 having low dimensional variation, heating the sheets 196 and films 81 while the sheets 196 and films 81 are positioned and/or compressed between the plates 129, cooling the sheets 196 and films 81 while positioned and/or compressed between the plates 129, and removing the shaped wall thickness 76 from the plates 129, wherein the layers of film 81 interconnect the layers of sheets 196. In an embodiment, the shaped wall thickness 76 is formed by positioning and/or compressing one or more sheets 196 comprised of preformed configurations 77 in the form of one or more fibers 78 and one or more films 81 between two or more plates 129 having low dimensional variation, heating the sheets 196 and films 81 while the sheets 196 and films 81 are positioned and/or compressed between the plates 129, cooling the sheets 196 and films 81 while positioned and/or compressed between the plates 129, and removing the shaped wall thickness 76 from the plates 129, wherein the material 82 comprising the layers of film 81 flows into the void space 84 in the layers of sheets 196 during heating and partially or fully retains this position after cooling. In an embodiment, the shaped wall thickness 76 is formed by positioning and/or compressing one or more sheets 196 and/or films 81 between two or more plates 129 having low dimensional variation, heating the sheets 196 and/or films 81 while the sheets 196 and/or films 81 are positioned and/or compressed between the plates 129, cooling the sheets 196 and/or films 81 while positioned and/or compressed between the plates 129, and removing the shaped wall thickness 76 from the plates 129, wherein some or all of said sheets 196 and/or films 81 are comprised of a material 82 having been surface treated to improve adhesion between sheets 196 and/or films 81. The amount of sheets 196 and configurations of sheets 196 is virtually unlimited in the present invention. The amount of sheets 196 and films 81, the configurations of sheets 196 and films 81, and the combinations of sheets 196 and films 81 employed in the present invention are virtually unlimited.

Figure 93:
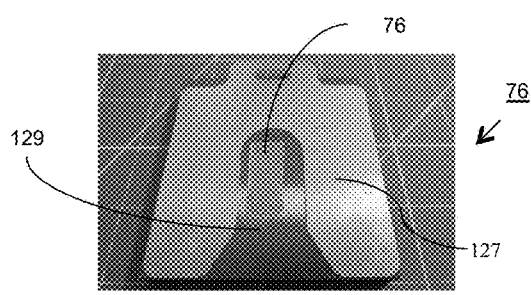
FIG. 93 is a photograph of the multiple sheets of preformed configurations in the form of fibers separated by void spaces of FIG. 89 and FIG. 90 after they have been assembled as in FIG. 92, heated, compressed, and cooled.
Figure 91:
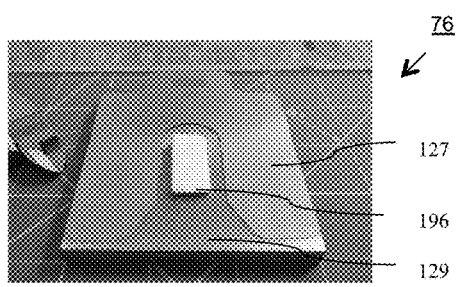
FIG. 91 is a photograph of multiple sheets of preformed configurations in the form of fibers separated by void spaces stacked on top of each other positioned on a flat steel plate and surrounded by a high tolerance shim.
Figure 94:
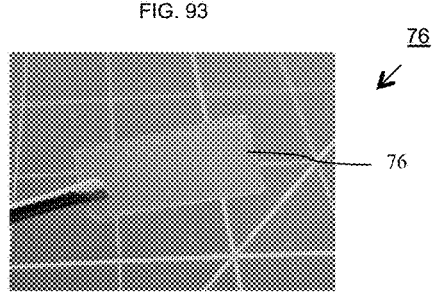
FIG. 94 is a photograph of the multiple sheets of preformed configurations in the form of fibers separated by void spaces of FIG. 89 and FIG. 90 after they have been assembled as in FIG. 92, heated, compressed, and cooled showing an example of densified fibers that have changed from an opaque white appearance to a translucent appearance and the material changes from a flexible to a substantially more rigid material.

In an embodiment, the wall thickness 76 is formed by a process of consisting of the steps of: (1) cutting the sheets 196 into any size and layering the sheets 196 if there are more that one sheet as shown in FIG. 82, FIG. 89, and FIG. 90; (2) positioning the sheets 196 on a bottom plate 129 having low dimensional variation as shown in FIG. 91; (3) placing a shim 127 or other device having low dimensional variation so that it can separate the bottom plate 129 from the top plate 129 as shown in FIG. 91 and FIG. 92 to set the thickness of the wall thickness 76; (4) heating the flat plates 129, shim 127, and sheets 196; (5) compressing the top plate 129 against the bottom plate 129 so that the gap between the two plates 129 is substantially equal to the thickness of the shim 127; (4) clamping the top plate 129 and bottom plate 129 together before, during, or after heating and allowing the assembly to slowly or quickly cool to produce a wall thickness 76 having low dimensional variation. If the sheets 196 are heated and not constrained by the plates 129 or other compression mold, the sheets 196 will distort and be unsuitable for producing a wall thickness 76 as shown in FIG. 83. The wall thickness 76 that was shaped between the two plates 129 is shown in FIG. 93 while the wall thickness 76 is resting on the bottom plate 129. FIG. 94 shows the wall thickness 76 after it was shaped between two flat plates in a close-up photograph. Other examples of embodiment of a shaped wall thickness 76 are shown FIG. 95 wherein some samples include greater or lesser porosity or experienced greater or lesser amount of thermal treatment. The white or opaque sheet 196 shown in FIG. 95 experienced lower temperatures than the more translucent wall thicknesses. The amount of sheets 196, the porosity of the sheets 196, and the thickness of the sheets 196 placed between the plates 129 influences the amount of porosity in the final wall thickness 76. In an embodiment, the starting wall thickness 76 comprised of the sheets 196, layers of sheets 196, or layers of sheets 196 and films 81 is larger than its ending wall thickness because the wall thickness is consolidated. In an embodiment, the starting wall thickness comprised of sheets, layers of sheets 196, or layers of sheets 196 and films 81 is larger than its ending wall thickness 76 and its ending width and/or length is larger than its beginning width and/or length after the wall thickness 76 is consolidated.

While several particular forms of the invention have been illustrated and described, it will also be apparent that various modifications can be made without departing from the scope of the invention. For example and without limitation, the strut pattern 60 can have a lesser or greater number of rings 58 than what is shown in FIG. 42. As a further non-limiting example, the strut pattern 60 can have any number of open or closed cells circumferentially arranged to encircle the stent central axis of other embodiments of the present invention. In FIG. 42, there are three W-shape or other shape closed or open cells that are circumferentially arranged, although a lesser or greater number may be implemented in a strut pattern of other embodiments. In yet another non-limiting example, the strut pattern 60 can have any number of W-shape or other shape open or closed cells arranged axially along the entire longitudinal length of a stent in other embodiments. In FIG. 43, there are eighteen W-shape closed cells axially arranged, although a lesser or greater number may be implemented in a strut pattern of other embodiments. In yet one more embodiment, any coating 180 or surface treatment of the preformed configurations 77, outer surface 70, inner surface 72, cutting edges 182, or combination thereof that temporarily serves as a moisture barrier between the wall thickness 76 and the anatomical lumen 88, delays the onset of hydrolysis/degradation of material 82 or controls the rate of degradation or resorption of material 82 is suitable for use and improving the performance of a endoprosthesis. Although in the present invention, the ability of the coating 180 to delay hydrolysis is defined in terms of "perm" and "moisture vapor transmission rate" there are other possible measurements that can characterize the ability of a coating to protect the stent 40 wall thickness 76 from moisture after the deployment of the stent 40 that have an equivalent result.

EXAMPLES

The following examples are presented to more particularly illustrate our invention and are not to be construed as limitations thereon.

Example 1—Bioresorbable (PLLA) Stent Made by Solution Electrospinning Process

Particles of PURASORB PL-38 having a somewhat translucent to opaque appearance, which is a homopolymer of L-lactide (PLLA) having molecular weights in the range of 121-298 kg/mol and 298-727 kg/mol, were dissolved in hexafluoroisopropanol (HFIP) at 2.5, 5, 11, and 15 weight percent. The solutions were clear in appearance. The PLLA solutions were electrospun from a syringe equipped with a 22 gauge needle using 15 kV potential, a throw distance of 12-16 cm, and a syringe flow rate of 5 mL/h. To form a mesh wall thickness for use in a precursor tubular construct, having a wall thickness of different diameter fibers, the 2.7 mm diameter drum or mandrel having a length of twelve inches was rotated at 600, 1000, and 1500 rpm to achieve the different degrees of fiber orientation and a wall thickness of 150 microns. The precursor tubular construct tubes were dried under vacuum for two days to remove the residual HFIP and moisture. The resultant fibers ranged in diameter from 0.5 to 1.5 microns depending on the rotational rate of the drum, solution concentration, and solution flow rate.

The resultant tubes were heated in a oven to a temperature near and above the glass transition temperature of PLLA, specifically at 55-75 degrees Celsius, 75-85 degrees Celsius, 85-95 degrees Celsius, 95-105 degrees Celsius, 105-115 degrees Celsius, 115-125 degree Celsius, 125-135 degrees Celsius, 135-145 degrees Celsius, 145-155 degrees Celsius, 155-165 degrees Celsius, and 165-235 degrees Celsius to interconnect the electrospun fibers and form the fibers around the mandrel to form tube 74. While at elevated temperature the wall thickness was compressed to consolidate the wall thickness so that the porosity in the wall thickness was reduced from 80 percent porosity to about 20 percent porosity or less.

The tubes were sized in the cavity of a mold having low dimensional variability. The tubes were cooled to room temperature at different cooling rates ranging from fast (quenching in ice water) to slower cooling. Some samples were annealing at a temperature in the range of 47-142 degrees Celsius. The tubes were cooled. The resultant crystallinity of the wall thickness was measured with a differential scanning calorimeter (DSC). The tube 74 was converted into sixteen 18 mm long stents 40 by cutting a strut pattern 60 into the tube wall thickness 76. This process produced sixteen stents 40 and about 17 mm of tube 74 was wasted because some length of tube was required to be gripped by laser during the cutting operation. The strut pattern as illustrated in FIG. 42 was cut into the wall thickness using a laser machining process (Service available from Rofin-Sinar Laser GmbH, Berzeliusstrabe 87, 22113, Hamburg or Peterbrunner Str. Lb, 82319, Starnberg, Germany).

A stent 40 was then coated with a hydrophobic C10 polymer coating containing antiproliferative agent zotarolimus at a dosage of 160 µg/cm$^2$ of stent surface so that 85% of drug is delivered in 60 days and the balance is delivered in 180 days. The hydrophobic coating delays hydration of fibers for 90 to 180 days. A second coating at least partially containing hydrophilic polyvinyl-pyrrolidinone is also added to improve biocompatibility.

Another stent 40 was coated with another hydrophobic polymer poly(vinylidene fluoride-co-hexafluoropropylene) containing everolimus at a dosage of 100 µg/cm$^2$ of stent surface so that 80% of everolimus is delivered in the first 30 days. One more stent 40 was coated with another hydrophobic polymer poly(vinylidene fluoride-co-hexafluoropropylene) containing sirolimus at a dosage of 100 µg/cm$^2$ of stent surface so that 80% of sirolimus is delivered in the first 30 days. One more stent 40 was coated with another controlled release polymer comprised of a copolymer comprised of 50/50 DL-lactide/glycolide (available from PURAC as PURASORB PDLG 5004) containing sirolimus at a dosage of 100 µg/cm$^2$ of stent surface so that 80% of sirolimus is delivered in the first 30 days. The stents were crimped onto a balloon catheter.

Example 2—Wall Thickness Suitable for Production of Prosthesis—Flat Sheet

A blend of poly L-Lactide (Trade name PURASORB PL-38 blended with PURASORB PL-32 available from Purac, Gorinchem, The Netherlands) was dissolved in HPLC-grade dichloromethane (CAS 75-09-2) (available from Fischer Scientific, Boston, Mass., USA) at a 5% weight percent in a 20 ml scintillation vial (available from Fischer Scientific, Boston, Mass., USA) and electrospun. The polymer solution pumped through a stainless 21 gauge by ½ inch steel blunt needle (Part NE-211 PL-25, Available from Amazon.com) at a rate of 1.5 ml/hour to 0.2 ml/minute. A high voltage power supply (available from Gamma High Voltage, Ormond Beach, Fla., USA) was connected to the syringe needle and a three inch diameter by eight inch long rotating cylindrical-shaped mandrel or collector plate wherein the power supply was set at 90 milliamps (mA) and 10-12 kilovolts (KV). The throw distance, which is the distance between the end of the syringe needle and the mandrel was set at twelve centimeters (cm). Varying the throw distance, voltage, and pumping rate controlled the amount of fiber wetness upon deposition. The fiber alignment was controlled by the speed of rotation of the mandrel and the amount of voltage. The solution exiting the needle consists of streaming jet or whipping jet sections depending on the viscosity of the solution, throw distance, voltage differential, and environmental conditions. Generally, the higher speed of mandrel rotation tended to align the fibers in the circumferential direction around the mandrel and the higher the voltage differential the more fiber "wagging" which resulted in a more nonwoven structure. As known by those skilled in the art of electrospinning the term "wagging" refers to the amount that the fiber oscillates as it travels from the tip of the syringe needle to the collection surface.

Figure 95:
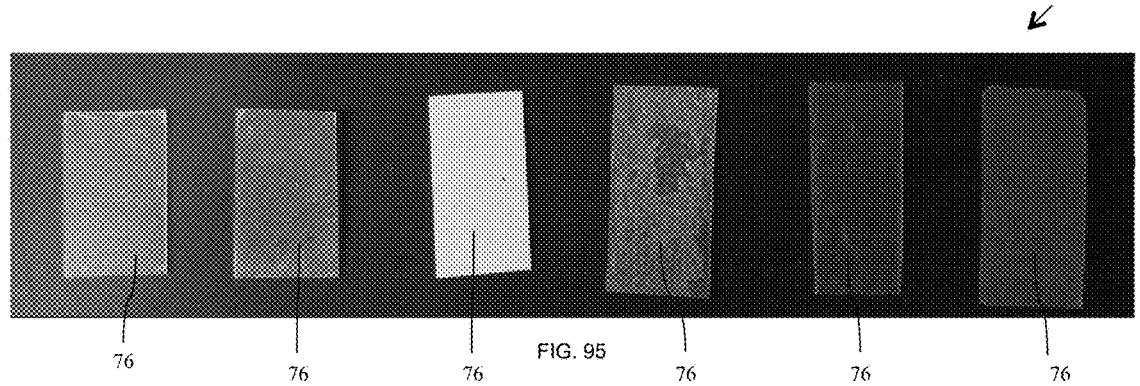
FIG. 95 is a photograph of various embodiments of multiple sheets of preformed configurations in the form of fibers at least partially separated by void spaces that were processed as shown in FIG. 91 to FIG. 94 wherein the heating and cooling conditions were varied as described herein so that in some cases the densified fibers were translucent after cooling, in some cases the fibers were still opaque and white after cooling, and in some cases the fibers were a combination of transparent and opaque and white appearance after cooling.

The fibers 78 collected on the mandrel 118 were removed from the mandrel by making a cut along the long dimension of the mandrel to form flat sheets 196 approximately 8 inches by 9.43 inches. A portion of the fibers 78 collected on the mandrel were examined under a microscope and a photograph of these fibers is shown in FIG. 53. These sheets were then cut into small strips of material approximately 0.5 inches by 1.0 inch as shown in FIGS. 82 and 83 and these strips were layered on top of each other until the multiple strips had a thickness of about 0.025 inches. In some cases the fiber alignment direction was the same in each layer and in other cases the fiber alignment direction varied from layer to layer. The layered sheets of fibers were placed on a 3.0 inch by 3.0 inch by 0.25 inch steel plate made of 4140/4142 alloy steel (model 4468T34 available from McMaster Carr, Robbinsville, N.J., USA) as shown in FIG. 91. The sheets were surrounded by a 0.005 inch thick shim (model 97235K138 available from McMaster Carr, Robbinsville, N.J., USA) and another 3.0 inch by 3.0 inch by 0.25 inch steel plate was placed on top of the layered fibers and shim as shown in FIG. 92. This assembly was placed on a hot plate and the temperature of the assembly was raised from about 80 degrees Fahrenheit to about 300-425 degrees Fahrenheit or until the sheets changed from a an opaque white appearance to a translucent appearance as shown in FIGS. 93 and 94. The two steel plates were clamped together to compress the 0.025 inch thick fiber sheets to the 0.005 thickness of the shim (which separated the two plates) so that there was a compression ratio of 5. The assembly was allowed to cooled in some cases rapidly by quenching ice water and in other cases slowly, and disassembled to remove the annealed, flattened sheet of polymeric fibers. The experiment was repeated numerous times varying the thickness of the sheets, fiber thickness, fiber manufacturing process, sheet porosity, fiber alignment, heating temperature, rate of heating, cooling temperature, rate of cooling, compression force, humidity, and other conditions so that various mechanical properties were obtained in of the produced wall thickness. As shown in FIG. 95, wall thicknesses 76 were produced that were opaque, white, translucent, flexible, rigid, stiff, solid, porous, and combinations thereof. The experiments were also repeated including strengthening additives 150 in the material 82 comprising the fibers 78.

A die capable of cutting dog bone shapes (available from Ceast, Norwood, Mass., USA) was used to cut "dog bone" shaped articles from the samples produced. The dog-bone articles were tested in a dynamic mechanical analyzer (model RSA-G2 Solids Analyzer available from TA Instruments, New Castle, Del., USA) to confirm superior mechanical properties versus virgin polymer in tests including strength at break, elongation at break, Young's modulus, flexural strength, flexural strain, and flexural modulus at room temperature and at physiological conditions. Test results confirmed that fibers formed into a wall thickness and compressed during heating and cooling provided a material suitable for use as a medical device or implant.

Example 3—Wall Thickness Suitable for Production of Prosthesis—Tube

The flat sheets approximately 8 inches by 9.43 inches prepared as described in EXAMPLE 2, were cut into longer strips 1 inch wide by 8 inches long and 1 inch wide by 9.43 inches long to obtain strips of fibrous material having fibers aligned in different directions. These strips were wound around a steel 5 mm diameter by 200 mm long steel shaft having dimensional variation of less than 0.008 mm (model 6112K37 available from McMaster Carr, Robbinsville, N.J., USA). The assembly was placed in an oven at 135-425 degrees Fahrenheit and baked until the fibrous material wrapped around the mandrel turned from an opaque white appearance to a translucent appearance. In some cases the assembly was removed from the heat prior to becoming fully translucent. In other cases the assembly was removed from the heat prior to losing it opaque white appearance. The heated fibrous material and shaft were then rolled over a flat plate having a 0.005 inch thick shim having clearance for the fibrous material in the middle as shown in FIG. 87. By rolling the heated shaft over the shim and the heated fibrous material over the plate, the tube's wall thickness comprised of fibers being was densified and formed into a thickness having low dimensional variation equal to about 0.005 inch. The material was cooled in some cases while fully positioned on the mandrel. In other cases, the material was cooled by sliding the tube-shaped material off the end of the mandrel into a bath of ice water to quench the wall thickness and lock in the formed shape. In some cases the material was reheated and annealed at a temperature in the range of 120 to 250 degrees Fahrenheit.

The polymeric tubes formed of annealed, consolidated fibers were removed from the mandrel. In some cases the tubes were removed from the mandrel while they were above room temperature, in some cases the tubes were removed from the mandrel while they were at room temperature, and in other cases the tubes were removed from the mandrel while they were below room temperature. In some cases the tubes were twisted while they were removed from the mandrel which created strain hardening in the wall thickness. The inventors found that slightly warming the assembly facilitated the removal of the polymeric tubes from the shafts without substantially distorting the parts from their original dimensions. These tubes were then converted into stents by cutting a stent pattern in the wall thickness of the tubes, coating the outside surface of the struts with a drug-polymer matrix, and crimping the coated stent onto the outside surface of a balloon catheter.

Example 4—Wall Thickness Suitable for Production of Prosthesis—Films

A wall thickness 76 was formed of multiple layers of films. The four films were produced by dissolving PURASORB Poly (L-lactide) in HPLC-grade dichloromethane and casting the films in a mold. The films were 0.010 millimeters thick. A rod-shaped mandrel having low dimensional variation was coated with a thin layer of Crisco as a release agent. The films were stacked on top of each other and formed around the outside diameter of the lubricated mandrel by spirally wrapping the films around the mandrel until the desired wall thickness was obtained. The ends of the films were tacked down at the short edge to prevent the films from unwrapping. The mandrel was placed in an autoclave preheated at a temperature of 210 degrees Celsius for a period of eight minutes or until the wall thickness became translucent. The mandrel was removed from the autoclave and rolled over a flat plate and shim preheated to a temperature of about 38 degrees Celsius as shown in FIG. 87 to size the wall thickness. Since the films were still hot from being heated in the autoclave the wall thickness conformed to the thickness of the gap between the mandrel and flat plate set by the shim during rolling. After rolling the mandrel about 5-10 rotations, the mandrel and hot films were quenched in cold ice water. The mandrel and cooled films were then replaced in the autoclave preheated at 100-150 degrees Celsius for about 10 minutes to increase crystallinity. Upon removal of the heated assembly, the wall thickness was cooled and twisted to remove the tube from mandrel.

Example 5—Wall Thickness Suitable for Production of Prosthesis—Films & Sheets

A wall thickness was formed into a three layer sandwich of two films of Poly (L-lactide) at the two outer layers and one layer of a fibers comprised of a copolymer of L-lactide and glycolide in a 10/90 molar ratio in the middle layer. The films were produced of PURASORB PL-38, PURASORB PL-32, PURASORB PL-65 (available from PURAC, the Netherlands), and combinations thereof at different ratios. The fibers were obtained in monofilament form from BIO-GENERAL, San Diego, Calif., USA and in multifilament form from RIVERPOINT MEDICAL, Portland, Oreg., USA. In one embodiment, the plurality of fibers comprised of the copolymer were laid in the wall thickness in the radial direction, axial direction, angled direction, and combinations thereof. In a second embodiment, the plurality of fibers comprised of the copolymer were first braided into a configuration like shown in FIG. 18 and then placed between the two films of Poly (L-lactide). In an embodiment, the films were substituted with sheets of fiber in nonwoven configuration produced by electrospinning. The sandwich was placed between two flat plates like shown in FIG. 91 and FIG. 92 and heated in an autoclave preheated to about 190-220 degrees Celsius for about 8 to 15 minutes. The two flat plates separated by a shim were compressed with a clamp to consolidate the wall thickness from a starting thickness of 0.250 mm to an ending thickness of 0.125 mm so that there was a compression ratio of 2. The wall thickness while still clamped between the two plates was then cooled by quenching. The plates were unclamped and the wall thickness was removed. The wall thickness had transformed form a white appearance to a clear appearance and was substantially more stiff than prior to being heated, consolidated, and cooled. In one case the top plate was much cooler so that the bottom of the wall thickness transformed into a translucent material but the top of the wall thickness remained white.

Example 6—Drawn & Expanded—Wall Thicknesses

Wall thicknesses comprised of Poly (L-lactide) having an as-polymerized molecular weight of 674,000 g/mol (Available from Purac as PL-38) and 1,534,000 g/mol (Available from Purac as PL-65) were formed into a wall thickness in the shape of a tubular precursor construct having an outer diameter of 12 mm and length of 5 cm. The wall thickness was formed by: (1) melting the Poly (L-lactide), extruding the melt through a tubular-shaped die, and cooling the tubular-shaped extrudate to produce a tubular precursor construct; (2) dissolving Poly (L-lactide) in a solvent comprised of chloroform at a ratio of 10 weight percent Poly (L-lactide):90 weight percent Chloroform, extruding the solution through a tubular-shaped die, and evaporating the solvent from the tubular-shaped extrudate to produce a tubular precursor construct; (3) melting the Poly (L-lactide), extruding the melt through a circular-shaped die, and cooling the circular-shaped extrudate to produce a fiber that was subsequently aligned in the wall thickness of a tubular precursor construct using braiding and winding processes; (4) dissolving Poly (L-lactide) in a solvent comprised of chloroform at a ratio of 8 weight percent Poly (L-lactide):92 weight percent Chloroform, extruding the solution through a circular-shaped die, and evaporating the solvent from the circular-shaped extrudate to produce a fiber that was subsequently aligned in a the wall thickness of a tubular precursor construct using braiding and winding processes; (5) melting the Poly (L-lactide), extruding the melt through a rectangular-shaped die, and cooling the rectangular-shaped extrudate to produce a film that was subsequently aligned in the wall thickness of a tubular precursor construct in multiple layers like a jelly roll; (6) dissolving Poly (L-lactide) in a solvent comprised of chloroform at a ratio of 8 weight percent Poly (L-lactide):92 weight percent Chloroform, extruding the solution through a rectangular-shaped die, and evaporating the solvent from the rectangular-shaped extrudate to produce a film that was subsequently aligned in a the wall thickness of a tubular precursor construct in multiple layers like a jelly roll, (7) dissolving Poly (L-lactide) in a solvent comprised of chloroform at a ratio of 10 weight percent Poly (L-lactide):90 weight percent Chloroform, casting the solution on a flat sheet, and evaporating the solvent from the rectangular-shaped casting to produce a film that was subsequently aligned in a the wall thickness of a tubular precursor construct in multiple layers like a jelly roll; and (8) dissolving Poly (L-lactide) in a solvent comprised of chloroform at a ratio of 5 weight percent Poly (L-lactice):95 percent Chloroform, casting the solution on a flat sheet, and evaporating the solvent to form a rectangular-shaped casting to produce a film and melting a co-polymer of L-lactide and glycolide, compressing the melted copolymer and forming into a rectangular shape to form a film, and positioning the two sheets on top of each other and forming a wall thickness of a tubular precursor construct from the two film as shown in FIG. 97 and FIG. 98.

The tubular precursor construct were then passed though a sizing die similar to the one shown in FIG. 108 having a entrance diameter of 12 mm and an exit diameter of 3 mm to draw down the tubes at a draw down ratio of 4. The length of the tubes was increased from 5 cm to 15 cm or an axial elongation ratio of 3. The tubes were drawn at a temperature of 100 degrees Celsius and held at constant tension until cooled to a temperature of below about 50 degrees Celsius. In some of the samples, the wall thickness of the tubular precursor construct was consolidated before drawing. In some of the samples, the wall thickness of the tubular precursor construct was formed into a network before drawing. A stent pattern was like the one shown in FIG. 42 was cut into the tube wall thickness using a StarFemto FX available from Rofin-Baasel Lasertech.

The wall thickness of the tubular precursor construct was cut into the shape of a dog-bone tensile bar and tensile tested using a dynamic mechanical analyzer (model RSA-G2 available from TA Instruments) at a crosshead speed of 25 millimeters/minute and found to have a maximum tensile strength of 300 MPa for melt processed wall thicknesses and 1 GPa for solution processed wall thicknesses. For samples including void spaces in the wall thickness, the maximum tensile strength was lower but the samples showed dramatically higher elongation to break results. Samples were prepared having higher draw down ratios than 4, which produced samples of even higher tensile strength.

It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

We claim:

1. A method of producing a tubular-shaped bioresorbable stent comprising the steps of:
   providing a solution-processed, flexible first film having a film thickness less than 0.100 millimeters, wherein the first film has major surfaces that are substantially parallel and distinctly greater than the minor surfaces, wherein the first film comprises a single solid bioresorbable material having a weight average molecular weight within the range of greater than 500,000 g/mol to 2,682,000 g/mol or a blend of multiple solid bioresorbable materials wherein at least one material within the blend has a weight average molecular weight within the range of greater than 500,000 g/mol to 2,682,000 g/mol,
   wrapping the first film around the circumference of a shape-forming device at least two times in a way that forms at least two overlaying separate film thicknesses surrounding at least part of the length of the shape-forming device in a tubular configuration,
   supporting the inner diameter of the wrapped first film with the shapeforming device substantially maintaining the wrapped film in tubular configuration,
   heating the supported first film to a temperature above the melting temperature of the material within the first film to form a tubular liquefied material on the outer surface of the shape-forming device, wherein heating the supported first film comprises increasing the temperature of the first film to a temperature between 110 degrees Celsius to 250 degrees Celsius,
   cooling the liquefied material at a rate within the range of 7 degrees Celsius per minute to 200 degrees Celsius per second on the shapeforming device until the liquefied material is solidified into a greater than 0 percent to 70 percent crystalline material and 30 percent to less than 100 percent amorphous material forming a self-supporting tube having a unified, tube wall thickness, and wherein the tube is suitable for inclusion of a strut pattern.

2. The method of claim 1 further comprises the steps of preparing at least one solution by dissolving one or more solid bioresorbable material(s) within one or more liquid solvent(s), wherein the concentration of the material(s) within the solution is equal to or less than 15 percent of the solution and the remainder of the solution is solvent(s) and/or forming at least one of the solutions into at least one liquid shape that has major surfaces that are substantially parallel and distinctly greater than the minor surfaces and removing the solvent(s) from at least one of the liquid shape(s) thereby converting at least one of the liquid shape(s) into at least one solution-processed, flexible film having major surfaces that are substantially parallel and distinctly greater than the minor surfaces.

3. The method of claim 1 further comprising removing portions of the tube wall thickness forming a strut pattern within the tube wall thickness.

4. The method of claim 1 further comprising removing the tube from the shape-forming device.

5. The method of claim 1 further comprising applying at least one coating that includes at least one active ingredient onto at least some or all the surfaces of the stent.

6. The method of claim 1 further comprising wrapping an additional second different film comprising at least one active ingredient and includes poly (DL-lactide) or a copolymer of DL-lactide and glycolide.

7. The method of claim 1 further comprising forming the film by solvent casting.

8. The method of claim 1 further comprises at least partially producing the stent within a protective environment that minimizes or prevents a reduction of molecular weight of the bioresorbable material(s).

9. The method of claim 1 further comprises sterilizing the stent by electron beam irradiation (e-beam), gamma irradiation, ethylene oxide (EtO), low temperature plasma, steam, dry heat, and/or ultraviolet light.

10. The method of claim 1 further comprises crimping the stent from a larger size to smaller size onto a catheter prior to delivery of the stent into an anatomical lumen and/or expanding the stent from a smaller size to a larger size during deployment of the stent within an anatomical lumen.

11. The method of claim 1, wherein the material comprises one material or a blend of multiple material(s) selected from the group of: amorphous polymers, polymerized lactic acid, hydrolysable polymers and/or copolymers, hydrolysable polyesters and/or copolymers thereof, semi crystalline polymers, homopolymers of L-lactide, poly (L-lactide), poly (glycolide), poly (caprolactone), poly (D-lactide), poly (DL-lactide), copolymers of L-lactide and glycolide, copolymers of L-lactide and D-lactide, copolymers of L-lactide and caprolactone, poly (dioxanone), poly (hydroxyalkanoate), poly (orthoester), poly (4-hydroxybutyrate), poly (anhydride), poly (trimethylene carbonate), poly (butylene succinate), polymers having an ester termination, polymers having an end group comprising free carboxylic acid, polymers having an end group comprising alkyl ester, polymers having an end group comprising decyl ester, polymers having end group comprising docecyl ester, semi-crystalline polymers or copolymers, a polymer containing an acid group, or thermoplastics.

12. The method of claim 1 further comprising strengthening the tube so that the material within the tube has a tensile strength greater than 40 MPa in at least one direction by deforming the tube prior to making a strut pattern in the tube wall thickness, wherein deforming is by first expanding the diameter of the tube and/or elongating the tube when the tube is at a temperature within the range of glass transition temperature (Tg) of the material(s) within the tube and the melting temperature (Tm) of the material(s) within the tube and second by cooling the tube to below the glass transition temperature (Tg) of the material(s) within the tube after expanding and/or elongating the tube to maintain the strengthened tube.

13. The method of claim 1 further comprising crystallizing some or all the material(s) within the tube so that some or all the material(s) within the tube have a crystallinity greater than 0 percent and the remainder of the material(s) within the tube are amorphous by deforming the tube prior to making a strut pattern in the tube wall thickness, wherein deforming is by first expanding the diameter of the tube and/or elongating the tube when the tube is at a temperature within the range of glass transition temperature (Tg) of the material(s) within the tube and the melting temperature (Tm) of the material(s) within the tube and second by cooling the tube to below the glass transition temperature (Tg) of the material(s) within the tube after expanding and/or elongating the tube to maintain the crystallization within the tube.

14. The method of claim 1 further comprising applying one or more coating(s) onto at least some or all the outer surfaces of the stent.

15. The method of claim 1 further comprising using the stent in an end-use application selected for the group of: a device for repair, reconstruction, replacement of hollow organ tissue; a balloon-expandable stent; a bifurcated stent; a biliary stent; a birth control device; a carotid stent; a cell growth platform; a cell transportation device; a cerebral stent; a device for delivering a drug or drugs to an anatomical lumen; a device for local delivery of active ingredients to tubular-shaped lumen or organs for treatment of cancer; a device for reinforcing an anatomical lumen; a device for supporting an anatomical lumen; a device for treatment of cancer within or near an anatomical lumen; a device for treatment of colon or rectal cancer; a device to assist in remodeling of diseased anatomical lumens; a drug delivery device; a drug delivery stent; a gastrointestinal stent; a graft; a iliac stent; a large bronchi stent; a mechanical support device; a modular stent; a nasal stent; a patch; a peripheral vascular stent; a reinforcement device; a renal stent; a repair device; a self-expandable stent; a stent-graft; a superficial femoral artery stent; a scaffold; a tissue engineering application; a trachea stent; a tracheal stent; at treatment; a ureter stent; a urethral stent; a urinary stent; a vascular stent; an anatomical lumen repair or splicing device; an attachment device; an esophageal stent; an implant; an implantable scaffold; an intrauterine device (IUD); an oncology treatment device; and a device for the treatment of cancer; an implantable device or patch; a regenerative medicine device; a coronary vascular stent.

16. The method of claim 1 further comprising incorporating one or more active ingredients into the stent.

17. The method of claim 1 further comprising incorporating one or more active ingredient(s) into the stent, wherein the active ingredients are selected from the group of: 5-Fluorauracil (5-FU); abciximab; ABT-578; actinomcin D; actinomycin; agents affecting extracellular matrix production and organization; agents that bind to the FKBP12 binding protein; agents that binds to the mammalian target of rapamycin (mTOR) and thereby blocks the cell cycle mainly of the smooth muscle cell from the G1 to S phase; agents that block T-cell activation or proliferation; agents that decrease cytokine expression on the cell surface membrane and results in an inhibition of T-cell activation and lower smooth muscle cell selectivity; agents that fight cancer; agents that have ability to stabilize microtubules and thereby inhibit cell division in the G0/G1 and G2/M phases; agents that inhibit platelet aggregation; agents that inhibit smooth muscle cell proliferation; agents that inhibits the calcineurin receptor; agents that interfere with endogenous vasoactive mechanisms; agents that interferes with endogenous vasoactive mechanisms; agents that prevent or reduce blood clotting; agents that prevent or reduce allergic reactions; agents that promote endothelialization; agents that reduce neointimal hyperplasia; agents that reduce the size of tumors; agents that reduce vascular hyperplasia; an inhibitor of mammalian target of rapamycin (mTOR); amorphous drugs; analgesics; anesthetic agents; anti-cancer agents; anticoagulants; anti-inflammatory agents; anti-irritant agents; anti-migratory agents; antimitotic agents; anti-proliferative agent; anti-sense nucleotides and transforming nucleic acids; anti-thrombotic agents; antibiotics; antibodies; antimicrobials; antineoplastic agents; antiproliferative drugs; Ap-17; bacteria; bARKct inhibitors; batistimat; beta-blockers; bevacizumab; bioactive agents; Biolimus A9; bisphosphonates; bleomycin; buffering agents; capecitabine; capox; carboplatin; carboplatin AUC 6; cetuximab; chaperone inhibitors; chemotherapeutic agents; cilostazole; cisplatin; clopidogrel; corticosteroids; crystalline forms of drugs; crystalline drugs; crystalline materials; cyclosporine; cytostatic drugs; dexamethasone; deoxyribonucleic acid (DNA); docetaxel; doxorubicin hydrochloride; drugs; drugs that interfere with cells ability to reproduce; endothelial progenitor cells (EPC); epidermal growth factor inhibitors; epirubicin; erythropoietin (Epo D); estradiol; estrogen; everolimus; everolimus (certican or RAD-001); FKBP-12 binding agents; flunisolide; fluorouracil; folfiri; folfiri-bevacizumab; folfiri-cetuximab; folfox; gefitinib; geldanamycin; gemcitabine; genetic therapeutic agents; genistein; glucocorticosteroids; growth factors and delivery vectors including recombinant micro-organisms and liposomes; halofuginone; hormones; human apolioproteins (e.g. AI, AII, AIM, AIV, AV, etc.); hydrocortisone; hypothemycin; imiquimod (as well as other imidazoquinoline immune response modifiers); immunosuppressive agents; irinotecan; irinotecan hydrochloride; leptomycin B; leucovorin calcium; limus drugs; liprostin; living cells; lomustine (CCNU); macrolide antibiotics including FKBP-12 binding compounds; at influence pH in environment surrounding endoprosthesis; materials that promote improvement in elasticity of anatomical lumen; materials that promote remodeling of anatomical lumen; materials that provide reparative effect on anatomical lumen; materials that slow down aging process of anatomical lumen; methotrexate; mineralocorticoids; mitomycin; mitotic inhibitors; modified DNA; mometasone furoate; mometasone furoate monohydrate; mTOR inhibitors; myolimus; natural materials; nitric oxide; non-genetic therapeutic agents; novolimus; nucleic acids; oxaliplatin; oxaliplatin and capecitabine; paclitaxel; panitumumab; pegylated liposomal doxorubicine; peptides; peroxisome proliferator-activated receptor gamma ligands (PPAR.gamma.); pharmaceutically active agents; pharmaceutically active agents having optimized morphology; pharmaceuticals; phospholamban inhibitors; pimecrolimus; polypeptides; progestin; protease inhibitors; proteasome inhibitors; protein-tyrosine kinase inhibitors; proteins; radiation; rapamcin hydroxyesters; rapamycin; rapamycin derivatives; regorafenib; regoranfenib, resiquimod; Resten-NG; Ridogrel; Serca 2 gene/protein; semi-crystalline drugs; sirolimus; sirolimus salicylate; statins; steroids; tacrolimus; tacrolimus (FK506); taxol, temsirolimus; temsirolimus (CCI-779 or amorphous rapamycin 42-ester with 3-hydroxy-2-(hydroxymethyl)-2- methyl-propionic acid); therapeutic agents; topotecan; toxic compounds; trapidil; trastuzumab; vascular cell growth inhibitor; vascular cell growth promoter; vascular endothelial growth factors (e.g. VEGF-2); vasodilating agents; vinorelbine; virus; ziv-afibercept; zotarolimus; or zotarolimus.

18. The method of claim 1, further comprising including at least one additive within the bioresorbable material.

19. The method of claim 1 further comprising wrapping at least one additional film around the shape-forming device prior to liquefying the first film and/or additional film(s) and cooling the first and/or additional film(s), wherein the additional film(s) comprise: a material or a blend of materials having a molecular weight equal to or less than 500,000 g/mol, a material or a blend of materials having a molecular weight equal to or greater than 2,682,000 g/mol, a material or a blend of materials having the same or a different chemical composition than the first film, a material or a blend of materials having the same or a different molecular weight than the first film, a material or a blend of materials having the same or a different degradation rate than the first film where the degradation rate is the rate at which the material(s) lose substantial strength at physiological conditions, a material or a blend of materials having the same or a different resorption rate than the first film where the resorption rate is the rate at which the material(s) lose substantial mass at physiological conditions, a material or blend of materials having the same or a different melting temperature than the first film, a material or blend of materials having the same or a different degree of crystallinity than the first film, a material or blend of materials having the same or one or more different physical properties than the first film where the physical properties minimally include the tensile strength, elastic modulus, and/or elongation-to-break properties.

20. The method of claim 1 further comprising wrapping at least one additional film around the shape-forming device prior to liquefying the first film and/or the additional film(s) and cooling the first film and/or additional films(s), wherein the first film comprises poly (L-lactide) or a copolymer of L-lactide and the additional film(s) comprise one bioresorbable material or a blend of multiple bioresorbable materials selected from the group of: poly (L-lactide) or copolymers of L-lactide having a different molecular weight than the first film; poly (L-lactide) or copolymers of L-lactide having a molecular weight equal to or greater than 2,682,000 g/mol; poly (L-lactide) or copolymers of L-lactide having a molecular weight equal to or less than 500,000 g/mol; poly (glycolide) or copolymers glycolide; poly (caprolactone) or copolymers of caprolactone; poly (D-lactide) or co-polymers of D-lactide; and poly (DL-lactide) or co-polymers of DL-lactide.

* * * * *